(12) United States Patent
Reich et al.

(10) Patent No.: US 7,232,912 B2
(45) Date of Patent: Jun. 19, 2007

(54) INDAZOLE COMPOUNDS, PHARMACEUTICAL COMPOSITIONS, AND METHODS FOR MEDIATING OR INHIBITING CELL PROLIFERATION

(75) Inventors: Siegfried Heinz Reich, Solana Beach, CA (US); Ted Michael Bleckman, La Jolla, CA (US); Susan Elizabeth Kephart, San Diego, CA (US); William Henry Romines, III, San Diego, CA (US); Michael Brennan Wallace, San Diego, CA (US)

(73) Assignee: Agouron Pharmaceuticals, Inc., La Jolla, CA (US)

( * ) Notice: Subject to any disclaimer, the term of this patent is extended or adjusted under 35 U.S.C. 154(b) by 1 day.

(21) Appl. No.: 11/112,423

(22) Filed: Apr. 22, 2005

(65) Prior Publication Data

US 2005/0239855 A1    Oct. 27, 2005

Related U.S. Application Data

(62) Division of application No. 10/291,158, filed on Nov. 8, 2002, now Pat. No. 6,919,461, which is a division of application No. 09/761,656, filed on Jan. 18, 2001, now Pat. No. 6,555,539.

(60) Provisional application No. 60/176,484, filed on Jan. 18, 2000.

(51) Int. Cl.
    C07D 235/04    (2006.01)

(52) U.S. Cl. .................................. 548/305.4

(58) Field of Classification Search ............. 548/362.5, 548/305.4
    See application file for complete search history.

(56) References Cited

U.S. PATENT DOCUMENTS

| | | | |
|---|---|---|---|
| 3,862,958 A | 1/1975 | Ruechardt et al. | |
| 3,994,890 A | 11/1976 | Fujimura et al. | |
| 4,051,145 A | 9/1977 | Dupre et al. | |
| 4,978,603 A | 12/1990 | Inoue et al. | |
| 5,221,601 A | 6/1993 | Graindourze et al. | |
| 5,612,360 A | 3/1997 | Boyd et al. | |
| 5,621,082 A | 4/1997 | Xiong et al. | |
| 5,733,920 A | 3/1998 | Mansuri et al. | |
| 5,760,028 A | 6/1998 | Jadhav et al. | |
| 6,020,336 A | 2/2000 | Lavielle et al. | |
| 6,046,205 A | 4/2000 | Lavielle et al. | |
| 6,919,461 B2 * | 7/2005 | Reich et al. | 548/362.5 |
| 2003/0105336 A1 * | 6/2003 | Schindler et al. | 548/364.1 |
| 2004/0092546 A1 * | 5/2004 | Wei et al. | 514/303 |

FOREIGN PATENT DOCUMENTS

WO    WO02/010137    * 7/2002

OTHER PUBLICATIONS

Greene, Theodora, Protective Groups in Organic Synthesis, Third Edition, John Wiley & Sons, Inc.*
Webster, Exp. Opin. Invest. Drugs, vol. 7 (1998), pp. 865-887.
Stover et al., Current Opinion in Drug Discovery and Development; vol. 2 (1999), pp. 274-285.
Sedlacek et al., Int. J. Oncol., vol. 9 (1996), pp. 1143-1168.
Schow et al., Bioorg. Med. Chem. Lett., vol. 7 (1997), pp. 2697-2702.
Legravend et al., Bioorg. Med. Chem. Lett., vol. 8 (1998), pp. 793-798.
Chang, et al., Chemistry & Biology, vol. 6 (1999), pp. 361-375.
Whitten et al., J. Org. Chem. 51, 1891 (1986).
Elpern et al., J. Amer. Chem. Soc., 68, 1946, 1436.
Weinreb et al., Tet. Lett. 27, 19, 1986, 2099-2102.
Gu, et al., Tet. Lett., 37, 15, 1996, 2565-2568.
Kwon et al., Synthesis, 1976, 249.
Harvey et al., J. Chem. Soc. Perk. Trans. 1, 1988, 1939-1944.
Daidone et al., Heterocycles (1996), 43(11), 2385-2396.
Hager et al., Acta Crystallogr., Sect. C: Cryst. Struct. Commun. (1996), 52(11), 2894-2896.
Kamel et al., Tetrahedron (1973), 29(1), 221-225.

* cited by examiner

*Primary Examiner*—Thomas McKenzie
*Assistant Examiner*—Binta Robinson
(74) *Attorney, Agent, or Firm*—Ye Hua; Stephen H. Prodnuk; Bryan C. Zielinski

(57) ABSTRACT

Indazole compounds that modulate and/or inhibit cell proliferation, such as the activity of protein kinases are described. These compounds and pharmaceutical compositions containing them are capable of mediating, e.g., kinases-dependent diseases to modulate and/or inhibit unwanted cell proliferation. The invention is also directed to the therapeutic or prophylactic use of pharmaceutical compositions containing such compounds, and to methods of treating cancer as well as other disease states associated with unwanted angiogenesis and/or cellular proliferation, such as diabetic retinopathy, neovascular glaucoma, rheumatoid arthritis, and psoriasis, by administering effective amounts of such compounds.

2 Claims, No Drawings

INDAZOLE COMPOUNDS, PHARMACEUTICAL COMPOSITIONS, AND METHODS FOR MEDIATING OR INHIBITING CELL PROLIFERATION

This is a Divisional of U.S. application Ser. No. 10/291,158, filed Nov. 8, 2002 now U.S. Pat. No. 6,919,461, which is a Divisional of U.S. application Ser. No. 09/761,656, filed Jan. 18, 2001, now U.S. Pat. No. 6,555,539, which claims the benefit of U.S. Provisional Application No. 60/176,484, filed Jan. 18, 2000, the disclosures of which are incorporated by reference herein in their entireties.

FIELD OF THE INVENTION

This invention is directed to indazole compounds that mediate and/or inhibit cell proliferation, for example, through the inhibition of the activity of protein kinases, such as VEGF, CHK-1, and cyclin-dependent kinases (CDKs), such as CDK1, CDK2, CDK4, and CDK6. The invention is further related to pharmaceutical compositions containing such compounds and compositions, and to methods of treating cancer as well as other disease states associated with unwanted angiogenesis and/or cellular proliferation, by administering effective amounts of such compounds.

BACKGROUND OF THE INVENTION

Uncontrolled cell proliferation is the insignia of cancer. Cell proliferation in response to various stimuli is manifested by a deregulation of the cell division cycle, the process by which cells multiply and divide. Tumor cells typically have damage to the genes that directly or indirectly regulate progression through the cell division cycle.

Hyperproliferative disease states, including cancer, are characterized by cells rampantly winding through the cell cycle with uncontrolled vigor due to, for example, damage to the genes that directly or indirectly regulate progression through the cycle. Thus, agents that modulate the cell cycle, and thus hyperproliferation, could be used to treat various disease states associated with uncontrolled or unwanted cell proliferation. In addition to cancer chemotherapeutic agents, cell cycle inhibitors are also proposed as antiparasitics (See, Gray et al., *Curr. Med. Chem.* 6, 859–875 (1999)) and recently demonstrated as potential antivirals (See, Schang et al., *J. Virol.* 74, 2107–2120 (2000)). Moreover, the applicability of antiproliferative agents may be expanded to treating cardiovascular maladies such as artherosclerosis or restenosis (See Braun-Dullaeus et al., *Circulation*, 98, 82–89 (1998)), and states of inflammation, such as arthritis (See, Taniguchi et al., *Nature Med.*, 5, 760–767(1999)) or psoriasis.

Mechanisms of cell proliferation are under active investigation at cellular and molecular levels. At the cellular level, de-regulation of signaling pathways, loss of cell cycle controls, unbridled angiogenesis or stimulation of inflammatory pathways are under scrutiny, while at the molecular level, these processes are modulated by various proteins, among which protein kinases are prominent suspects. Overall abatement of proliferation may also result from programmed cell death, or apoptosis, which is also regulated via multiple pathways, some involving proteolytic enzyme proteins.

Among the candidate regulatory proteins, protein kinases are a family of enzymes that catalyze phosphorylation of the hydroxyl group of specific tyrosine, serine, or threonine residues in proteins. Typically, such phosphorylation dramatically perturbs the function of the protein, and thus protein kinases are pivotal in the regulation of a wide variety of cellular processes, including metabolisim, cell proliferation, cell differentiation, and cell survival. Of the many different cellular functions in which the activity of protein kinases is known to be required, some processes represent attractive targets for therapeutic intervention for certain disease states. Two examples are cell-cycle control and angiogenesis, in which protein kinases play a pivotal role; these processes are essential for the growth of solid tumors as well as for other diseases.

CDKs constitute a class of enzymes that play critical roles in regulating the transitions between different phases of the cell cycle, such as the progression from a quiescent stage in $G_1$ (the gap between mitosis and the onset of DNA replication for a new round of cell division) to S (the period of active DNA synthesis), or the progression from $G_2$ to M phase, in which active mitosis and cell-division occur. See, e.g., the articles compiled in *Science*, vol. 274 (1996), pp. 1643–1677; and *Ann. Rev. Cell Dev. Biol.*, vol. 13 (1997), pp. 261–291. CDK complexes are formed through association of a regulatory cyclin subunit (e.g., cyclin A, B1, B2, D1, D2, D3, and E) and a catalytic kinase subunit (e.g., cdc2 (CDK1), CDK2, CDK4, CDK5, and CDK6). As the name implies, the CDKs display an absolute dependence on the cyclin subunit in order to phosphorylate their target substrates, and different kinase/cyclin pairs function to regulate progression through specific portions of the cell cycle.

The D cyclins are sensitive to extracellular growth signals and become activated in response to mitogens during the $G_1$ phase of the cell cycle. CDK4/cyclin D plays an important role in cell cycle progression by phosphorylating, and thereby inactivating, the retinoblastoma protein (Rb). Hypophosphorylated Rb binds to a family of transcriptional regulators, but upon hyperphosphorylation of Rb by CDK4/cyclin D, these transcription factors are released to activate genes whose products are responsible for S phase progression. Rb phosphorylation and inactivation by CDK4/cyclin D permit passage of the cell beyond the restriction point of the $G_1$ phase, whereupon sensitivity to extracellular growth or inhibitory signals is lost and the cell is committed to cell division. During late $G_1$, Rb is also phosphorylated and inactivated by CDK2/cyclin E, and recent evidence indicates that CDK2/cyclin E can also regulate progression into S phase through a parallel pathway that is independent of Rb phosphorylation (see Lukas et al., "Cyclin E-induced S Phase Without Activation of the pRb/E2F Pathway," *Genes and Dev.*, vol. 11 (1997), pp. 1479–1492).

The progression from $G_1$ to S phase, accomplished by the action of CDK4/cyclin D and CDK2/cyclin E, is subject to a variety of growth regulatory mechanisms, both negative and positive. Growth stimuli, such as mitogens, cause increased synthesis of cyclin D1 and thus increased functional CDK4. By contrast, cell growth can be "reined in," in response to DNA damage or negative growth stimuli, by the induction of endogenous inhibitory proteins. These naturally occurring protein inhibitors include $p21^{WAF1/CIP1}$, $p27^{KIP1}$, and the $p16^{INK4}$ family, the latter of which inhibit CDK4 exclusively (see Harper, "Cyclin Dependent Kinase Inhibitors," *Cancer Surv.*, vol. 29 (1997), pp. 91–107). Aberrations in this control system, particularly those that affect the function of CDK4 and CDK2, are implicated in the advancement of cells to the highly proliferative state characteristic of malignancies, such as familial melanomas, esophageal carcinomas, and pancreatic cancers (see, e.g., Hall and Peters, "Genetic Alterations of Cyclins, Cyclin-Dependent Kinases, and CDK Inhibitors in Human Cancer," *Adv. Cancer Res.*, vol. 68 (1996), pp. 67–108; and Kamb et al., "A Cell Cycle Regulator Potentially Involved in Genesis of Many Tumor Types," *Science*, vol. 264 (1994), pp. 436–440). Overexpression of cyclin D1 is linked to esophageal, breast, and squamous cell carcinomas (see, e.g., DelSal et al., "Cell Cycle and Cancer: Critical Events at the $G_1$ Restriction Point," *Critical Rev. Oncogenesis*, vol. 71 (1996), pp. 127–142). Genes encoding the CDK4-specific inhibitors of the p16 family frequently have deletions and mutations in familial melanoma, gliomas, leukemias, sarcomas, and pancreatic, non-small cell lung, and head and neck carcinomas (see Nobori et al., "Deletions of the Cyclin-Dependent Kinase-4 Inhibitor Gene in Multiple Human Cancers," *Nature*, vol. 368 (1994), pp. 753–756). Amplification and/or overexpression of cyclin E has also been observed in a wide variety of solid tumors, and elevated cyclin E levels have been correlated with poor prognosis. In addition, the cellular levels of the CDK inhibitor p27, which acts as both a substrate and inhibitor of CDK2/cyclin E, are abnormally low in breast, colon, and prostate cancers, and the expression levels of p27 are inversely correlated with the stage of disease (see Loda et al., "Increased Proteasome-dependent Degradation of the Cyclin-Dependent Kinase Inhibitor p27 in Aggressive Colorectal Carcinomas," *Nature Medicine*, vol. 3 (1997), pp. 231–234). Recently there is evidence that CDK4/cyclin D might sequester p27, as reviewed in Sherr, et al., *Genes Dev.*, Vol. 13 (1999), pp. 1501–1512. The p21 proteins also appear to transmit the p53 tumor-suppression signal to the CDKs; thus, the mutation of p53 in approximately 50% of all human cancers may indirectly result in deregulation of CDK activity.

The emerging data provide strong validation for the use of compounds inhibiting CDKs, and CDK4 and CDK2 in particular, as anti-proliferative therapeutic agents. Certain biomolecules have been proposed for this purpose. For example, U.S. Pat. No. 5,621,082 to Xiong et al. discloses nucleic acid encoding of inhibitors of CDK6, and WO 99/06540 for CDK's. Peptides and peptidomimetic inhibitors are described in European Patent Publication No. 0 666 270 A2, Bandara, et al., *Nature Biotechnology*, Vol. 15 (1997), pp. 896–901 and Chen, et al., *Proceedings of the National Academy of Science, USA*, Vol. 96 (1999), pp. 4325–4329. Peptide aptamers were identified from screening in Cohen, et al., *Proc. Natl. Acad. Sci. U.S.A.*, Vol. 95 (1998), pp. 14272–14277. Several small molecules have been identified as CDK inhibitors (for recent reviews, see Webster, "The Therapeutic Potential of Targeting the Cell Cycle," *Exp. Opin. Invest. Drugs*, vol. 7 (1998), pp. 865–887, and Stover, et al., "Recent advances in protein kinase inhibition: current molecular scaffolds used for inhibitor synthesis," *Current Opinion in Drug Discovery and Development*, Vol. 2 (1999), pp. 274–285). The flavone flavopiridol displays modest selectivity for inhibition of CDKs over other kinases, but inhibits CDK4, CDK2, and CDK1 equipotently, with $IC_{50}$s in the 0.1–0.3 μM range. Flavopiridol is currently in Phase II clinical trials as an oncology chemotherapeutic (Sedlacek et al., "Flavopiridol (L86-8275; NSC 649890), A New Kinase Inhibitor for Tumor Therapy," *Int. J. Oncol.*, vol. 9 (1996), pp. 1143–1168). Analogs of flavopiridol are the subject of other publications, for example, U.S. Pat. No. 5,733,920 to Mansuri et al. (International Publication No. WO 97/16447) and International Publication Nos. WO 97/42949, and WO 98/17662. Results with purine-based derivatives are described in Schow et al., *Bioorg. Med. Chem. Lett., vol.* 7 (1997), pp. 2697–2702; Grant et al., *Proc. Amer. Assoc. Cancer Res,.* vol. 39 (1998), Abst. 1207; Legravend et al., *Bioorg. Med. Chem. Lett., vol.* 8 (1998), pp. 793–798; Gray et al., *Science*, vol. 281 (1998), pp. 533–538; Chang, et al., *Chemistry & Biology*, Vol. 6 (1999), pp. 361–375, WO 99/02162, WO 99/43675, and WO 99/43676. In addition, the following publications disclose certain pyrimidines that inhibit cyclin-dependent kinases and growth-factor mediated kinases: International Publication No. WO 98/33798; Ruetz et al., *Proc. Amer. Assoc. Cancer Res,.* vol. 39 (1998), Abst. 3796; and Meyer et al., *Proc. Amer. Assoc. Cancer Res.*, vol. 39 (1998), Abst. 3794.

Benzensulfonamides that block cells in G1 are in development by Eisai, see Owa, et al., *J. Med. Chem.*, Vol. 42 (1999), pp. 3789–3799. An oxindole CDK inhibitor is in development by Glaxo-Wellcome, see Luzzio, et al., *Proc. Amer. Assoc. Cancer Res.*, Vol. (1999), Abst. 4102 and WO99/15500. Paullones were found in collaboration with the NCI, Schultz, et al., *J. Med. Chem.*, Vol. (1999), pp. 2909–2919. Indenopyrazoles are described in WO99/17769 and by Seitz, et al, $218^{th}$ ACS Natl. Mtg. (Aug. 22–26, 1999, New Orleans), Abst MEDI 316. Aminothiazoles are used in WO99/24416 and WO99/21845.

CHK1 is another protein kinase. CHK 1 plays an important role as a checkpoint in cell cycle progression. Checkpoints are control systems that coordinate cell cycle progression by influencing the formation, activation and subsequent inactivation of the cyclin-dependent kinases. Checkpoints prevent cell cycle progression at inappropriate times, maintain the metabolic balance of cells while the cell is arrested, and in some instances can induce apoptosis (programmed cell death) when the requirements of the checkpoint have not been met. See, e.g., O'Connor, *Cancer Surveys*, 29, 151–182 (1997); Nurse, *Cell*, 91, 865–867 (1997); Hartwell et al., *Science*, 266, 1821–1828 (1994); Hartwell et al., *Science*, 246, 629–634 (1989).

One series of checkpoints monitors the integrity of the genome and, upon sensing DNA damage, these "DNA damage checkpoints" block cell cycle progression in $G_1$ & $G_2$ phases, and slow progression through S phase. O'Connor, *Cancer Surveys*, 29, 151–182 (1997); Hartwell et al., *Science*, 266, 1821–1828 (1994). This action enables DNA repair processes to complete their tasks before replication of the genome and subsequent separation of this genetic material into new daughter cells takes place. Importantly, the most commonly mutated gene in human cancer, the p53 tumor suppressor gene, produces a DNA damage checkpoint protein that blocks cell cycle progression in $G_1$ phase and/or induces apoptosis (programmed cell death) following DNA damage. Hartwell et al., *Science*, 266, 1821–1828 (1994). The p53 tumor suppressor has also been shown to strengthen the action of a DNA damage checkpoint in $G_2$ phase of the cell cycle. See, e.g., Bunz et al., *Science*, 28, 1497–1501 (1998); Winters et al., *Oncogene*, 17, 673–684 (1998); Thompson, Oncogene, 15, 3025–3035 (1997).

Given the pivotal nature of the p53 tumor suppressor pathway in human cancer, therapeutic interventions that exploit vulnerabilities in p53-defective cancer have been actively sought. One emerging vulnerability lies in the operation of the $G_2$ checkpoint in p53 defective cancer cells. Cancer cells, because they lack $G_1$ checkpoint control, are particularly vulnerable to abrogation of the last remaining barrier protecting them from the cancer killing effects of DNA-damaging agents: the $G_2$ checkpoint. The $G_2$ checkpoint is regulated by a control system that has been conserved from yeast to humans. Important in this conserved system is a kinase, CHK1, which transduces signals from the DNA-damage sensory complex to inhibit activation of the cyclin B/Cdc2 kinase, which promotes mitotic entry. See, e.g., Peng et al., *Science*, 277, 1501–1505 (1997); Sanchez et al., *Science*, 277, 1497–1501 (1997). Inactivation of CHK1 has been shown to both abrogate $G_2$ arrest induced by DNA damage inflicted by either anticancer agents or endogenous DNA damage, as well as result in preferential killing of the resulting checkpoint defective cells. See, e.g., Nurse, *Cell*, 91, 865–867 (1997); Weinert, *Science*, 277, 1450–1451 (1997); Walworth et al., *Nature*, 363, 368–371 (1993); and Al-Khodairy et al., *Molec. Biol. Cell*, 5, 147–160 (1994).

Selective manipulation of checkpoint control in cancer cells could afford broad utilization in cancer chemotherapeutic and radiotherapy regimens and may, in addition, offer a common hallmark of human cancer "genomic instability" to be exploited as the selective basis for the destruction of cancer cells. A number of factors place CHK1 as a pivotal target in DNA-damage checkpoint control. The elucidation of inhibitors of this and functionally related kinases such as CDS1/CHK2, a kinase recently discovered to cooperate with CHK1 in regulating S phase progression (see Zeng et al., *Nature*, 395, 507–510 (1998); Matsuoka, *Science*, 282, 1893–1897 (1998)), could provide valuable new therapeutic entities for the treatment of cancer.

Another group of kinases are the tyrosine kinases. Tyrosine kinases can be of the receptor type (having extracellular, transmembrane and intracellular domains) or the non-receptor type (being wholly intracellular). At least one of the non-receptor protein tyrosine kinases, namely, LCK, is believed to mediate the transduction in T-cells of a signal from the interaction of a cell-surface protein (Cd4) with a cross-linked anti-Cd4 antibody. A more detailed discussion of non-receptor tyrosine kinases is provided in Bolen, *Oncogene*, 8, 2025–2031 (1993), which is incorporated herein by reference.

In addition to its role in cell-cycle control, protein kinases also play a crucial role in angiogenesis, which is the mechanism by which new capillaries are formed from existing vessels. When required, the vascular system has the potential to generate new capillary networks in order to maintain the proper functioning of tissues and organs. In the adult, however, angiogenesis is fairly limited, occurring only in the process of wound healing and neovascularization of the endometrium during menstruation. See Merenmies, J., Parada, L. F., Henkemeyer, M., *Cell Growth & Differentiation*, 8, 3–10 (1997). On the other hand, unwanted angiogenesis is a hallmark of several diseases, such as retinopathies, psoriasis, rheumatoid arthritis, age-related macular degeneneration, and cancer (solid tumors). Folkman, *Nature Med.*, 1, 27–31 (1995). Protein kinases which have been shown to be involved in the angiogenic process include three members of the growth factor receptor tyrosine kinase family: VEGF-R2 (vascular endothelial growth factor receptor 2, also know as KDR (kinase insert domain receptor) and as FLK-1); FGF-R (fibroblast growth factor receptor); and TEK (also known as Tie-2).

VEGF-R2, which is expressed only on endothelial cells, binds the potent angiogenic growth factor VEGF and mediates the subsequent signal transduction through activation of its intracellular kinase activity. Thus, it is expected that direct inhibition of the kinase activity of VEGF-R2 will result in the reduction of angiogenesis even in the presence of exogenous VEGF (see Strawn et al., *Cancer Research*, 56, 3540–3545 (1996)), as has been shown with mutants of VEGF-R2 which fail to mediate signal transduction. Millauer et al., *Cancer Research*, 56, 1615–1620 (1996). Furthermore, VEGF-R2 appears to have no function in the adult beyond that of mediating the angiogenic activity of VEGF. Therefore, a selective inhibitor of the kinase activity of VEGF-R2 would be expected to exhibit little toxicity.

Similarly, FGF-R binds the angiogenic growth factors aFGF and bFGF and mediates subsequent intracellular signal transduction. Recently, it has been suggested that growth factors such as bFGF may play a critical role in inducing angiogenesis in solid tumors that have reached a certain size. Yoshiji et al., *Cancer Research*, 57, 3924–3928 (1997). Unlike VEGF-R2, however, FGF-R is expressed in a number of different cell types throughout the body and may or may not play important roles in other normal physiological processes in the adult. Nonetheless, systemic administration of a small molecule inhibitor of the kinase activity of FGF-R has been reported to block bFGF-induced angiogenesis in mice without apparent toxicity. Mohammad et al., *EMBO Journal*, 17, 5996–5904 (1998).

TEK (also known as Tie-2) is another receptor tyrosine kinase expressed only on endothelial cells which has been shown to play a role in angiogenesis. The binding of the factor angiopoietin-1 results in autophosphorylation of the kinase domain of TEK and results in a signal transduction process which appears to mediate the interaction of endothelial cells with peri-endothelial support cells, thereby facilitating the maturation of newly formed blood vessels. The factor angiopoietin-2, on the other hand, appears to antagonize the action of angiopoietin-1 on TEK and disrupts angiogenesis. Maisonpierre et al., *Science*, 277, 55–60 (1997).

As a result of the above-described developments, it has been proposed to treat angiogenesis by the use of compounds inhibiting the kinase activity of VEGF-R2, FGF-R, and/or TEK. For example, WIPO International Publication No. WO 97/34876 discloses certain cinnoline derivatives that are inhibitors of VEGF-R2, which may be used for the treatment of disease states associated with abnormal angiogenesis and/or increased vascular permeability such as cancer, diabetes, psoriasis, rheumatoid arthritis, Kaposi's sarcoma, haemangioma, acute and chronic nephropathies, atheroma, arterial restinosis, autoimmune diseases, acute inflammation and ocular diseases with retinal vessel proliferation.

In addition to the protein kinases identified above, many other protein kinases have been considered to be therapeutic targets, and numerous publications disclose inhibitors of kinase activity, as reviewed in the following: McMahon et al., *Current Opinion in Drug Discovery & Development*, 1, 131–146 (1998); Strawn et al., *Exp. Opin. Invest. Drugs*, 7, 553–573 (1998).

There is still a need, however, for other small-molecule compounds that may be readily synthesized and are potent inhibitors of cell proliferation, for example, inhibitors of one or more protein kinases, such as CHK1, VEGF, CDKs or CDK/cyclin complexes. Because CDK4 may serve as a general activator of cell division in most cells, and because complexes of CDK4/cyclin D and CDK2/cyclin E govern the early $G_1$ phase of the cell cycle, there is a need for effective and specific inhibitors of CDK4 and/or CDK2 for treating one or more types of tumors.

SUMMARY OF THE INVENTION

An object of the invention is to provide potent antiproliferative agents. Accordingly, one object of the invention is to attain compounds and drug compositions that inhibit the activity of one or more kinases, such as CDKs, VEGF, and CHK-1, or cyclin complexes thereof. A further object is to provide an effective method of treating cancer indications through kinases inhibition, such as through inhibition of VEGF, CHK-1, CDK4 or CDK4/D-type cyclin complexes and/or CDK2 or CDK2/E-type cyclin complexes. Another object is to achieve pharmaceutical compositions containing compounds effective to block the transition of cancer cells into their proliferative phase. These and other objects and advantages of the invention, which will become apparent in light of the detailed description below, are achieved through use of cell-cycle control agents of the invention described below.

According to these objectives, there is provided in accordance with the present invention a compound represented by the Formula I

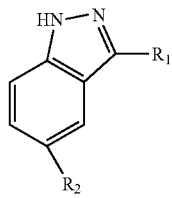

wherein:
R$_1$ is a substituted or unsubstituted alkyl, aryl, heteroaryl, carbocycle, or heterocycle group, or

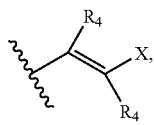

wherein R$_4$ is H or lower alkyl, and X is a substituted or unsubstituted alkyl, aryl, heteroaryl, carbocycle, or heterocycle group; and R$_2$ is a substituted or unsubstituted alkyl, aryl, heteroaryl, carbocycle, or heterocycle group, or

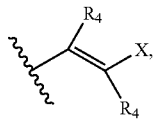

wherein R$_4$ is H or lower alkyl, and X is a substituted or unsubstituted aryl, heteroaryl, carbocycle, or heterocycle group; or a pharmaceutically acceptable salt of a compound of the Formula I; or a prodrug or pharmaceutically active metabolite of a compound of the Formula I, or a pharmaceutically acceptable salt of the prodrug or metabolite.

According to these objectives, there is also provided a compound represented by Formula II:

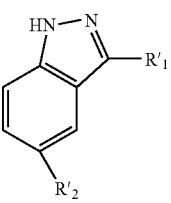

wherein R'$_1$ is a substituted or unsubstituted alkyl, aryl, heteroaryl, carbocycle, heterocycle,

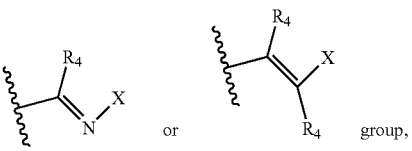

wherein each R$_4$ is individually H or lower alkyl and X is a substituted or unsubstituted alkyl, aryl, heteroaryl, carbocycle, or heterocycle group; and R'$_2$ is a substituted or unsubstituted amino, nitro, alkenyl, alkyl, aryl, heteroaryl, carbocycle, heterocycle,

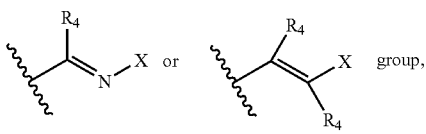

wherein R$_4$ is independently H or lower alkyl, and X is a substituted or unsubstituted aryl, heteroaryl, carbocycle, or heterocycle group; or a pharmaceutically acceptable salt of a compound of the Formula II; or a prodrug or pharmaceutically active metabolite of a compound of the Formula II, or a pharmaceutically acceptable salt of the prodrug or metabolite thereof.

There is also provided in accordance with the invention, a pharmaceutical composition comprising:
(a) a cell-cycle control agent selected from:
  (i) a compound of the Formula I or II,
  (ii) a pharmaceutically acceptable salt of a compound of the Formula I or II; or
  (iii) a prodrug or pharmaceutically active metabolite of a compound of the Formula I or II, or a pharmaceutically acceptable salt of the prodrug or metabolite; and
(b) a pharmaceutically acceptable carrier.

The invention also provides methods for making compounds of Formula I and II.

There is further provided in accordance with the invention, a method of using a compound as a cell-cycle control agent for treating a disease or disorder mediated by inhibition of kinase comprising administering to a patient in need thereof, a compound of Formula I or II, or a pharmaceutically acceptable salt of a compound of the Formula I or II; or a prodrug or pharmaceutically active metabolite of a compound of the Formula I or II, or a pharmaceutically acceptable salt of the metabolite or prodrug.

The invention further provides a method of treating mycotic infection, malignancies or cancer as well as other disease states associated with unwanted angiogenesis and/or cellular proliferation, comprising administering effective amounts of a compound of Formula I or II or a pharmaceutically acceptable salt of a compound of the Formula I or II; or a prodrug or pharmaceutically active metabolite of a compound of the Formula I or II, or a pharmaceutically acceptable salt of the metabolite or prodrug, to a patient in need of such treatment.

The invention also provides a method of modulating and/or inhibiting kinase activity by administering a compound of the Formula I or II or a pharmaceutically acceptable salt of a compound of the Formula I or II; or a prodrug or pharmaceutically active metabolite of a compound of the Formula I or II, or a pharmaceutically acceptable salt of the metabolite or prodrug, to a patient in need thereof.

There is also provided in accordance with the invention, a pharmaceutical composition containing a compound of the Formula I or II or a pharmaceutically acceptable salt of a compound of the Formula I or II; or a prodrug, or pharmaceutically active metabolite of a compound of the Formula I or II, or a pharmaceutically acceptable salt of the metabolite or prodrug, and the therapeutic use of the composition in treating diseases mediated by kinase activity, such as cancer, as well as other disease states associated with unwanted angiogenesis and/or cellular proliferation, such as diabetic retinopathy, neovascular glaucoma, rheumatoid arthritis, and psoriasis.

For the pharmaceutical composition and method aspects of the invention, $R_1$ can also be hydrogen, in Formula I and II.

The inventive agents and compositions containing such agents may be useful in treating various disorders or disease states associated with uncontrolled or unwanted cellular proliferation, such as cancer, autoimmune disorders, viral diseases, fungal diseases, neurodegenerative disorders, and cardiovascular diseases. Thus, the invention is also directed to methods of treating such diseases by administering an effective amount of the inventive agent.

Other aspects, advantages, and features of the invention will become apparent from the detailed description below.

DETAILED DESCRIPTION AND PREFERRED EMBODIMENTS OF THE INVENTION

The compounds and compositions of the present invention, are useful as anti-proliferative agents and as inhibitors of mammalian kinase complexes, insect kinase or fungal kinase complexes. For example, VEGF, CHK-1, and/or CDK complexes can be inhibited. Such compounds and compositions are also useful for controlling proliferation, differentiation, and/or apoptosis.

Examples of $R_1$, $R_2$, $R'_1$, and $R'_2$ preferred in compounds of Formula I or II groups are set forth below:

$R_1$ and $R'_1$

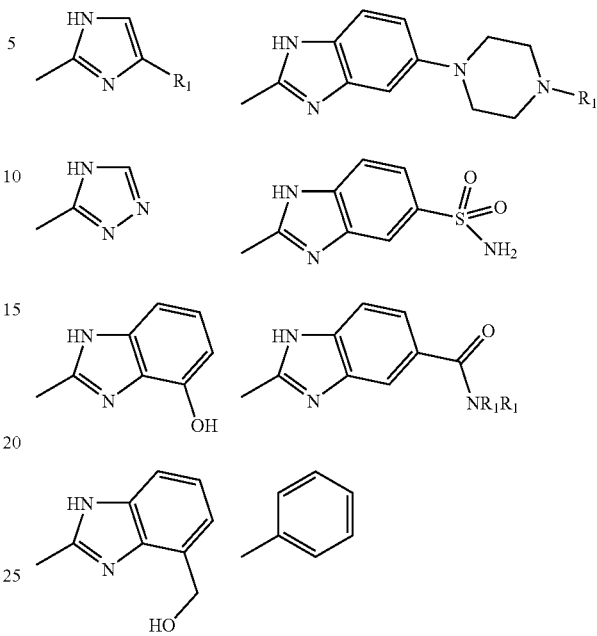

-continued

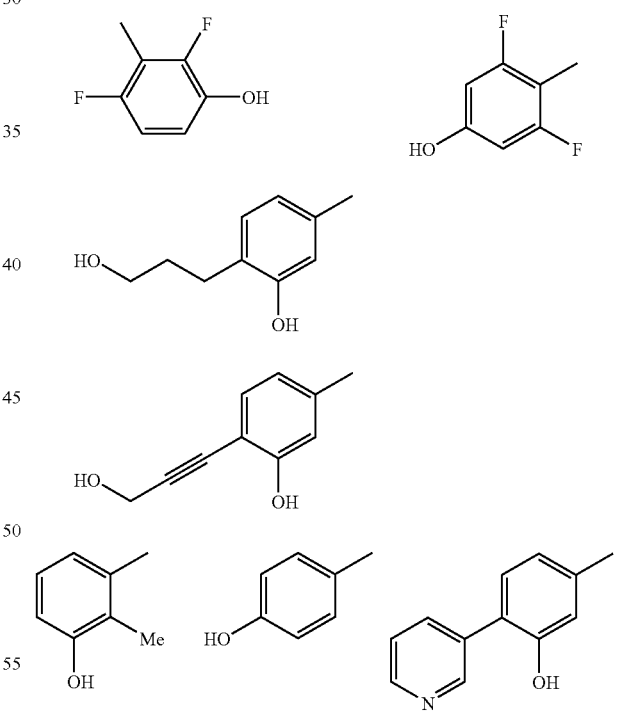

$R_2$ and $R'_2$

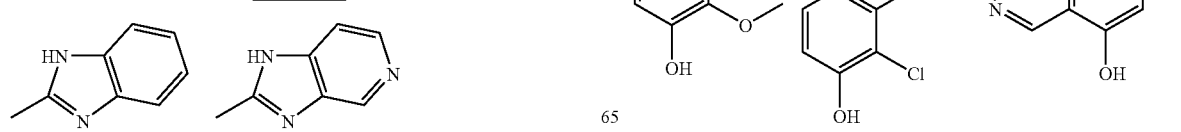

-continued

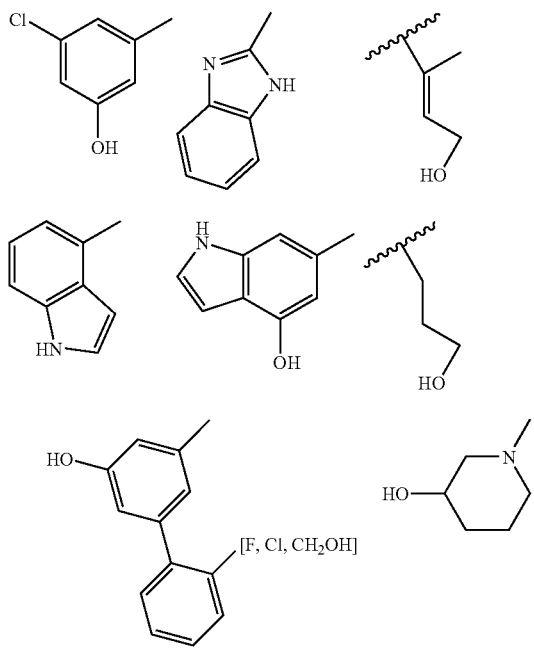

Preferably $R_1$ and $R'_1$ are:

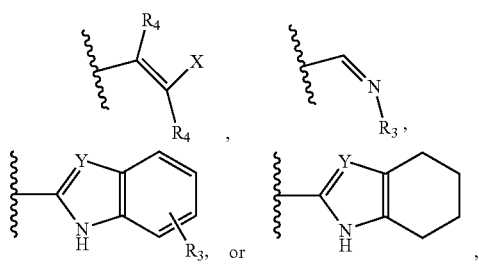

wherein Y is CH or N or $CR_3$, X is as defined above and $R_3$ is H, or one or more substituents located on the ring, such as a substituted or unsubstituted alkyl, alkenyl, aryl, heteroaryl, carbocycle, heterocycle, hydroxy, halogen, alkoxy, aryloxy, heteroaryloxy, thioalkyl, thioaryl, thioacyl, thioheteroaryl or amino;

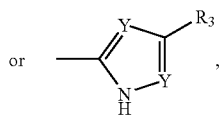

wherein the two Y's can be the same or different.
In those embodiments, wherein $R_1$ or $R'_1$ is

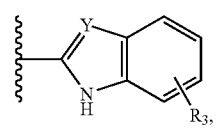

there can be one or more $R_3$ substituents on the phenyl ring.

More preferably, $R_1$ and $R'_1$ are substituted or unsubstituted

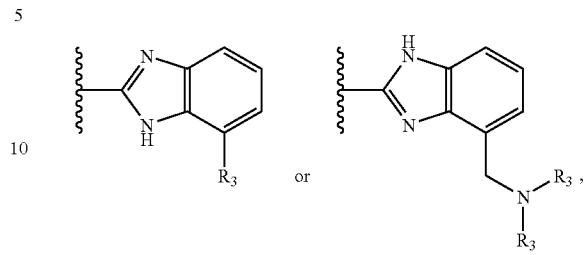

wherein the $R_3$ groups are as defined above. Also, two $R_3$'s together with an adjacent nitrogen can form a heteroaryl or heterocycle ring.

Preferably, $R_2$ and $R'_2$ are unsubstituted or substituted phenyl or

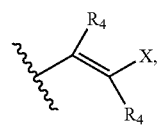

wherein $R_4$ is H or lower alkyl, and X is a substituted or unsubstituted group selected from alkyl, aryl, heteroaryl, carbocycle, or heterocycle.

Other preferred $R_2$ and $R_{12}$ groups are substituted or unsubstituted heteroaryls such as

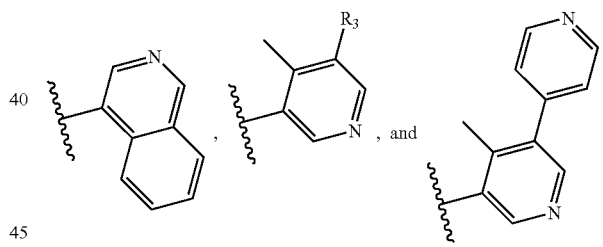

Other preferred $R_2$ and $R'_2$ groups are

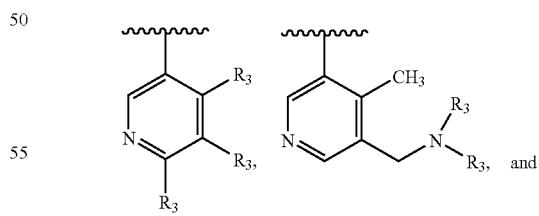

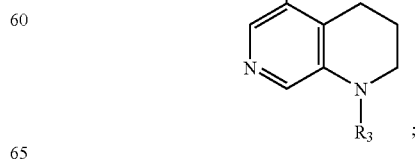

where $R_3$ is as defined above.

Especially preferred substituents for the phenyl of $R_2$ include fluorine, chlorine, hydroxyl, or an alkoxy group, such as methoxy. Examples of preferred R groups, X, and Y groups are found in the exemplary compounds that follow.

Y is preferably nitrogen.

X is preferably aryl, heteroaryl, carbocycle, or heterocycle, most preferably phenyl.

$R_2$ and $R'_2$ can also be an amino (—NR'R"), wherein R' and R" are independently as defined for $R_3$ above, and together with an adjacent nitrogen can form a ring.

$R_4$ is preferably hydrogen, or can be a lower alkyl having 1–6 carbon atoms, which may be substituted or unsubstituted. The two $R_4$'s can be the same or different.

Other preferred $R_1$, $R_2$, $R'_1$, and $R'_2$ groups are found in the exemplary compounds that follow.

Any desired alkyl group can be used, e.g., as $R_1$ or $R_2$ or $R'_1$ or $R'_2$ or $R_3$ or X. The alkyl group can be a straight- or branched-chain alkyl group having one to twelve carbon atoms. Exemplary alkyl groups include methyl, ethyl, n-propyl, isopropyl, butyl, isobutyl, sec-butyl, tert-butyl, pentyl, isopentyl, tert-pentyl, hexyl, isohexyl, and the like. The alkyl can be substituted or unsubstituted. Preferred substituted alkyls include fluoromethyl, difluoromethyl, trifluoromethyl, 2-fluoroethyl, 3-fluoropropyl, hydroxymethyl, 2-hydroxyethyl, 3-hydroxypropyl, and the like.

Any desired aryl, heteroaryl, carbocycle, or heterocycle group can be used as, e.g., $R_1$ or $R_2$ or $R'_1$ or $R'_2$ or $R_3$ or X. The groups can be fused or non-fused, monocyclic or polycyclic.

Preferred aryl and heteroaryl groups include monocyclic and polycyclic unsaturated or aromatic ring structures, with "aryl" referring to those that are carbocycles and "heteroaryl" referring to those that are heterocycles. Examples of ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzothiophenyl(thianaphthenyl), furanyl, thiophenyl, imidazolyl, oxazolyl, isoxazolyl, thiazolyl, triazolyl, tetrazolyl, isoquinolinyl, acridinyl, pyrimidinyl, benzimidazolyl, benzofuranyl, and the like.

Preferred carbocyclic groups include those having from three to twelve carbon atoms, including bicyclic and tricyclic cycloalkyl structures. Preferred carbocyclic groups include cyclopropyl, cyclobutyl, cyclopentyl, cyclohexyl, cycloheptyl, and the like.

Preferred heterocyclic groups include saturated rings containing carbon atoms, for example containing 4 or 5 ring carbon atoms, and at least one heteroatom selected from nitrogen, oxygen and sulfur, and having no unsaturation. Preferred heterocyclic groups include pyrrolidinyl, piperidinyl, thiazinyl, and morpholinyl.

$R_1$, $R_2$, $R_3$, Y, X, and other R groups can be unsubstituted or substituted with any desired substituent or substituents that do not adversely affect the desired activity of the compound. Examples of preferred substituents are those found in the exemplary compounds that follows, as well as halogen (chloro, iodo, bromo, or fluoro); $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano; amido; phosphonato; phosphine; carboxyl; thiocarbonyl; sulfonyl; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O.

These substituents may optionally be further substituted with a substituent selected from such groups.

Preferred compounds are shown in the examples that follow as well as:

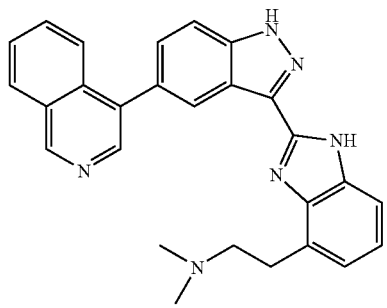

The present invention also relates to intermediates useful in the preparation of compounds of Formula I or II. A particularly preferred intermediate has the structure

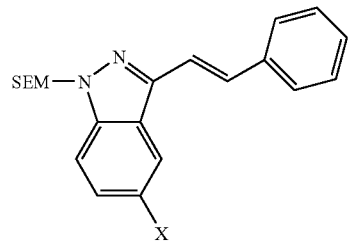

Another preferred intermediate has the structure

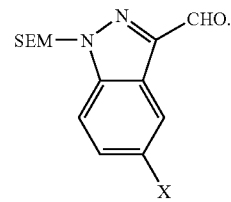

Another preferred intermediate has the structure

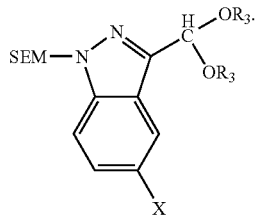

X = halogen, NO₂

In place of SEM, in the above three intermediates, other known protecting groups, such as benzyloxycarbonyl (CBZ), tert-butoxycarbonyl (BOC), tetra hydropyranyl (THP), and fluorene-9-methyloxycarbonyl (FMOC), can be used.

Other preferred intermediates include

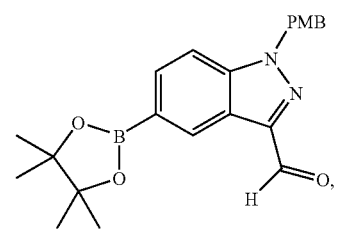
19e

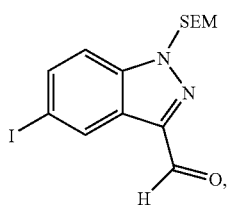
7b'

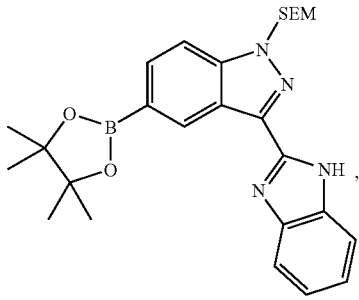
7c'

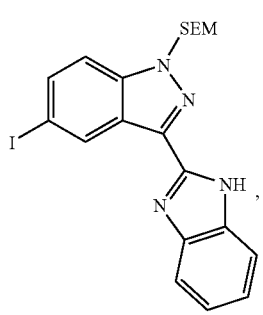

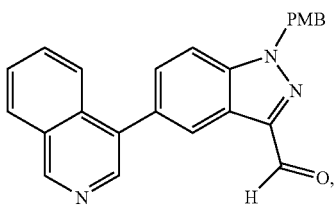
19f

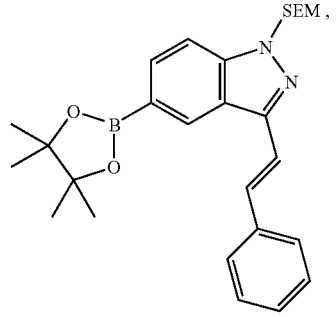
16a

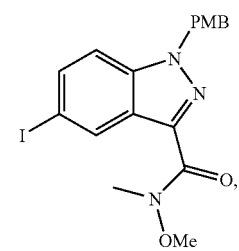
19c

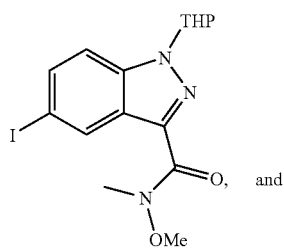
x

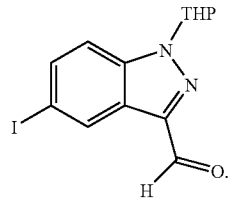
and
y

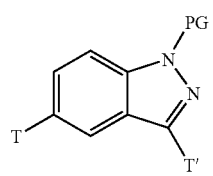

The abbreviations "SEM" and "PMB" refer to (trimethyl silyl) ethoxy methyl and p-methoxybenzyl, respectively.

A preferred intermediate has the structure wherein PG is a protecting group, T is a reactive group such as a substituted or unsubstituted boron, halogen, NO₂, or $NH_2$ group, and T' is a reactive group such as CHO, $CO_2H$, $CO_2R_3$, $CONR_3R_3$, where $R_3$ groups are as defined above.

Pharmaceutical compositions according to the invention may, alternatively or in addition to a compound of the Formula I or II, comprise as an active ingredient a pharmaceutically acceptable salt of a compound of the Formula I or II, or a prodrug or pharmaceutically active metabolite of such a compound or salt or a salt of the prodrug or metabolite. Such compounds, salts, prodrugs, and metabolites are sometimes referred to herein collectively as "cell-cycle control agents."

The term "prodrug" refers to a metabolic precursor of a compound of the Formula I or II (or a salt thereof) that is pharmaceutically acceptable. A prodrug may be inactive when administered to a subject but is converted in vivo to an active compound of the Formula I or II. The term "active metabolite" refers to a metabolic product of a compound of the Formula I or II that is pharmaceutically acceptable and effective. Prodrugs and active metabolites of compounds of the Formula I or II may be determined using techniques known in the art.

Prodrugs and active metabolites of a compound may be identified using routine techniques known in the art. See, e.g., Bertolini et al., J. Med. Chem., 40, 2011–2016 (1997); Shan, et al., J. Pharm. Sci., 86 (7), 765–767; Bagshawe, Drug Dev. Res., 34, 220–230 (1995); Bodor, Advances in Drug Res., 13, 224–331 (1984); Bundgaard, Design of Prodrugs (Elsevier Press 1985); and Larsen, Design and Application of Prodrugs, Drug Design and Development (Krogsgaard-Larsen et al., eds., Harwood Academic Publishers, 1991).

Within the invention it is understood that a compound of Formula I or II may exhibit the phenomenon of tautomerism and that the formula drawings within this specification represent only one of the possible tautomeric forms. It is to be understood that the invention encompasses any tautomeric form which modulates and/or inhibits kinase activity and is not to be limited merely to any one tautomeric form utilized within the formula drawings.

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, Formulas I and II are intended to cover solvated as well as unsolvated forms of the identified structures. For example, Formulas I and II include compounds of the indicated structure in both hydrated and non-hydrated forms. Other examples of solvates include the structures in combination with isopropanol, ethanol, methanol, DMSO, ethyl acetate, acetic acid, or ethanolamine.

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrovic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

Cell-cycle control agents in accordance with the invention are useful as pharmaceuticals for treating proliferative disorders in mammals, especially humans, marked by unwanted proliferation of endogenous tissue. Compounds of the Formula I or II may be used for treating subjects having a disorder associated with excessive cell proliferation, e.g., cancers, psoriasis, immunological disorders involving undesired proliferation of leukocytes, and restenosis and other smooth-muscle disorders. Furthermore, such compounds may be used to prevent de-differentiation of post-mitotic tissue and/or cells.

Diseases or disorders associated with uncontrolled or abnormal cellular proliferation include, but are not limited to, the following:

a variety of cancers, including, but not limited to, carcinoma, hematopoietic tumors of lymphoid lineage, hematopoietic tumors of myeloid lineage, tumors of mesenchymal origin, tumors of the central and peripheral nervous system and other tumors including melanoma, seminoma and Kaposi's sarcoma and the like.

a disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

defective apoptosis-associated conditions, such as cancers (including but not limited to those types mentioned hereinabove), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus erythematosus, rheumatoid arthritis, psoriasis, autoimmune mediated glomerulonephritis, inflammatory bowel disease and autoimmune diabetes mellitus), neurodegenerative disorders (including but not limited to Alzheimer's disease, amyotrophic lateral sclerosis, retinitis pigmentosa, Parkinson's disease, AIDS-related dementia, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteroporosis and arthritis), aspirin-sensitive rhinosinusitis, cystic fibrosis, multiple sclerosis, kidney diseases and cancer pain.

The active agents of the invention may also be useful in the inhibition of the development of invasive cancer, tumor angiogenesis and metastasis.

Moreover, the active agents of the invention, for example, as inhibitors of the CDKs, can modulate the level of cellular RNA and DNA synthesis and therefore are expected to be useful in the treatment of viral infections such as HIV, human papilloma virus, herpes virus, Epstein-Barr virus, adenovirus, Sindbis virus, pox virus and the like.

Compounds and compositions of the invention inhibit the kinase activity of, for example, CDK/cyclin complexes, such as those active in the $G_0$ or $G_1$ stage of the cell cycle, e.g., CDK2, CDK4, and/or CDK6 complexes.

The specific dosage amount of a cell-cycle control agent being administered to obtain therapeutic or inhibitory effects may be determined in a manner known in the art according to the particular circumstances surrounding the case, including, e.g., the specific agent being administered, the route of administration, the condition being treated, and the subject or host being treated. An exemplary total daily dose of a cell-cycle control agent, which may be administered in single or multiple doses, contains a dosage level of from about 0.01 mg/kg body weight to about 50 mg/kg body weight.

The cell-cycle control agents of the invention may be administered by any of a variety of suitable routes, such as orally, rectally, transdermally, subcutaneously, intravenously, intramuscularly, or intranasally. The cell-cycle control agents are preferably formulated into compositions suitable for the desired routes before being administered.

A pharmaceutical composition or preparation according to the invention comprises an effective amount of a cell-cycle control agent, optionally one or more other active agents, and a pharmaceutically acceptable carrier, such as a diluent or excipient for the agent; when the carrier serves as a diluent, it may be a solid, semi-solid, or liquid material acting as a vehicle, excipient, or medium for the active ingredient(s). Compositions according to the invention may be made by admixing the active ingredient(s) with a carrier, or diluting it with a carrier, or enclosing or encapsulating it within a carrier, which may be in the form of a capsule, sachet, paper container, or the like. Exemplary ingredients, in addition to one or more cell-cycle control agents and any other active ingredients, include Avicel (microcrystalline cellulose), starch, lactose, calcium sulfate dihydrate, terra alba, sucrose, talc, gelatin, agar, pectin, acacia, magnesium stearate, stearic acid, peanut oil, olive oil, glyceryl monostearate, Tween 80 (polysorbate 80), 1,3-butanediol, cocoa butter, beeswax, polyethylene glycol, propylene glycol, sorbitan monostearate, polysorbate 60, 2-octyldodecanol, benzyl alcohol, glycine, sorbic acid, potassium sorbate, disodium hydrogen phosphate, sodium chloride, and water.

The compositions may be prepared in any of a variety of forms suitable for the desired mode of administration. For example, pharmaceutical compositions may be prepared in the form of tablets, pills, powders, lozenges, sachets, cachets, elixirs, suspensions, emulsions, solutions, syrups, aerosols (as solids or in liquid media), ointments (e.g., containing up to 10% by weight of a cell-cycle control agent), soft-gel and hard-gel capsules, suppositories, sterile injectable solutions, sterile packaged powders, and the like.

Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation can be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, gylcerin and the like in concentrations ranging from 0–60% of the total volume. A compound of Formula I or II may be dissolved in DMSO and diluted with water. The composition may also be in the form of a solution of a salt form of the active ingredient in an appropriate aqueous vehicle such as water or isotonic saline or dextrose solution.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, hydroxypropylmethyl-cellulose, sodium carboxymethylcellulose, methyl cellulose, or polyvinylpyrrolidone (PVP). It desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

For administration to the eye, the active agent is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/ciliary, lens, choroid/retina and sclera. The pharmaceutically acceptable ophthalmic vehicle may be an ointment, vegetable oil, or an encapsulating material. A compound of the invention may also be injected directly into the vitreous and aqueous humor.

Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

The compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

A pharmaceutical composition according to the invention comprises a cell-cycle control agent and, optionally, one or more other active ingredients, such as a known antiproliferative agent that is compatible with the cell-cycle control agent and suitable for the indication being treated.

The compounds are useful as anti-angiogenesis agents and as agents for modulating and/or inhibiting the activity of protein kinases, thus providing treatments for cancer or other diseases associated with cellular proliferation mediated by protein kinases.

Therapeutically effective amounts of the agents of the invention may be used to treat diseases mediated by modulation or regulation of protein kinases. An "effective amount" is intended to mean that amount of an agent that, when administered to a mammal in need of such treatment, is sufficient to effect treatment for a disease mediated by the activity of one or more kinases. Thus, e.g., a therapeutically effective amount of a compound of the Formula I or II, salt, active metabolite or prodrug thereof is a quantity sufficient to modulate, regulate, or inhibit the activity of one or more kinases such that a disease condition which is mediated by that activity is reduced or alleviated.

"Treating" is intended to mean at least the mitigation of a disease condition in a mammal, such as a human, that is affected, at least in part, by the activity of one or more kinases, and includes: preventing the disease condition from occurring in a mammal, particularly when the mammal is found to be predisposed to having the disease condition but has not yet been diagnosed as having it; modulating and/or inhibiting the disease condition; and/or alleviating the disease condition.

The inventive agents may be prepared using the reaction routes and synthesis schemes as described below, employing the techniques available in the art using starting materials that are readily available.

Exemplary general Schemes 1–6, shown below, can be used to make the compounds of the invention.

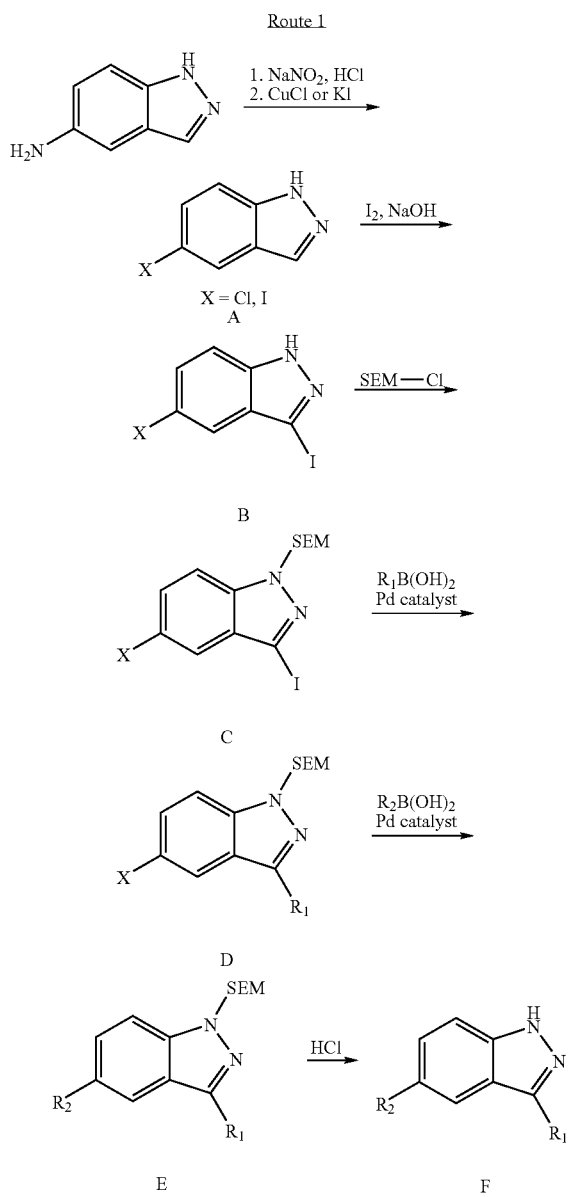

The halogenated intermediate A can be obtained by standard diatozation of 5-amino indazole and treatment of the resulting diazonium salt with an appropriate halide salt, such as CuCl or KI. Further halogenation to afford the 3-haloindazole B is achieved by treatment with a suitable base such as sodium hydroxide or potassium hydroxide and elemental halogen such as iodine. Intermediate B is protected using any number of suitable protecting groups and treated with a (preferably stoichiometric) alkyl or aryl boronic acid or ester and a suitable Pd catalyst, for example, Pd(PPh$_3$)$_4$, to affect selective reaction at the C-3 position. Further reaction with a second alkyl or aryl boronic acid or ester and a suitable Pd catalyst affords the desired 3,5-disubstituted intermediate E which is then deprotected to afford the final compound F. Deprotection conditions are consistent with the specific protecting group employed, for example, acidic conditions for removal of a THP protecting group. $R_1$ and $R_2$ are as defined above, and can be $R'_1$ and $R'_2$.

Route 1 variation

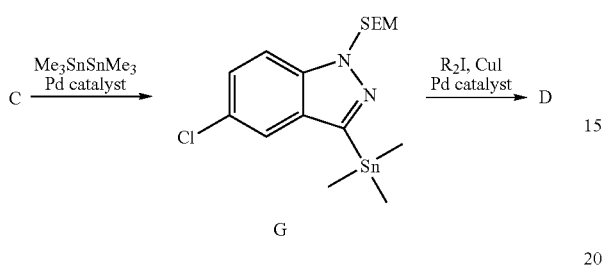

G

The above alternative synthetic variation to Route 1 involves treatment of intermediate C wherein X is Cl with an alkyl ditin species, such as hexamethyl ditin, and an appropriate Pd catalyst, to afford intermediate G. Reaction of intermediate G with an alkyl or aryl halide and a suitable Pd catalyst provides the desired intermediate D which can be further elaborated as described above.

Route 2

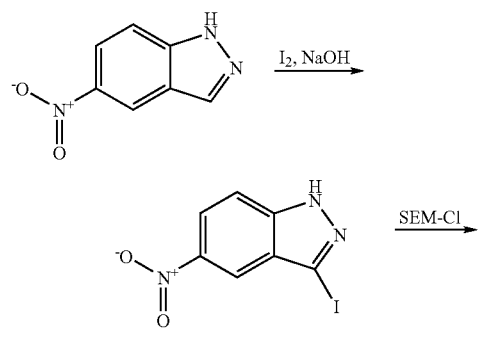

H

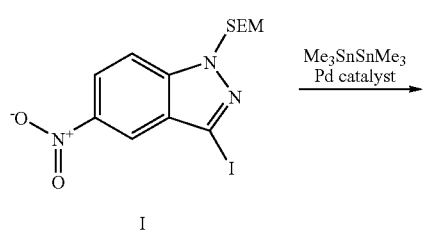

I

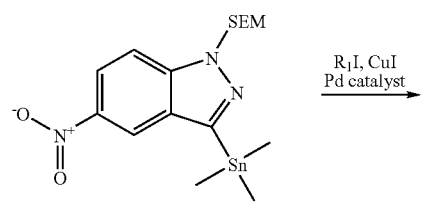

J

-continued

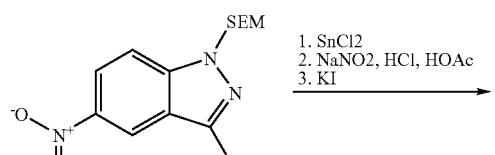

K

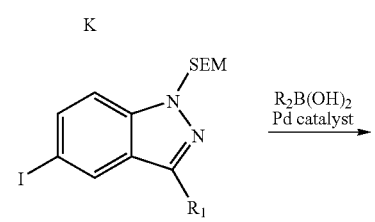

L

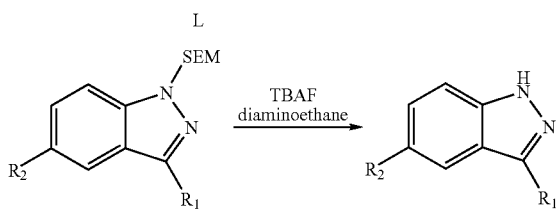

M                F

Alternatively, as shown in Route 2 above, a 5-nitro indazole can be halogenated as described above for intermediate A, to afford nitro compound H, by treatment with a suitable base such as sodium hydroxide or potassium hydroxide and elemental halogen such as iodine to yield an intermediate I after standard protection with an appropriate protecting group. Treatment of intermediate I with an alkyl ditin species, such as hexamethyl ditin, and a suitable Pd catalyst, can afford intermediate J. Further reaction of nitro compound J with an alkyl or aryl boronic acid or ester and a suitable Pd catalyst affords the 3-substituted indazole K. Reduction of K with a suitable reducing agent, such as hydrogen with palladium catalyst or $SnCl_2$, affords the amine. Diazotization of the resulting 5-amino indazole and treatment of the resulting diazonium salt with a suitable halide salt, such as CuCl or KI affords intermediate halo compound L. Reaction of L with an alkyl or aryl boronic acid or ester and a suitable Pd catalyst affords the intermediate M which is deprotected as before to yield final compound F. $R_1$ and $R_2$ are as defined above, and can be $R'_1$ and $R'_2$.

Route 3

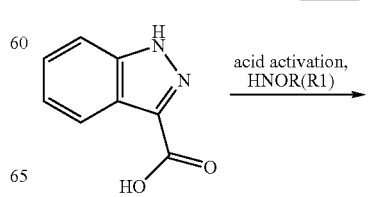

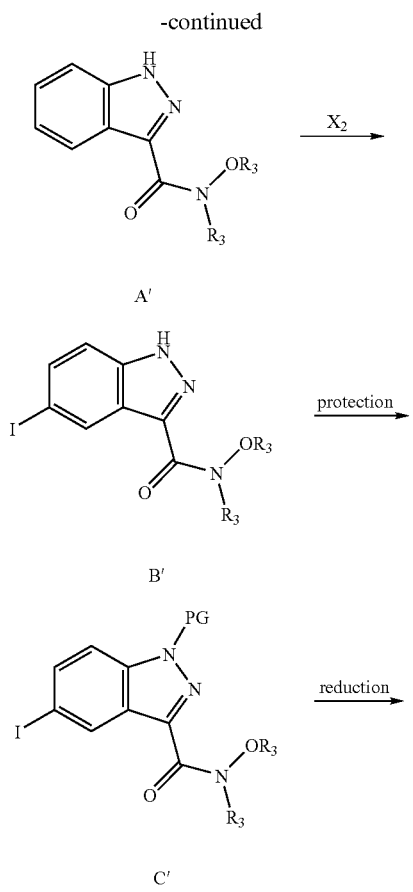

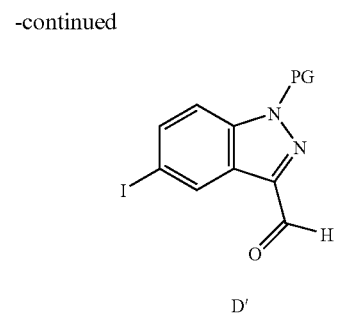

In Route 3 shown above, 3-carboxyindazole is activated to provide an active acylating species, such as with carbonyldiimidazole, which is then treated with a suitable alkoxyalkyl amine, such N,N-dimethylhydroxylamine, to afford the amide A'. Selective halogenation of intermediate A' with elemental halogen such as bromine or iodine and preferably with a catalyst such as bis(trifluoroacetoxy)iodosobenzene or bis(acetoxy)iodosobenzene yields the 5-halo indazole B'. Protection of intermediate B' under standard conditions with a suitable protecting group such as PMB or THP affords protected amide C'. Reduction of C' with an appropriate reductant such as lithium aluminum hydride or an equivalent hydride reducing agent yields key intermediate aldehyde D'. $R_3$ is as defined above, and is preferably substituted or unsubstituted alky, preferably lower alkyl.

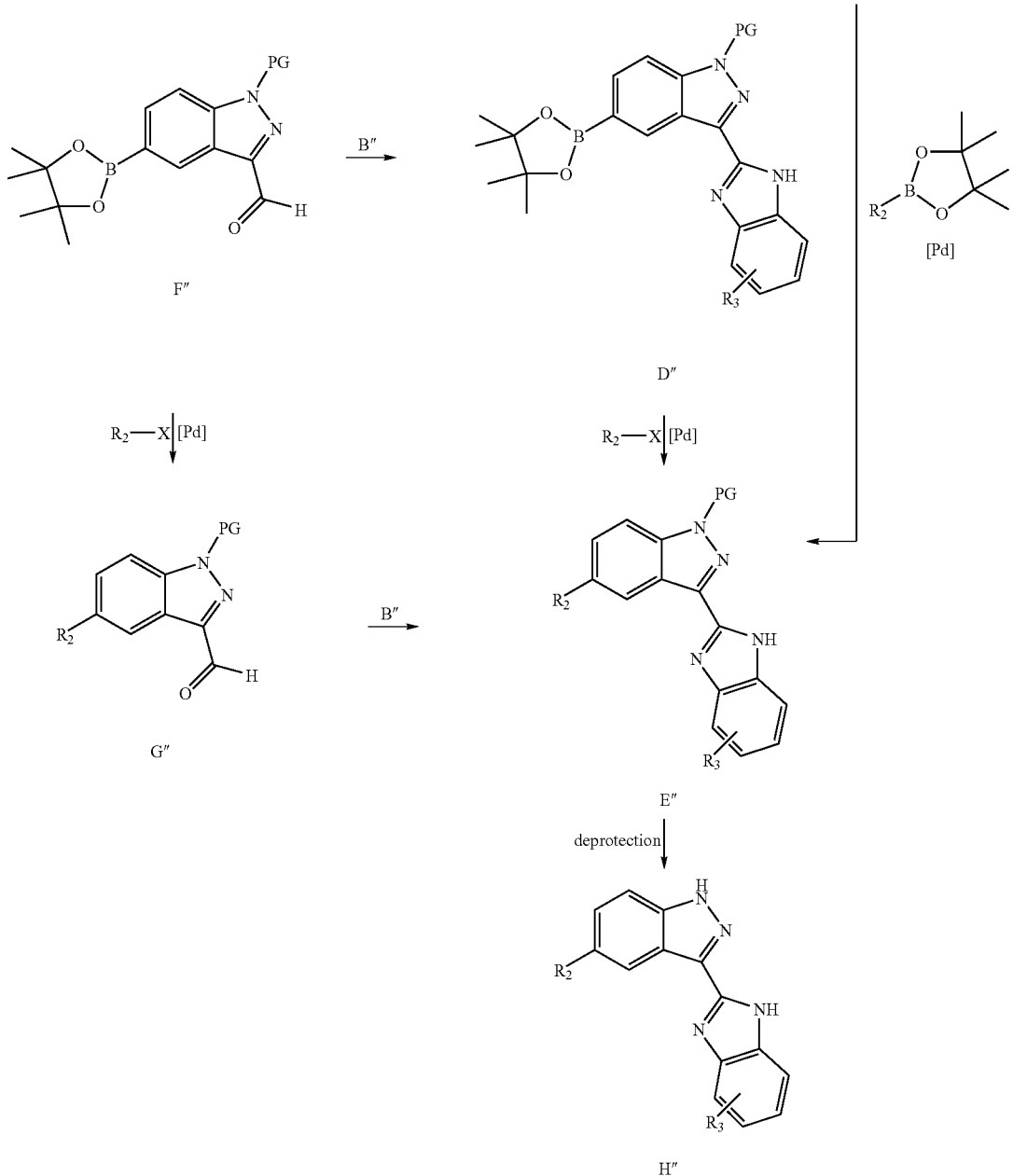

In Route 4 shown above, intermediate D' is reacted with a substituted diamine B" and a suitable oxidizing agent such as sulfur to afford the benzimidazole C'. Conversion of compound C' to the corresponding borinate ester D" is accomplished by reacting with a suitable diboron species, such as dipinacoiatodiboron, or other electrophilic source of boron, with an appropriate palladium catalyst. Intermediate D' is further reacted with a halogenated aryl or alkyl halide under palladium catalysis to give 5-substituted indazole intermediate E", which after appropriate deprotection affords the final compound H".

Alternatively, starting compound D' is reacted with a suitable diboron species, such as bis(pinacolato)diboron, or other suitable electrophilic source of boron, and an appropriate palladium catalyst to give boron ester F'". Elaboration of compound F'" into intermediate D" is accomplished as described before for intermediate D'.

Another alternative conversion can be accomplished by reacting intermediate aldehyde F'" with a substituted aryl or alkyl halide to provide $R_2$ with a palladium catalyst to afford G" which is further reacted with a substituted diamine B" and a suitable oxidizing agent such as sulfur to afford the benzimidazole E". Deprotection as before yields final compound H". $R_2$ is as defined above and can be $R'_2$. $R_3$ is as defined above.

Yet another preparation of intermediate E" can be accomplished by reacting compound such as C" directly with a suitable alkyl borinic acid or ester under suitable palladium catalysis.

Additional electrophilic boron species that can be used have the structure:

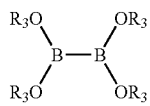

where $R_3$ is as defined above and two $R_3$ groups can form a ring.

Specific examples include:

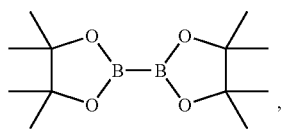

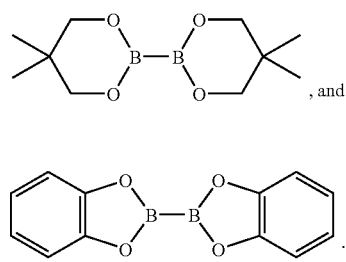

Route 5

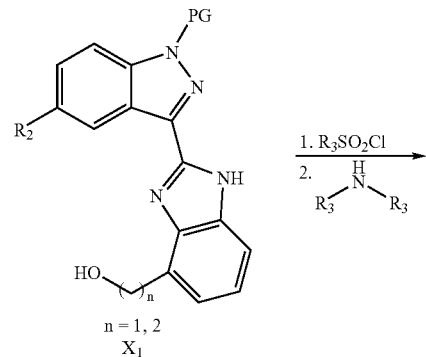

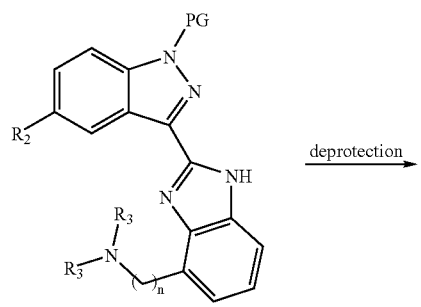

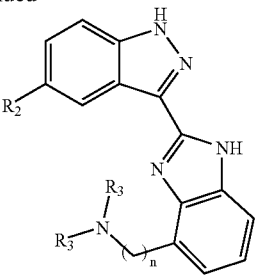

In Route 5 above, alcohol intermediate $X_1$ can be activated for example by reaction with a sulfonyl halide such as methanesulfonyl chloride and a suitable base such as triethylamine and this electrophilic species reacted further with a nucleophile such as a substituted amine to afford the intermediate $X_2$ which is then deprotected under the appropriate conditions. $R_2$ is as defined above, and can be $R'_2$. $R_3$ is as defined above.

Route 6

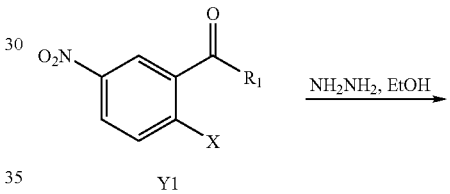

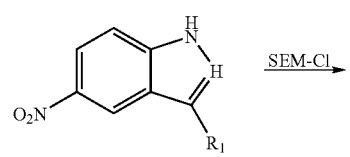

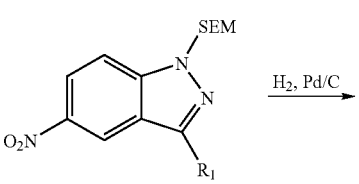

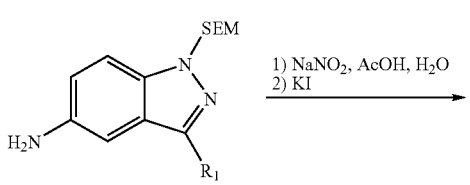

-continued

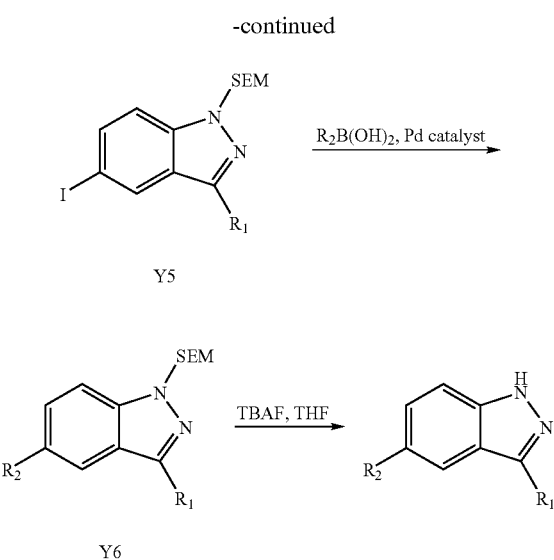

In Route 6 shown above, the core indazole structure is formed in an annulation of a 2-halo-5-nitrophenyl aryl ketone Y1 with hydrazine to provide the requisite 3-aryl-5-nitroindazole Y2. Subsequent protection and reduction provides the amine Y4. As described for Route 2, diazotization, treatment of the diazonium salt with KI, followed by Pd catalyzed coupling of the iodo intermediate with an aryl boronic acid affords the protected 3,5-bisarylindazole intermediate Y6. Standard deprotection then yields the final products. $R_1$ and $R_2$ are as defined above, and can be $R'_1$ and $R'_2$.

The preparation of specific preferred compounds of the invention is described in detail in the following examples. The artisan will recognize that the chemical reactions described may be readily adapted to prepare a number of other kinase inhibitors of the invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius and all parts and percentages are by weight. Reagents were purchased from commercial suppliers such as Aldrich Chemical Company or Lancaster Synthesis Ltd. and were used without further purification unless otherwise indicated. Tetrahydrofuran (THF) distilled from calcium hydride and N,N-dimethylformamide (DMF) were purchased from Aldrich in Sure seal bottles and used as received. All solvents were purified using standard methods readily known to those skilled in the art, unless otherwise indicated.

The reactions set forth below were done generally under a positive pressure of argon or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed on glass-backed silica gel 60 F 254 plates Analtech (0.25 mm) and eluted with the appropriate solvent ratios (v/v), and are denoted where appropriate. The reactions were assayed by TLC and terminated as judged by the consumption of starting material.

Visualization of the TLC plates was done with a p-anisaldehyde spray reagent or phosphomolybdic acid reagent (Aldrich Chemical 20 wt % in ethanol) and activated with heat. Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ or $MgSO_4$ prior to filtration and evaporation of the solvents under reduced pressure on a rotary evaporator and noted as solvents removed in vacuo. Flash column chromatography (Still et al., *J. Org. Chem.*, 43, 2923 (1978)) was done using Baker grade flash silica gel (47–61 μm) and a silica gel: crude material ratio of about 20:1 to 50:1 unless otherwise stated. Hydrogenation was done at the pressure indicated in the examples or at ambient pressure.

$^1$H-NMR spectra were recorded on a Bruker instrument operating at 300 MHz or 500 MHz and $^{13}$C-NMR spectra were recorded operating at 75 MHz. NMR spectra were obtained as $CDCl_3$ solutions (reported in ppm), using chloroform as the reference standard (7.25 ppm and 77.00 ppm) or $CD_3OD$ (3.4 ppm and 4.8 ppm and 49.3 ppm), or internal tetramethylsilane (0.00 ppm) when appropriate. Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Infrared (IR) spectra were recorded on a Perkin-Elmer FT-IR Spectrometer as neat oils, or as KBr pellets, and when given are reported in wave numbers ($cm^{-1}$). The mass spectra were obtained using LSIMS or electrospray. All melting points (mp) are uncorrected.

The starting materials used in the examples are commercially available and/or can be prepared by techniques known in the art.

EXAMPLE 1

5-Phenyl-3-Styryl-1H-Indazole

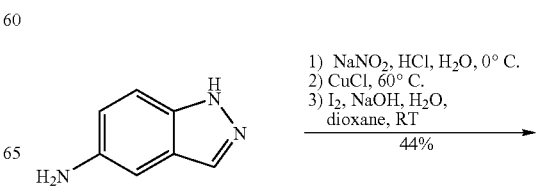

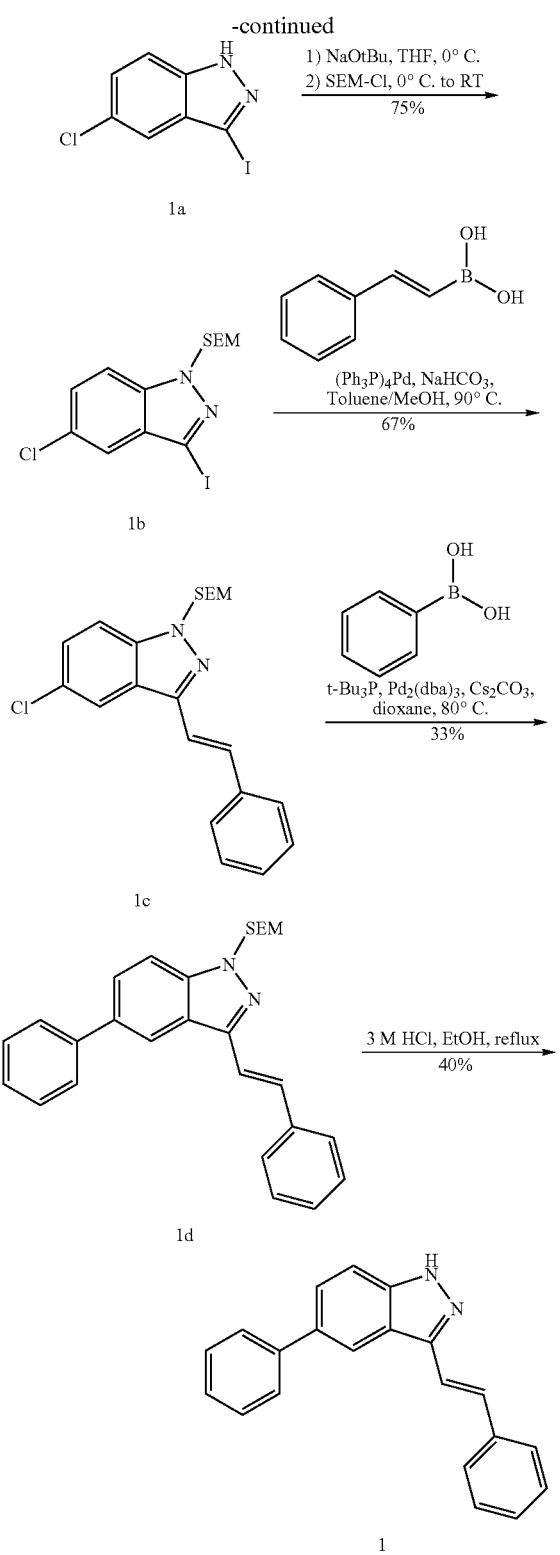

(a) Intermediate 1a—5-Chloro-3-iodo-1H-indazole

5-Amino-1H-indazole (15.41 g, 116 mmol) was suspended in a mixture of water (250 mL), ice (250 mL), and concentrated HCl (100 mL). The mixture was cooled in an ice-salt bath to an internal temperature of −5° C. To this mixture, was added a solution of sodium nitrite (8.78 g, 127 mmol) in water (75 mL), which had been cooled to 0° C. The resulting diazonium solution was stirred for 15 minutes at −5° C. A solution of copper (I) chloride (14.9 g, 151 mmol) in concentrated HCl (150 mL) was cooled to 0° C. and then added to the diazonium solution dropwise, causing an orange precipitate to form. The cooling bath was removed to allow the reaction to warm to room temperature. Gas evolution began at 10° C. internal temperature. After stirring at room temperature for 1.5 hours, the gas evolution subsided. The flask was then heated to 60° C. for 30 minutes, then cooled to ~15° C. A brown precipitate formed. The precipitate was collected by suction filtration and dried in a vacuum dessicator over NaOH for 16 hours to give crude 5-chloro-1H-indazole (25.6 g) as a tan powder.

This crude intermediate was dissolved in 1,4-dioxane (400 mL). 3 M Aqueous NaOH (400 mL) and iodine flakes (35.3 g, 139 mmol) were added to the solution. After stirring at room temperature for 2 hours, the reaction mixture was neutralized to pH=6 with 20% aqueous citric acid, causing the dark color to change to light green. Saturated aqueous sodium thiosulfate (~400 mL) was added to the solution, causing the color to change from green to yellow, and the solution extracted with ethyl acetate (3×1000 mL). The combined organic extracts were dried over sodium sulfate, suction filtered through a coarse frit, and concentrated to a green sludge which was then redissolved in ethyl acetate (500 mL), filtered through a Celite pad, and concentrated to a green solid. Purification by silica gel chromatography (25% ethyl acetate in hexanes) yielded 5-Chloro-3-iodo-1H-indazole 1a (14.18 g, 44% from 5-amino-1H-indazole) as an off-white solid: mp=198–199° C.; $R_f$=0.53 (50% ethyl acetate/hexanes); $^1$H NMR (DMSO-$d_6$) δ 7.44 (m, 2H), 7.60 (d, 1H, J=8.7 Hz), 13.68 (s, 1H). Anal. ($C_7H_4ClIN_2$) C, H, N.

(b) Intermediate 1b—5-Chloro-3-iodo-1-[2-(trimethylsilanyl)-ethoxymethyl]-1H-indazole 5-Chloro-3-iodo-1H-indazole 1a (8.86 g, 31.8 mmol) was dissolved in THF (100 mL) and cooled in an ice-salt bath to 0° C. Solid sodium t-butoxide (3.67 g, 38.2 mmol) was added, and the mixture stirred at 0° C. for 1 hour. 2-(Trimethylsilyl)ethoxymethyl chloride (7.96 g, 38.2 mmol) was then added, and stirring continued at 0° C. for 1 hour more. The solution was diluted with ethyl acetate (200 mL), washed with water (100 mL), and brine (100 mL). The organic layer was dried over magnesium sulfate, filtered, and concentrated. Silica gel chromatography (5 to 20% ethyl acetate in hexanes) afforded 1 b (9.75 g, 75%) as a yellow oil: $R_f$=0.39 (5% ethyl acetate/hexanes); $^1$H NMR (CDCl$_3$) δ −0.06 (s, 9H), 0.87 (t, 2H, J=8.1 Hz), 3.55 (t, 2H, J=8.1 Hz), 5.70 (s, 2H), 7.43 (dd, 1H, J=8.9, 1.7 Hz), 7.49 (m, 2H). Anal. ($C_{13}H_{18}ClIN_2OSi$) C, H, N.

(c) Intermediate 1c—5-Chloro-3-styryl-1-[2-(trimethylsilanyl)-ethoxymethyl]-1H-indazole 5-Chloro-3-iodo-2-SEM-indazole 1b (553 mg, 1.35 mmol), styryl boronic acid (300 mg, 2.03 mmol), and tetrakis(triphenylphosphine)palladium (78.2 mg, 0.068 mmol) were dissolved in toluene (10 mL) and methanol (1.4 mL). Saturated aqueous sodium bicarbonate solution (1.7 mL) was added, and the mixture heated in a 90° C. oilbath for 3 hours. Slight refluxing was observed. After cooling to room temperature, the solution was diluted with water (15 mL) and extracted with ethyl acetate (4×50 mL). The combined organic extracts were dried over magnesium sulfate, filtered, and concentrated. Purification by silica gel chromatography (toluene) gave pure 1c (350.7 mg, 67%) as a yellow oil: $R_f$=0.20 (toluene); $^1$H NMR (CDCl$_3$) δ -0.09 (s, 9H), 0.86 (t, 2H, J=8.1 Hz), 3.55 (t, 2H, J=8.3 Hz), 5.65 (s, 2H), 7.2–7.4 (m, 7H), 7.54 (d, 2H, J=7.6 Hz), 7.93 (d, 1H, J=1.6 Hz). $^{13}$C NMR (CDCl$_3$) δ -1.5, 17.7, 66.5, 77.9, 111.0, 119.2, 120.3, 123.6, 126.5, 127.3, 127.4, 128.0, 128.7, 131.6, 136.9, 139.4, 142.5. Anal. (C$_{21}$H$_{25}$ClN$_2$OSi.0.02 CHCl$_3$) C, H, N, Cl.

(d) Intermediate 1d—5-Phenyl-3-styryl-1-[2-(trimethylsilanyl)-ethoxymethyl]-1H indazole To a solution of 5-chloro-3-styryl-2-SEM-indazole 1c (209.4 mg, 0.544 mmol) in dry 1,4-dioxane (0.5 mL) was added phenyl boronic acid (69.6 mg, 0.571 mmol), cesium carbonate (213 mg, 0.653 mmol), and tris(dibenzylidineacetone)dipalladium (10.0 mg, 0.0108 mmol). A solution of tri-tert-butyl phosphine in 1,4-dioxane (0.1 M, 0.217 mL) was added, and the mixture heated to 80° C. for 6 hours. After cooling to room temperature, the solution was diluted with ethyl ether (20 mL), and filtered through a Celite pad to remove the black palladium precipitate. The filtrate was dried over magnesium sulfate, filtered, concentrated, and purified by silica gel chromatography (toluene) to give 1d (77.2 mg, 33%) as a colorless oil: $R_f$=0.09 (toluene); $^1$H NMR (CDCl$_3$) δ-0.04 (s, 9H), 0.93 (t, 2H, J=8.1 Hz), 3.62 (t, 2H, J=8.1 Hz), 5.76 (s, 2H, J), 7.3–7.7 (m, 14H) 8.17 (s, 1H). Anal. (C$_{27}$H$_{30}$N$_2$OSi.0.2 H$_2$O) C, H, N.

(e) Example 1—5-Phenyl-3-Styryl-1H-indazole

Intermediate 1d (68.1 mg, 0.16 mmol) was dissolved in absolute ethanol (2.0 mL) and 3 M HCl (2.0 mL). The solution was heated to reflux for 20 hours, cooled to room temperature, and extracted with ethyl acetate (3×30 mL). The combined organic extracts were dried over magnesium sulfate, filtered, concentrated, and purified by silica gel chromatography (25 to 50% ethyl acetate in hexanes), affording the title compound (19.2 mg, 40%) as a white solid: $R_f$=0.14 (25% ethyl acetate/hexanes); $^1$H NMR (CDCl$_3$) δ 6.92 (d, 1H, J=6.3 Hz), 7.3–7.7 (m, 13H), 8.20 (s, 1H), 10.3 (br s, 1H). HRMS calculated for C$_{21}$H$_{17}$N$_2$ 297.1392 (MH$^+$). found 297.1398. Anal. (C$_{21}$H$_{16}$N$_2$.0.7 H$_2$O) C, H, N.

EXAMPLE 2

3,5-Distyryl-1H-Indazole

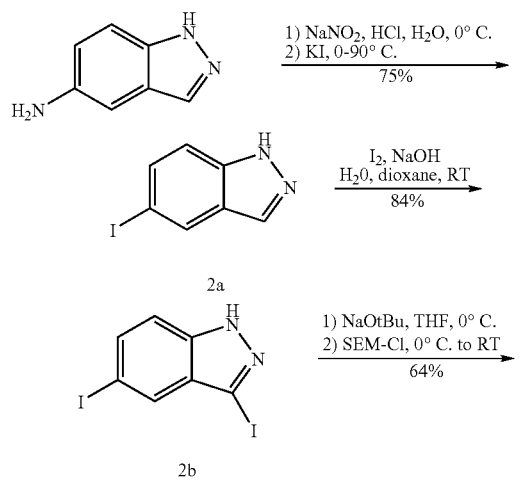

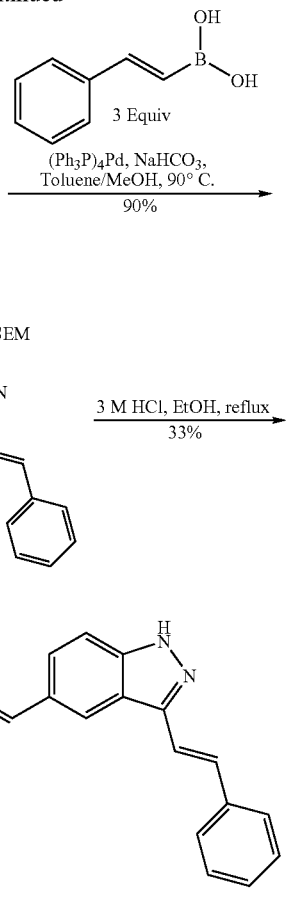

(a) Intermediate 2a—5-Iodo-1H-indazole

5-Amino-1H-indazole (10.21 g, 76.7 mmol) was suspended in a mixture of water (100 mL), ice (100 mL), and concentrated HCl (35 mL). The mixture was cooled in an ice-salt bath to an internal temperature of -5° C. To this mixture was added a solution of sodium nitrite (5.82 g, 84.4 mmol) in water (30 mL), which had been cooled to 0° C. The resulting diazonium solution was stirred for 10 minutes at -5° C., then a solution of potassium iodide (15.3 g, 92 mmol) in water (50 mL) was added slowly dropwise. Significant foaming occurred with the first few drops of KI solution, and then a black, tarry gum formed. After the addition was completed, the mixture was heated to 90° C. for 1 hour. The tarry precipitate dissolved and purple vapor was evolved during heating. The reaction was then cooled to room temperature, causing a fine brown precipitate to form. This precipitate was collected by suction filtration, and dried under vacuum to give 5-iodoindazole 2a (14.12 g, 75%) as a brown powder: $R_f$=0.28 (50% ethyl acetate/hexanes); $^1$H NMR (DMSO-d$_6$) δ 7.40 (d, 1H, J=9.0 Hz), 7.56 (dd, 1H, J=8.5, 1.5 Hz), 8.01 (s, 1H) 8.16 (s, 1H), 13.23 (s, 1H). Anal. (C$_7$H$_5$IN$_2$) C, H, I, N.

(b) Intermediate 2b—3,5-Diiodo-1H-indazole

Intermediate 2b was prepared by a synthetic method analogous to intermediate 1a synthesis. Treatment of intermediate 2a with iodine and sodium hydroxide yielded 3,5-diiodo-1H-indazole 2b (84%) as a yellow solid: $R_f$=0.39 (30% ethyl acetate/hexanes); $^1$H NMR (DMSO-d$_6$) δ 7.41 (d, 1H, J=8.7 Hz), 7.66 (dd, 1H, J=8.7, 1.5 Hz), 7.77 (d, 1H, J=0.9 Hz) 13.65 (s, 1H).

(c) Intermediate 2c—3,5-Diiodo-1-[2-(trimethylsilanyl)-ethoxymethyl]-1H-indazole By a synthetic method similar to intermediate 1b, treatment of 3,5-diiodoindazole 2b with sodium t-butoxide and 2-(trimethylsilyl)ethoxymethyl chloride afforded 2c (64%) as a yellow oil: $R_f$=0.53 (30% ethyl acetate/hexanes); $^1$H NMR (CDCl$_3$) δ −0.05 (s, 9H), 0.86 (t, 2H, J=8.1 Hz), 3.54 (t, 2H, J=8.1 Hz), 5.69 (s, 2H), 7.34 (d, 1H, J=8.7 Hz), 7.69 (dd, 1H, J=8.7, 1.5 Hz), 7.87 (d, 1H, J=1.5 Hz).

(d) Intermediate 2d—3,5-Distyryl-1-[2-(trimethylsilanyl)-ethoxymethyl]-1H-indazole Styryl boronic acid (186 mg, 1.26 mmol) was added to a solution of 2c (210.0 mg, 0.42 mmol) and tetrakis(triphenylphosphine)palladium (48.5 mg, 0.042 mmol) in toluene (3.5 mL) and methanol (0.5 mL). Saturated aqueous sodium bicarbonate solution (1.05 mL) was added, and the mixture heated in a 90° C. oilbath (slight reflux) for 4 hours. After cooling to room temperature, the reaction was poured into water (15 mL) and extracted with ethyl acetate (4×50 mL). The combined organic extracts were dried over magnesium sulfate, filtered, concentrated, and purified by silica gel chromatography (toluene), to give 2d (170.9 mg, 90%) as a yellow oil: $R_f$=0.10 (toluene); $^1$H NMR (CDCl$_3$) δ 0.01 (s, 9H), 0.98 (t, 2H, J=8.5 Hz), 3.67 (t, 2H, J=8.5 Hz), 5.73 (s, 2H), 7.17 (d, 1H, J=16 Hz), 7.3–7.7 (m, 15H), 8.05 (s, 1H). $^{13}$C NMR (CDCl$_3$) δ −1.5, 17.6, 66.4, 77.7, 110.1, 119.4, 119.8, 123.3, 125.1, 126.3, 126.5, 127.8, 128.6, 128.7, 128.9, 131.3, 137.1, 137.3, 140.6, 143.3. Anal. ($C_{29}H_{32}N_2OSi\cdot0.1CHCl_3$) C, H, N.

(e) Example 2—3,5-Distyryl-1H-Indazole

Example 2 was prepared analogous to example 1, by treatment of 2d with 3M HCl which afforded 3,5-distyryl-1H-indazole (33%) as a bright yellow solid: $R_f$=0.11 (25% ethyl acetate/hexanes); $^1$H NMR (CDCl$_3$) δ 7.2–7.7 (m, 16H) 8.076 (s, 1H), 10.05 (br s, 1H). HRMS calculated for $C_{23}H_{19}N_2$ 323.1548 (MH$^+$). found 323.1552. Anal. ($C_{23}H_{18}N_2\cdot0.5\,H_2O$) C, H, N.

EXAMPLE 3

3-(1H-Benzoimidazol-2-yl)-5-Phenyl-1H-indazole

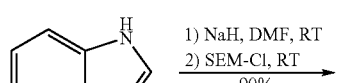
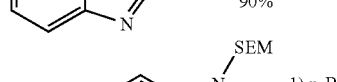
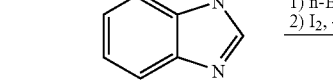

-continued

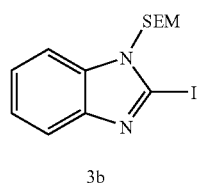
3b

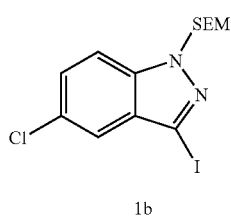
1b

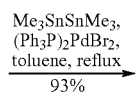

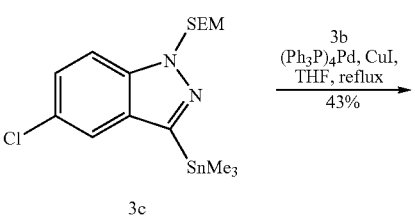
3c

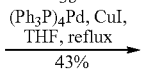

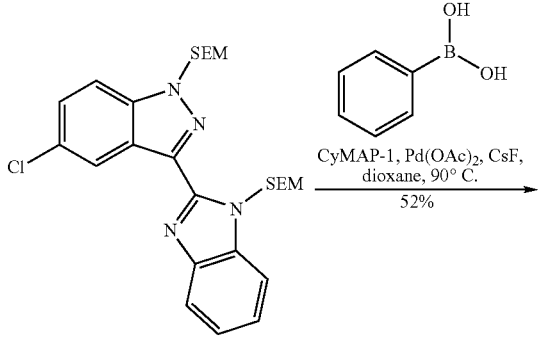
3d

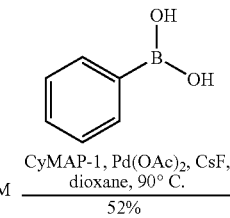

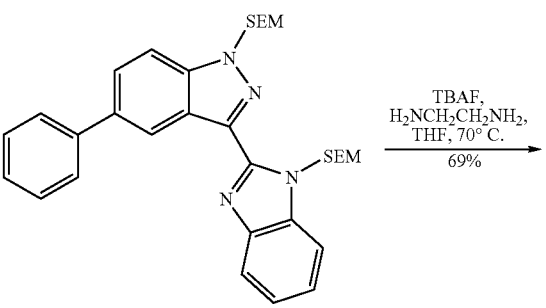
3e

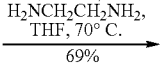

-continued

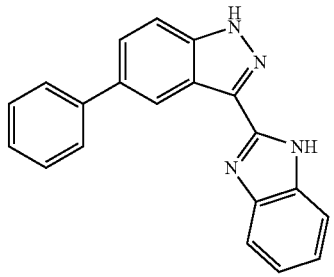

3

(a) Intermediate 3a—1-[2-(Trimethylsilanyl)-ethoxymethyl]-1H benzoimidazole (See Whitten et. al., *J. Org. Chem.* 51, 1891 (1986) incorporated herein by reference, for a similar procedure): Solid 1H-benzoimidazole (30 g, 254 mmol) was added in small portions to a suspension of sodium hydride (10.2 g of 60% dispersion in mineral oil, 254 mmol) in DMF (350 mL) at room temperature. The mixture was stirred for 3 hours, and then cooled to 0° C. in an ice bath. 2-(Trimethylsilyl) ethoxymethyl chloride (46.57 g, 279 mmol) was added dropwise over 10 minutes. The reaction was stirred for 16 hours, warming to room temperature as the ice bath melted, then poured into water (1 L), and extracted with ethyl acetate. The organic layer was washed with brine, dried over sodium sulfate, filtered, concentrated, and purified by silica gel chromatography (50 to 85% ethyl acetate in hexanes) to give 3a (56.63 g, 90%) as an amber oil: $R_f$=0.40 (50% ethyl acetate/hexanes); $^1$H NMR (CDCl$_3$) δ −0.04 (s, 9H), 0.90 (t, 2H, J=8.1 Hz), 3.50 (t, 2H, J=8.1 Hz), 5.53 (s, 2H), 7.31 (m, 2H), 7.54 (m, 1H), 7.81 (m, 1H), 7.96 (s, 1H). Anal. ($C_{13}H_{20}N_2OSi.0.5\ H_2O$) C, H, N.

(b) Intermediate 3b—2-Iodo-1-[2-(trimethylsilanyl)-ethoxymethyl]-1H-benzoimidazole A solution of N-SEM-benzimidazole (intermediate 3a) (19.19 g, 77.25 mmol) in dry ethyl ether (150 mL) and cooled to −78° C. in a dry ice/acetone bath, was added dropwise via cannula to a solution of n-butyllithium (46 mL of 2.5 M in hexanes, 116 mmol) in dry ethyl ether (150 mL), also cooled to −78° C. in a dry ice/acetone bath. Addition of the benzimidazole solution took 10 minutes. Stirring was continued 15 minutes longer, during which time a dark red color developed. The resulting aryllithium solution was added dropwise via cannula to a solution of iodine flakes (49 g, 193 mmol) in dry ether (500 mL), itself cooled to −78° C. in a dry ice/acetone bath. After the addition was complete (10 minutes), the cooling bath was removed, and the reaction mixture was allowed to warm for 30 minutes to an internal temperature of −10° C. Water (250 mL) was added, and the mixture was washed with saturated aqueous sodium bisulfite solution (2×200 mL). The organic layer was dried over sodium sulfate, filtered, concentrated, and purified by silica gel chromatography to give 3-iodo-n-SEM-benzimidazole 3b (22.84 g, 80%) as a yellow solid: mp=60–63° C.; $R_f$=0.70 (ethyl acetate); $^1$H NMR (CDCl$_3$) δ −0.04 (s, 9H), 0.92 (t, 2H, J=8.1 Hz), 3.58 (t, 2H, J=8.1 Hz), 5.53 (s, 2H), 7.27 (m, 2H), 7.51 (m, 1H), 7.73 (m, 1H). HRMS calculated for $C_{13}H_{19}IN_2OSiNa$ 397.0209 (MNa$^+$). found 397.0204. Anal. ($C_{13}H_{19}IN_2OSi$) C, H, I, N.

(c) Intermediate 3c—5-Chloro-1-[2-(trimethylsilanyl)-ethoxymethyl]-3-(trimethylstannyl)-1H-indazole A mixture of intermediate 1b (6.25 g, 15.3 mmol), hexamethylditin (10.2 g, 30.5 mmol), and bis(triphenylphosphine)palladium(II)dibromide (242 mg, 0.306 mmol) in toluene (50 mL) was heated to reflux for 30 minutes, then cooled, filtered, and concentrated. Purification by silica gel chromatography (5 to 50% ethyl acetate in hexanes) gave 3c (6.34 g, 93%) as a slightly yellow oil: $R_f$=0.21 (5% ethyl acetate/hexanes), $R_f$=0.23 (toluene); $^1$H NMR (CDCl$_3$) δ −0.06 (s, 9H), 0.56 (s with small side bands, 9H), 0.87 (t, 2H, J=8.4 Hz), 3.54 (t, 2H, J=8.4 Hz), 5.75 (s, 2H), 7.34 (dd, 1H, J=8.7, 1.8 Hz), 7.51 (d, 1H, J=8.7 Hz), 7.66 (d, 1H, J=1.8 Hz). Anal. ($C_{16}H_{27}ClN_2OSiSn$) C, H, Cl, N.

(d) Intermediate 3d—5-Chloro-1-[2-(trimethylsilanyl)-ethoxymethyl]-3-{1-[2-(trimethylsilanyl)-ethoxymethyl]-1H-benzoimidazol-2-yl}-1H-indazole A mixture of 3c (4.47 g, 10.03 mmol), 3b (4.12 g, 11.03 mmol), tetrakis(triphenylphosphine)palladium(0) (579 mg, 0.50 mmol), and copper(I) iodide (190 mg, 1.00 mmol) in THF (100 mL) was heated to reflux for 1 hour. Additional catalyst (580 mg, 0.50 mmol) and CuI (200 mg, 1.05 mmol) were added, and refluxing continued for 20 hours. After cooling to room temperature, the black precipitate was filtered off, the filtrate concentrated, and the residue purified by silica gel chromatography (toluene) to give pure 3d (2.29 g, 43%) as a colorless oil which crystallizes on standing: mp=80–82° C.; $R_f$=0.12 (10% ethyl acetate/hexanes), $R_f$=0.13 (toluene); $^1$H NMR (CDCl$_3$) δ −0.15 (s, 9H), −0.06 (s, 9H), 0.85 (t, 2H, J=8.1 Hz), 0.91 (t, 2H, J=8.4 Hz), 3.60 (t, 2H, J=8.4 Hz), 3.61 (t, 2H, J=8.1 Hz), 5.80 (s, 2H), 6.24 (s, 2H), 7.36 (m, 2H), 7.47 (dd, 1H, J=9.0, 2.1 Hz), 7.57 (d, 1H, J=9.0 Hz), 7.62 (m, 1H), 7.91 (m, 1H), 8.73 (d, 1H, J=2.1 Hz). Anal. ($C_{26}H_{37}ClN_4O_2Si_2$) C, H, Cl, N.

(e) Intermediate 3e—5-Phenyl-1-[2-(trimethylsilanyl)-ethoxymethyl]-3-{1-[2-(trimethylsilanyl)-ethoxymethyl]-1H-benzoimidazol-2-yl}-1H-indazole A mixture of 3d (192.0 mg, 0.363 mmol), phenylboronic acid (66.4 mg, 0.544 mmol), palladium(II) acetate (3.3 mg, 0.0145 mmol), CyMAP-1 (See Old et. al., *J. Am. Chem. Soc.*, 120, 9722 (1998) for a similar procedure) (5.7 mg, 0.0145 mmol), and cesium fluoride (165 mg, 1.09 mmol) in 1,4-dioxane (3.6 mL) was heated in a 100° C. oilbath for 1 hour. After cooling to room temperature, the mixture was diluted with ethyl acetate (20 mL) and filtered to remove the black precipitate. The filtrate was washed with 1M aqueous sodium hydroxide (20 mL), dried over magnesium sulfate, concentrated, and purified by silica gel chromatography (0 to 4% methanol in dichloromethane) to give 3e (107.0 mg, 52%) as a slightly yellow oil: $R_f$=0.26 (dichloromethane); $^1$H NMR (CDCl$_3$) δ −0.15 (s, 9H), −0.04 (s, 9H), 0.86 (t, 2H, J=8.1 Hz), 0.95 (t, 2H, J=8.1 Hz), 3.61 (t, 2H, J=8.1 Hz), 3.66 (t, 2H, J=8.1 Hz), 5.85 (s, 2H), 6.28 (s, 2H), 7.37 (m, 3H), 7.49 (2H, J=7.5 Hz), 7.63–7.80 (m, 5H), 7.91 (m, 1H), 8.88 (s, 1H). Anal. ($C_{32}H_{42}N_4O_2Si_2.0.4H_2O$) C, H, N.

EXAMPLE 3

3-(1H-Benzoimidazol-2-yl)-5-phenyl-1H-indazole

Tetrabutylammonium fluoride (1.0 M in THF, 3.16 mL) and 1,2-diaminoethane (95 mg, 1.58 mmol) were added to intermediate 3e (90.2 mg, 0.158 mmol). The solution was heated in a 70° C. oilbath for 20 hours, then heated to reflux for 24 hours longer. After cooling to room temperature, the solution was diluted with ethyl acetate (30 mL) and washed with saturated aqueous sodium bicarbonate solution (20 mL). The organic layer was dried over magnesium sulfate, filtered, concentrated, and purified by silica gel chromatography (25 to 50% ethyl acetate in hexanes) to give 3-(1H-Benzoimidazol-2-yl)-5-Phenyl-1H-Indazole 3 (33.9 mg, 69%) as a white solid: $R_f$=0.30 (50% ethyl acetate/hexanes); $^1$H NMR (CDCl$_3$) δ 7.21 (quintet of d, 2H, J=5.7, 1.5 Hz), 7.39 (t, 1H, J=7.4 Hz), 7.53 (t, 3H, J=7.5 Hz), 7.76 (m, 5H), 8.71 (s, 1H), 13.01 (s, 1H), 13.70 (s, 1H). HRMS calculated for C$_{20}$H$_{15}$N$_4$ 311.1297 (MH$^+$). found 311.1283.

EXAMPLE 4

3-[3-(1H-Benzoimidazol-2-yl)-1H-indazol-5-yl]-phenol

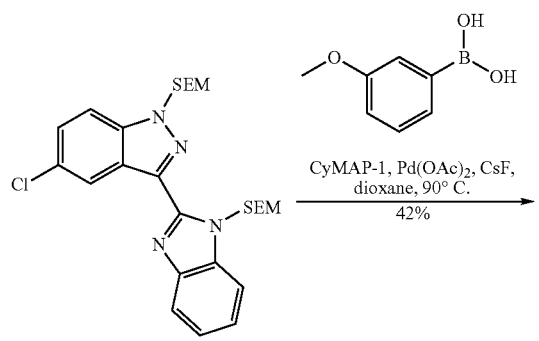

3d

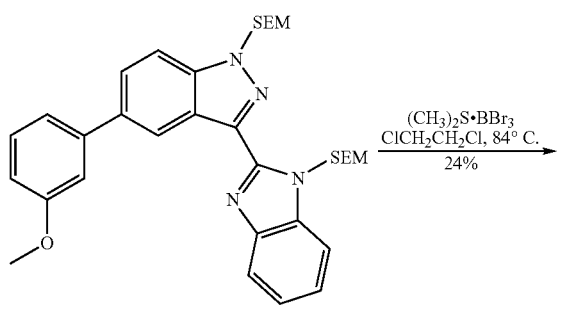

4a

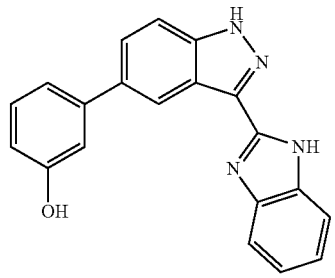

4

(a) Intermediate 4a—5-(3-Methoxyphenyl)-1-[2-(trimethylsilanyl)-ethoxymethyl]-3-{1-[2-(trimethylsilanyl)-ethoxymethyl]-1H-benzoimidazol-2-yl}-1H-indazole A mixture of intermediate 3d (371.5 mg, 0.702 mmol), 3-methoxyphenylboronic acid (160 mg, 1.05 mmol), palladium(II) acetate (7.9 mg, 0.0355 mmol), CyMAP-1 (See Old et. al., *J. Am. Chem. Soc.*, 120, 9722 (1998), incorporated herein by reference, for a similar procedure) (14 mg, 0.0355 mmol), and cesium fluoride (320 mg, 2.11 mmol) in 1,4-dioxane (7.1 mL) was heated in a 90° C. oilbath for 22 hours. After cooling to room temperature, the mixture was diluted with ethyl acetate (50 mL) and filtered to remove the black precipitate. The filtrate was dried over magnesium sulfate, concentrated, and purified by silica gel chromatography (10% ethyl acetate in hexanes) to give 4a (178.3 mg, 42%) as a slightly yellow oil: $R_f$=0.20 (10% ethyl acetate/hexanes); $^1$H NMR (CDCl$_3$) δ −0.14 (s, 9H), −0.03 (s, 9H), 0.86 (t, 2H, J=8.1 Hz), 0.95 (t, 2H, J=8.1 Hz), 3.61 (t, 2H, J=8.1 Hz), 3.66 (t, 2H, J=8.1 Hz), 3.91 (s, 3H), 5.85 (s, 2H), 6.27 (s, 2H), 6.93 (ddd, 1H, J=1.1, 2.5, 8.1 Hz), 7.27–7.40 (m, 5H), 7.63–7.70 (m, 2H), 7.77 (dd, 1H, J=1.5, 8.7 Hz), 7.93 (m, 1H) 8.87 (s, 1H). Anal. (C$_{33}$H$_{44}$N$_4$O$_3$Si$_2$) C, H, N.

(b) Example 4—3-[3-(1H-Benzoimidazol-2-yl)-1H-indazol-5-yl]-phenol

A solution of intermediate 4a (88.3 mg, 0.147 mmol) in 1,2-dichloroethane (3.0 mL) was treated with boron tribromide-methyl sulfide complex (1.0 M in dichloromethane, 0.588 mL) and heated to reflux for 1 hour. Stirring was continued at room temperature for 16 hours. Water (5.0 mL) was added, and stirring continued for 30 minutes at room temperature. The mixture was diluted with diethyl ether (30 mL), and washed with saturated aqueous sodium bicarbonate solution (20 mL). The organic layer was washed with 1 M NaOH (3×30 mL). The combined aqueous washes were acidified to pH=1 with 6 M HCl and extracted sequentially with ether (30 mL), ethyl acetate (30 mL), and dichloromethane (2×20 mL). These organic extracts were combined, dried over magnesium sulfate, filtered, concentrated, and purified by silica gel chromatography (50 to 75% ethyl acetate in hexanes) to give the phenol 4 (11.6 mg, 24%) as a white powder: $^1$H NMR (DMSO-$d_6$) δ 6.78 (dd, 1H, J=1.9, 7.7 Hz), 7.12–7.27 (m, 4H), 7.31 (t, 1H, J=7.7 Hz), 7.52 (dd, 1H, J=2.1, 6.6 Hz), 7.71 (d, 2H, J=1.1 Hz), 7.76 (dd, 1H, J=1.5, 6.8 Hz), 8.67 (s, 1H), 9.57 (s, 1H), 13.00 (s, 1H), 13.68 (s, 1H). HRMS calculated for $C_{20}H_{15}N_4O$ 327.1246 (MH$^+$). found 327.1231.

EXAMPLE 5

3-(1H-Benzoimidazol-2-yl)-5-(3-methoxyphenyl)-1H-indazole

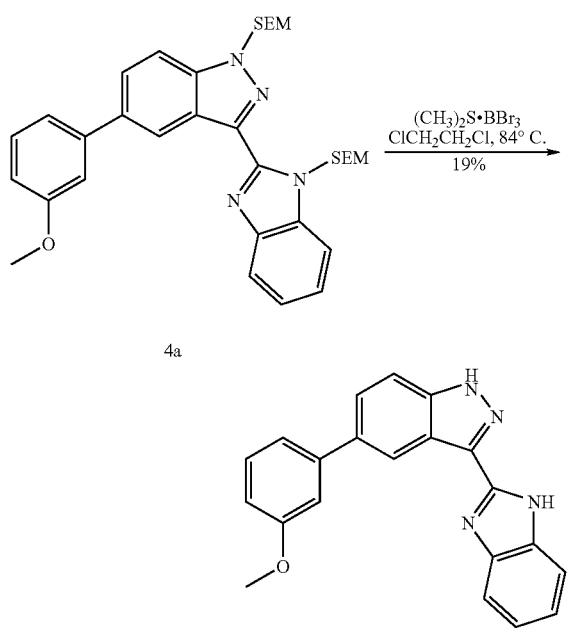

(a) Example 5—3-(1H-Benzoimidazol-2-yl)-5-(3-methoxyphenyl)-1H-indazole

The same crude reaction mixture from which example 4 was obtained also yielded the methoxyphenyl analog 5 as follows:

A solution of intermediate 4a (88.3 mg, 0.147 mmol) in 1,2-dichloroethane (3.0 mL) was treated with boron tribromide-methyl sulfide complex (1.0 M in dichloromethane, 0.588 mL) and heated to reflux for 1 hour. Stirring was then continued at room temperature for 16 hours. Water (5.0 mL) was added, and stirring continued for 30 minutes at room temperature. The mixture was diluted with diethyl ether (30 mL), and washed with saturated aqueous sodium bicarbonate solution (20 mL). The organic layer was washed with 1 M NaOH (3×30 mL). The organic layer was then dried, filtered, concentrated, and purified by silica gel chromatography (50 to 75% ethyl acetate in hexanes) to give 5 (9.3 mg, 19%) as a white powder: $^1$H NMR (DMSO-$d_6$) δ 3.86 (s, 3H), 6.98 (dd, 1H, J=2.1, 7.8 Hz), 7.19–7.23 (m, 3H), 7.30 (d, 1H, J=7.8 Hz), 7.45 (t, 1H, J=7.8 Hz), 7.52 (dd, 1H, J=1.8, 5.7 Hz), 7.75 (m, 3H), 8.70 (s, 1H), 13.00 (s, 1H), 13.70 (s, 1H). HRMS calculated for $C_{21}H_{16}N_4ONa$ 363.1222 (MNa$^+$). found 363.1225.

EXAMPLE 6

3-(1H-Benzoimidazol-2-yl)-5-(2-fluorophenyl)-1H-Indazole

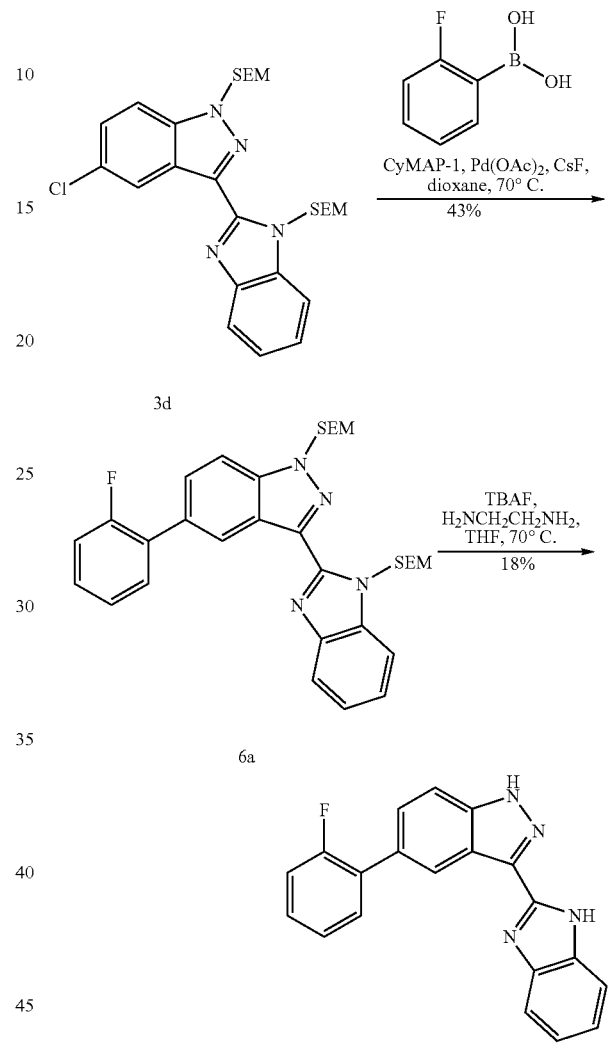

(a) Intermediate 6a—5-(2-Fluorophenyl)-1-[2-(trimethylsilanyl)-ethoxymethyl]-3-{1-[2-(trimethylsilanyl)-ethoxymethyl]-1H-benzoimidazol-2-yl}-1H-indazole A mixture of intermediate 3d (419.0 mg, 0.792 mmol), 2-fluorophenylboronic acid (166 mg, 1.19 mmol), palladium (II) acetate (9.0 mg, 0.04 mmol), CyMAP-1 (See Old et. al., J. Am. Chem. Soc., 120, 9722 (1998) incorporated herein by reference, for a similar procedure) (16 mg, 0.04 mmol), and cesium fluoride (361 mg, 2.38 mmol) in 1,4-dioxane (8.0 mL) was heated in a 70° C. oilbath for 1 hour. As only partial conversion was observed, more palladium (II) acetate (12 mg, 0.05 mmol) and CyMAP-1 (14 mg, 0.035 mmol) were added, and stirring continued at 70° C. for 16 hr. After cooling to room temperature, the mixture was diluted with ethyl acetate (50 mL) and filtered to remove the black precipitate. The filtrate was dried over magnesium sulfate, concentrated, and purified by silica gel chromatography (10% ethyl acetate in hexanes) to give 6a (155.6 mg, 43%) as a colorless oil: $^1$H NMR (CDCl$_3$) δ −0.14 (s, 9H), −0.03 (s, 9H), 0.86 (t, 2H, J=8.1 Hz), 0.95 (t, 2H, J=8.1 Hz), 3.61 (t, 2H, J=8.1 Hz), 3.66 (t, 2H, J=8.1 Hz), 5.86 (s, 2H), 6.27 (s, 2H), 7.15–7.39 (m, 5H), 7.57–7.75 (m, 4H), 7.88 (m, 1H) 8.82 (s, 1H). Anal. (C$_{32}$H$_{41}$FN$_4$O$_2$Si$_2$.0.4H$_2$O) C, H, N.

(b) Example 6—3-(1H-Benzoimidazol-2-yl)-5-(2-fluorophenyl)-1H-indazole

Example 6 was prepared by a synthetic method analogous to example 3. Treatment of intermediate 6a with tetrabutylammonium fluoride afforded 6 (21.2 mg, 18%) as a white powder: R$_f$=0.35 (50% ethyl acetate/hexanes); $^1$H NMR (DMSO-d$_6$) δ 7.20 (m, 2H), 7.33–7.52 (m, 4H), 7.62 (m, 2H), 7.74 (m, 2H), 8.65 (s, 1H), 13.02 (s, 1H), 13.75 (s, 1H). HRMS calculated for C$_{20}$H$_{14}$FN$_4$ 329.1202 (MH$^+$). found 329.1212. Anal. (C$_{20}$H$_{13}$FN$_4$.1.1H$_2$O) C, H, N.

EXAMPLE 7'

3-(1H-Benzoimidazol-2-yl)-5-(4-methoxyphenyl)-1H-indazole

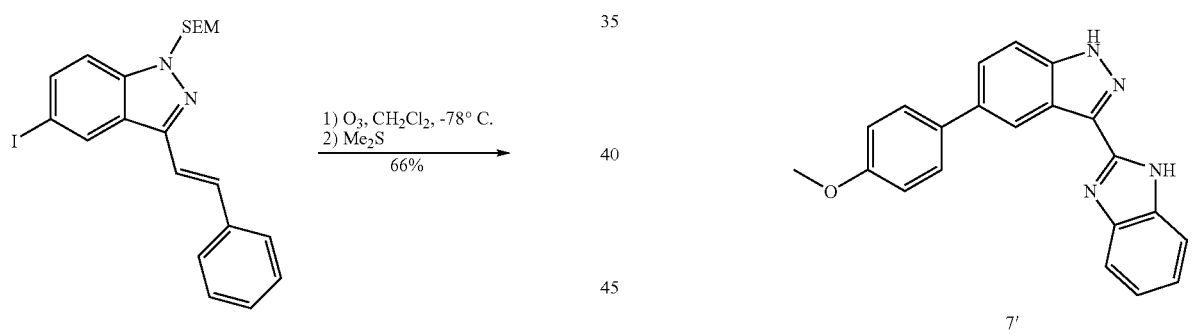

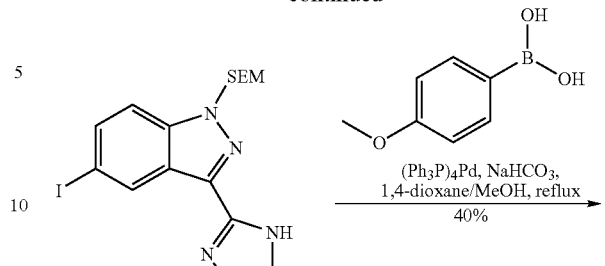

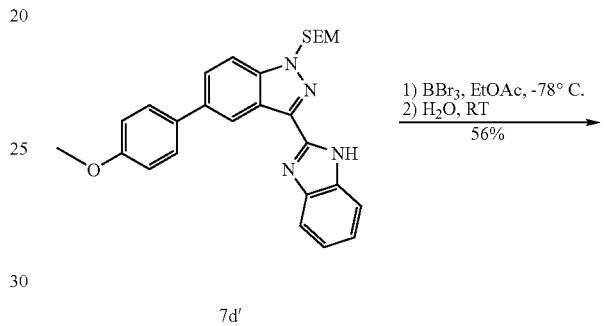

(a) Intermediate 7a'—5-Iodo-3-((E)-styryl)-1-(2-trimethylsilanyl-ethoxymethyl)-1H-indazole Intermediate 7a' was prepared from 5-nitroindazole (Acros organics, a division of Fisher Scientific, Pittsburg, Pa.) in five steps according to the method used to prepare 6-Iodo-3-((E)-styryl)-1-(2-trimethylsilanyl-ethoxymethyl)-1H-indazole from 6-nitroindazole (Found in: Kania, Braganza, et al., patent application "Compounds and Pharmaceutical Compositions for Inhibiting Protein Kinases, and Methods for Their Use", p. 52, line 10 to p. 53, line 26; and p. 59, line 16 to p. 60, line 4, U.S. Provisional Ser. No. 60/142,130, filed Jul. 2, 1999, incorporated by reference herein in its entirety.): $^1$H NMR (CDCl$_3$) δ −0.06 (s, 9H),

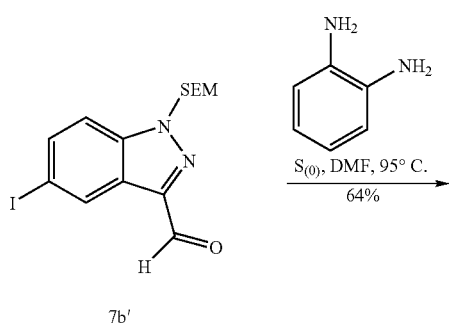

0.89 (t, 2H, J=8.4 Hz), 3.57 (t, 2H, J=8.4 Hz), 5.70 (s, 2H), 7.29–7.44 (m, 6H), 7.59 (d, 2H, J=7.0 Hz), 7.67 (dd, 1H, J=8.7, 1.5 Hz), 8.36 (s, 1H).

(b) Intermediate 7b'—5-Iodo-1-(2-trimethylsilanyl-ethoxymethyl)-1H-indazole-3-carbaldehyde Ozone was bubbled into a solution of 5-iodo-3-styryl-2-SEM-indazole 7a' (4.93 g, 10.35 mmol) in dichloromethane (500 mL) at −78° C. After 20 minutes the solution color had changed from orange to deep blue. The mixture was purged with Argon for 30 minutes to remove excess ozone, then dimethylsulfide (1.29 g, 20.7 mmol) was added. The cooling bath was removed, and stirring continued until the internal temperature reached 15° C., about 2 hours. The solution was washed with water (2×200 mL), dried over magnesium sulfate, filtered and concentrated. Purification by silica gel chromatography (10% ethyl acetate in hexanes) afforded aldehyde 7b' (2.74 g, 66%) as a yellow oil: $^1$H NMR (CDCl$_3$) δ −0.05 (s, 9H), 0.89 (t, 2H, J=8.4 Hz), 3.56 (t, 2H, J=8.4 Hz), 5.79 (s, 2H), 7.43 (d, 1H, J=8.7 Hz), 7.76 (dd, 1H, J=8.8, 1.5 Hz), 8.71 (s, 1H), 10.22 (s, 1H).

(c) Intermediate 7c'—3-(1H-Benzoimidazol-2-yl)-5-iodo-1-(2-trimethylsilanyl-ethoxymethyl)-1H-indazole To a solution of aldehyde 7b' (2.74 g, 6.81 mmol) in DMF (130 mL) were added 1,2-phenylenediamine (0.74 g, 6.81 mmol) and elemental sulfur (0.26 g, 8.2 mmol). The mixture was heated in a 95° C. oilbath for 14.5 hours, cooled to room temperature, and diluted with ethyl acetate (500 mL). The solution was washed with a mixture of saturated aqueous sodium chloride (100 mL) and water (100 mL). The organic layer was then washed with saturated aqueous sodium bicarbonate (100 mL), followed by water (100 mL), dried over magnesium sulfate, filtered, concentrated, and purified by silica gel chromatography (20% ethyl acetate in hexanes) to give impure 7c' as a pale yellow solid. Precipitation from chloroform/hexanes afforded pure 7c' (2.15 g, 64%) as a white powder: R$_f$=0.23 (20% ethyl acetate/hexanes); $^1$H NMR (DMSO-d$_6$) δ −0.12 (s, 9H), 0.82 (t, 2H, J=7.9 Hz), 3.59 (t, 2H, J=7.9 Hz), 5.87 (s, 2H), 7.23 (m, 2H), 7.52 (d, 1H, J=7.2 Hz), 7.73–7.84 (m, 3H), 8.94 (s, 1H), 13.13 (s, 1H). HRMS calculated for C$_{20}$H$_{23}$IN$_4$OSi 491.0759 (MH$^+$). found 491.0738.

(d) Intermediate 7d'—3-(1H-Benzoimidazol-2-yl)-5-(4-methoxy-phenyl)-1-(2-trimethylsilanyl-ethoxymethyl)-1H-indazole 2M aqueous sodium carbonate solution (6.4 mL) was added to a solution of 7c' (2.50 g, 5.10 mmol), 4-methoxyphenyl boronic acid (1.01 g, 6.63 mmol), and tetrakis(triphenylphosphine)palladium (0.59 g, 0.51 mmol) in 1,4-dioxane (35 mL) and methanol (15 mL). The mixture was heated to reflux for 5 hours, then cooled and partitioned between ethyl acetate (300 mL) and a mixture of saturated aqueous sodium chloride (100 mL) and water (100 mL). The organic layer was dried over magnesium sulfate, filtered, concentrated, and purified by silica gel chromatography (20% ethyl acetate in hexanes) to give a dark brown solid. Precipitation from dichloromethane/hexanes afforded pure 7d' (948.6 mg, 40%) as a white powder: R$_f$=0.13 (20% ethyl acetate/hexanes); $^1$H NMR (DMSO-d$_6$) δ −0.10 (s, 9H), 0.85 (t, 2H, J=7.9 Hz), 3.63 (t, 2H, J=7.9 Hz), 3.82 (s, 3H), 5.91 (s, 2H), 7.10 (d, 2H, J=8.7 Hz), 7.23 (m, 2H), 7.43 (m, 1H), 7.54 (d, 1H, J=6.8 Hz), 7.69 (d, 2H, J=8.7 Hz), 7.80 (m, 1H), 7.92 (d, 1H, J=8.9 Hz), 8.70 (s, 1H), 13.08 (s, 1H).

(e) Example 7'—3-(1H-Benzoimidazol-2-yl)-5-(4-methoxy-phenyl)-1H-indazole

A solution of intermediate 7d' (148.4 mg, 0.315 mmol) in ethyl acetate (15 mL) at −78° C. was treated with boron tribromide (1.0 M in dichloromethane, 4.73 mL). The solution was stirred for 17 hours, allowing the mixture to gradually warm to room temperature. Water (10 mL) was added, and the mixture allowed to stir at room temperature for 6 days. The solution was treated with 3M sodium hydroxide solution to bring the pH to 10, then extracted with ethyl acetate (3×20 mL). The combined organic extracts were dried over magnesium sulfate, filtered, and concentrated. Purification by silica gel chromatography (50% ethyl acetate in hexanes) afforded 7' (60.5 mg, 56%) as a white solid: R$_f$=0.21 (50% ethyl acetate/hexanes); $^1$H NMR (DMSO-d$_6$) δ 3.82 (s, 3H), 7.08 (d, 2H, J=8.9 Hz), 7.21 (m, 2H), 7.53–7.78 (m, 6H), 8.66 (s, 1H), 12.96 (s, 1H), 13.63 (s, 1H). Anal. (C$_{21}$H$_{16}$N$_4$O·0.25CH$_2$Cl$_2$) C, H, N.

EXAMPLE 8'

4-[3-(1H-Benzoimidazol-2-yl)-1H-indazol-5-yl]-phenol

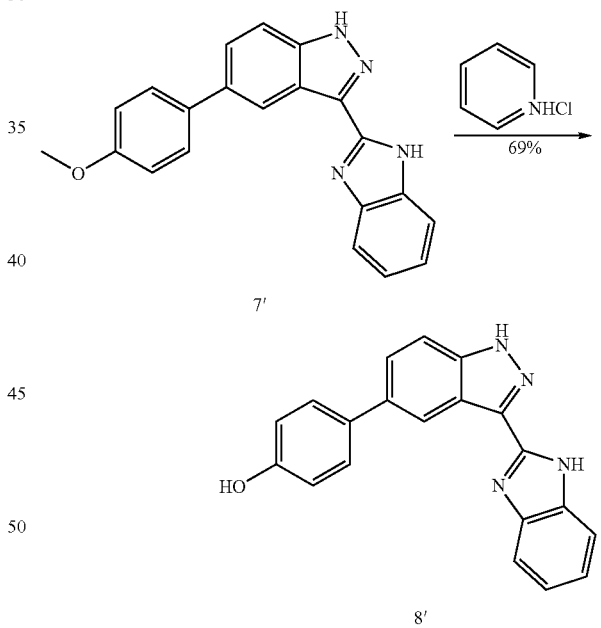

A mixture of anisole 7' (44.6 mg, 0.131 mmol) and pyridine hydrochloride (912 mg, 7.9 mmol) was heated in a 180° C. oilbath for 3 hours. The pyridine salt is liquid at this temperature. After cooling to room temperature, the mixture was partitioned between ethyl acetate (20 mL) and saturated aqueous sodium bicarbonate (15 mL). The aqueous layer was further extracted with ethyl acetate (3×20 mL). The combined organic extracts were dried over magnesium sulfate, filtered, concentrated and purified by silica gel chromatography (50% ethyl acetate/hexanes) to give pure phenol 8' (29.4 mg, 69%) as a pale yellow solid: R$_f$=0.23 (60% ethyl acetate/hexanes); $^1$H NMR (DMSO-d$_6$) δ 6.91

(d, 2H, J=8.4 Hz), 7.21 (m, 2H), 7.53 (m, 3H), 7.68 (s, 2H), 7.75 (d, 1H, J=6.9 Hz), 8.61 (s, 1H), 9.53 (s, 1H), 12.98 (s, 1H), 13.63 (s, 1H). HRMS calculated for $C_{20}H_{14}N_4O$ 327.1246 (MH$^+$). found 327.1253. Anal. ($C_{20}H_{13}N_4O$·0.8 DMSO) C, H, N.

EXAMPLE 9'

3-(1H-Benzoimidazol-2-yl)-5-(3-methoxy-2-methyl-phenyl)-1H-indazole

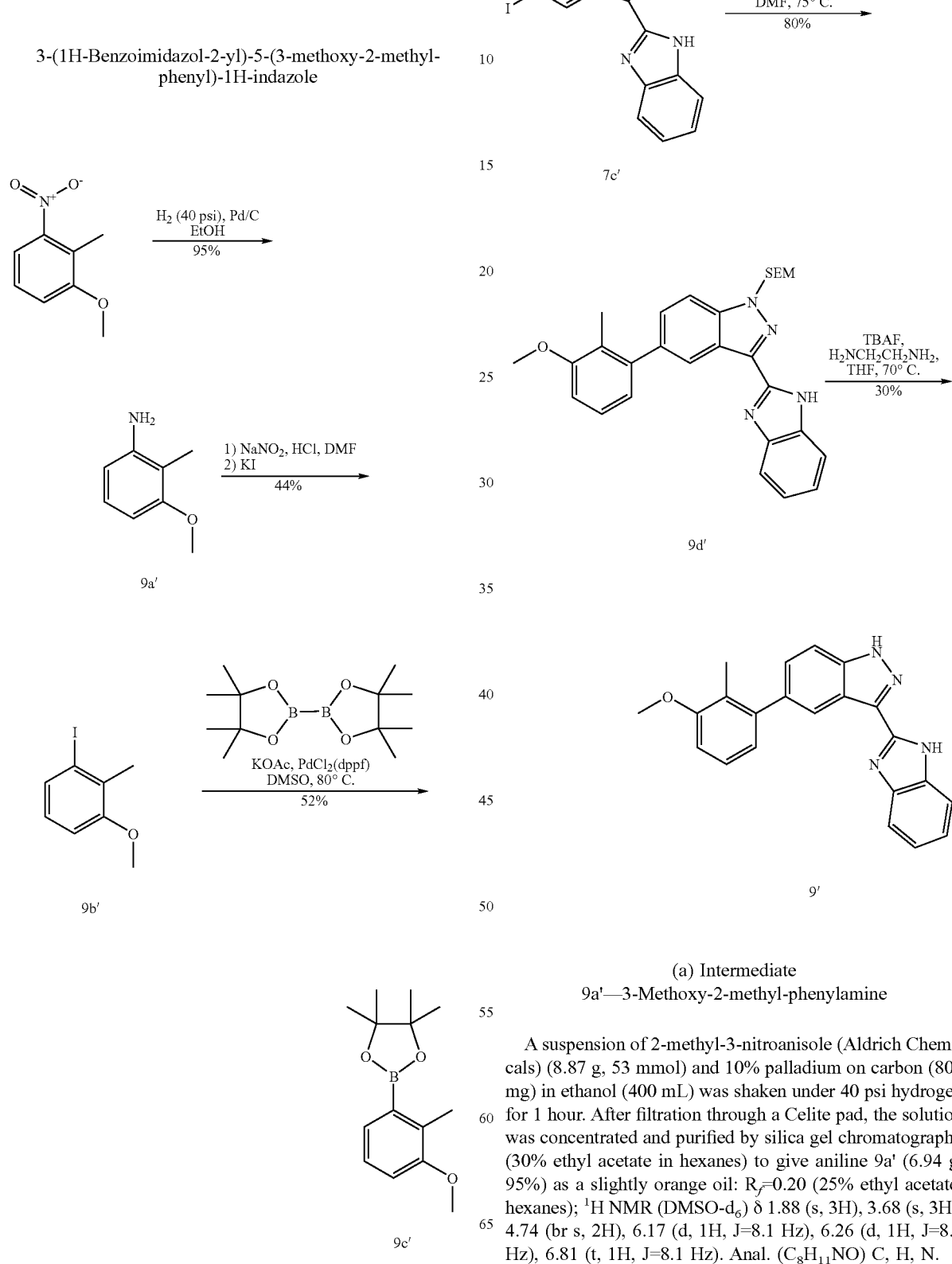

(a) Intermediate
9a'—3-Methoxy-2-methyl-phenylamine

A suspension of 2-methyl-3-nitroanisole (Aldrich Chemicals) (8.87 g, 53 mmol) and 10% palladium on carbon (800 mg) in ethanol (400 mL) was shaken under 40 psi hydrogen for 1 hour. After filtration through a Celite pad, the solution was concentrated and purified by silica gel chromatography (30% ethyl acetate in hexanes) to give aniline 9a' (6.94 g, 95%) as a slightly orange oil: $R_f$=0.20 (25% ethyl acetate/hexanes); $^1$H NMR (DMSO-d$_6$) δ 1.88 (s, 3H), 3.68 (s, 3H), 4.74 (br s, 2H), 6.17 (d, 1H, J=8.1 Hz), 6.26 (d, 1H, J=8.1 Hz), 6.81 (t, 1H, J=8.1 Hz). Anal. ($C_8H_{11}NO$) C, H, N.

(b) Intermediate
9b'—1-Iodo-3-methoxy-2-methyl-benzene

3-Methoxy-2-methyl-phenylamine (5.28 g, 38.5 mmol) was diazotized according to the method of DeGraw, et al. [DeGraw, J. I.; Brown, V. H.; Colwell, W. T.; Morrison, N. E., *J. Med. Chem.*, 17, 762 (1974)], incorporated herein by reference, affording aryl iodide 9b' (4.17 g, 44%) as a yellow oil:: $R_f$=0.53 (10% ethyl acetate/hexanes); $^1$H NMR (CDCl$_3$) δ 2.36 (s, 3H), 3.80 (s, 3H), 6.81 (m, 2H), 7.42 (dd, 1H, J=7.5, 1.5 Hz).

(c) Intermediate 9c'—2-(3-Methoxy-2-methyl-phenyl)-4,4,5,5-tetramethyl-[1,3,2] dioxaborolane 1-Iodo-3-methoxy-2-methyl-benzene (3.80 g, 15.3 mmol), Bis(pinacolato)diboron (4.28 g, 16.8 mmol), potassium acetate (4.51 g, 46.0 mmol), and 1,1'-bis(diphenylphosphino)ferrocenedichloropalladium(II) (625 mg, 0.766 mmol) were dissolved in DMSO (70 mL) and heated to 80° C. internal temperature for 1 hour. After cooling, the mixture was diluted with toluene (400 mL), washed with water (2×100 mL), dried over magnesium sulfate, filtered, and concentrated. Purification by silica gel chromatography (5 to 20% ethyl acetate in hexanes) yielded boronic ester 9c' (19.6 g, 52%) as a white, crystalline solid: $R_f$=0.27 (5% ethyl acetate/hexanes); $^1$H NMR (CDCl$_3$) δ 1.34 (s, 12H), 2.42 (s, 3H), 3.81 (s, 3H), 6.91 (d, 1H, J=8.1 Hz), 7.14 (t, 1H, J=7.8 Hz), 7.34 (d, 1H, J=7.5 Hz). Anal. (C$_{14}$H$_{21}$BO$_3$) C, H.

(d) Intermediate 9d'—3-(1H-Benzoimidazol-2-yl)-5-(3-methoxy-2-methyl-phenyl)-1-(2-trimethylsilanyl-ethoxymethyl)-1H-indazole Aqueous sodium carbonate solution (2M, 2.65 mL) was added to a solution of 7c' (519.4 mg, 1.06 mmol), boronic ester 9c' (262.8 mg, 1.06 mmol), and 1,1'-bis(diphenylphosphino)ferrocenedichloropalladium(II) (43.2 mg, 0.053 mmol) in DMF (12 mL). The mixture was heated in a 75° C. oilbath for 4.5 hours, then cooled and partitioned between ethyl acetate (100 mL) and a mixture of saturated aqueous sodium chloride (50 mL) and water (50 mL). The organic layer was dried over magnesium sulfate, filtered, concentrated, but $^1$H NMR of this crude material showed only 60% conversion. The crude mixture was redissolved in DMF (12 mL) and additional boronic ester (253 mg, 1.01 mmol), catalyst (140 mg, 0.17 mmol), and sodium carbonate solution (2.65 mL) were added. Stirring was continued at 80° C. for 15.5 hours. After the same workup as above, crude $^1$H NMR showed less than 5% 7c' remaining. Purification by silica gel chromatography (10 to 30% ethyl acetate in hexanes) afforded 9d' (410.7 mg, 80%) as a white foam: $R_f$=0.37 (30% ethyl acetate/hexanes, same as 7c'); $^1$H NMR (DMSO-d$_6$) δ −0.10 (s, 9H), 0.85 (t, 2H, J=7.9 Hz), 2.06 (s, 3H), 3.64 (t, 2H, J=7.9 Hz), 3.85 (s, 3H), 5.92 (s, 2H), 6.92 (d, 1H, J=7.2 Hz), 7.02 (d, 1H, J=8.3 Hz), 7.17–7.30 (m, 3H), 7.47–7.53 (m, 2H), 7.70 (d, 1H, J=7.7 Hz), 7.90 (d, 1H, J=8.7 Hz), 8.45 (s, 1H), 13.09 (s, 1H). Anal. (C$_{28}$H$_{32}$N$_4$O$_2$Si.0.3H$_2$O) C, H, N.

(e) Example 9'—3-(1H-Benzoimidazol-2-yl)-5-(3-methoxy-2-methyl-phenyl)-1H-indazole In an analogous manner to example 3, treatment of intermediate 9d' with tetrabutylammonium fluoride afforded 9' (47.2 mg, 30%) as a white powder: $R_f$=0.23 (5% methanol/dichloromethane); $^1$H NMR (DMSO-d$_6$) δ 2.07 (s, 3H), 3.85 (s, 3H), 6.91 (d, 1H, J=7.4 Hz), 7.01 (d, 1H, J=8.1 Hz), 7.24 (m, 3H), 7.39 (dd, 1H, J=8.7, 1.5 Hz), 7.50 (m, 1H), 7.68 (d, 2H, J=8.5 Hz), 8.40 (s, 1H), 12.96 (s, 1H), 13.66 (s, 1H). Anal. (C$_{22}$H$_{18}$N$_4$O.0.3H$_2$O) C, H, N.

EXAMPLE 10'

3-[3-(1H-Benzoimidazol-2-yl)-1H-indazol-5-yl]-2-methyl-phenol

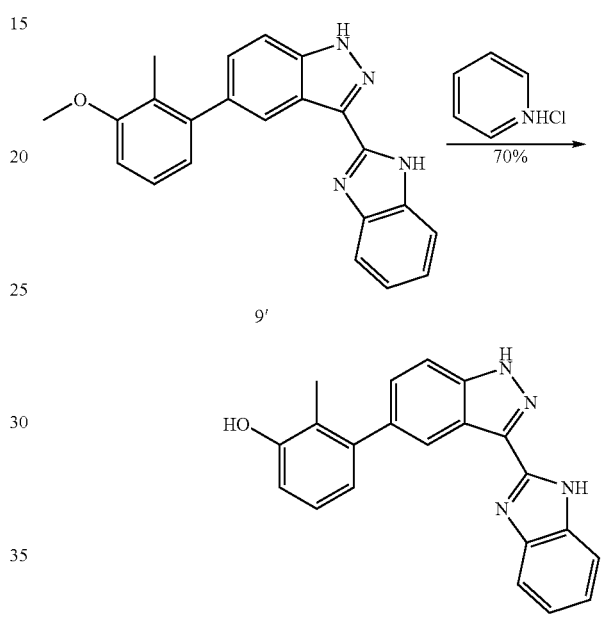

Phenol 10' was prepared by a synthetic method analogous to phenol 8', by treatment of 9' (31.6 mg, 0.089 mmol) with pyridine hydrochloride yielded phenol 10' (20.8 mg, 70%) as an off-white solid: $R_f$=0.21 (60% ethyl acetate/hexanes); $^1$H NMR (DMSO-d$_6$) δ 2.04 (s, 3H), 6.75 (d, 1H, J=7.0 Hz), 6.85 (d, 1H, J=7.7 Hz), 7.08 (t, 1H, J=7.7 Hz), 7.19 (quint, 2H, J=7.7 Hz), 7.39 (dd, 1H, J=8.7, 1.5 Hz), 7.50 (d, 1H J=7.5 Hz), 7.68 (m, 2H), 8.39 (s, 1H), 9.39 (s, 1H), 12.95 (s, 1H), 13.64 (s, 1H). HRMS calculated for C$_{21}$H$_{16}$N$_4$O 341.1402 (MH$^+$), found 341.1410. Anal. (C$_{21}$H$_{16}$N$_4$O.1.0MeOH) C, H, N.

EXAMPLE 11

5-(2-Methylphenyl)-3-phenyl-1H-indazole

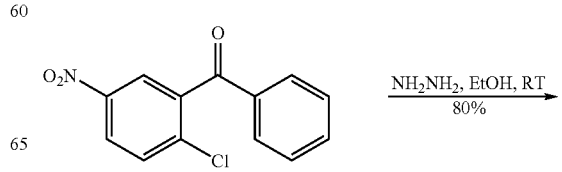

-continued

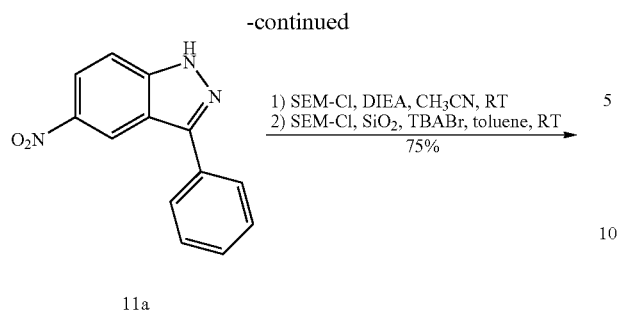

11a

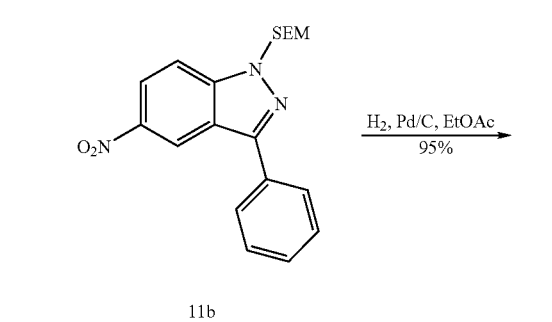

11b

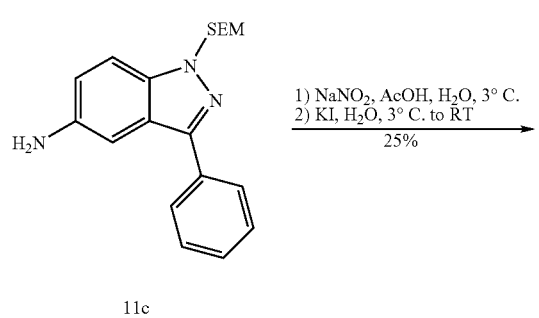

11c

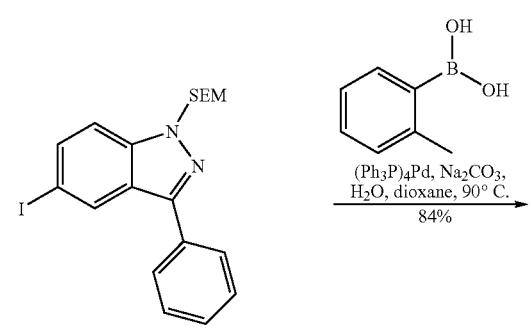

11d

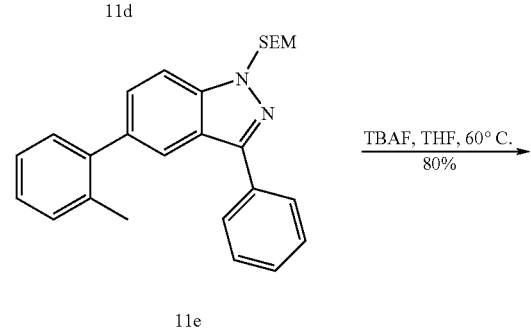

11e

-continued

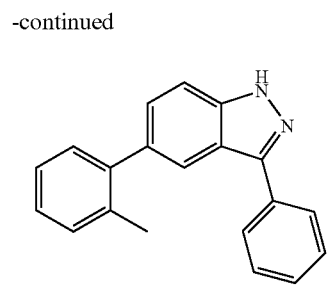

11

(a) Intermediate 11a—5-Nitro-3-phenyl-1H-indazole

To a solution of 2-chloro-5-nitrobenzophenone (15 g, 57 mmol) in ethanol (300 mL) was added hydrazine monohydrate (50 mL, 1 mol). The resultant solution was stirred overnight (16 hrs.) at ambient temperature, then poured into water (2L) and stirred for an additional 2 hours. The precipitate that formed was collected by filtration, washed with water (2×100 mL) and air dried to give 5-Nitro-3-phenyl-1H-indazole 11a (13.1 g, 80%) as a yellow solid: $^1$H NMR (DMSO-$d_6$) δ 7.48 (tt, 1H, J=1.3, 7.4 Hz), 7.58 (dd, 2H, J=7.1, 7.4 Hz), 7.78 (d, 1H, J=9.2 Hz), 8.01 (dd, 2H, J=1.3, 7.1 Hz), 8.25 (dd, 1H, J=2.1, 9.2 Hz), 8.91 (d, 1H, J=2.1 Hz), 13.88 (s, 1H). Anal. ($C_{13}H_9N_3O_2$) C, H, N.

(b) Intermediate 11b—5-Nitro-3-phenyl-1-[2-(trimethylsilanyl)ethoxymethyl]-1H-indazole Diisopropylethylamine (15 mL, 86.1 mmol) was added, dropwise, to a solution of 5-nitro-3-phenyl-1H-indazole 11a (13 g, 54.3 mmol) and 2-(trimethylsilyl)ethoxymethyl chloride (15 g, 90 mmol) in acetonitrile (400 mL). The resultant reaction mixture was stirred at ambient temperature for 2 hours, then poured into water (1 L) and extracted with ethyl acetate (3×300 mL). The combined organic extracts were dried over sodium sulfate and concentrated. The residue obtained was dissolved in toluene (40 mL). To this solution were added 2-(trimethylsilyl)ethoxymethyl chloride (3 mL, 17 mmol), tetrabutylammonium bromide (500 mg) and silica (40 g). This mixture was stirred overnight at ambient temperature, then filtered. The filtrate was subsequently concentrated. Silica gel chromatography (5% ethyl acetate/hexanes) provided 11b (15 g, 75%) as a yellow solid: $^1$H NMR (DMSO-$d_6$) δ −0.11 (s, 9H), 0.83 (t, 2H, J=7.9 Hz), 3.62 (t, 2H, J=7.9 Hz), 5.91 (s, 2H), 7.52 (tt, 1H, J=0.7, 7.4 Hz), 7.60 (dd, 2H, J=7.1, 7.4 Hz), 8.00 (d, 1H, J=9.2 Hz), 8.02 (dd, 2H, J=0.7, 7.1 Hz), 8.35 (dd, 1H, J=2.1, 9.2 Hz), 8.91 (d, 1H, J=2.1 Hz).

(c) Intermediate 11c—5-Amino-3-phenyl-1-[2-(trimethylsilanyl)ethoxymethyl]-1H-indazole A mixture of 5-nitro-3-phenyl-1-[2-(trimethylsilanyl) ethoxymethyl]-1H-indazole 11 b (14 g, 37.9 mmol) and 10% palladium on carbon (1 g) in ethyl acetate (500 mL) was stirred under an atmosphere of hydrogen overnight. The reaction mixture was filtered through celite, then concentrated to provide 11c (12.2 g, 95%) as a white solid: $^1$H NMR (DMSO-$d_6$) δ −0.12 (s, 9H), 0.80 (t, 2H, J=8.0 Hz), 3.54 (t, 2H, J=8.0 Hz), 5.01 (br s, 2H), 5.67 (s, 2H), 6.89 (dd, 1H, J=1.8, 8.8 Hz), 7.12 (d, 1H, J=1.8 Hz) 7.37 (tt, 1H, J=0.5, 7.4 Hz), 7.47 (d, 1H, J=8.8 Hz), 7.50 (dd, 2H, J=7.2, 7.4 Hz), 7.87 (dd, 2H, J=0.5, 7.2 Hz).

(d) Intermediate 11d—5-Iodo-3-phenyl-1-[2-(trimethylsilanyl)ethoxymethyl]-1H-indazole Intermediate 11c (12 g, 35.3 mmol) was dissolved in a mixture of acetic acid (300 mL) and water (50 mL). The mixture was cooled in an ice-salt bath to −5° C. To this mixture was slowly added a solution of sodium nitrite (4.5 g, 65.2 mmol) in water (10 mL) at such a rate to maintain the reaction temperature below 3° C. The resultant diazonium solution was stirred at 0° C. for 20 minutes. A solution of potassium iodide (6.5 g, 39.2 mmol) in water (10 mL) was then slowly added to the reaction, again at a rate to maintain the reaction temperature below 3° C. The reaction was left stirring overnight, gradually equilibrating to room temperature. The crude reaction mixture was poured into water (300 mL) and extracted with ethyl acetate (2×500 mL). The combined organic extracts were dried over sodium sulfate and concentrated. Silica gel chromatography (5% ethyl acetate/hexanes) provided 11d (4 g, 25%) as a yellow oil: $^1$H NMR (DMSO-$d_6$) δ −0.12 (s, 9H), 0.83 (t, 2H, J=7.9 Hz), 3.57 (t, 2H, J=7.9 Hz), 5.80 (s, 2H), 7.45 (tt, 1H, J=1.3, 7.5 Hz), 7.54 (dd, 2H, J=7.1, 7.5 Hz), 7.67 (d, 1H, J=8.8 Hz), 7.75 (dd, 1H, J=1.5, 8.8 Hz), 7.94 (dd, 2H, J=1.3, 7.1 Hz), 8.40 (d, 1H, J=1.5 Hz).

(e) Intermediate 11e—5-(2-Methylphenyl)-3-phenyl-1-[2-(trimethylsilanyl) ethoxymethyl]-1H-indazole Aqueous saturated sodium bicarbonate (2 mL) was added to a mixture of intermediate 11d (130 mg, 0.3 mmol), 2-methylphenylboronic acid (120 mg, 0.9 mmol) and tetrakis(triphenylphosphine)palladium(0) (25 mg, 0.02 mmol) in 1,4-dioxane (10 mL). The resultant reaction mixture was heated in a 90° C. oil bath for 18 hours. After cooling to room temperature, the crude reaction mixture was poured into water (50 mL) and extracted with ethyl acetate (2×25 mL). The combined organic extracts were dried over sodium sulfate and concentrated. Silica gel chromatography (10% ethyl acetate/hexanes) afforded 11e (100 mg, 84%) as an off-white solid: $^1$H NMR (DMSO-$d_6$) δ −0.10 (s, 9H), 0.85 (t, 2H, J=8.0 Hz), 2.24 (s, 3H), 3.62 (t, 2H, J=8.0 Hz), 5.85 (s, 2H), 7.29 (m, 4H), 7.42 (tt, 1H, J=1.4, 7.4 Hz), 7.47 (dd, 1H, J=1.5, 8.3 Hz), 7.52 (dd, 2H, J=7.1, 7.4 Hz), 7.84 (d, 1H, J=8.3 Hz), 7.93 (d, 1H, J=1.5 Hz), 7.99 (dd, 2H, J=1.4, 7.1 Hz).

(f) Example 11—5-(2-Methylphenyl)-3-phenyl-1H-indazole

Tetrabutylammonium fluoride (1.0 M in THF, 2 mL) was added to a solution of intermediate 11e (100 mg, 0.24 mmol) in tetrahydrofuran (5 mL). This solution was heated in a 60° C. oil bath for 18 hours, then poured into water (25 mL) and extracted with ethyl acetate (2×25 mL). The combined organic extracts were dried over sodium sulfate and concentrated. Silica gel chromatography (20% ethyl acetate/hexanes) provided 5-(2-methylphenyl)-3-phenyl-1H-indazole 11 (55 mg, 80%) as an off-white solid: $^1$H NMR (DMSO-$d_6$) δ 2.24 (s, 3H), 7.28 (m, 4H), 7.37 (dd, 1H, J=1.5, 8.6 Hz), 7.38 (tt, 1H, J=1.4, 7.5 Hz), 7.50 (dd, 2H, J=7.1, 7.5 Hz), 7.64 (d, 1H, J=8.6 Hz), 7.91 (d, 1H, J=1.5 Hz), 7.99 (dd, 2H, J=1.4, 7.1 Hz), 13.30 (s, 1H). Anal. ($C_{20}H_{16}N_2.0.25H_2O$) C, H, N.

EXAMPLE 12

3-Phenyl-5-[2-(trifluormethyl)phenyl]-1H-indazole

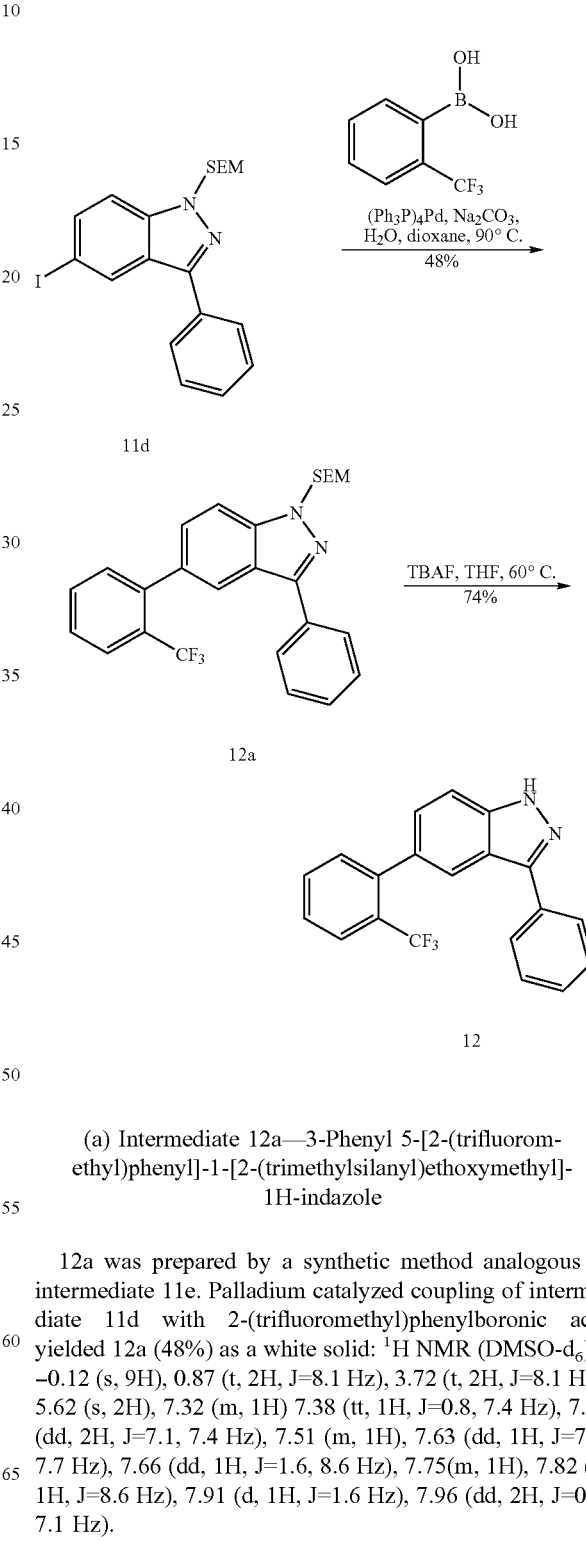

(a) Intermediate 12a—3-Phenyl 5-[2-(trifluoromethyl)phenyl]-1-[2-(trimethylsilanyl)ethoxymethyl]-1H-indazole 12a was prepared by a synthetic method analogous to intermediate 11e. Palladium catalyzed coupling of intermediate 11d with 2-(trifluoromethyl)phenylboronic acid yielded 12a (48%) as a white solid: $^1$H NMR (DMSO-$d_6$) δ −0.12 (s, 9H), 0.87 (t, 2H, J=8.1 Hz), 3.72 (t, 2H, J=8.1 Hz), 5.62 (s, 2H), 7.32 (m, 1H) 7.38 (tt, 1H, J=0.8, 7.4 Hz), 7.48 (dd, 2H, J=7.1, 7.4 Hz), 7.51 (m, 1H), 7.63 (dd, 1H, J=7.2, 7.7 Hz), 7.66 (dd, 1H, J=1.6, 8.6 Hz), 7.75 (m, 1H), 7.82 (d, 1H, J=8.6 Hz), 7.91 (d, 1H, J=1.6 Hz), 7.96 (dd, 2H, J=0.8, 7.1 Hz).

(b) Example 12—3-Phenyl 5-[2-(trifluoromethyl)phenyl]-1H-indazole 12 was prepared similar to example 11. Treatment of 12a with tetrabutylammonium fluoride afforded 3-phenyl 5-[2-(trifluoromethyl)phenyl]-1H-indazole 12 (74%) as a white solid: $^1$H NMR (DMSO-d$_6$) δ 7.34 (m, 1H), 7.38 (tt, 1H, J=1.3, 7.3 Hz), 7.49 (dd, 2H, J 7.1, 7.3 Hz), 7.52 (m, 1H), 7.62 (dd, 1H, J=7.4, 7.7 Hz), 7.65 (dd, 1H, J=1.9, 8.6 Hz), 7.73 (dd, J=7.2, 7.5 Hz), 7.85 (d, 1H, J=8.6 Hz), 7.94 (d, 1H, J=1.9 Hz), 7.96 (dd, 2H, J=1.3, 7.1 Hz). Anal. (C$_{20}$H$_{13}$N$_2$F$_3$.0.1H$_2$O) C, H, N.

EXAMPLE 13

5-(4-Hydroxy-2-methylphenyl)-3-phenyl-1H-indazole

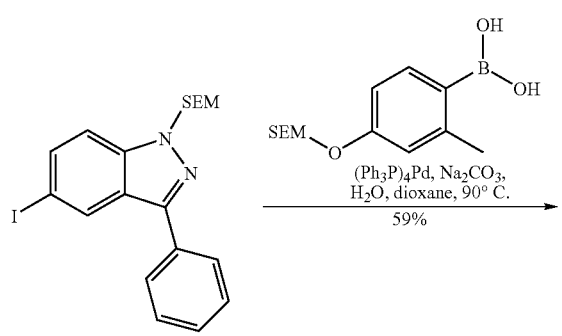

11d

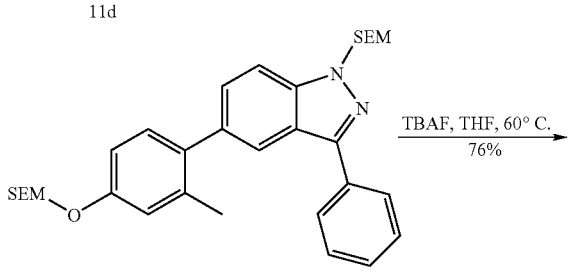

13a

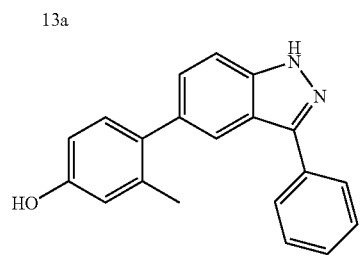

13

(a) Intermediate 13a—5-(2-methyl-4-[2-(trimethyl-silanyl)ethoxymethoxy]phenyl)-3-phenyl-1-[2-(trimethylsilanyl)ethoxymethyl]-1H-indazole 13a was prepared similar to intermediate 11e. Palladium catalyzed coupling of intermediate 11d with (2-methyl-4-[2-(trimethylsilanyl)ethoxymethoxy]phenyl)boronic acid yielded 13a (59%) as a pale yellow foam: $^1$H NMR (DMSO-d$_6$) δ −0.09 (s, 9H), 0.00 (s, 9H), 0.85 (t, 2H, J=8.0 Hz), 0.92 (t, 2H, J=8.1 Hz), 2.22 (s, 3H), 3.62 (t, 2H, J=8.0 Hz), 3.73 (t, 2H, J=8.1 Hz), 5.25 (s, 2H), 5.85 (s, 2H), 6.93 (dd, 1H, J=2.6, 8.3 Hz), 6.98 (d, 1H, J=2.6 Hz), 7.22 (d, 1H, J=8.3 Hz), 7.43 (tt, 1H, J=0.9, 7.7 Hz), 7.45 (dd, 1H, J=1.3, 8.6 Hz), 7.52 (dd, 2H, J=7.2, 7.7 Hz), 7.82 (d, 1H, J=8.6 Hz), 7.89 (d, 1H, J=1.3 Hz), 7.99 (dd, 2H, J=0.9, 7.2 Hz).

(b) Example 13—5-(4-Hydroxy-2-methylphenyl)-3-phenyl-1H-indazole 13 was prepared similar to example 11. Treatment of 13a with tetrabutylammonium fluoride afforded 5-(4-hydroxy-2-methylphenyl)-3-phenyl-1H-indazole 13 (75%) as a pale yellow solid: $^1$H NMR (DMSO-d$_6$) δ 2.17 (s, 3H), 6.66 (dd, 1H, J=2.3, 8.2 Hz), 6.70 (d, 1H, J=2.3 Hz), 7.08 (d, 1H, J=8.2 Hz), 7.32 (dd, 1H, J=1.5, 8.6 Hz), 7.39 (tt, 1H, J=1.4, 7.7 Hz), 7.50 (dd, 2H, J=7.2, 7.7 Hz), 7.59 (d, 1H, J=8.6 Hz), 7.83 (d, 1H, J=1.5 Hz), 7.97 (dd, 2H, J=1.4, 7.2 Hz) 9.28 (s, 1H), 13.22 (s, 1H). Anal. (C$_{20}$H$_{16}$N$_2$O00.8H$_2$O) C, H, N.

EXAMPLE 14

3-Phenyl-5-(Pyrid-4-yl)-1H-indazole

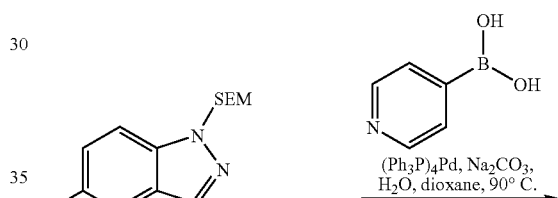

11d

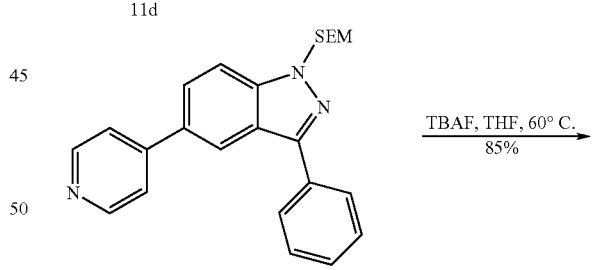

14a

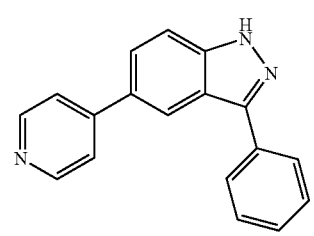

14

(a) Intermediate 14a—3-Phenyl-5-(pyrid-4-yl)-1-[2-trimethylsilanyl)ethoxymethyl]-1H-indazole 14a was prepared similar to example 11e. Palladium catalyzed coupling of intermediate 11d with pyridine-4-lboronic acid yielded 14a (76%) as a white solid: ¹H NMR (DMSO-d₆) δ −0.11 (s, 9H), 0.84 (t, 2H, J=7.9 Hz), 3.62 (t, 2H, J=7.9 Hz), 5.86 (s, 2H), 7.46 (tt, 1H, J=1.1, 7.4 Hz), 7.51 (d, 1H, J=8.3 Hz), 7.56 (dd, 2H, J=7.1, 7.4 Hz), 7.80 (dd, 1H, J=1.4, 8.3 Hz), 7.85 (dd, 2H, J=1.6, 4.5 Hz), 8.07 (dd, 2H, J=1.1, 7.1 Hz), 8.41 (d, 1H, J=1.4 Hz), 8.64 (dd, 2H, J=1.6, 4.5 Hz).

(b) Example 14—3-Phenyl 5-(pyrid-4-yl)-1H-indazole 14 was prepared similar to example 11. Treatment of 14a with tetrabutylammonium fluoride afforded 3-phenyl-5-(pyrid-4-yl)-1H-indazole 14 (85%) as a white solid: ¹H NMR (DMSO-d₆) δ 7.43 (tt, 1H, J=1.2, 7.6 Hz), 7.54 (dd, 2H, J=7.1, 7.6 Hz), 7.72 (d, 1H, J=8.8 Hz), 7.83 (dd, 2H, J=1.6, 4.5 Hz), 7.84 (dd, 1H, J=1.5, 8.8 Hz), 8.07 (dd, 2H, J=1.2, 7.1 Hz), 8.40 (d, 1H, J=1.5 Hz), 8.63 (dd, 2H, J=1.6, 4.5 Hz) 13.39 (s, 1H). Anal. (C₁₈H₁₃N₃.0.2H₂O) C, H, N.

EXAMPLE 14B

3-Phenyl-5-(pyrid-3-yl)-1H-indazole

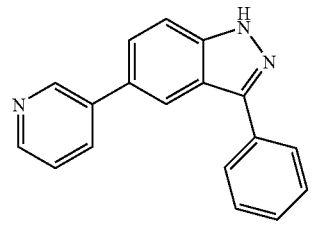

14b (a) Intermediate 14b'—3 phenyl-5-(pyrid-3-yl)-1-[2-(trimethylsilanyl)ethoxymethyl]-1H-indazole 14b' was prepared similar to intermediate 11e. Palladium catalyzed coupling of intermediate 11d with pyridine-3-boronic acid yielded 14b' (66%) as a white solid: ¹H NMR (DMSO-d₆) δ −0.10 (s, 9H), 0.83 (t, 2H, J=7.9 Hz), 3.63 (t, 2H, J=7.9 Hz), 5.86 (s, 2H), 7.43 (tt, 1H, J=1.2, 7.5 Hz), 7.51 (dd, 1H, J=4.7, 8.0 Hz), 7.54 (dd, 2H, J=7.1, 7.5 Hz), 7.65 (d, 1H, J=8.6 Hz), 7.73 (dd, 1H, J=1.5, 8.6 Hz), 8.07 (dd, 2H, J=1.2, 7.1 Hz), 8.18 (ddd, 1H, J=1.6, 2.3, 8.0 Hz), 8.32 (d, 1H, J=1.5 Hz), 8.56 (dd, 1H, J=1.6, 4.7 Hz), 8.90 (d, 1H, J=2.3 Hz).

(b) Example 14b—3-Phenyl 5-(pyrid-3-yl)-1H-indazole

Similar to example 11, treatment of 14b' with tetrabutylammonium fluoride afforded 3-phenyl-5-(pyrid-3-yl)-1H-indazole 14b (79%) as a white solid:: ¹H NMR (DMSO-d₆) δ 7.41 (tt, 1H, J=1.3, 7.4 Hz), 7.49 (dd, 1H, J=4.7, 7.9 Hz), 7.53 (dd, 2H, J=7.1, 7.4 Hz), 7.70 (d, 1H, J=8.7 Hz), 7.76 (dd, 1H, J=1.5, 8.7 Hz), 8.08 (dd, 2H, J=1.3, 7.1 Hz), 8.17 (ddd, 1H, J=1.7, 2.0, 7.9 Hz), 8.31 (d, 1H, J=1.5 Hz) 8.56 (dd, 1H, J=1.7, 4.7 Hz), 8.99 (d, 1H, J=2.0 Hz), 13.35 (s, 1H). Anal. (C₁₈H₁₃N₃) C, H, N.

EXAMPLE 15

2-Methyl-3-[3-((E)-styryl)-1H-indazol-5-yl]-phenol

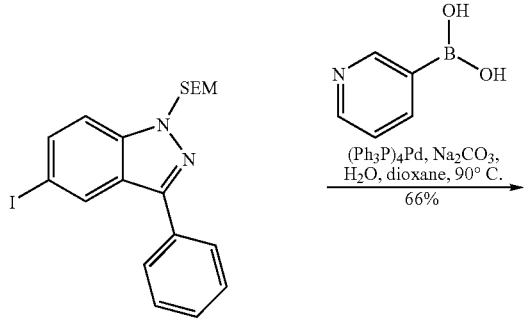

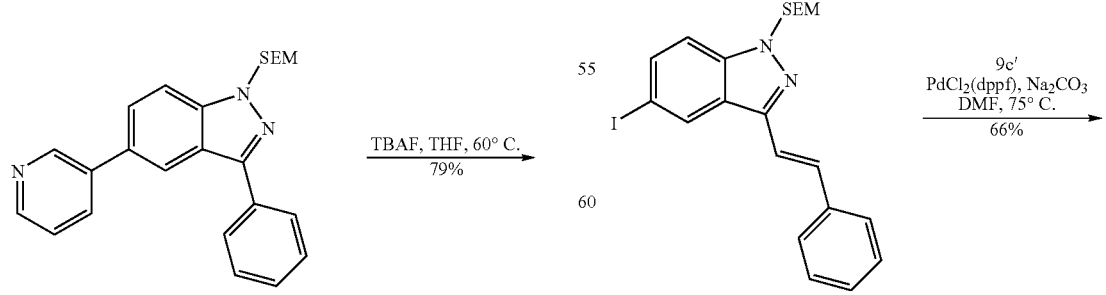

-continued

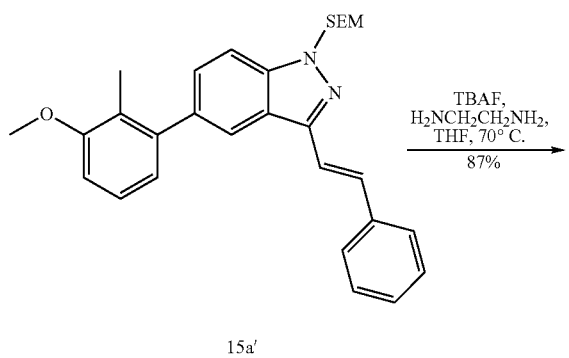

15a'

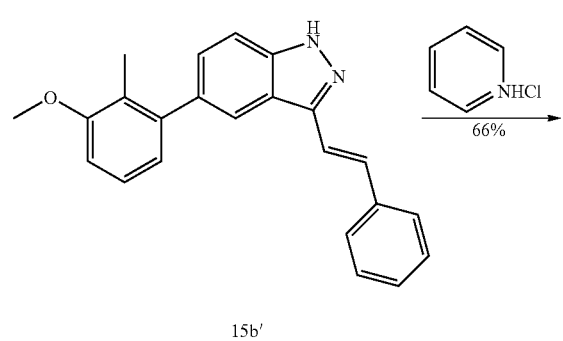

15'

(a) Intermediate 15a'—5-(3-Methoxy-2-methyl-phenyl)-3-((E)-styryl)-1-(2-trimethylsilanyl-ethoxymethyl)-1H-indazole Intermediate 15a' was prepared from 7a' (571.8 mg, 1.42 mmol) by a synthetic method analogous to 9d', yielding styryl analog 15a' (442.5 mmol, 66%) as a yellow oil: $^1$H NMR (DMSO-$d_6$) δ −0.10 (s, 9H), 0.83 (t, 2H, J=8.1 Hz), 2.07 (s, 3H), 3.58 (t, 2H, J=7.9 Hz), 3.84 (s, 3H), 5.79 (s, 2H), 6.91 (d, 1H, J=7.6 Hz), 6.99 (d, 1H, J=8.3 Hz), 7.22–7.41 (m, 5H), 7.56 (d, 2H, J=5.1 Hz), 7.70–7.78 (m, 3H), 8.09 (s, 1H).

(b) Intermediate 15b'—5-(3-Methoxy-2-methyl-phenyl)-3-((E)styryl)-1H-indazole

15b' was prepared similar to example 3. Treatment of 15a' (211.4 mg, 0.449 mmol) yielded 15b' (132.7 mg, 87%) as a white foam: $R_f$=0.38 (50% ethyl acetate/hexanes); $^1$H NMR (DMSO-$d_6$) δ 1.98 (s, 3H), 3.84 (s, 3H), 6.91 (d, 1H, J=7.5 Hz), 6.98 (d, 1H, J=8.1 Hz), 7.21–7.61 (m, 8H), 7.70 (d, 2H, J=7.4 Hz), 8.05 (s, 1H), 13.18 (s, 1H). HRMS calculated for $C_{23}H_{20}N_2O$ 341.1648 (MH$^+$). found 341.1638. Anal. ($C_{23}H_{20}N_2O \cdot 0.2H_2O$) C, H, N.

(c) Example 15—2-Methyl-3-[3-((E)-styryl)-1H-indazol-5-yl]-phenol

Phenol 15' was prepared similar to phenol 8'. Treatment of intermediate 15b' (63.1 mg, 0.185 mmol) with pyridine hydrochloride yielded phenol 15' (39.7 mg, 66%) as an off-white solid: $R_f$=0.24 (50% ethyl acetate/hexanes); $^1$H NMR (DMSO-$d_6$) δ 2.05 (s, 3H), 6.74 (d, 1H, J=7.5 Hz), 6.83 (d, 1H, J=7.9 Hz), 7.05 (t, 1H, J=7.7 Hz), 7.25–7.62 (m, 7H), 7.70 (d, 2H, J=7.2 Hz), 8.03 (s, 1H), 9.34 (s, 1H), 13.16 (s, 1H). HRMS calculated for $C_{22}H_{18}N_2O$ 327.1497 (MH$^+$), found 327.1487. Anal. ($C_{22}H_{18}N_2O \cdot 0.5H_2O$) C, H, N.

EXAMPLE 16

4-[3-((E)-Styryl)-1H-indazol-5-yl-isoquinoline

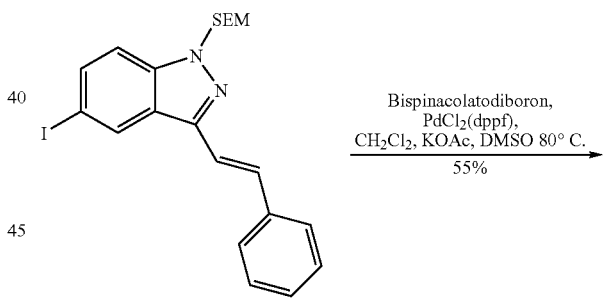

7a'

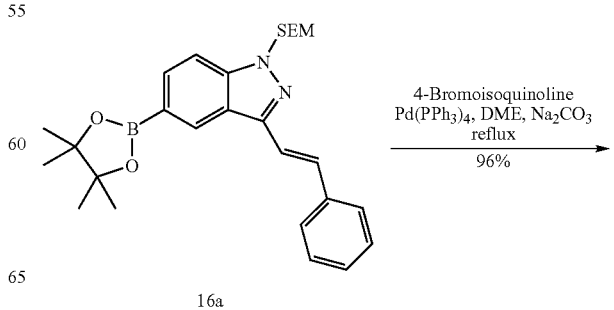

16a

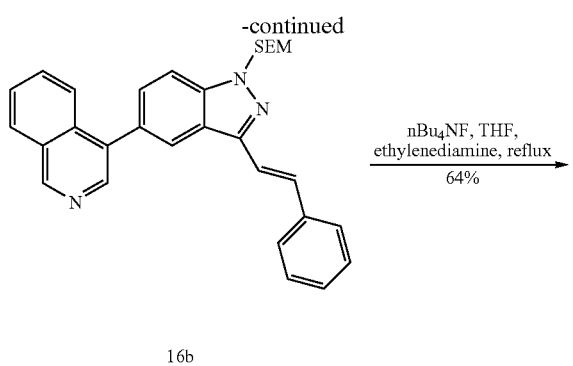

(a) Intermediate 16a—3-((E)-Styryl)-5-(4,4,5,5-tetramethyl-[1,3,2]dioxaborolan-2-yl)-1-(2-trimethylsilanyl-ethoxymethyl)-1H-indazole A mixture of 7a' (2.0 g, 4.2 mmol), bis(pinacolato)diboron (1.17 g, 4.6 mmol), potassium acetate (1.24 g, 12.6 mmol) and DMSO (25 mL) was degassed under vacuum with argon replacement three times. 1,1-Bis(Diphenylphosphino)ferrocenedichloropalladium(II)-CH$_2$Cl$_2$ (0.172 g, 0.21 mmol) was added and the degassing procedure was repeated. The reaction was heated to 80° C. for 1 hour and the mixture was poured into water and extracted with ethyl acetate-hexanes (2:1), washed with brine, dried over MgSO$_4$, and concentrated. Chromatography on silica 6:1 hexanes-Et$_2$O afforded 1.09 g 16a (55%). $^1$H NMR (CDCl$_3$) δ 8.51 (s, 1H), 7.88 (d, 1H, J=8.4 Hz), 7.64 (d, 1H, J=7.2 Hz), 7.58 (m, 2H), 7.48 (s, 1H), 7.41 (m, 3H), 7.31 (m, 1H), 3.59 (t, 2H, J=7.3 Hz), 1.41 (s, 12H), 0.91 (t, 2H, J=8.3 Hz), −0.06 (s, 9H). Anal. (C$_{27}$H$_{37}$N$_2$O$_3$SiB) C, H, N.

(b) Intermediate 16b—4-[3-((E)-Styryl)-1-(2-trimethylsilanyl-ethoxymethyl)-1H indazol-5-yl]-isoquinoline Intermediate 16a (0.218 g, 0.47 mmol), 4-bromoisoquinoline (0.082 g, 0.39 mmol) and Na$_2$CO$_3$ (0.1 g, 0.95 mol) were combined with 3 mL DME and 0.5 mL water and the mixture was degassed and purged with argon. Tetrakis(triphenylphosphino)palladium(0) (0.023 g, 0.02 mmol) was added and the mixture was again degassed and then heated to reflux under argon for 15 hours. Aqueous work up as with 16a and chromtagraphy on silica (4:1 hexanes-ethyl acetate) yielded 0.181 g (96%) of 16b.; $^1$H NMR (CDCl$_3$) δ 8.59 (s, 1H), 8.13 (m, 2H), 7.97 (d, 1H, J=7.6 Hz), 7.73 (m, 3H), 7.58 (m, 3H), 7.50 (d, 2H, J=9.5 Hz), 7.26 (m, 4H), 5.82 (s, 2H), 3.68 (t, 2H, J=8.1 Hz), 0.97 (t, 2H, J=8.3 Hz), −0.03 (s, 9H). Anal. (C$_{30}$H$_{31}$N$_3$OSi.0.75H$_2$O) C, H, N.

(c) Example 16—4-[3-((E)-Styryl)-1H-indazol-5-yl]-isoquinoline

A solution of 16b (0.17 g, 0.35 mmol) in 3.6 mL of 1M tetrabutylammonium fluoride in THF and ethylenediamine (0.475 uL, 0.427 g, 7.1 mmol) was heated to reflux for 1 hour. The reaction was diluted with ethyl acetate and brought to pH 7 with 0.4 M HCl, washed with brine, dried over MgSO$_4$, and concentrated. Chromtagraphy on silica (1:1 hexanes-ethyl acetate) yielded 0.079 g (64%) of 16 as a white solid. $^1$H NMR (CDCl$_3$) δ 10.20 (brs, 1H), 9.31 (s, 1H), 8.59 (s, 1H), 8.16 (s, 1H), 8.09 (d, 1H, J=7.2 Hz), 7.93 (d, 1H, J=7.2 Hz), 7.20–7.75 (m, 11H). Anal. (C$_{24}$H$_{17}$N$_3$.0.4H$_2$O) C, H, N.

EXAMPLE 17

4-[3-((E)-Styryl)-1H-indazol-5-yl]-quinoline

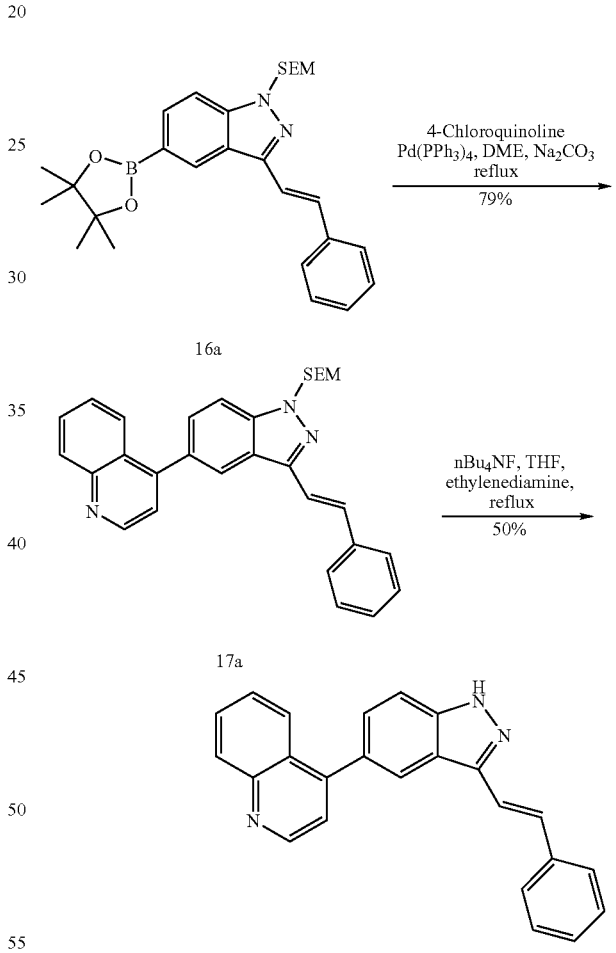

(a) Intermediate 17a—4-[3-((E)Styryl)-1-(2-trimethylsilanyl-ethoxymethyl)-1H-indazol-5-yl]-quinoline 17a was prepared by a synthetic method analogous to intermediate 16b. Employing 4-chloroquinoline, 17a was prepared in 79% yield. $^1$H NMR (CDCl$_3$) δ 8.99 (d, 1H, J=4.4 Hz), 8.21 (d, 1H, J=7.9 Hz), 8.15 (s, 1H,), 7.95 (d, 1H, J=8.4 Hz), 7.72 (m, 2H), 7.42–7.62 (m, 10H), 5.82 (s, 2H), 3.67 (t, 2H, J=9.3 Hz), 0.97 (t, 2H, J=8.3 Hz), −0.02 (s, 9H). Anal. (C$_{30}$H$_{31}$N$_3$OSi.0.5H$_2$O) C, H, N.

(b) Example 17—4-[3-((E)-Styryl)-1H-indazol-5-yl]-quinoline

Example 17 was prepared similar to intermediate 16. 17a was deprotected to afford 17 in 50% yield as a white solid. $^1$H NMR (CDCl$_3$) δ 13.10 (brs, 1H), 8.98 (d, 1H, J=4.4 Hz), 8.37 (s, 1H), 8.15 (d, 1H, J=8.4 Hz), 8.00 (d, 1H, J=8.4 Hz), 7.54–7.79 (m, 9H), 7.37 (m, 2H), 7.26 (m, 1H). Anal. (C$_{24}$H$_{17}$N$_3$.1.0 H$_2$O) C, H, N.

EXAMPLE 18

5-(4Pyridyl)-3-(2-Pyrrolyl)-1H-indazole

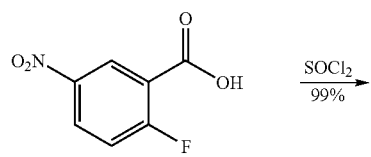

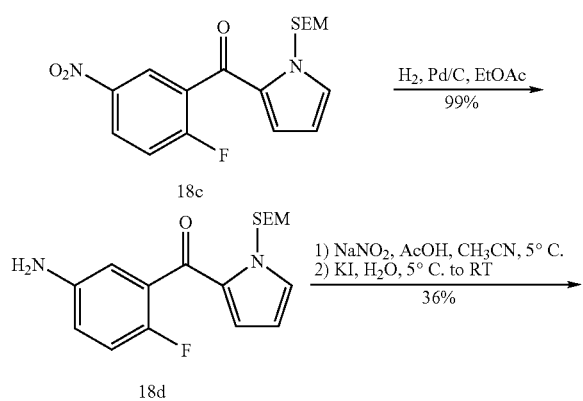

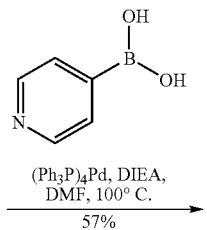

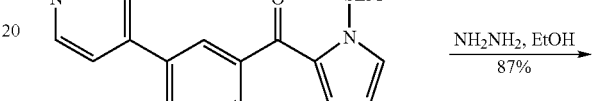

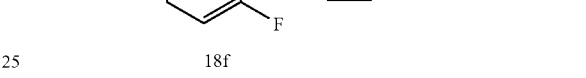

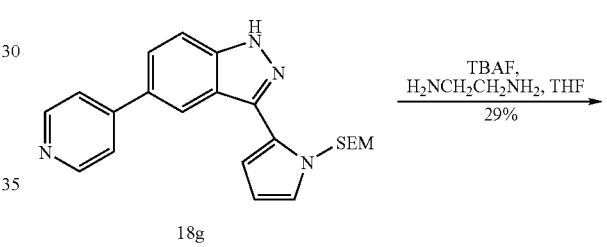

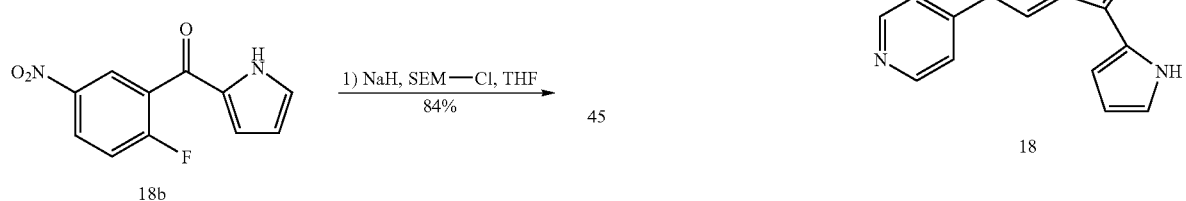

(a) Intermediate 18a—2-Fluoro-5-nitrobenzoyl chloride

A solution of 2-chloro-5-nitrobenzoic acid (10.3 g, 56 mmol) in thionyl chloride (90 ml, 1.2 mol) was heated at reflux for 2 hours. Excess thionyl chloride was removed by concentration, in vacuo. The residue obtained was dissolved in ether (150 ml), then concentrated to provide 2-fluoro-5-nitrobenzoyl chloride 18a (11.21 g, 99%) as an off-white solid: $^1$H NMR (DMSO-d$_6$) δ 7.62 (dd, 1H, J=9.1, 9.6 Hz), 8.48 (ddd, 1H, J=3.0, 6.9, 9.1 Hz), 8.60 (dd, 1H, J=3.0, 6.3 Hz). Anal. (C$_7$H$_3$NO$_3$ClF) C, H, N. Cl.

(b) Intermediate 18b—1-(2-Fluoro-5-nitrophenyl)-1-(1H-pyrrol-2-yl)methanone

A solution of 2-chloro-5-nitrobenzoyl chloride 18a (10.04 g, 49 mmol) and pyrrole (3.4 ml, 3.29 g, 49 mmol) in 1,2-dichloroethane (110 ml) was cooled to 0° C. prior to addition of AlCl$_3$ (6.61 g, 49.6 mmol) as the solid. The resultant reaction mixture was stirred overnight, gradually warming to room temperature. The crude reaction was, subsequently, poured into a mixture of concentrated HCl (20 ml) and ice water (200 ml). After stirring for an additional 90 minutes, the layers were separated and the aqueous phase was extracted with CH$_2$Cl$_2$ (2×200 ml). The combined organic extracts were washed with water (200 ml) and saturated NaHCO$_3$ (200 ml), dried over sodium sulfate and concentrated. Silica gel chromatography (25% ethyl acetate/hexanes) provided 18b (7.23 g, 63%) as a pale yellow solid: $^1$H NMR (DMSO-d$_6$) δ 6.28 (ddd, 1H, J=2.1, 2.3, 3.6 Hz), 6.74 (ddd, 1H, J=1.3, 2.3, 2.5 Hz), 7.32 (ddd, 1H, J=1.3, 2.4, 3.6 Hz), 7.65 (dd, 1H, J=9.0, 9.1 Hz), 8.39 (dd, 1H, J=3.0, 5.8 Hz), 8.45 (ddd, 1H, J=3.0, 4.4, 9.1 Hz), 12.33 (broad, 1H). Anal. (C$_1$H$_7$N$_2$O$_3$F.0.1HCl) C, H, N.

(c) Intermediate 18c—1-(2-Fluoro-5-nitrophenyl)-1-(1-[2-(trimethylsilanyl)ethoxymethyl]-1H-pyrrol-2-yl)methanone A solution of 1-(2-fluoro-5-nitrophenyl)-1-(1H-pyrrol-2-yl)methanone 18b (1.72 g, 7.3 mmol) in THF (30 ml) was added dropwise, under an argon atmosphere, to a stirred suspension of NaH (350 mg, 8.75 mmol) in THF (15 ml) at 0° C. This mixture was stirred at 0° C. for 45 minutes prior to addition of 2-(trimethylsilyl)ethoxymethyl chloride (1.70 g, 10.2 mmol) in a single portion as the neat liquid. The resultant reaction mixture was stirred at ambient temperature overnight, then poured into saturated NaHCO$_3$ (80 ml). The layers were separated and the aqueous phase was extracted with ethyl acetate (2×50 ml). The combined organic extracts were washed with brine (60 ml), dried over sodium sulfate and concentrated. Silica gel chromatography (10% ethyl acetate/hexanes) provided 18c (2.24 g, 84%) as a yellow syrup: $^1$H NMR (DMSO-d$_6$) δ −0.07 (s, 9H), 0.83 (t, 2H, J=7.8 Hz), 3.53 (t, 2H, J=7.8 Hz), 5.74 (s, 2H), 6.27 (dd, 1H, J=2.5, 4.0 Hz), 6.75 (dd, 1H, J=1.4, 4.0 Hz), 7.57 (dd, 1H, J=1.4, 2.5 Hz), 7.64 (dd, 1H, J=9.0, 9.1 Hz), 8.29 (dd, 1H, J=3.0, 5.8 Hz), 8.45 (ddd, 1H, J=3.0, 4.6, 9.1 Hz). Anal. (C$_{17}$H$_{21}$N$_2$O$_4$FSi) C, H, N.

(d) Intermediate 18d—1-(5-Amino-2-fluorophenyl)-1-(1-[2-(trimethylsilanyl)ethoxymethyl]-1H-pyrrol-2-yl)methanone A mixture of 1-(2-fluoro-5-nitrophenyl)-1-(1-[2-(trimethylsilanyl)ethoxymethyl]-1H-pyrrol-2-yl)methanone 18c (3.63 g, 10 mmol) and 10% palladium on carbon (365 mg) in ethyl acetate (90 ml) was stirred under an atmosphere of hydrogen overnight. The reaction mixture was filtered through celite, then concentrated to provide 18d (3.30 g, 99%) as an amber syrup: $^1$H NMR (DMSO-d$_6$) δ −0.07 (s, 9H), 0.82 (t, 2H, J=8.0 Hz), 3.50 (t, 2H, J=8.0 Hz), 5.12 (br s, 2H), 5.71 (s, 2H), 6.20 (dd, 1H, J=2.5, 3.9 Hz), 6.59 (dd, 1H, J=2.9, 5.6 Hz) 6.60 (dd, 1H, J=1.8, 3.9 Hz), 6.66 (ddd, 1H, J=2.9, 4.3, 8.8 Hz), 6.93 (dd, 1H, J=8.8, 9.7 Hz), 7.42 (dd, 1H, J=1.8, 2.5 Hz). Anal. (C$_{17}$H$_{23}$N$_2$O$_2$FSi) C, H, N.

(e) Intermediate 18e—1-(2-Fluoro-5-iodophenyl)-1-(1-[2-(trimethylsilanyl)ethoxymethyl]-1H-pyrrol-2-yl)methanone Intermediate 18d (332 mg, 1.0 mmol) was dissolved in a mixture of acetic acid (10 ml) and acetonitrile (10 ml). This vigorously stirred solution was cooled in an ice-salt bath to −5° C., prior to addition of a solution of sodium nitrite (83 mg, 1.2 mmol) in water (10 ml). The resultant diazonium solution was stirred for 45 minutes, gradually warming to 5° C. The reaction was, again, cooled to −5° C. preceding the addition of a solution of potassium iodide (232 mg, 1.4 mmol) in water (3 ml). The resultant mixture was stirred for an additional 2 hours, warming to 15° C., then poured into a mixture of K$_2$CO$_3$ (30 g) and ice water (100 ml). This aqueous mixture was extracted with ethyl acetate (2×50 ml). The combined organic extracts were washed with 10% aqueous Na$_2$S$_2$O$_3$ (50 ml), dried over sodium sulfate and concentrated. Silica gel chromatography (5% ethyl acetate/hexanes) provided 18e (160 mg, 36%) as a colorless oil: $^1$H NMR (DMSO-d$_6$) δ −0.08 (s, 9H), 0.81 (t, 2H, J=7.9 Hz), 3.50 (t, 2H, J=7.9 Hz), 5.71 (s, 2H), 6.24 (dd, 1H, J=2.6, 4.0 Hz), 6.63 (dd, 1H, J=1.7, 4.0 Hz) 7.18 (dd, 1H, J=8.7, 9.7 Hz), 7.51(dd, 1H, J=1.7, 2.6 Hz), 7.74 (dd, 1H, J=2.3, 6.4 Hz), 7.90 (ddd, 1H, J=2.3, 4.9, 8.7 Hz). Anal. (C$_{17}$H$_{21}$NO$_2$FSiI) C, H, N, I.

(f) Intermediate 18f—1-[2-Fluoro-5-(4-pyridyl)phenyl]-1-(1-[2-(trimethylsilanyl)ethoxymethyl]-1H-pyrrol-2-yl)methanone Diisopropylethylamine (1.3 ml, 7.5 mmol) was added to a mixture of 1-(2-fluoro-5-iodophenyl)-1-(1-[2-(trimethylsilanyl)ethoxymethyl]-1H-pyrrol-2-yl)methanone 18e (798 mg, 1.8 mmol), tetrakis(triphenylphosphine)palladium(0) (65 mg, 0.06 mmol) and pyridine-4-boronic acid (323 mg, 2.6 mmol) in DMF (20 ml). The resultant reaction mixture was heated in a 90° C. oil bath for 18 hours, under an argon atmosphere. After cooling to room temperature, the crude reaction mixture was poured into water (100 ml) and extracted with ethyl acetate (2×75 ml). The combined organic extracts were washed with water (6×75 ml), dried over sodium sulfate and concentrated. Silica gel chromatography (20% ethyl acetate/CH$_2$Cl$_2$) afforded 18f (407 mg, 57%) as a pale yellow oil: $^1$H NMR (DMSO-d$_6$) δ −0.06 (s, 9H), 0.84 (t, 2H, J=7.9 Hz), 3.54 (t, 2H, J=7.9 Hz), 5.76 (s, 2H), 6.24 (dd, 1H, J=2.6, 4.0 Hz), 6.68 (dd, 1H, J=1.8, 4.0 Hz) 7.49 (dd, 1H, J=8.7, 9.3 Hz), 7.51(dd, 1H, J=1.8, 2.6 Hz), 7.72 (d, 2H, J=6.2 Hz), 7.87 (dd, 1H, J=2.4, 6.5 Hz), 8.02 (ddd, 1H, J=2.4, 4.9, 8.7 Hz), 8.63 (d, 2H, J=6.2 Hz). Anal. (C$_{22}$H$_{25}$N$_2$O$_2$FSi) C, H, N.

(g) Intermediate 18g—5-(4-Pyridyl)-3-(1-[2-(trimethylsilanyl)ethoxymethyl]-1]pyrrol-2-yl)-1H-indazole A solution of 1-[2-fluoro-5-(4-pyridyl)phenyl]-1-(1-[2-(trimethylsilanyl)ethoxymethyl]-1H-pyrrol-2-yl)methanone 18f (504 mg, 1.3 mmol) and hydrazine monohydrate (1.7 ml, 35 mmol) in ethanol (35 ml) was heated at reflux for 42 hours. The ethanol was then removed by concentration, in vacuo. The residue obtained was partitioned between water (25 ml) and ethyl acetate (25 ml). The layers were separated and the aqueous phase was extracted with ethyl acetate (25 ml). The combined organic extracts were washed with saturated NaHCO$_3$ (30 ml), dried over sodium sulfate and concentrated. Silica gel chromatography (3% CH$_3$OH/CH$_2$Cl$_2$) provided 18g (430 mg, 87%) as an off-white solid: $^1$H NMR (DMSO-d$_6$) δ −0.28 (s, 9H), 0.63 (t, 2H, J=8.0 Hz), 3.28 (t, 2H, J=8.0 Hz), 5.72 (s, 2H), 6.26 (dd, 1H, J=2.8, 3.5 Hz), 6.79 (dd, 1H, J=1.7, 3.5 Hz) 7.10 (dd, 1H, J=1.7, 2.8 Hz), 7.67 (d, 1H, J=8.9 Hz), 7.77 (d, 2H, J=6.2 Hz), 7.81 (dd, 1H, J=1.6, 8.9 Hz), 8.19 (d, 1H, J=1.6 Hz), 8.61 (d, 2H, J=6.2 Hz), 13.25 (s, 1H). Anal. (C$_{22}$H$_{26}$N$_4$OSi) C, H, N.

(h) Example 18—5-(4-Pyridyl)-3-(2-pyrrolyl)-1H-indazole

Tetrabutylammonium fluoride (1.0 M in THF, 5 ml) was added to a solution of intermediate 18g (366 mg, 0.9 mmol) and 1,2-diaminoethane (150 mg, 2.5 mmol) in tetrahydrofuran (20 ml). This solution was heated at reflux for 42 hours, then poured into saturated NaHCO$_3$ (30 ml) and extracted with ethyl acetate (2×25 ml). The combined organic extracts were dried over sodium sulfate and concentrated. Silica gel chromatography (3% CH$_3$OH/CH$_2$Cl$_2$) provided 5-(4-Pyridyl)-3-(2-pyrrolyl)-1H-indazole 18 (71 mg, 29%) as an off-white solid: $^1$H NMR (DMSO-d$_6$) δ 6.20 (dd, 1H, J=2.6, 5.6 Hz), 6.82–6.92 (m, 2H), 7.64 (d, 1H, J=8.7 Hz), 7.81 (dd, 1H, J=1.4, 8.7 Hz), 7.83 (d, 2H, J=6.1 Hz), 8.37 (d, 1H, J=1.4 Hz), 8.62 (d, 2H, J=6.1 Hz), 11.37 (s, 1H), 13.09 (s, 1H). Anal. (C$_{16}$H$_{12}$N$_4$·0.05CH$_2$Cl$_2$) C, H, N.

EXAMPLE 18b'

5-Nitro-3-(2-Pyrrolyl)-1H-indazole

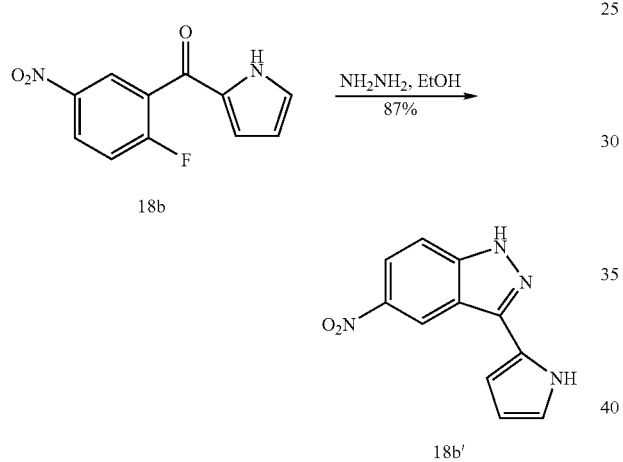

18b' was prepared similar to intermediate 11a. Treatment of 1-(2-fluoro-5-nitrophenyl)-1-(1H-pyrrol-2-yl)methanone 18b with hydrazine hydrate afforded 5-nitro-3-(2-pyrrolyl)-1H-indazole 18b' (75%) as an orange-red solid: $^1$H NMR (DMSO-d$_6$) δ 6.23 (ddd, 1H, J=2.4, 2.6, 3.6 Hz), 6.81 (ddd, 1H, J=1.5, 2.5, 3.6 Hz), 6.93 (ddd, 1H, J=1.5, 2.1, 2.6 Hz), 7.70 (d, 1H, J=9.2 Hz), 8.21 (dd, 1H, J=2.0, 9.2 Hz), 8.90 (d, 1H, J=2.0 Hz), 11.57 (broad, 1H), 13.62 (s, 1H). Anal. (C$_{11}$H$_8$N$_4$O$_2$) C, H, N.

EXAMPLE 19

4-[3-(4-Chloro-1H-benzoimidazol-2-yl)-1H-indazol-5-yl]-isoquinoline

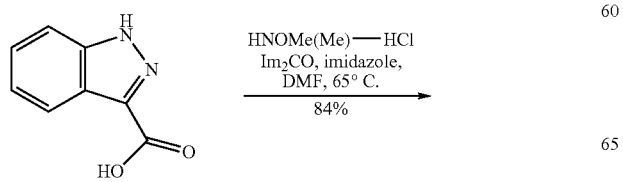

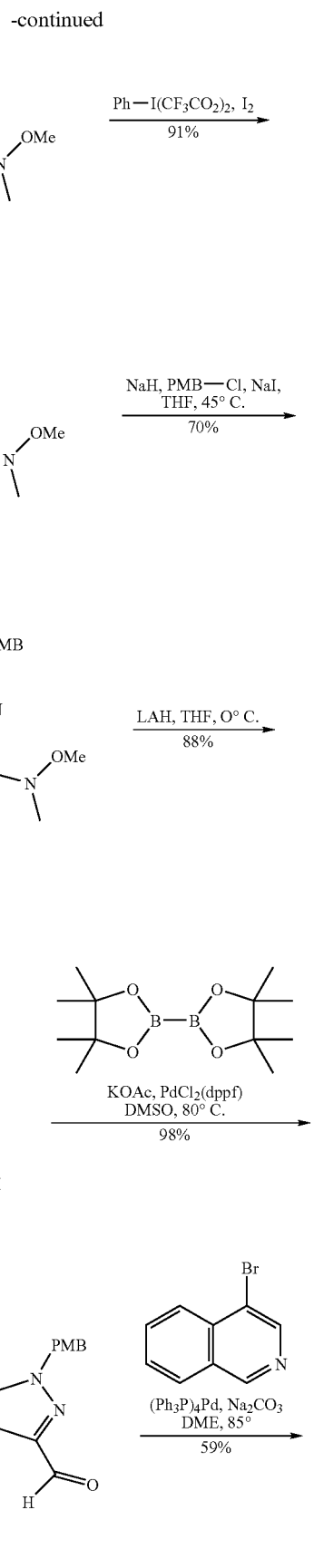

-continued

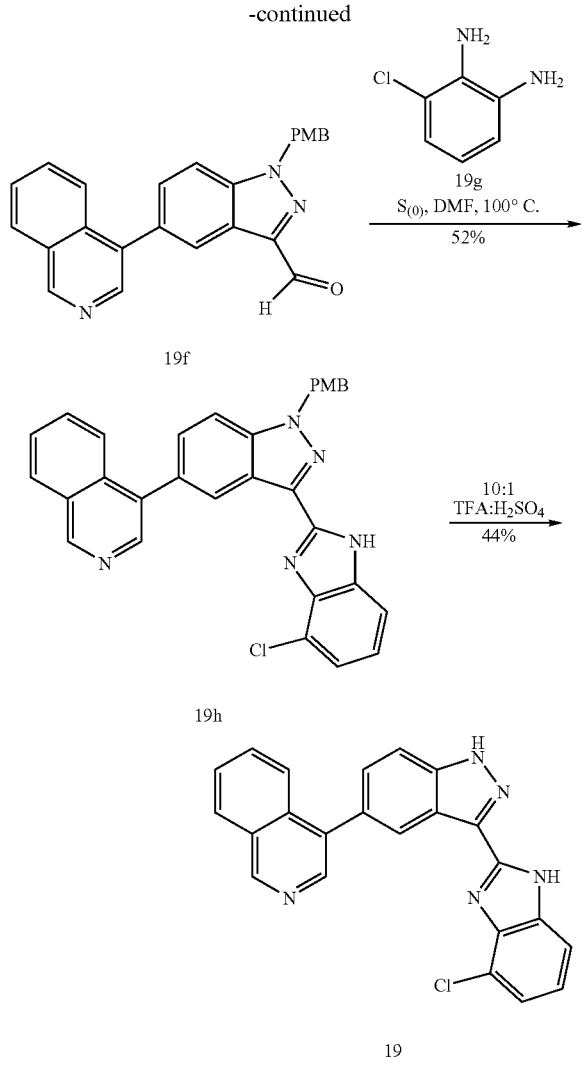

(a) Intermediate 19a—1H-indazole-3-carboxylic acid methoxy-methyl-amide

3-Carboxyindazole (100 g, 617 mmol) in 1 L DMF was treated with carbonyldiimidazole (110 g, 678 mmol) at 25° C. with gas evolution for 15 minutes. The reaction was heated to 60–65° C. for 2 hours and then allowed to cool to 25° C. N,O-Dimethylhydroxylamine-HCl (66.2 g, 678 mmol) was added as a solid and the mixture was heated to 65° C. for 3 hours The reaction was concentrated to a paste and taken up in 2L $CH_2Cl_2$, washed with water, and then 2N HCl. Product was visibly coming out of solution. Solid was filtered and rinsed separately with ethyl acetate. The ethyl acetate and $CH_2Cl_2$ layers were separately washed with $NaHCO_3$, and brine, dried over MgSO4 and concentrated. The resulting solids were combined, triturated with a 1:1 mixture of $CH_2Cl_2$-ether, filtered, and dried to afford 106 g (84%) of intermediate 19a as a white solid: $R_f$=0.38 (75% ethyl acetate in hexanes); $^1H$ NMR (DMSO-$d_6$) δ 13.60 (s, 1H,), 7.80 (d, 1H, J=8.2 Hz), 7.60 (d, 1H, J=8.2 Hz), 7.41 (t, 1H, J=8.0 Hz), 7.22 (t, 1H, J=8.0 Hz), 3.77(s, 3H), 3.44 (s, 3H). Anal. ($C_{10}H_{11}N_3O_2$) C, H, N.

(b) Intermediate 19b—5-Iodo-1H-indazole-3-carboxylic acid methoxy-methyl-amide

To the amide 19a (20g, 97.4 mmol) in 1 L $CH_2Cl_2$ was added bis(trifluoroacetoxy)iodobenzene (46 g, 107 mmol) followed by portionwise addition of iodine (14.84 g, 58.5 mmol) at 25° C. After 1 hour, 600 mL of saturated $Na_2HSO_3$ was added and a solid began to precipitate which was filtered and rinsed with excess $CH_2Cl_2$. The filtrate was washed with brine, dried over MgSO4, concentrated, and the remaining solid triturated with a minimal amount of $CH_2Cl_2$. The combined solids were dried under vacuum over KOH to give 29.26 g (91%) of iodide 19b as a pale white solid: $R_f$=0.31 (50% ethyl acetate in hexanes); $^1H$ NMR (DMSO-$d_6$) δ 13.79 (s, 1H), 8.39 (s, 1H), 7.65 (d, 1H, J=8.7 Hz), 7.48 (d, 1H, J=8.7 Hz), 3.76 (s, 3H), 3.44 (s, 3H). Anal. ($C_{10}H_{10}N_3IO_2$) C, H.

(c) Intermediate 19c—5-Iodo-1-(4methoxy-benzyl)-1H-indazole-3-carboxylic acid methoxy-methyl-amide To the iodide 19b (15g, 45.3 mmol) in 200 mL THF was added NaH (1.9 g of a 60% mineral oil dispersion, 1.14 g, 47.6 mmol), portionwise with gas evolution. After 15 minutes the reaction was cooled to 0° C. and p-methoxybenzyl chloride (8.51 g, 54.4 mmol) was added followed by NaI (679 mg, 4.5 mmol). The mixture was heated to 45° C. for 9h and allowed to cool to 25° C. The solution was diluted with ethyl acetate, washed with saturated aqueous $NH_4Cl$, brine and dried over MgSO4 and concentrated to a viscous oil. Ether was added to the oil and a solid formed which was filtered and rinsed with ether to provide 14.18g (70%) of 19c as a faint yellow solid.: $R_f$=0.42 (50% ethyl acetate in hexanes); $^1H$ NMR ($CDCl_3$) δ 8.60 (s, 1H), 7.56 (dd, 1H, J=8.8, 1.6 Hz), 7.11 (m, 3H), 6.80 (dd, 2H, J=6.7, 2.1 Hz), 5.52 (s, 2H), 3.81 (s, 3H), 3.75 (s, 3H), 3.51 (s, 3H). Anal. ($C_{18}H_{18}N_3O_3I$) C, H, N, I.

(d) Intermediate 19d—5-Iodo-1-(4-methoxy-benzyl)-1H-indazole-3-carbaldehyde

The amide 19c (12.8 g, 28.3 mmol) in 300 mL THF was cooled to −5° C. and $LiAlH_4$ (1.29 g, 34 mmol) was added portionwise over 10 minutes. After 30 minutes the reaction was quenched by the slow addition of ethyl acetate at −5° C. and the whole was poured into 0.4 N $NaHSO_4$. The organic layer was washed with brine, dried over MgSO4, and concentrated to afford a slightly offwhite solid which was triturated with a minimal amount of ether, filtered, washed with ether, and dried to give 9.79 g (88%) of aldehyde 19d as a white solid: $R_f$=0.57 (50% ethyl acetate in hexanes); $^1H$ NMR ($CDCl_3$) δ 10.20 (s, 1H), 8.96 (s, 1H), 7.63 (dd, 1H, J=8.8, 1.6 Hz), 7.18 (m, 3H), 6.83 (d, 1H, J=8.7 Hz), 5.57 (s, 3H), 3.75 (s, 3H). Anal. ($C_{16}H_{13}N_2O_2I$.0.1 ethyl acetate) C, H, N, I.

(e) Intermediate 19e—1-(4-Methoxy-benzyl)-5-(4,4,5,5-tetramethyl-[1,3,2]-dioxaborolan-2-yl)-1H-indazole-3-carbaldehyde Bis(pinacolato)diboron (Aldrich Chemicals) (7.05 g, 27.8 mmol), iodide 19d (9.90 g, 25.24 mmol), potassium acetate (12.4 g, 126 mmol), and 1,1'-bis(diphenyl-phosphino)ferrocenedichloropalladium(II) (515 mg, 0.631 mmol) were dissolved in dimethysulfoxide (150 mL), degassed, and heated in an 80° C. oilbath for 1 hour. After cooling to room temperature, the mixture was partitioned between ethyl acetate (200 mL) and water (150 mL). The organic layer was dried over magnesium sulfate, filtered, concentrated, and purified by silica gel chromatography (25% ethyl acetate in hexanes) to give boronic ester 19e (9.75 g, 98%) as an off-white solid: $R_f$=0.37 (25% ethyl acetate in hexanes); $^1$H NMR (DMSO-$d_6$) δ 1.31 (s, 12H), 3.69 (s, 3H), 5.75 (s, 2H), 6.87 (d, 2H, J=8.7 Hz), 7.27 (d, 2H, J=8.7 Hz), 7.74 (d, 1H, J=8.4 Hz), 7.91 (d, 1H, J=8.4 Hz), 8.52 (s, 1H), 10.17 (s, 1H). Anal. ($C_{22}H_{25}BN_2O_4$) C, H, N.

(f) Intermediate 19f—5-Isoquinolin-4-yl-1-(4-methoxy-benzyl)-1H-indazole-3-carbaldehyde To a degassed solution of boronic ester 19e (6.00g, 15.30 mmol) and 4-bromoisoquinoline (5.17 g, 24.8 mmol) in ethylene glycol dimethyl ether (DME, 76 mL) was added aqueous sodium carbonate solution (2.0 M, 38.2 mL, 76.4 mmol) followed by tetrakis(triphenylphosphine)palladium (0) (883 mg, 0.76 mmol). The mixture was heated in an 80° C. oilbath for 5 hours, attaining a maximum internal temperature of 78° C. After cooling to room temperature, the mixture was diluted with ethyl acetate (200 mL), washed with water (100 mL), and saturated aqueous sodium chloride solution (50 mL). The organic extracts were dried over magnesium sulfate, filtered, concentrated and columned (silica gel, 30 to 70% ethyl acetate in hexanes), affording 19f (3.56 g, 59%) as an off-white solid: $R_f$=0.16 (50% ethyl acetate in hexanes); $^1$H NMR (DMSO-$d_6$) δ 3.71 (s, 3H), 5.83 (s, 2H), 6.92 (d, 2H, J=8.7 Hz), 7.38 (d, 2H, J=8.7 Hz), 7.74 (m, 4H), 8.10 (d, 1H, J=8.7 Hz), 8.22 (m, 2H), 8.48 (s, 1H), 9.37 (s, 1H), 10.21 (s, 1H).

(g) Intermediate 19g—3-Chloro-benzene-1,2-diamine

A solution of sodium borohydride (1.90 g, 50.2 mmol) in water (40 mL) was added to a suspension of 10% palladium on carbon (250 mg) in water (50 mL) while bubbling argon into the latter solution via pipette. To this was added a solution of 3-chloro-2-nitroaniline (Astatech Chemicals) (4.33 g, 25.1 mmol) in 2N aqueous sodium hydroxide (125 mL) dropwise via addition funnel, slowly enough to keep gas evolution under control. The mixture was stirred at room temperature for 10 minutes, filtered through a Celite pad, acidified with 3N aqueous hydrochloric acid, and extracted with dichloromethane (3×200 mL). The combined organic layers were dried over magnesium sulfate, filtered, concentrated, and purified by silica gel chromatography (1 to 20% ethyl acetate in dichloromethane) to give diamine 19g (2.13 g, 60%) as yellow oil: $R_f$=0.30 (dichloromethane); $^1$H NMR (DMSO-$d_6$) δ 4.60 (br s, 2H), 4.80 (br s, 2H), 6.37 (t, 1H, J=7.8 Hz), 6.48 (m, 2H). Anal. ($C_6H_7ClN$) C, H, Cl, N.

(h) Intermediate 19h—4-[3-(4-Chloro-1H-benzoimidazol-2-yl)-1-(4methoxy-benzyl)-1H-indazol-5-yl]-isoquinoline Aldehyde 19f (405.6 mg, 1.03 mmol) and diamine 19g (147 mg, 1.03 mmol) were condensed in the presence of elemental sulfur (50 mg, 1.55 mmol) analogous to the synthesis of intermediate 7c', affording intermediate 19h (275.5 mg, 52%) as a pale yellow solid: $R_f$=0.12 (50% ethyl acetate in hexanes); $^1$H NMR (DMSO-$d_6$) δ 3.74 (s, 3H), 5.83 (s, 2H), 6.93 (d, 2H, J=8.8 Hz), 7.22 (m, 2H), 7.38 (d, 2H, J=8.5 Hz), 7.48 (d, 1H, J=7.2 Hz), 7.67 (dd, 1H, J=8.7, 1.5 Hz), 7.76 (m, 3H), 8.04 (d, 1H, J=8.7 Hz), 8.26 (dd, 1H, J=7.4, 1.5 Hz), 8.54 (s, 1H), 8.64 (s, 1H), 9.40 (s, 1H), 13.41 (s, 1H).

(i) Example 19

4-[3-(4-Chloro-1H-benzoimidazol-2-yl)-1H-indazol-5-yl]-isoquinoline

Concentrated sulfuric acid (0.3 mL) was added to a solution of 19h (121.6 mg, 0.236 mmol) in trifluoroacetic acid (3.0 mL), and stirred at room temperature for 19 hours. The mixture was then diluted with water (50 mL), treated with concentrated aqueous ammonium hydroxide until pH=8, and extracted with ethyl acetate (3×50 mL). The combined organic extracts were dried over magnesium sulfate, filtered, concentrated, and purified by silica gel chromatography to give 19 (41.5 mg, 44%) as a white solid: $R_f$=0.40 (75% ethyl acetate in hexanes); $^1$H NMR (DMSO-$d_6$) [Some peaks are doubled due to tautomeric isomerization] δ 7.22 (m, 2H), 7.48 (d, 1H, J=7.2 Hz), 7.64 (d, 1H, J=8.7), 7.79 (m, 4H), 8.27 (d, 1H, J=7.5), 8.55 (s, 1H), 8.63 (s, 1H), 9.40 (s, 1H), 13.39 and 13.56 (2 s, 1H together), 13.94 (s, 1H). Anal. ($C_{23}H_{14}ClN_5$.1.2 $CH_3OH$) C, H, Cl, N.

EXAMPLE 20

4-{3-[5-(4-Methyl-piperazin-1-yl)-1H-benzoimidazol-2-yl]-1H-indazol-5-yl}-isoquinoline

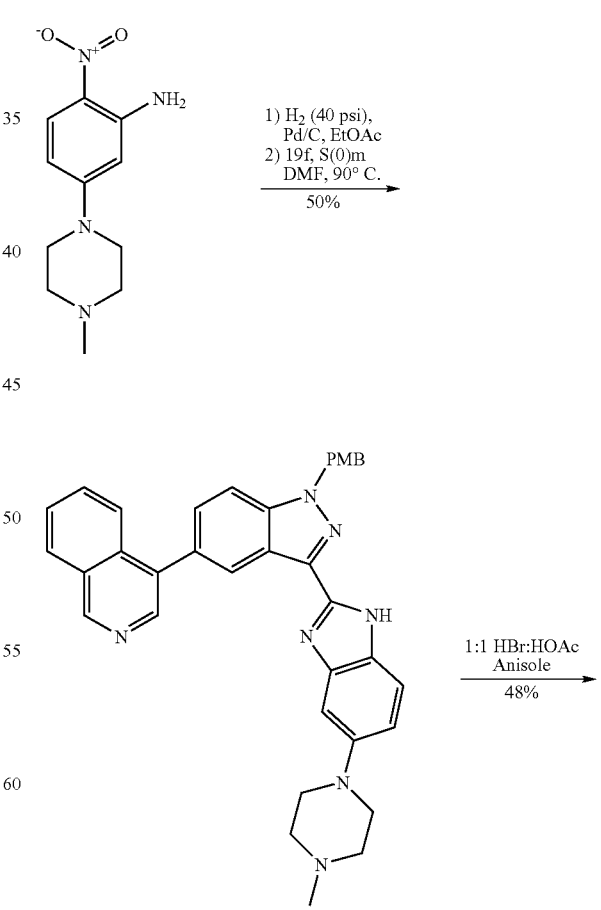

20a

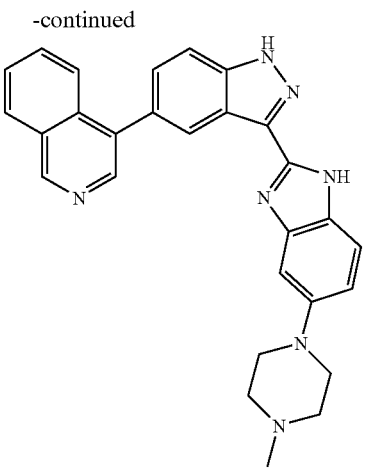

20

(a) Intermediate 20a—41{-(4Methoxy-benzyl)-3-[5-(4-methyl-piperazin-1-yl)-1H-benzoimidazol-2-yl]-1H-indazol-5-yl}-isoquinoline A suspension of 5-(4-Methyl-piperazin-1-yl)-2-nitro-phenylamine (513.0 mg, 2.17 mmol) [See Kim, Jung Sun; et al.; *J. Med. Chem.*; 39; 992 (1996) for the synthesis of this compound] and 10% palladium on carbon (200.8 mg) in ethyl acetate (50 mL) was shaken under 40 psi $H_2$ for 17 hours. The catalyst was removed by filtration through a Celite pad, and the mixture concentrated to afford crude 4-(4-Methyl-piperazin-1-yl)-benzene-1,2-diamine (522 mg) as a yellow foam. This crude diamine was added to a solution of aldehyde 19f (853.7 mg, 2.17 mmol) and elemental sulfur (83 mg, 2.60 mmol) in anhydrous dimethylformamide (40 mL), and the solution heated in an 80° C. oilbath for 6 hours. After cooling to room temperature, the solution was diluted with ethyl acetate (150 mL) and washed with water (50 mL) and saturated aqueous sodium chloride solution (50 mL). The organic layer was dried over magnesium sulfate, filtered, concentrated, and purified by silica gel chromatography (1:20:400 concentrated aqueous $NH_4OH$: EtOH:$CH_2Cl_2$), affording 20a (623 mg, 50%) as an orange-brown foam: $R_f$=0.20 (10% ethanol in dichloromethane); $^1H$ NMR (DMSO-$d_6$) [Some peaks are doubled due to tautomeric isomerization] δ 2.23 (s, 3H), 2.49 (m, 4H), 3.10 (m, 4H), 3.71 (s, 3H), 5.80 (s, 2H), 6.91 (m, 4H), 7.36 and 7.47 (2 d, 3H together, J=8.3, 8.7 Hz), 7.64 (d, 1H, J=8.9 Hz), 7.77 (m, 3H), 7.99 (m, 1H), 8.25 (d, 1H, J=7.2 Hz), 8.53 (s, 1H), 8.62 and 8.64 (2 s, 1H together), 9.39 (s, 1H), 12.78 and 12.83 (2 s, 1H together). Anal. ($C_{36}H_{33}N_7$0.9$H_2O$) C, H, N.

EXAMPLE 20

4-{3-[5-(4-Methyl-piperazin-1-yl)-1H-benzoimidazol-2-yl]-1H indazol-5-yl}-isoquinoline Anisole (229.4 mg, 2.12 mmol) was added to a solution of 20a (123.0 mg, 0.212 mmol) in glacial acetic acid (2.12 mL). Concentrated aqueous hydrobromic acid (2.12 mL) was added, and the mixture heated to reflux for 21 hours. After cooling, the reaction solution was added dropwise to a rapidly stirred mixture of dichloromethane (50 mL), tetrahydrofuran (20 mL), and saturated aqueous sodium bicarbonate (30 mL). The layers were separated, and the organic layer was washed with saturated aqueous sodium bicarbonate (20 mL), followed by water (20 mL). The organic layer was dried over magnesium sulfate, filtered, concentrated, and purified by silica gel chromatography (1:20:100 concentrated aqueous $NH_4OH$: EtOH:$CH_2Cl_2$), yielding slightly impure 20 (76.0 mg, 78%) as a red foam. Further purification by precipitation from dichloromethane/hexanes afforded pure 20 (47.1 mg, 48%) as a pink solid: $R_f$=0.20 (1:20:50 concentrated aqueous $NH_4OH$: EtOH:$CH_2Cl_2$); $^1H$ NMR (DMSO-$d_6$) [Some peaks are doubled due to tautomeric isomerization] δ 2.23 (s, 3H), 2.49 (m, 4H), 3.11 (m, 4H), 6.91 (m, 2H), 7.35 and 7.47 (2 d, 1H together, J=9.0, 8.9 Hz), 7.61 (d, 1H, J=8.9 Hz), 7.80 (m, 4H), 8.26 (d, 1H, J=7.7 Hz), 8.54 (s, 1H), 8.59 and 8.62 (2 s, 1H together), 9.39 (s, 1H), 12.74 and 12.79 (2 s, 1H together), 13.73 and 13.76 (2 s, 1H together). Anal. ($C_{28}H_{25}N_7$.0.7 $H_2O$) C, H, N.

EXAMPLE 21

2-[5-(3-Hydroxy-2-methyl-phenyl)-1H-indazol-3-yl]-1H-benzoimidazol-4-ol

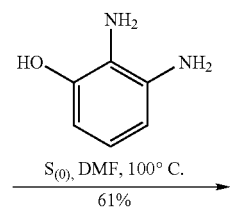

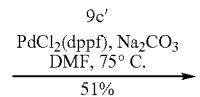

21a

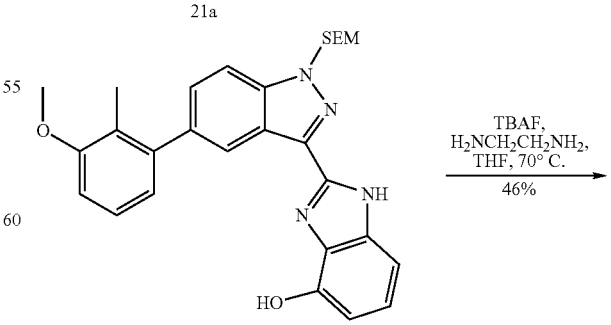

21b

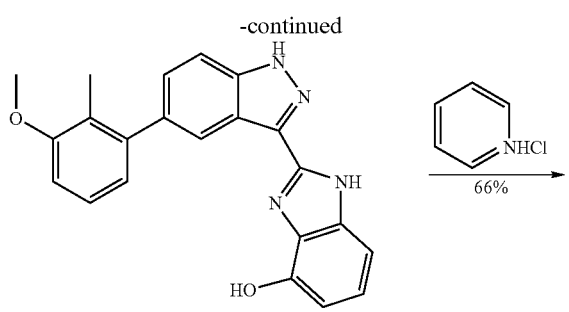

21c

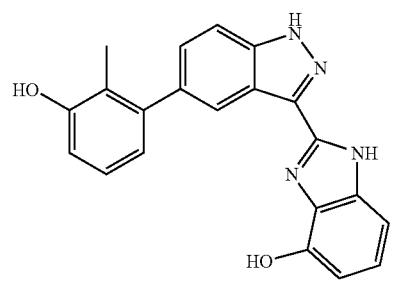

21

(a) Intermediate 21a—2-[5-Iodo-1-(2-trimethylsilanyl-ethoxymethyl)-1H-indazol-3-yl]-1H-benzoimidazol-4-ol Aldehyde 7b' (2.66 g, 6.62 mmol), and 2,3-diaminophenol (available from Aldrich Chemicals) (822 mg, 6.62 mmol) were condensed in the presence of elemental sulfur analogous to the synthesis of intermediate 7c', affording 21a (2.04 g, 61%) as a yellow solid: $R_f$=0.15 (25% ethyl acetate in hexanes); $^1$H NMR (DMSO-$d_6$) [Some peaks are doubled due to tautomeric isomerization] δ −0.13 (s, 9H), 0.82 (t, 2H, J=8.1 Hz), 3.59 (t, 2H, J=7.8 Hz), 5.85 (s, 2H), 6.59 (d, 1H, J=7.5 Hz), 7.01 (m, 2H), 7.71 (d, 1H, J=8.7 Hz), 7.81 (dd, 1H, J=8.8, 1.5 Hz), 8.90 and 9.04 (2 s, 1H together), 9.49 and 9.74 (2 s, 1H together), 12.69 and 12.96 (2 s, 1H together). Anal. ($C_{20}H_{23}IN_4O_2Si$) C, H, N.

(b) Intermediate 21b—2-[5-(3-Methoxy-2-methyl-phenyl)-1-(2-trimethylsilanyl-ethoxymethyl)-1H-indazol-3-yl]-1H-benzoimidazol-4-ol Boronic ester 9c' (250 mg, 1.01 mmol) and iodide 21a (510.6 mg, 1.01 mmol) were coupled by the procedure analogous to intermediate 9d' synthesis, affording 21b (256.7 mg, 51%) as a yellow foam: $R_f$=0.22 (30% ethyl acetate in hexanes, co-spots with 21a); $^1$H NMR (DMSO-$d_6$) [Some peaks are doubled due to tautomeric isomerization] δ −0.11 (s, 9H), 0.85 (t, 2H, J=8.1 Hz), 2.06 (s, 3H), 3.64 (t, 2H, J=7.7 Hz), 3.85 (s, 3H), 5.90 (s, 2H), 6.55 (dd, 1H, J=7.2, 1.1 Hz), 6.96 (m, 4H), 7.26 (t, 1H, J=7.9 Hz), 7.46 (dd, 1H, J=8.7, 1.5 Hz), 7.87 (d, 1H, J=8.7 Hz), 8.40 and 8.55 (2 s, 1H together), 9.45 and 9.61 (2 s, 1H together), 12.62 and 12.91 (2 s, 1H together). Anal. ($C_{28}H_{32}N_4O_3Si \cdot 0.4H_2O$) C, H, N.

(c) Intermediate 21c—2-[5-(3-Methoxy-2-methyl-phenyl)-1H-indazol-3-yl]-1H benzoimidazol-4-ol In an analogous manner to example 3, treatment of 21b (174.5 mg, 0.349 mmol) with tetrabutylammonium fluoride afforded 21c (59.8 mg, 46%) as an off-white solid: $R_f$=0.26 (5% methanol in dichloromethane); $^1$H NMR (DMSO-$d_6$) [Some peaks are doubled due to tautomeric isomerization] δ 2.07 (s, 3H), 3.85 (s, 3H), 6.53 and 6.62 (2 d, 1H together, J=7.4, 7.7 Hz), 6.96 (m, 4H), 7.26 (t, 1H, J=7.9 Hz), 7.37 (d, 1H, J=8.5 Hz), 7.66 (d, 1H, J=8.5 Hz), 8.35 and 8.49 (2 s, 1H together), 9.45 and 9.55 (2 s, 1H together), 12.53 and 12.78 (2 s, 1H together), 13.57 and 13.62 (2 s, 1H together). HRMS calculated for $C_{22}H_{19}N_4O_2$ 371.1508 (MH$^+$). found 371.1523.

(d) Example 21—2-[5-(3-Hydroxy-2-methyl-phenyl)-1H-indazol-3-yl]-1H-benzoimidazol-4-ol By a procedure analogous to phenol 8' synthesis, treatment of 21c (45.9 mg, 0.124 mmol) with pyridine hydrochloride afforded 21 (29.0 mg, 66%) as a tan powder: $R_f$=0.28 (10% methanol in dichloromethane); $^1$H NMR (DMSO-$d_6$) [Some peaks are doubled due to tautomeric isomerization] δ 2.04 (s, 3H), 6.54 and 6.62 (dd and d, 1H together, J=7.2, 1.3 and 7.7 Hz), 6.75 (d, 1H, J=7.4 Hz), 6.85 (d, 1H, J=7.9 Hz) 7.01 (m, 3H), 7.37 and 7.38 (dd and dd, 1H together, J=8.5, 1.5 Hz for each), 7.65 and 7.66 (2 d, 1H together, J=8.7 Hz for each), 8.35 and 8.48 (2 s, 1H together), 9.38 and 9.39 (2 s, 1H together), 9.46 and 9.56 (2 s, 1H together), 12.52 and 12.77 (2 s, 1H together), 13.55 and 13.60 (2 s, 1H together). HRMS calculated for $C_{21}H_{17}N_4O_2$ 357.1351 (MH$^+$). found 357.1360. Anal. ($C_{21}H_{16}N_4O_2 \cdot 0.8\ CH_3OH$) C, H, N.

EXAMPLE 22

6-(3-Hydroxy-propyl)-2-methyl-3-[3-((E)-styryl)-1H-indazol-5-yl]-phenol

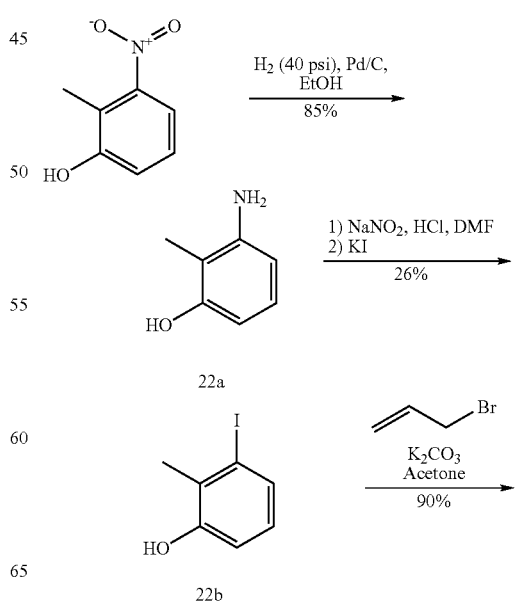

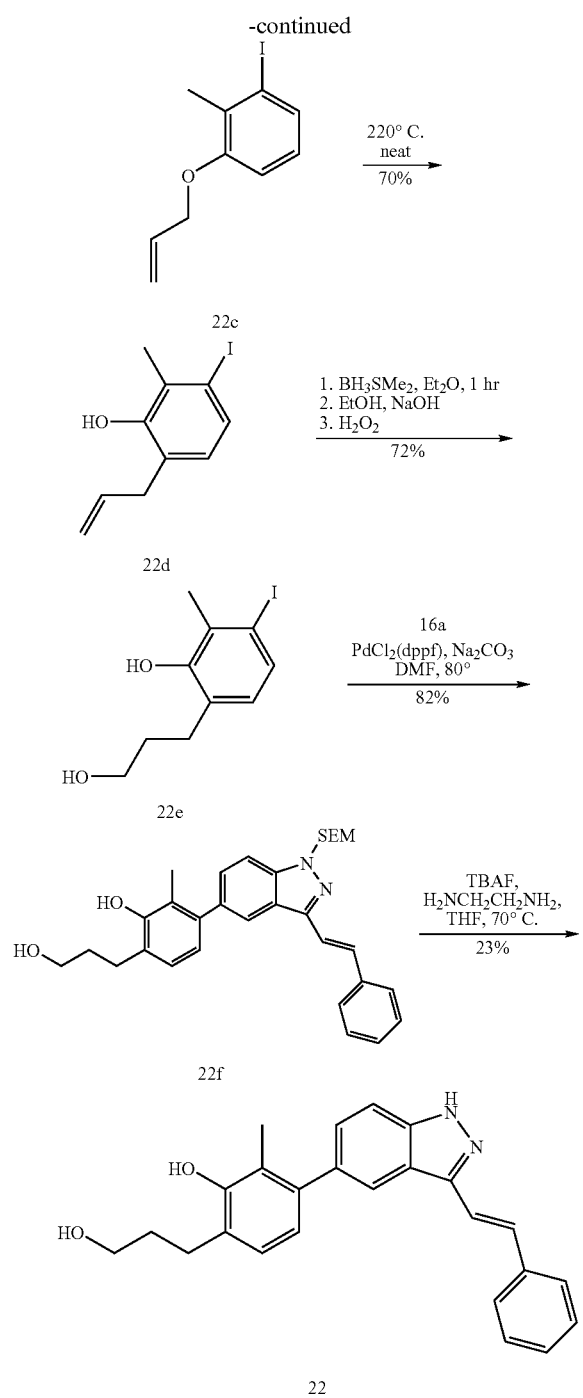

(a) Intermediate 22a—3-Amino-2-methyl-phenol

A suspension of 2-methyl-3-nitro-phenol (Aldrich Chemicals) (29.8 g, 194.6 mmol) and 10% palladium on carbon (3.01 g) in ethanol (350 mL) was shaken under 40 psi hydrogen for 3.5 hours. After filtration through a Celite pad, the solution was concentrated and purified by silica gel chromatography (50% ethyl acetate in hexanes) to give aniline 22a (20.32 g, 85%) as a colorless solid: $R_f$=0.50 (50% ethyl acetate/hexanes); $^1$H NMR (DMSO-$d_6$) δ 1.87 (s, 3H), 4.63 (s, 2H), 6.08 (dd, 2H, J=7.9, 10.5 Hz), 6.64 (t, 1H, J=7.9 Hz), 8.76 (s, 1H). Anal. ($C_7H_9NO$) C, H, N.

(b) Intermediate 22b—3-Iodo-2-methyl-phenol

3-Amino-2-methyl-phenol 22a (18.35 g, 149 mmol) was diazotized according to the method of DeGraw, et al. [DeGraw, J. I.; Brown, V. H.; Colwell, W. T.; Morrison, N. E., *J. Med. Chem.*, 17, 762 (1974)]. After column chromatography (10–50% ethyl acetate in hexanes), aryl iodide 22b (9.06 g, 26%) was isolated as an orange solid. Further purification by recrystallization from hexanes afforded 5.63 g pale orange needles: $R_f$=0.35 (20% ethyl acetate/hexanes); $^1$H NMR (DMSO-$d_6$) δ 2.22 (s, 3H), 6.80 (m, 2H), 7.24 (dd, 1H, J=7.5, 1.5 Hz), 9.75 (s, 1H).

(c) Intermediate 22c—1-Allyloxy-3-iodo-2-methyl-benzene

Allyl bromide (1.57 g, 13.0 mmol) was added to a solution of 3-iodo-2-methyl phenol (2.026g, 8.66 mmol) in acetone (18 mL). The solution was heated at reflux for 2 hours, then cooled to room temperature, diluted with ethyl acetate (50 mL), and acidified with 1N aqueous hydrochloric acid until an aqueous of pH=2 was obtained. The layers were separated, and the aqueous layer extracted with ethyl acetate (2×10 mL). The combined organic extracts were dried over magnesium sulfate, filtered, concentrated and purified by silica gel chromatography (5% ethyl acetate in hexanes) to give allyl ether 22c (2.1353 g, 90%) as a yellow oil: $R_f$=0.60 (20% ethyl acetate/hexanes); $^1$H NMR (CDCl$_3$) δ 2.40 (s, 3H), 4.53 (d of t, 2H, J=5.1, 1.5 Hz), 5.28 (d of q, 1H, J=10.6, 1.5 Hz), 5.42 (d of q, 1H, J=17.3, 1.5 Hz), 6.05 (m, 1H), 6.82 (m, 2H), 7.43 (dd, 1H. J=7.2, 1.9 Hz).

(d) Intermediate 22d—6-Allyl-3-iodo-2-methyl-phenol

Intermediate 22c (1.0954 g, 3.996 mmol) was heated in a sealed tube in a 200° C. oil bath for 2 hours. After cooling and column chromatography, phenol 22d (767.2 mg, 70%) was obtained as an amber oil: $R_f$=0.31 (10% ethyl acetate/hexanes); $^1$H NMR (DMSO-$d_6$) δ 2.30 (s, 3H), 3.28 (d, 2H, J=6.6 Hz), 5.02 (m, 2H), 5.90 (m, 1H), 6.66 (d, 1H, J=7.9 Hz), 7.26 (d, 1H, J=8.1 Hz), 8.63 (s, 1H).

(e) Intermediate 22e—6-(3-Hydroxy-propyl)-3-iodo-2-methyl-phenol

Borane-dimethylsulfide complex (0.159 mL, 1.68 mmol borane) was added dropwise to a chilled solution (0° C.) of intermediate 22d (459.8 mg, 1.677 mmol) in dry ether (5.0 mL). The cooling bath was removed, and stirring continued for 1 hour. Absolute ethanol (2.5 mL) was added, followed by aqueous sodium hydroxide (2.5 N, 3.35 mL). The mixture was recooled to 0° C., and hydrogen peroxide added (30 wt % in H$_2$O, 0.27 mL). After stirring at 0° C. for 15 minutes, the cooling bath was removed, and the mixture was allowed to warm to room temperature over 1 hour. The solution was partitioned between ether (50 mL) and 1N aqueous hydrochloric acid (final aqueous pH 2–3). The organic layer was dried over magnesium sulfate, filtered, and concentrated to an orange oil. Purification by silica gel chromatography yielded alcohol 22e (353.1 mg, 72%) as a yellow oil $R_f$=0.11 (20% ethyl acetate/hexanes); $^1$H NMR (DMSO-$d_6$) δ 1.64 (quint, 2H, J=7.0 Hz), 2.29 (s, 3H), 2.54 (t, 2H, J=7.5 Hz)

3.39 (t, 2H, J=6.5 Hz), 4.54, (br s, 1H), 6.68 (d, 1H, J=8.1 Hz), 7.23 (d, 1H, J=8.1 Hz), 8.58 (s, 1H).

(f) Intermediate 22f—6-(3-Hydroxy-propyl)-2-methyl-3-[3-((E)-styryl)-1-(2-trimethylsilanyl-ethoxymethyl)-1H-indazol-5-yl]-phenol Aqueous sodium carbonate solution (2M, 1.79 mL) was added to a degassed solution of boronic ester 16a (534.1 mg, 1.12 mmol), aryl iodide 22e (209.1 mg, 0.716 mmol), and 1,1'-bis(diphenylphosphino)ferrocenedichloropalladium(II) (29 mg, 0.036 mmol) in DMF (3.2 mL). The mixture was heated in an 80° C. oilbath for 1.5 hours, then cooled and partitioned between ethyl acetate (50 mL) and water (10 mL). The organic layer was dried over magnesium sulfate, filtered, and concentrated. Purification by silica gel chromatography (20 to 50% ethyl acetate in hexanes) afforded 22f (301.9 mg, 82%) as a yellow foam: $R_f$=0.07 (20% ethyl acetate/hexanes); $^1$H NMR (DMSO-$d_6$) δ −0.09 (s, 9H), 0.83 (t, 2H, J=7.9 Hz), 1.73 (quint, 2H, J=7.5 Hz), 2.09 (s, 3H), 2.65 (t, 2H, J=7.5 Hz), 3.46 (t, 2H, J=6.5 Hz), 3.58 (t, 2H, J=8.0 Hz), 5.78 (s, 2H), 6.74 (d, 1H, J=7.7 Hz), 6.98 (d, 1H, J=7.9 Hz), 7.27 (m, 1H), 7.37 (m, 3H), 7.56 (m, 2H), 7.73 (m, 3H), 8.06 (s, 1H), 8.25 (br s, 1H). Anal. ($C_{31}H_{38}N_2O_3Si \cdot 0.5\ CH_2Cl_2$) C, H, N.

(g) Intermediate 22—6-(3-Hydroxy-propyl)-2-methyl-3-[3-((E)-styryl)-1H-indazol-5-yl]-phenol 22 was prepared similar to example example 3, treatment of intermediate 22f (202.9 mg, 0.394 mmol) with tetrabutylammonium fluoride afforded 22 (34.3 mg, 23%) as a white powder: $R_f$=0.19 (50% ethyl acetate/hexanes); $^1$H NMR (DMSO-$d_6$) δ1.72 (quint, 2H, J=7.4 Hz) 2.10 (s, 3H), 2.64 (t, 2H, J=7.4 Hz), 3.45 (t, 2H, J=6.2 Hz), 4.59 (br s, 1H), 6.74 (d, 1H, J=7.7 Hz), 6.97 (d, 1H, J=7.7 Hz), 7.33 (m, 4H), 7.45 (m, 5H), 8.02 (s, 1H), 8.26 (s, 1H), 13.18 (s, 1H). Anal. ($C_{25}H_{24}N_2O_2 \cdot 0.6H_2O$) C, H, N.

EXAMPLE 23

3-[3-(4Hydroxymethyl-1H-benzoimidazol-2-yl)-1H-indazol-5-yl]-2-methyl-phenol

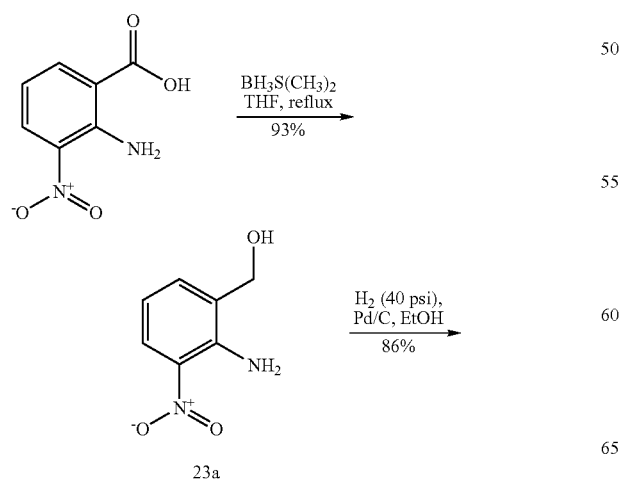

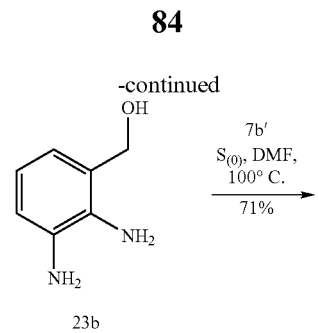

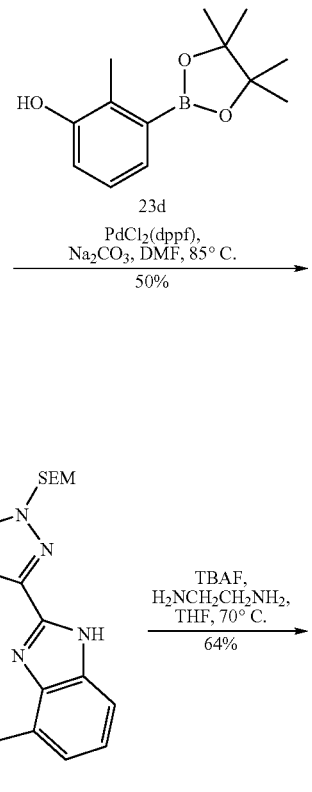

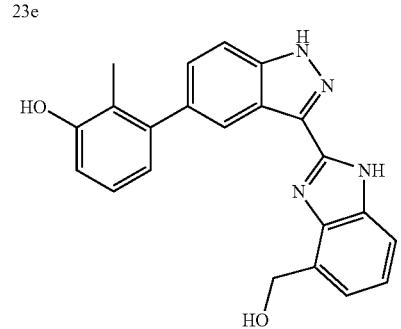

(a) Intermediate 23a—(2-Amino-3-nitro-phenyl)-methanol

3-Nitroanthranilic acid [See Chapman, E. and Stephen, H. J. Chem. Soc., 127, 1791, (1925) for the synthesis of this reagent] (5.00 g, 27.45 mmol) was reduced with borane-dimethylsulfide complex according to the method of Mikelson, et al. [Mickelson, John W.; et al. *J. Med. Chem.;* 39; 4654 (1996)], affording benzyl alcohol 23a (4.27 g, 93%) as an orange crystalline solid: $R_f$=0.22 (75% ethyl acetate in hexanes); $^1$H NMR (DMSO-d$_6$) δ 4.50 (d, 2H, J=5.4 Hz), 5.43 (t, 1H, J=5.4 Hz), 6.65 (dd, 1H, J=8.7, 7.2 Hz), 7.10 (br s, 2H), 7.47 (d, 1H, J=7.0 Hz), 7.94 (dd, 1H, J=8.8, 1.5 Hz). Anal. (C$_7$H$_8$N$_2$O$_3$) C, H, N.

(b) Intermediate 23b—(2,3-Diamino-phenyl)-methanol

In a manner analogous to the synthesis of 9a', intermediate 23a (3.16 g, 18.8 mmol) was hydrogenated in ethanol (300 mL) to give 23b (2.23g, 86%) as a yellow-brown solid. Further purification by recrystalization from ethanol gave 23b (1.04 g, 40%) as yellow needles: $R_f$=0.17 (75% ethyl acetate in hexanes); $^1$H NMR (DMSO-d$_6$) δ 4.36 (br s, 6H), 4.90 (br s, 1H), 6.42 (m, 3H). Anal. (C$_7$H N$_2$O) C, H, N.

(c) Intermediate 23c—{2-[5-Iodo-1-(2-trimethylsilanyl-ethoxymethyl)-1H-indazol-3-yl]-1H-benzoimidazol-4-yl}-methanol 23c was prepared similar to 7c' synthesis. Condensation of diamine 23b (587.3 mg, 4.25 mmol) with aldehyde 7b' (1.71 g, 4.25 mmol) in the presence of elemental sulfur afforded 23c (1.57 g, 71%) as a yellow solid: $^1$H NMR (DMSO-d$_6$) [Some peaks are doubled due to tautomeric isomerization] δ −0.13 (s, 9H), 0.82 (t, 2H, J=7.7 Hz), 3.58 (t, 2H, J=7.9 Hz), 4.87 (br s, 1H), 5.04 (br s, 1H), 5.22 (br s, 1H), 5.87 (s, 2H), 7.26 (m, 2H), 7.39 and 7.67 (m and br s, 1H together), 7.75 (d, 1H, J=8.7 Hz), 7.83 (dd, 1H, J=8.8, 1.5 Hz), 8.95 (d, 1H, J=1.1 Hz), 12.97 and 13.13 (2s, 1H together). Anal. (C$_{21}$H$_{251}$N$_4$O$_2$Si) C, H, I, N.

(d) Intermediate 23d—2-Methyl-3-(4,4,5,5-tetramethyl-[1,3,2]dioxaborolan-2-yl)-phenol By a synthetic method analogous to 9c' synthesis, iodide 22b (1.21 g, 5.17 mmol) was converted to boronic ester 23d (1.15 g, 95%), a white, crystalline solid: $R_f$=0.18 (10% ethyl acetate in hexanes); $^1$H NMR (CDCl$_3$) δ 1.35 (s, 12H), 2.46 (s, 3H), 6.87 (dd, 1H, J=7.9, 1.0 Hz), 7.08 (t, 1H, J=7.5 Hz), 7.35 (dd, 1H, J=7.4, 1.1 Hz). Anal. (C$_{13}$H$_{19}$BO$_3$.0.2 H$_2$O) C, H.

(e) Intermediate 23e—3-[3-(4-Hydroxymethyl-1H-benzoimidazol-2-yl)-1-(2-trimethylsilanyl-ethoxymethyl)-1H-indazol-5-yl]-2-methyl-phenol 23e was prepared similar to 9d' synthesis. Iodide 23c (276.3 mg, 0.514 mmol) and boronic ester 23d (300 mg, 1.28 mmol) were coupled to give 23e (128.2 mg, 50%) as a yellow solid: $R_f$=0.16 (40% ethyl acetate in hexanes); $^1$H NMR (DMSO-d$_6$) [Some peaks are doubled due to tautomeric isomerization] δ −0.11 (s, 9H), 0.85 (t, 2H, J=7.9 Hz), 2.03 and 2.07 (2 s, 3H together), 3.63 (t, 2H, J=7.7 Hz), 4.87 and 4.97 (2 d, 2H together, J=5.8 and 5.5 Hz), 5.11 and 5.25 (2 t, 1H together, J=5.6 and 6.1 Hz), 5.92 and 5.93 (2 s, 2H together), 6.76 (dd, 1H, J=7.5, 3.4 Hz), 6.86 (d, 1H, J=7.9 Hz), 7.17 (m, 3H), 7.39 and 7.60 (dd and d, 1H together, J=6.8, 2.1 and 7.9 Hz), 7.49 (d, 1H, J=8.7 Hz), 7.89 (d, 1H, J=8.9 Hz), 8.44 and 8.47 (2 s, 1H together), 9.46 and 9.48 (2s, 1H together), 12.91 and 13.09 (2s, 1H together). Anal. (C$_{28}$H$_{32}$N$_4$O$_3$Si.0.3H$_2$O) C, H, N.

(f) Example 23—3-[3-(4-Hydroxymethyl-1H-benzoimidazol-2-yl)-1H-indazol-5-yl]-2-methyl-phenol 23 was prepared similar to example 3. Treatment of 23e (130.7 mg, 0.261 mmol) with tetrabutylammonium fluoride afforded 23 (61.6 mg, 64%) as a white solid: $R_f$=0.22 (70% ethyl acetate in hexanes); $^1$H NMR (DMSO-d$_6$) [Some peaks are doubled due to tautomeric isomerization] δ2.04 and 2.07 (2 s, 3H together), 4.86 and 4.97 (2 d, 2H together, J=6.0 and 5.7 Hz), 5.10 and 5.23 (2 t, 1H together, J=5.6 and 6.0 Hz), 6.76 (d, 1H, J=7.2 Hz), 6.85 (d, 1H, J=8.1 Hz), 7.14 (m, 3H), 7.37 and 7.58 (dd and d, 1H together, J=7.2, 1.9 and 7.7 Hz), 7.40 (dd, 1H, J=8.5, 1.5 Hz), 7.67 (d, 1H, J=8.1 Hz), 8.39 and 8.42 (2 s, 1H together), 9.43 and 9.45 (2s, 1H together), 12.81 and 12.96 (2 s, 1H together), 13.65 and 13.70 (2 s, 1H together). Anal. (C$_{224}$H$_{18}$N$_4$O$_2$.1.0 CH$_3$OH) C, H, N.

EXAMPLE 24

7-[3-((E)Styryl)-1H-indazol-5-yl]-isoquinoline

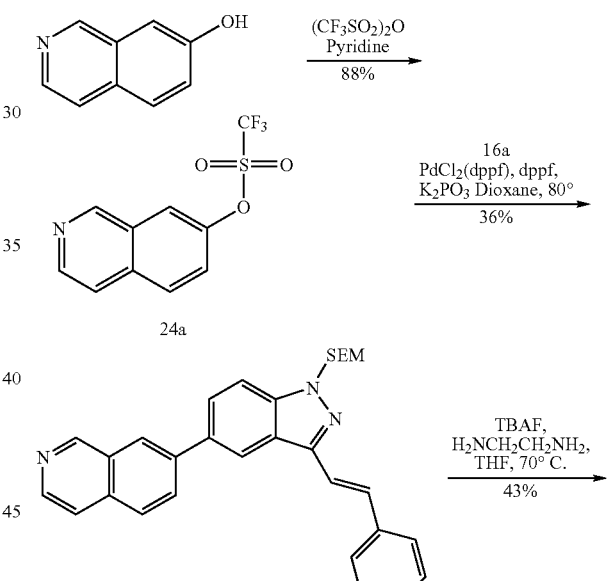

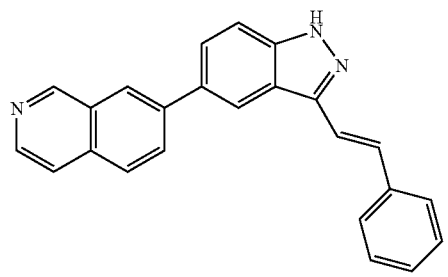

24

(a) Intermediate 24a—1,1,1-Trifluoro-methanesulfonic acid isoquinolin-7-yl ester Trifluoromethanesulfonic anhydride (4.54 g, 16.10 mmol) was added dropwise to a chilled (0° C.) mixture of 7-hydroxyisoquinoline (1.9477 g, 13.24 mmol, Lancaster Chemicals) in pyridine (14 mL). Stirring was continued at 0° C. for 1 hour, then at room temperature for 24 hours. The solution was partitioned between dichloromethane and saturated aqueous sodium bicarbonate solution. The organic layer was dried over magnesium sulfate, filtered, concentrated, and purified by silica gel chromatography (50% ethyl acetate in hexanes) to give triflate 24a (3.27 g, 88%) as a pale yellow oil: $R_f$=0.23 (50% ethyl acetate/hexanes); $^1$H NMR (DMSO-$d_6$) δ 7.72 (dd, 1H, J=9.0, 2.5 Hz), 7.80 (d, 1H, J=5.8 Hz), 8.06 (d, 1H, J=9.0 Hz), 8.23 (d, 1H, J=2.5 Hz), 8.55 (d, 1H, J=5.7 Hz), 9.39 (s, 1H). $^{13}$C NMR (DMSO-$d_6$) δ118.33 (q, J=320 Hz), 119.35, 119.99, 124.17, 128.03, 129.9, 134.31, 144.09, 147.02, 152.46. Anal. ($C_{10}H_6F_3NO_3S$·0.1$H_2O$) C, H, N, S.

(b) Intermediate 24b—7-[3-((E)-Styryl)-1-(2-trimethylsilanyl-ethoxymethyl)-1H-indazol-5-yl]-isoquinoline Isoquinoline triflate 24a (150 mg, 0.540 mmol) was added to a degassed solution of boronic ester 16a (282.9 mg, 0.594 mmol), powdered potassium phosphate (344 mg, 1.62 mmol), 1,1'-bis(diphenylphosphino)ferrocene dichloropalladium(II) (13 mg, 0.016 mmol), and 1,1'-bis(diphenylphosphino)ferrocene (9 mg, 0.016 mmol) in 1,4-dioxane (10 mL). The mixture was heated in an 80° C. oilbath for 6 hours, then cooled and partitioned between ethyl acetate (50 mL) and saturated aqueous sodium chloride solution (25 mL). The organic layer was dried over magnesium sulfate, filtered, and concentrated. Purification by silica gel chromatography (10 to 75% ethyl acetate in hexanes) afforded 24b (92.7 mg, 36%) as a fluorescent pink gel: $R_f$=0.06 (20% ethyl acetate/hexanes); $^1$H NMR (CDCl$_3$) δ –0.04 (s, 9H), 0.94 (t, 2H, J=8.4 Hz), 3.64 (t, 2H, J=8.1 Hz), 5.79 (s, 2H), 7.30–8.09 (m, 14H), 8.26 (d, 2H, J=12.9 Hz).

(c) Example 24—7-[3-((E)-Styryl)-1H-indazol-5-yl]-isoquinoline

Similar to example 3, treatment of intermediate 24b (86 mg, 0.18 mmol) with tetrabutylammonium fluoride afforded 24 (27.2 mg, 43%) as a white solid: $R_f$=0.11 (70% ethyl acetate in hexanes); $^1$H NMR (DMSO-$d_6$) δ 7.29 (t, 1H, J=7.2 Hz), 7.41 (t, 2H, J=7.2 Hz), 7.66 (m, 5H), 7.88 (t, 2H, J=5.7 Hz), 8.09 (d, 1H, J=8.7 Hz), 8.29 (dd, 1H, J=8.4, 1.8 Hz), 8.51 (m, 3H), 9.41 (s, 1H), 13.28 (s, 1H). Anal. ($C_{24}H_{17}N_3$·0.6$CH_2OH$) C, H, N.

EXAMPLE 25

4-[3-(1H-Benzoimidazol-2-yl)-1H-indazol-5-yl]-isoquinoline

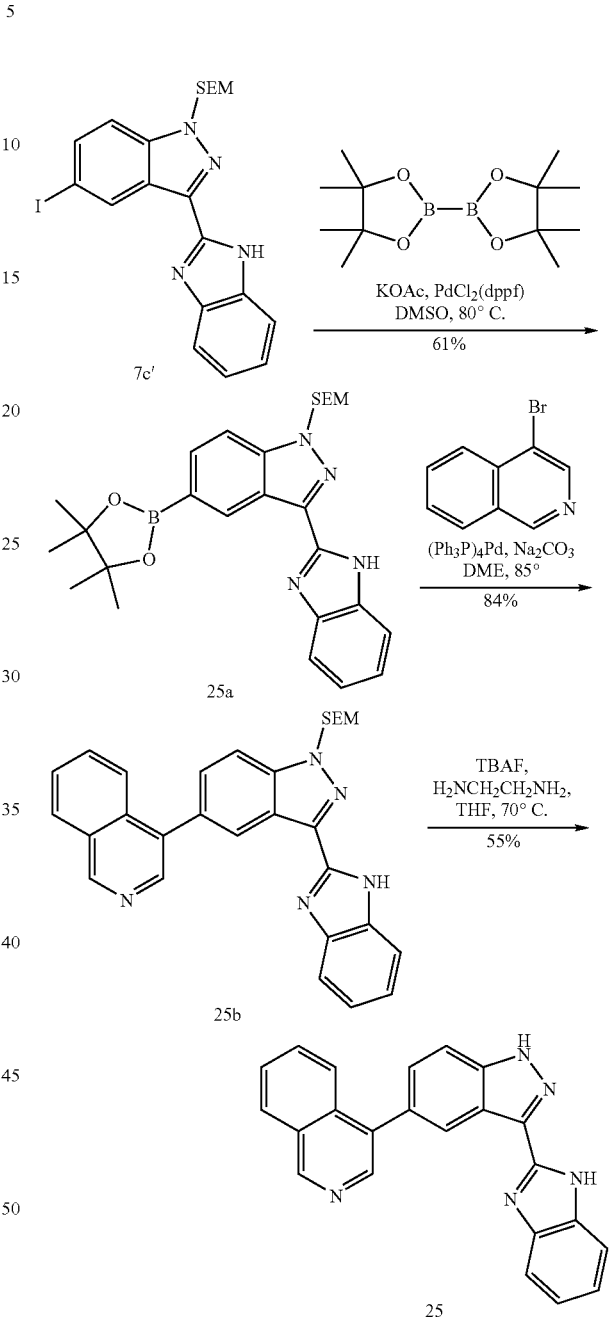

(a) Intermediate 25a—3-(1H-Benzoimidazol-2-yl)-5-(4,4,5,5-tetramethyl-[1,3,2]-dioxaborolan-2-yl)-1-(2-trimethylsilanyl-ethoxymethyl)-1H-indazole By a procedure analogous to boronic ester 19e synthesis, iodide 7c' (2.36 g, 4.81 mmol) was converted to boronic ester 25a (1.43g, 61%), a white, crystalline solid: $^1$H NMR (DMSO-$d_6$) δ –0.13 (s, 9H), 0.82 (t, 2H, J=7.7 Hz), 1.35 (s, 12H), 3.59 (t, 2H, J=7.9 Hz), 5.89 (s, 2H), 7.24 (m, 2H), 7.53 (m, 1H), 7.83 (m, 3H), 8.95 (s, 1H), 13.15 (s, 1H). Anal. ($C_{26}H_{35}BN_4O_3Si$) C, H, N.

(b) Intermediate 25b—4-[3-(1H-Benzoimidazol-2-yl)-1-(2-trimethylsilanyl-ethoxymethyl)-1H-indazol-5-yl]-isoquinoline By a procedure analogous to 19f synthesis, 4-bromoisoquinoline (238 mg, 1.14 mmol) was coupled with boronic ester 25a (280.4 mg, 0.572 mmol) to give 25b (237.5 mg, 84%) as a white solid: $R_f$=0.20 (50% ethyl acetate in hexanes); $^1$H NMR (DMSO-$d_6$) δ −0.07 (s, 9H), 0.86 (m, 2H), 3.67 (t, 2H, J=7.9 Hz), 5.98 (s, 2H), 7.20 (br m, 2H), 7.55 (br m, 1H), 7.65 (br m, 1H), 7.71 (m, 4H), 8.07 (d, 1H, J=8.7 Hz), 8.27 (dd, 1H, J=7.2, 1.7 Hz), 8.56 (s, 1H), 8.66 (d, 1H, J=0.8 Hz), 9.41 (s, 1H), 13.17 (s, 1H).

(c) Example 25—4-[3-(1H-Benzoimidazol-2-yl)-1H-indazol-5-yl]-isoquinoline 25 was prepared similar to example 3. Intermediate 25b (152.4 mg, 0.310 mmol) was treated with tetrabutylammonium fluoride to give 25 (61.9 mg, 55%) as a white foam: $R_f$=0.16 (70% ethyl acetate in hexanes); $^1$H NMR (DMSO-$d_6$) δ 7.18 (br m, 2H), 7.56 (br m, 2H), 7.63 (dd, 1H, J=8.5, 1.7 Hz), 7.81 (m, 4H), 8.27 (dd, 1H, J=7.4, 1.2 Hz), 8.55 (s, 1H), 8.62 (s, 1H), 9.40 (s, 1H), 13.05 (br s, 1H), 13.84 (s, 1H).

EXAMPLE 26

3-[3-(1H-Benzoimidazol-2-yl)-1H-indazol-5-yl]-6-(3-hydroxy-propyl)-2-methyl-phenol

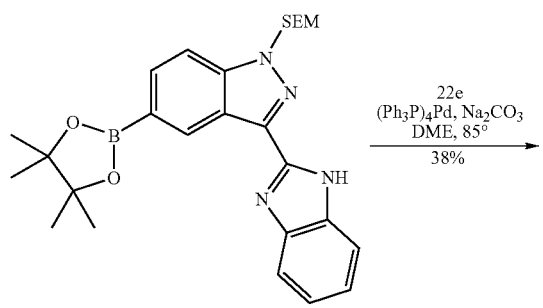

25a

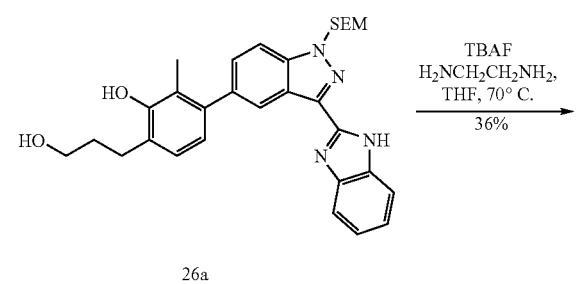

26a

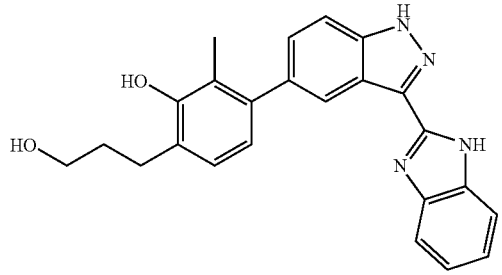

26

(a) Intermediate 26a—3-[3-(1H-Benzoimidazol-2-yl)-1-(2-trimethylsilanyl-ethoxymethyl)-1H-indazol-5-yl]-6-(3-hydroxy-propyl)-2-methyl-phenol By a procedure analogous to the synthesis of 25b, boronic ester 25a (303 mg, 0.618 mmol) was coupled with iodide 22e (180.5 mg, 0.618 mmol), affording 26a (124.4 mg, 38%) as a white solid: $R_f$=0.30 (50% ethyl acetate in hexanes); $^1$H NMR (DMSO-$d_6$) δ −0.11 (s, 9H), 0.85 (t, 2H, J=7.9 Hz), 1.74 (quint, 2H, J=7.0 Hz), 2.08 (s, 3H), 2.66 (t, 2H, J=7.7 Hz), 3.47 (q, 2H, J=5.3 Hz), 3.63 (t, 2H, J=7.9 Hz), 4.60 (t, 1H, J=5.0 Hz), 5.91 (s, 2H), 6.75 (d, 1H, J=7.7 Hz), 7.01 (d, 1H, J=7.7 Hz), 7.20 (quint, 2H, J=8.1 Hz), 7.49 (m, 2H), 7.71 (d, 1H J=7.7 Hz), 7.88 (d, 1H, J=8.7 Hz), 8.33 (s, 1H), 8.42 (s, 1H), 13.11 (s, 1H). Anal. ($C_{30}H_{36}N_4O_3Si$·0.6 ethyl acetate) C, H, N.

(b) Example 26—3-[3-(1H-Benzoimidazol-2-yl)-1H-indazol-5-yl]-6-(3-hydroxy-propyl)-2-methyl-phenol By a procedure analogous to example 3, deprotection of 26a (99.4 mg, 0.188 mmol) with tetrabutylammonium fluoride afforded 26 (26.9 mg, 36%) as a white solid: $R_f$=0.19 (70% ethyl acetate in hexanes); $^1$H NMR (DMSO-$d_6$) δ 1.74 (quint, 2H, J=7.4 Hz), 2.08 (s, 3H), 2.66 (t, 2H, J=7.4 Hz), 3.47 (q, 2H, J=5.1 Hz), 4.59 (t, 1H, J=5.1 Hz), 6.74 (d, 1H, J=7.7 Hz), 7.00 (d, 1H, J=7.7 Hz), 7.19 (quint, 2H, J=7.9 Hz), 7.38 (dd, 1H J=8.5, 1.5 Hz), 7.50 (d, 1H, J=7.4 Hz), 7.67 (m, 2H), 8.30 (s, 1H), 8.37 (s, 1H), 12.96 (s, 1H), 13.66 (s, 1H). Anal. ($C_{24}H_{22}N_4O_2$·0.4 ethyl acetate) C, H, N.

EXAMPLE 27

1-[3-((E)Styryl)-1H-indazol-5-yl]-piperidin-4-ol

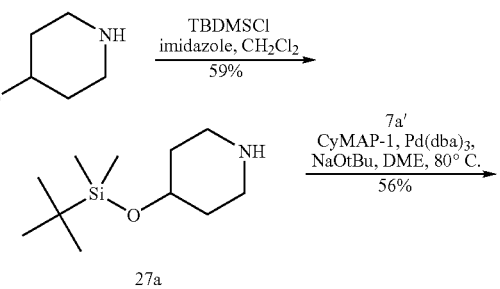

27a

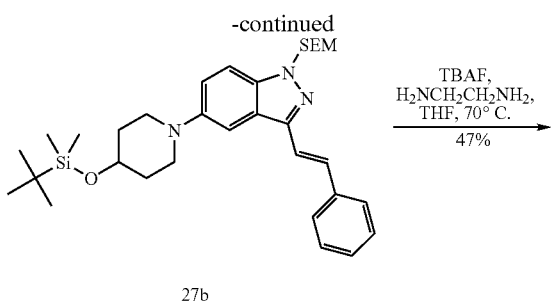

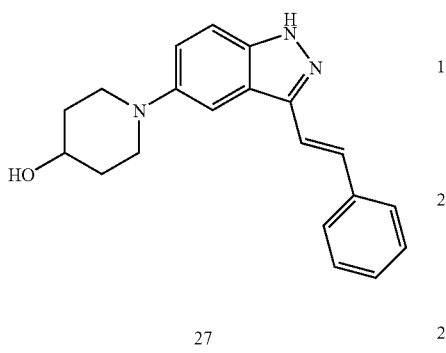

27

(a) Intermediate 27a—4-(tert-Butyl-dimethyl-silanyloxy)-piperidine

Imidazole (4.18 g, 61.4 mmol), 4-hydroxypiperidine (2.07 g, 20.46 mmol), and tert-butyldimethylsilyl chloride (4.63 g, 30.7 mmol) were dissolved in dichloromethane (50 mL) and stirred at 23° C. for 4 hours. The mixture was then washed with saturated aqueous sodium bicarbonate solution (3×50 mL) and water (50 mL), dried over magnesium sulfate, filtered, and concentrated under high vacuum to give 27a (2.60 g, 59%) as a yellow oil which crystallizes on standing.: $^1$H NMR (CDCl$_3$) δ 0.05 (s, 6H), 0.90 (s, 9H), 1.46 (m, 2H), 1.81 (m, 2H), 2.71 (m, 2H), 3.09 (m, 3H), 3.77 (septet, 1H, J=3.9 Hz),. Anal. ($C_{11}H_{25}NOSi.0.2CH_2Cl_2$) C, H, N.

(b) Intermediate 27b—5-{4-[(Dimethyl-ethyl)-dimethyl-silanyloxy]-piperidin-1-yl}-3-((E)-styryl)-1-(2-trimethylsilanyl-ethoxymethyl)-1H-indazole Sodium tert-butoxide (163 mg, 1.70 mmol), tris(dibenzylideneacetone)-dipalladium(0) (26 mg, 0.03 mmol), and CyMAP-1 (See Old et. al., *J. Am. Chem. Soc.*, 120, 9722 (1998) for the structure of this ligand) (33 mg, 0.085 mmol) were added to a degassed solution of 27a (241.1 mg, 1.12 mmol) and iodide 7a' (269.3 mg, 0.565 mmol), in ethylene glycol dimethyl ether (DME, 2.0 mL). The mixture was heated in an 80° C. oilbath for 17 hours. After cooling to room temperature, the mixture was diluted with ethyl acetate (50 mL) and filtered to remove the black precipitate. The filtrate was washed with water (10 mL) and saturated aqueous sodium chloride (10 mL), dried over magnesium sulfate, filtered, concentrated, and purified by silica gel chromatography (10 to 50% ethyl acetate in hexanes) to give 27b (177.7 mg, 56%) as an orange oil: R$_f$=0.28 (20% ethyl acetate in hexanes); $^1$H NMR (CDCl$_3$) δ –0.06 (s, 9H), 0.09 (s, 6H), 0.90 (m, 2H), 0.92 (s, 9H), 1.80 (m, 2H), 1.97 (m, 2H), 3.07 (m, 2H), 3.44 (m, 2H), 3.58 (t, 2H, J=8.4 Hz), 3.92 (m, 1H), 5.69 (s, 2H), 7.29 (m, 2H), 7.41 (m, 6H), 7.61 (d, 2H, J=8.7 Hz).

(c) Example 27—1-[3-((E)-Styryl)-1H-indazol-5-yl]-piperidin-4-ol

By a procedure analogous to example 3, treatment of intermediate 27b (121.4 mg, 0.22 mmol) with tetrabutylammonium fluoride afforded 27 (33.1 mg, 47%) as a yellow foam: R$_f$=0.15 (70% ethyl acetate/hexanes); $^1$H NMR (DMSO-d$_6$) δ 1.55 (m, 2H), 1.86 (m, 2H), 2.83 (m, 2H), 3.47 (m, 2H), 3.61 (m, 1H), 4.68 (d, 1H, J=4.2 Hz), 7.22 (m, 2H), 7.37 (m, 5H), 7.55 (d, 1H, J=16.5 Hz), 7.69 (d, 2H, J=7.2 Hz), 12.89 (s, 1H). Anal. ($C_{20}H_{21}N_3O.0.4H_2O.0.4$ ethyl acetate) C, H, N.

EXAMPLE 28

1-[3-((E)Styryl)-1H-indazol-5-yl]-piperidin-3-ol

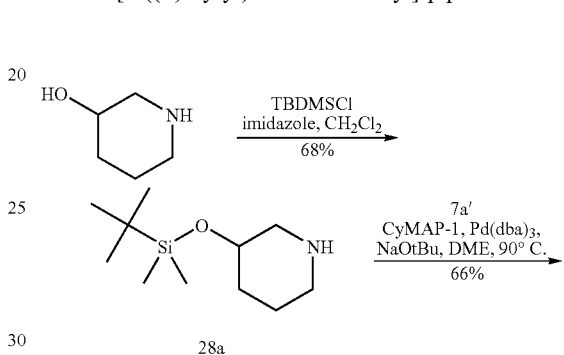

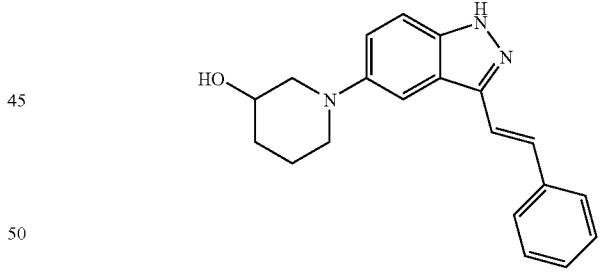

28

(a) Intermediate 28a—3-(tert-Butyl-dimethyl-silanyloxy)-piperidine

By a procedure analogous to the synthesis of 27a, 3-hydroxypiperidine hydrochloride (2.76 g, 20.06 mmol) was converted to 28a (2.92 g, 68%), a yellow oil which crystallizes on standing.: $^1$H NMR (CDCl$_3$) δ 0.05 (s, 6H), 0.89 (s, 9H), 1.46 (m, 2H), 1.77 (m, 2H), 2.39 (br s, 1H), 2.61 (m, 2H), 2.82 (m, 1H), 2.97 (dd, 1H, J=12.3, 2.7 Hz), 3.66 (septet, 1H, J=3.6 Hz). Anal. ($C_{11}H_{25}NOSi.0.2$ CH$_2$Cl$_2$) C, H, N.

(b) Intermediate 28b—5-{3-[(Dimethyl-ethyl)-dimethyl-silanyloxy]-piperidin-1-yl}-3-((E)-styryl)-1-(2-trimethylsilanyl-ethoxymethyl)-1H-indazole 28b was prepared by a procedure analogous to 27b synthesis. Intermediates 7a' (269.3 mg, 0.565 mmol) and 28a (244 mg, 1.13 mmol) were used to form 28b (212.0 mg, 66%) as a brown oil: $R_f$=0.17 (10% ethyl acetate in hexanes); $^1$H NMR (CDCl$_3$) δ −0.05 (s, 9H), 0.09 (s, 6H), 0.92 (m, 2H), 0.96 (s, 9H), 1.44 (m, 1H), 1.65–2.05 (m, 3H), 2.69 (m, 2H), 3.56 (m, 4H), 3.92 (m, 1H), 5.70 (s, 2H), 7.25 (m, 2H), 7.40 (m, 6H), 7.60 (d, 2H, J=8.4 Hz). Anal. (C$_{32}$H$_{49}$N$_3$O$_2$Si$_2$.0.6H$_2$O) C, H, N.

(c) Example 28—1-[3-((E)-Styryl)-1H-indazol-5-yl]-piperidin-3-ol

By a procedure analogous to example 3, treatment of intermediate 28b (181.5 mg, 0.322 mmol) with tetrabutylammonium fluoride afforded 28 (47.6 mg, 46%) as a yellow foam: $R_f$=0.19 (70% ethyl acetate/hexanes); $^1$H NMR (DMSO-d$_6$) δ 1.34 (m, 1H), 1.70 (m, 1H), 1.95 (m, 2H), 2.55 (m, 1H), 2.72 (m 1H), 3.46 (m, 1H), 3.63 (m, 1H), 3.74 (m, 1H), 4.88 (d, 1H, J=4.5 Hz), 7.24 (dd, 1H, J=9.0, 1.8 Hz), 7.33 (t, 1H, J=7.2 Hz), 7.42 (m, 5H), 7.63 (d, 1H, J=16.5 Hz), 7.76 (d, 2H, J=7.2 Hz), 12.97 (s, 1H). Anal. (C$_{20}$H$_{21}$N$_3$O.0.3H$_2$O) C, H, N.

EXAMPLE 29

[2-(5-Isoquinolin-4-yl-1H-indazol-3-yl)-1H-benzoimidazol-4-yl]-methanol

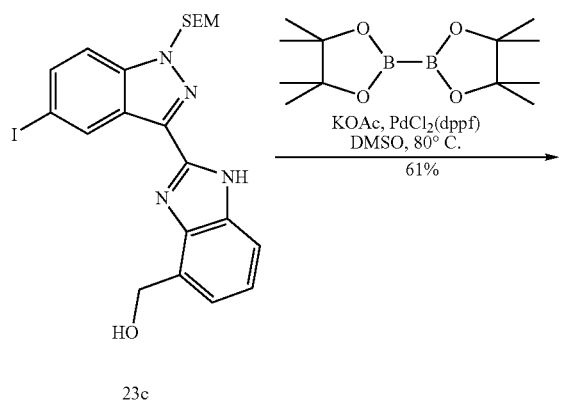

23c

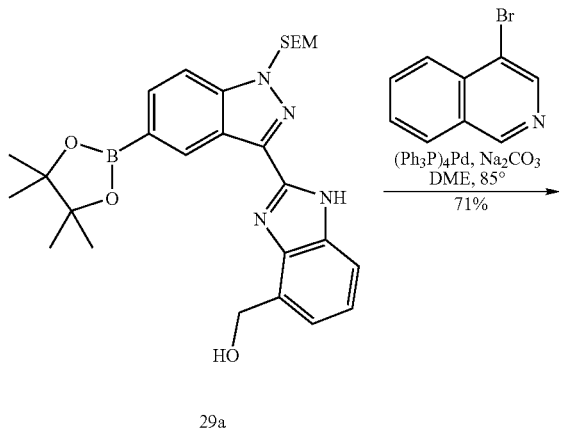

29a

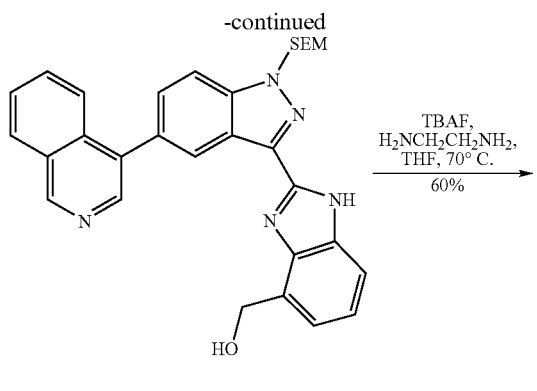

29b

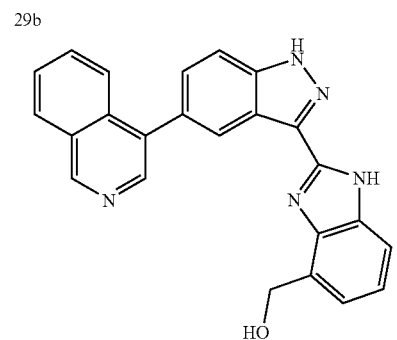

29

(a) Intermediate 29a—{2-[5-(4,4,5,5-Tetramethyl-[1,3,2]dioxaborolan-2-yl)-1-(2-trimethylsilanyl-ethoxymethyl)-1H-indazol-3-yl]-1H-benzoimidazol-4-yl}-methanol By a procedure similar to the synthesis of boronic ester 19e, iodide 23c (512.8 mg, 0.985 mmol) was converted to boronic ester 29a (312.0 mg, 61%), a white foam: $R_f$=0.28 (5% methanol in dichloromethane); $^1$H NMR (DMSO-d$_6$) [Some peaks are doubled due to tautomeric isomerization] δ −0.13 (s, 9H), 0.83 (t, 2H, J=7.7 Hz), 1.35 (s, 12H), 3.60 (t, 2H, J=8.1 Hz), 4.87 (br s, 1H), 5.06 (br s, 1H), 5.24 (m, 1H), 5.90 (s, 2H), 7.26 (m, 2H), 7.40 and 7.71 (2 d, 1H together, J=7.2 and 7.9 Hz), 7.82 (m, 2H), 8.95 (s, 1H), 12.93 and 13.10 (2 s, 1H together). Anal. (C$_{27}$H$_{37}$BN$_4$O$_4$Si.0.5H$_2$O) C, H, N.

(b) Intermediate 29b—{2-[5-Isoquinolin-4-yl-1-(2-trimethylsilanyl-ethoxy-methyl)-1H-indazol-3-yl]-1H-benzoimidazol-4-yl}-methanol By a procedure similar to the synthesis of 19f, 4-bromoisoquinoline (193 mg, 0.927 mmol) was coupled with boronic ester 29a (241.2 mg, 0.463 mmol) to give 29b (171.1 mg, 71%) as a white foam: $R_f$=0.22 (75% ethyl acetate in hexanes); $^1$H NMR (DMSO-d$_6$) [Some peaks are doubled due to tautomeric isomerization] δ-0.08 (s, 9H), 0.88 (t, 2H, J=7.7 Hz), 3.68 (t, 2H, J=7.9 Hz), 4.88 (d, 2H, J=5.3 Hz), 5.05 and 5.25 (2 br s, 1H together), 5.98 (s, 2H), 7.22 (m, 2H), 7.40 and 7.57 (2m, 1H together), 7.77 (m, 4H), 8.07 (d, 1H, J=8.5 Hz), 8.27 (dd, 1H, J=7.2, 1.5 Hz), 8.57 (s, 1H), 8.70 (br s, 1H), 9.41 (s, 1H), 12.97 and 13.14 (2s, 1H together). Anal. (C$_{30}$H$_{31}$N$_5$O$_2$Si.0.4H$_2$O) C, H, N.

(c) Example 29—[2-(5-Isoquinolin-4-yl-1H-indazol-3-yl)-1H-benzoimidazol-4-yl]-methanol 29 was prepared similar to example 3. Treatment of intermediate 29b (129.0 mg, 0.247 mmol) with tetrabutylammonium fluoride afforded 29 (58.3 mg, 60%) as a white powder: $^1$H NMR (DMSO-$d_6$) [Some peaks are doubled due to tautomeric isomerization] δ 4.88 (t, 2H, J=6.2 Hz), 5.03 and 5.23 (2 t, 1H together, J=5.6 and 6.2 Hz), 7.20 (m, 2H), 7.38 and 7.53 (m and d, 1H together, J=7.4 Hz for the doublet), 7.63 (dd, 1H, J=8.7, 1.3 Hz), 7.82 (m, 4H), 8.27 (d, 1H, J=7.4 Hz), 8.55 (s, 1H), 8.63 and 8.66 (2 s, 1H together), 9.40 (s, 1H), 12.87 and 13.02 (2 s, 1H together), 13.81 and 13.86 (2 s, 1H together). Anal. ($C_{24}H_{17}N_5O·0.4$ $H_2O·0.3$ $CH_2Cl_2$) C, H, N.

EXAMPLE 30

2-[2-(5-Isoquinolin-4-yl-1H-indazol-3-yl)-1H-benzoimidazol-4-yl-ethanol

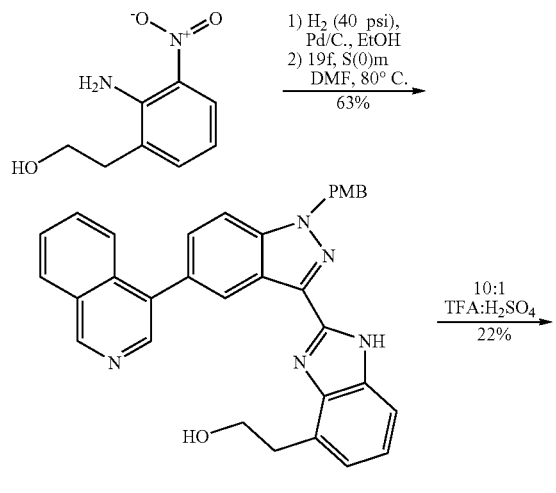

30a

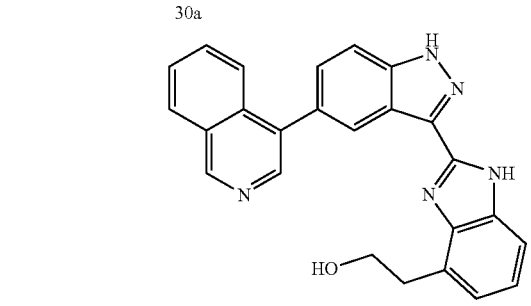

30

(a) Intermediate 30a—2-{2-[5-Isoquinolin-4-yl-1-(4methoxy-benzyl)-1H-indazol-3-yl]-1H-benzoimidazol-4-yl}-ethanol A suspension of 10% palladium on carbon (66 mg) and 2-(2-amino-3-nitrophenyl)ethanol [See Seno, Kaoru; Hagishita, Sanji; Sato, Tomohiro; Kuriyama, Kaoru; *J. Chem. Soc. Perkin Trans. 1*; 2012 (1984) for the synthesis of this reagent] (531.5 mg, 2.92 mmol) in absolute ethanol (50 mL) was shaken under 40 psi hydrogen for 3 hours. After filtration and concentration, crude 2-(2,3-diaminophenyl)ethanol (474.4 mg) was obtained as a red oil, which crystallized on standing: $R_f$=0.08 (75% ethyl acetate in hexanes); $^1$H NMR (DMSO-$d_6$) δ 2.58 (t, 2H, J=6.9 Hz), 3.53 (t, 2H, J=7.2 Hz), 4.32 (br s, 5H), 6.29 (m, 2H), 6.40 (dd, 1H, J=6.9, 2.1 Hz).

Without further purification, this crude diamine was condensed with aldehyde 19f (1.10 g, 2.81 mmol) in the presence of sulfur, similar to the synthesis of intermediate 7c', affording 30a (930.8 mg, 63%) as a yellow foam: $R_f$=0.19 (ethyl acetate); $^1$H NMR (DMSO-$d_6$) [Some peaks are doubled due to tautomeric isomerization] δ 3.10 (m, 2H), 3.71 (s, 3H), 3.74 (m, 2H), 4.66 and 4.80 (2 br s, 1H together), 5.82 (s, 2H), 6.93 (d, 2H, J=8.7 Hz), 7.05 (m, 2H), 7.39 (m, 3H), 7.65 (d, 1H, J=9.2 Hz), 7.81 (m, 3H), 8.00 (m, 1H), 8.26 (dd, 1H, J=7.2, 2.1 Hz), 8.54 (s, 1H), 8.65 (s, 1H), 9.39 (s, 1H), 12.96 and 13.02 (2 s, 1H together).

(b) Example 30—2-[2-(5-Isoquinolin-4-yl-1H-indazol-3-yl)-1H-benzoimidazol-4-yl]-ethanol Intermediate 30a (169.1 mg, 0.322 mmol) was deprotected by a synthetic method analogous to example 19, affording 30 (28.2 mg, 22%) as a white powder: $R_f$=0.33 (ethyl acetate); $^1$H NMR (DMSO-$d_6$) [Some peaks are doubled due to tautomeric isomerization] δ 3.11 (m, 2H), 3.73 (m, 2H), 4.68 and 4.85 (2 t, 1H together, J=5.2 and 5.5 Hz), 7.04 (m, 2H), 7.35 and 7.47 (2 d, 1H together, J=7.9 and 7.2 Hz), 7.63 (d, 1H, J=8.7 Hz), 7.83 (m, 4H), 8.26 (d, 1H, J=7.5), 8.55 (s, 1H), 8.63 (s, 1H), 9.39 (s, 1H), 12.97 and 13.01 (2 s, 1H together), 13.86 and 13.87 (2 s, 1H together). Anal. ($C_{25}H_{19}N_5O·0.3H_2O·0.4$ ethyl acetate·0.06 S)C, H, N.

EXAMPLE 31

[2-(5-Isoquinolin-4-yl-1H-indazol-3-yl)-1H-benzoimidazol-4-ylmethyl]-dimethyl-amine

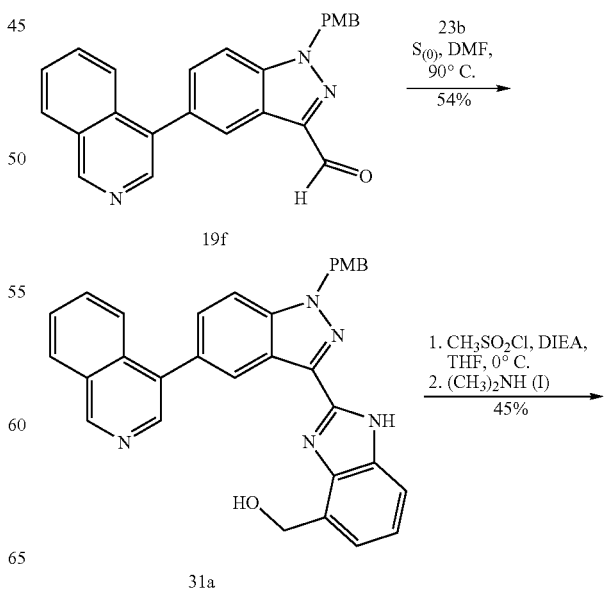

31a

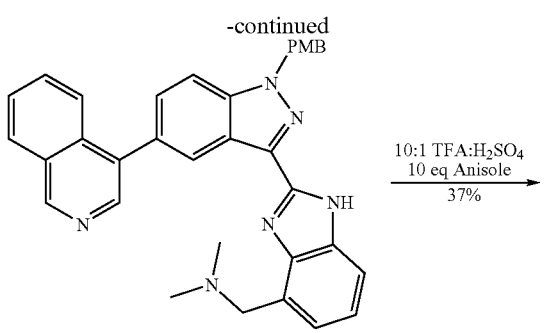

31b

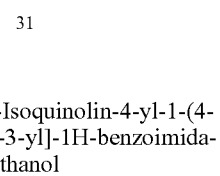

31

(a) Intermediate 31a—{2-[5-Isoquinolin-4-yl-1-(4-methoxy-benzyl)-1H-indazol-3-yl]-1H-benzoimidazol-4-yl}-methanol By a synthesis similar to the synthesis of 19h, aldehyde 19f (3.67 g, 9.33 mmol) and diamine 23b (1.29 g, 9.33 mmol) were condensed in the presence of sulfur to give 31a (2.60 g, 54%) as a yellow solid: $R_f$=0.19 (75% ethyl acetate in hexanes); $^1$H NMR (DMSO-d$_6$) [Some peaks are doubled due to tautomeric isomerization] δ 3.71 (s, 3H), 4.88 (d, 2H, J=5.5 Hz), 5.04 and 5.25 (2 t, 1H together, J=5.6 and 6.1 Hz), 5.81 and 5.83 (2 s, 2H together), 6.93 (d, 2H, J=8.5 Hz), 7.21 (m, 2H), 7.38 and 7.54 (2 d, 3H together, J=7.4 and 7.5 Hz), 7.66 (d, 1H, J=8.7 Hz), 7.77 (m, 3H), 8.01 (dd, 1H, J=8.7, 4.0 Hz), 8.26 (d, 1H, J=7.7 Hz), 8.54 and 8.55(2 s, 1H together), 8.65 and 8.68 (2 s, 1H together), 9.39 (s, 1H), 12.88 and 13.05 (2 s, 1H together). Anal. (C$_{32}$H$_{25}$N$_5$O$_2$.0.3H$_2$O) C, H, N.

(b) Intermediate 31b—(2-[5-Isoquinolin-4-yl-1-(4methoxy-benzyl)-1H-indazol-3-yl]-1H-benzoimidazol-4-ylmethyl}-dimethyl-amine Methane sulfonyl chloride (119.3 mg, 1.04 mmol) was added dropwise to a solution of 31a (527.5 mg, 1.03 mmol) and diisopropylethyl amine (153.3 mg, 1.19 mmol) in tetrahydrofuran (12.0 mL), cooled to 0° C. in an icebath. After stirring at 0° C. for 2.5 hours, the reaction flask was fitted with a dry ice-cooled cold finger condenser, and dimethyl amine gas was condensed into the reaction solution until the volume had increased by about 5 mL. Stirring was continued at 0° C. for 4 hours, then at room temperature for 15 hours. The mixture was partitioned between ethyl acetate (100 mL) and saturated aqueous sodium bicarbonate solution (20 mL). The organic extracts were dried over magnesium sulfate, filtered, concentrated, and columned (silica gel, 5 to 10% methanol in dichloromethane), affording 31 b (250.2 mg, 45%) as a pale yellow solid: $R_f$=0.26 (10% methanol in dichloromethane); $^1$H NMR (DMSO-d$_6$) δ 2.20 (s, 6H), 3.71 (s, 3H), 3.84 (s, 2H), 5.83 (s, 2H), 6.93 (d, 2H, J=8.7 Hz), 7.14 (m, 2H), 7.36 (d, 2H, J=8.5 Hz), 7.48 (m, 1H), 7.67 (d, 1H, J=8.9 Hz), 7.77 (quintet, 2H, J=6.4 Hz), 7.89 (m, 1H), 8.00 (d, 1H, J=8.9 Hz), 8.26 (d, 1H, J=7.5 Hz), 8.55 (s, 1H), 8.71 (s, 1H), 9.39 (s, 1H), 13.03 (brs, 1H). Anal. (C$_{34}$H$_{30}$N$_6$O.1.1H$_2$O) C, H, N.

(c) Example 31—[2-(5-Isoquinolin-4-yl-1H-indazol-3-yl)-1H-benzoimidazol-4-ylmethyl]-dimethyl-amine A mixture of 31b (125.7 mg, 0.233 mmol), anisole (252 mg, 2.33 mmol), trifluoroacetic acid (2.3 mL), and concentrated sulfuric acid (0.2 mL) was stirred at room temperature for 66 hours, then added dropwise to a rapidly stirred mixture of saturated aqueous sodium bicarbonate (75 mL) and ethyl acetate (25 mL). The layers were separated and the aqueous layer extracted with ethyl acetate (2×50 mL). The combined organic layers were dried over magnesium sulfate, filtered, concentrated, and purified by silica gel chromatography (25 to 40% methanol in dichloromethane) to give 31 (35.8 mg, 37%) as a white powder: $R_f$=0.09 (10% methanol in dichloromethane); $^1$H NMR (DMSO-d$_6$) [Some peaks are doubled due to tautomeric isomerization] δ 2.15 and 2.21 (2 br s, 6H together), 3.80 (s, 2H), 7.12 (br s, 2H), 7.40 and 7.54 (2 m, 1H together), 7.64 (d, 1H, J=9.0 Hz), 7.83 (m, 4H), 8.26 (d, 1H, J=7.5 Hz), 8.55 (s, 1H), 8.63 and 8.73 (2 br s, 1H together), 9.39 (s, 1H), 13.02 (br s, 1H), 13.83 (br s, 1H). Anal. (C$_{26}$H$_{22}$N$_6$.0.7H$_2$O.1.0CH$_3$OH) C, H, N.

EXAMPLE 32

[2-(5-Isoquinolin-4-yl-1H-indazol-3-yl)-1H-benzoimidazol-4-yl-methyl]-methyl-amine

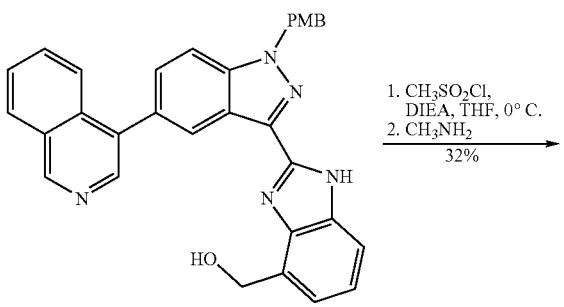

31a

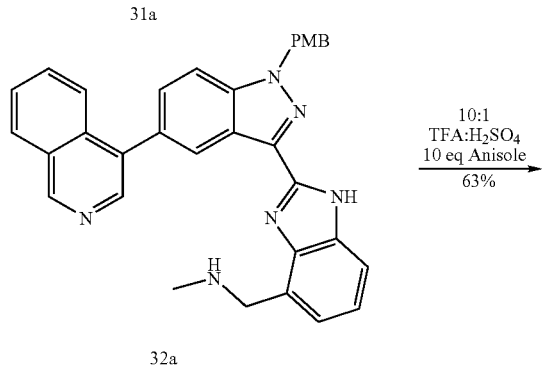

32a

-continued

32

(a) Intermediate 32a—{2-[5-Isoquinolin-4-yl-1-(4-methoxy-benzyl)-1H-indazol-3-yl]-1H-benzoimidazol-4-ylmethyl}-methyl-amine By a procedure similar to the synthesis of 31 b, alcohol 31a (516.6 mg, 1.01 mmol) was treated with methanesulfonyl chloride and diisopropylethyl amine at 0° C. for 1 hour. Instead of condensed gas, however, a solution of methylamine in tetrahydrofuran (2.0 M, 5.0 mL) was then added, and stirring continued at room temperature for 15 hours. Extractive workup and silica gel chromatography similar to 31 b afforded mono-methyl analog 32a (170.5 mg, 32%) as an off-white solid: $R_f$=0.16 (1:20:300 concentrated aqueous NH$_4$OH:ethanol:dichloromethane); $^1$H NMR (DMSO-d$_6$) δ 2.26 (s, 3H), 3.71 (s, 3H), 4.03 (s, 2H), 5.82 (s, 2H), 6.93 (d, 2H, J=8.7 Hz), 7.14 (d, 2H, J=4.7 Hz), 7.37 (d, 2H, J=8.7 Hz), 7.46 (m, 1H), 7.67 (dd, 1H, J=8.7, 1.3 Hz), 7.77 (m, 2H), 7.89 (d, 1H, J=7.7 Hz), 8.01 (d, 1H, J=8.5 Hz), 8.25 (dd, 1H, J=7.0, 1.8 Hz), 8.55 (s, 1H), 8.68 (s, 1H), 9.39 (s, 1H). Anal. (C$_{33}$H$_{28}$N$_6$0·0.6H$_2$O) C, H, N.

(b) Example 32—[2-(5-Isoquinolin-4-yl-1H-indazol-3-yl)-1H-benzoimidazol-4-ylmethyl]-methyl-amine Deprotection by a procedure similar to the synthesis of 31 afforded 32 (47.5 mg, 63%) as an off-white foam: $R_f$=0.29 (1:20:100 concentrated aqueous NH$_4$OH:ethanol:dichloromethane); $^1$H NMR (DMSO-d$_6$) δ 2.30 (s, 3H), 4.07 (s, 2H), 7.15 (d, 2H, J=4.5 Hz), 7.47 (m, 1H), 7.64 (dd, 1H, J=8.5, 1.5 Hz), 7.83 (m, 4H), 8.26 (d, 1H, J=7.2 Hz), 8.56 (s, 1H), 8.66 (s, 1H), 9.39 (s, 1H). Anal. (C$_{25}$H$_{20}$N$_6$·1.0EtOH·0.2 hexanes) C, H, N.

EXAMPLE 33

4-[3-(4Pyrrolidin-1-ylmethyl-1H-benzoimidazol-2-yl)-1H-indazol-5-yl]-isoquinoline

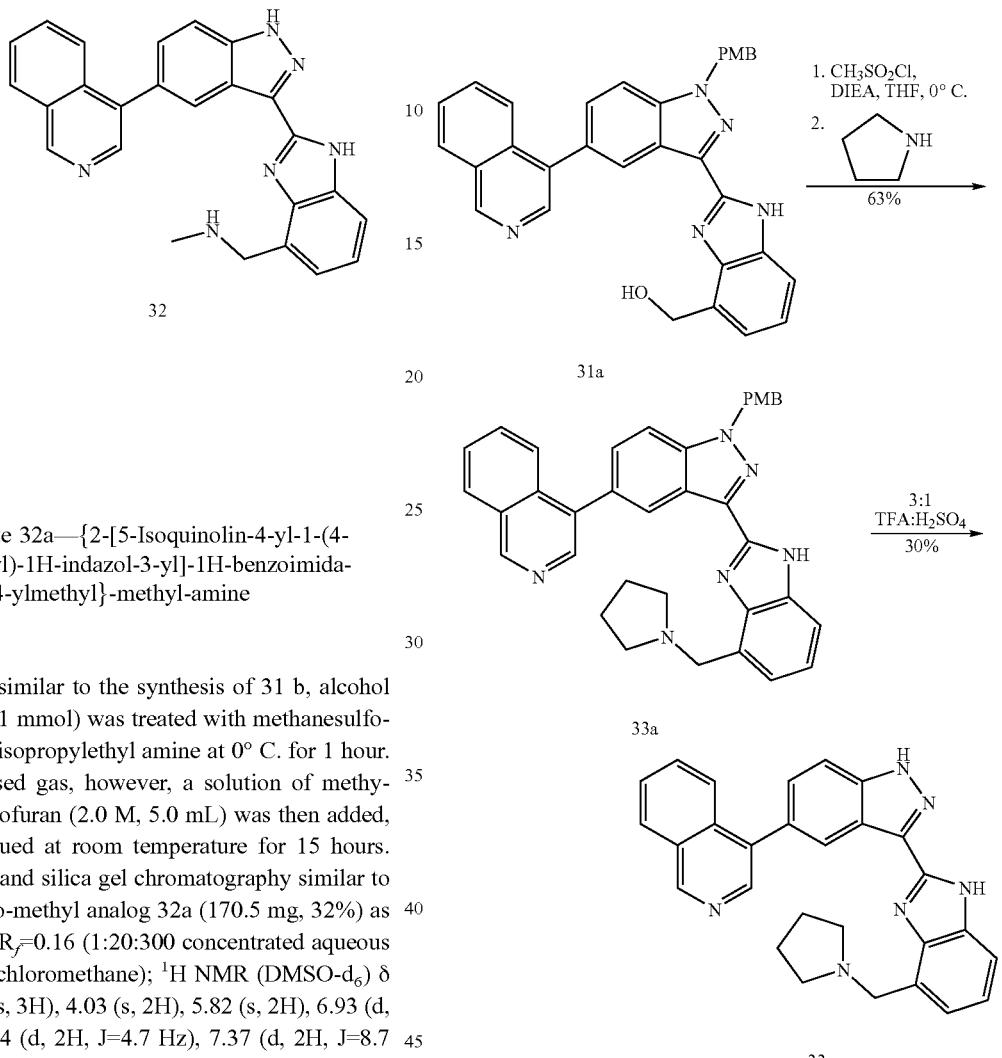

(a) Intermediate 33a—4-[i-(4-Methoxy-benzyl)-3-(4-pyrrolidin-1-ylmethyl-1i benzoimidazol-2-yl)-1H-indazol-5-yl]-isoquinoline By a synthetic method analogous to the synthesis of 31b, alcohol 31a (435.0 mg, 0.850 mmol) was treated with methanesulfonyl chloride and diisopropylethyl amine at 0° C. for 2 hours. Pyrrolidine (605 mg, 8.5 mmol) was added, and the mixture allowed to warm to room temperature over 20 hours. Extractive workup and silica gel chromatography similar to 31b afforded 33a (303.0 mg, 63%) as a yellow foam: $R_f$=0.13 (1:20:400 concentrated aqueous. NH$_4$OH:ethanol:dichloromethane); $^1$H NMR (DMSO-d$_6$) δ 1.61 (br s, 4H), 2.51 (br s, 4H), 3.71 (s, 3H), 3.97 (s, 2H), 5.83 (s, 2H), 6.93 (d, 2H, J=8.8 Hz), 7.14 (d, 2H, J=3.6 Hz), 7.36 (d, 2H, J=8.7 Hz), 7.45 (m, 1H), 7.67 (d, 1H, J=8.5 Hz), 7.76 (m, 2H), 7.89 (m, 1H), 8.00 (d, 1H, J=8.7 Hz), 8.25 (d, 1H, J=6.6 Hz), 8.54 (s, 1H), 8.70 (br s, 1H), 9.39 (s, 1H), 13.03 (br s, 1H). Anal. (C$_{36}$H$_{32}$N$_6$O·0.2CH$_2$Cl$_2$) C, H, N.

(b) Example 33—4-[3-(4-Pyrrolidin-1-ylmethyl-1H-benzoimidazol-2-yl)-1H-indazol-5-yl]-isoquinoline A solution of 33a (109.2 mg, 0.193 mmol) in 25% concentrated sulfuric acid/trifluoroacetic acid (2.0 mL) was stirred at room temperature for 21 hours, then added dropwise to a rapidly stirred mixture of tetrahydrofuran (25 mL), and saturated aqueous sodium carbonate (25 mL). Ethyl acetate (25 mL) and water (15 mL) were added, and the layers separated. The aqueous layer was extracted with ethyl acetate (3×50 mL), and the combined organic fractions dried over magnesium sulfate, filtered and concentrated. Purification by silica gel chromatography (1:20:100 concentrated aqueous NH$_4$OH:ethanol:dichloromethane) afforded 33 (25.4 mg, 30%) as a white powder: $^1$H NMR (CD$_3$OD) δ 1.77 (br s, 4H), 2.69 (br s, 4H), 4.12 (s, 2H), 7.24 (d, 2H, J=4.0 Hz), 7.80 (m, 5H), 8.06 (d, 1H, J=7.9 Hz), 8.23 (d, 1H, J=7.5 Hz), 8.53 (s, 1H), 8.69 (s, 1H), 9.29 (s, 1H). Anal. (C$_{28}$H$_{24}$N$_6$.0.9 MeOH) C, H, N.

EXAMPLE 34

4-{3-[4-(2-Pyrrolidin-1-yl-ethyl)-1H-benzoimidazol-2-yl]-1H-indazol-5-yl]-isoquinoline (a) Intermediate 34a—4{1-(4-Methoxy-benzyl)-3-[4-(2-pyrrolidin-1-yl-ethyl)-1H-benzoimidazol-2-yl]-1H-indazol-5-yl}-isoquinoline By a procedure similar to the synthesis of 33a, alcohol 30a (441.5 mg, 0.84 mmol) was converted into 34a (204.6 mg, 42%), an off-white foam: R$_f$=0.08 (1:20:400 concentrated aqueous NH$_4$OH:ethanol:dichloromethane); $^1$H NMR (DMSO-d$_6$) δ 1.38 (br s, 4H), 2.31 (br s, 4H), 2.79 (m, 2H), 3.07 (m, 2H), 3.71 (s, 3H), 5.81 (s, 2H), 6.93 (d, 2H, J=8.8 Hz), 6.98 (d, 1H, J=7.2 Hz), 7.08 (t, 1H, J=7.7 Hz), 7.36 (d, 2H, J=8.7 Hz), 7.39 (m, 1H), 7.66 (dd, 1H, J=8.5, 1.5 Hz), 7.76 (m, 2H), 7.89 (d, 1H, J=7.7 Hz), 8.01 (d, 1H, J=8.7 Hz), 8.25 (d, 1H, J=7.4 Hz), 8.53 (s, 1H), 8.75 (br s, 1H), 9.38 (s, 1H), 13.00 (br s, 1H). Anal. (C$_{37}$H$_{34}$N$_6$0.6H$_2$O) C, H, N.

(b) Example 34—4-{3-[4-(2-Pyrrolidin-1-yl-ethyl)-1H-benzoimidazol-2-yl]-1H-indazol-5-yl}-isoquinoline 34 was prepared similar to example 33. Treatment of 34a (66.2 mg, 0.114 mmol) with 3:1 trifluoroacetic acid/sulfuric acid yielded 34 (24.7 mg, 47%) as a white powder: R$_f$=0.38 (1:20:100 concentrated aqueous NH$_4$OH:ethanol:dichloromethane); $^1$H NMR (DMSO-d$_6$) δ1.37 (br m, 6H), 2.27 (br m, 2H), 2.80 (m, 2H), 3.07 (m, 2H), 6.98 (d, 1H, J=7.2 Hz), 7.09 (t, 1H, J=7.5 Hz), 7.36 (br s, 1H), 7.63 (dd, 1H, J=8.5, 1.5 Hz), 7.82 (m, 4H), 8.26 (d, 1H, J=7.4 Hz), 8.54 (s, 1H), 8.75 (br s, 1H), 9.39 (s, 1H), 12.98 (br s, 1H), 13.79 (s, 1H). Anal. (C$_{29}$H$_{26}$N$_6$.0.7 EtOH) C, H, N.

EXAMPLE 35

3-{[2-(5-Isoquinolin-4-yl-1H-indazol-3-yl)-1H-benzoimidazol-4-ylmethyl]-amino}-2-methyl-propan-1-ol

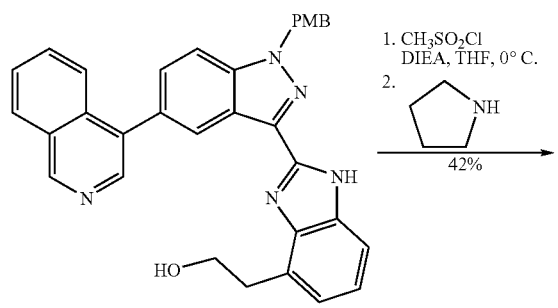

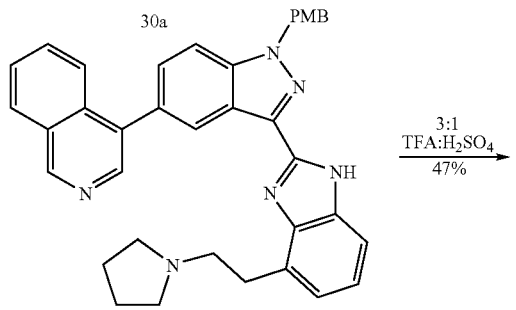

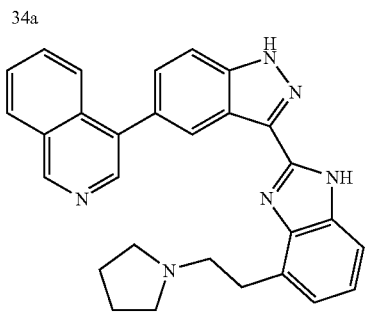

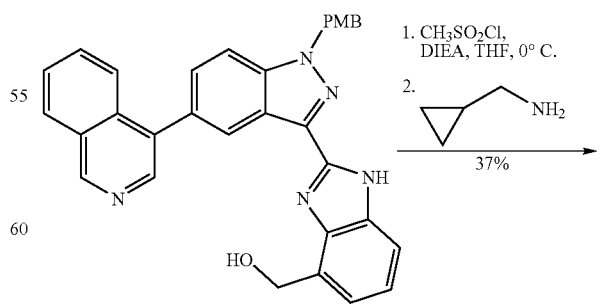

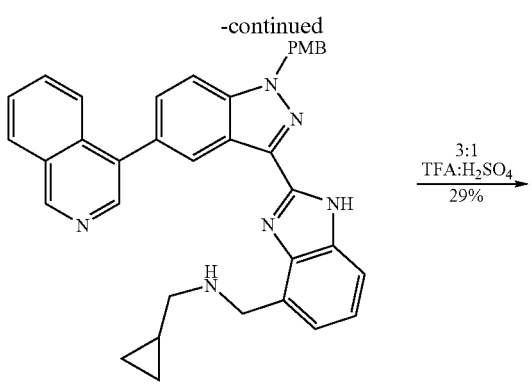

35a

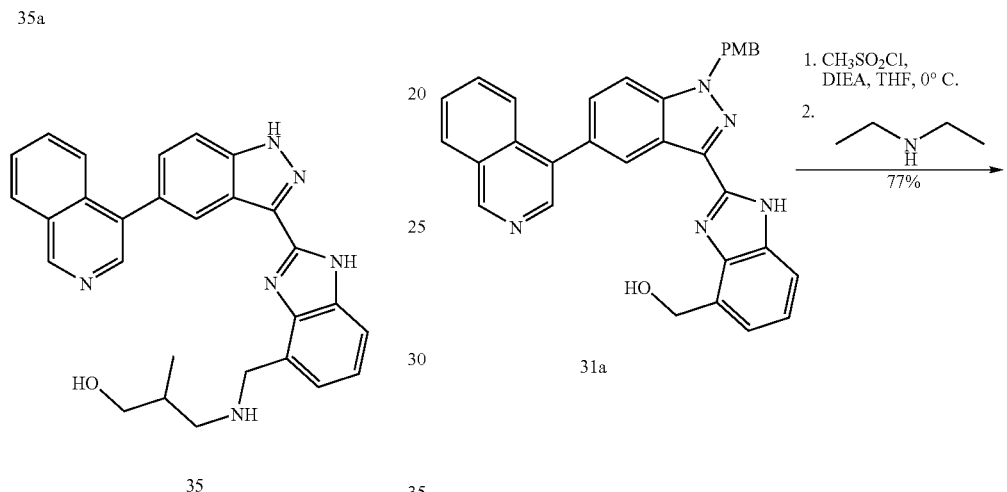

(a) Intermediate 35a—Cyclopropylmethyl-{2-[5-isoquinolin-4-yl-1-(4-methoxy-benzyl)-1H-indazol-3-yl]-1H-benzoimidazol-4-ylmethyl}-amine By a procedure similar to 31b synthesis, alcohol 31a (512.0 mg, 1.00 mmol) was treated with methanesulfonyl chloride and diisopropylethyl amine at 0° C. for 1 hour. Aminomethylcyclopropane (712 mg, 10.0 mmol) was then added, and stirring continued at room temperature for 15 hours. After extractive workup and column chromatography similar to 31b, intermediate 35a (209.3 mg, 37%) was obtained as an off-white powder: $R_f$=0.16 (1:20:300 concentrated aqueous NH$_4$OH:ethanol:dichloromethane); $^1$H NMR (DMSO-d$_6$) δ −0.24 (br s, 2H), −0.04 (br s, 2H), 0.66 (br s, 1H), 2.30 (br s, 2H), 3.71 (s, 3H), 4.04 (br s, 2H), 5.83 (s, 2H), 6.93 (d, 2H, J=8.7 Hz), 7.11 (m, 2H), 7.37 (d, 2H, J=8.7 Hz), 7.42 (m, 1H), 7.67 (dd, 1H, J=8.7, 1.5 Hz), 7.76 (m, 2H), 7.87 (d, 1H, J=8.1 Hz), 8.02 (d, 1H, J=8.7 Hz), 8.25 (dd, 1H, J=6.8, 1.9 Hz), 8.53 (s, 1H), 8.68 (br s, 1H), 9.38 (s, 1H). Anal. (C$_{36}$H$_{32}$N$_6$O0.5H$_2$O) C, H, N.

(b) Example 35—3-{[2-(5-Isoquinolin-4-yl-1H-indazol-3-yl)-1H-benzoimidazol-4-ylmethyl]-amino}-2-methyl-propan-1-ol 35 was prepared similar to example 33. Treatment of 35a (107.1 mg, 0.19 mmol) with 3:1 trifluoroacetic acid/sulfuric acid yielded ring-opened analog 35 (25.3 mg, 29%) as a white powder: $R_f$=0.35 (1:20:100 concentrated aqueous NH$_4$OH:ethanol: dichloromethane); $^1$H NMR (CD$_3$OD) δ 0.67 (d, 3H, J=6.8 Hz), 1.33 (m, 1H), 1.80 (m, 1H), 2.60 (m, 1H), 2.75 (m, 1H), 3.20 (m, 1H), 4.26 (s, 2H), 7.22 (m, 2H), 7.57 (d, 1H, J=7.7 Hz), 7.63 (dd, 1H, J=8.7, 1.7 Hz), 7.79 (m, 3H), 7.99 (d, 1H, J=7.5 Hz), 8.22 (d, 1H, J=7.5 Hz), 8.51 (s, 1H), 8.72 (br s, 1H), 9.29 (s, 1H). $^{13}$C NMR (CD$_3$OD, DEPT) δ 15.0 (CH$_3$), 35.6 (CH), 50.9 (CH$_2$), 54.0 (CH$_2$), 67.4 (CH$_2$), 111.7 (CH), 123.4 (CH), 124.0 (CH), 124.3 (CH), 125.8 (CH), 128.9 (CH), 129.3 (CH), 130.4 (CH), 132.6 (CH), 142.9 (CH), 152.6 (CH). Anal. (C$_{28}$H$_{26}$N$_6$O0.6 CH$_2$Cl$_2$-0.4 hexanes) C, H, N.

EXAMPLE 36

Diethyl-[2-(5-isoquinolin-4-yl-1H-indazol-3-yl)-1H-benzoimidazol-4-ylmethyl]-amine

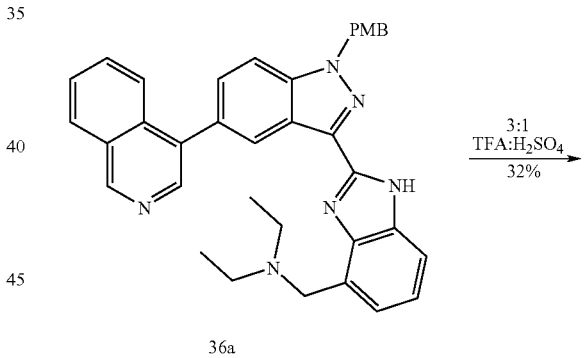

31a

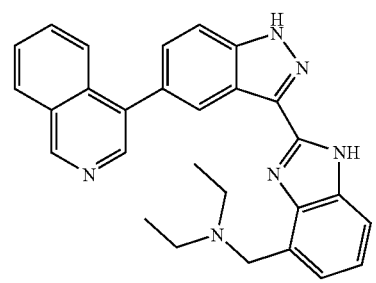

36

(a) Intermediate 36a—Diethyl-{2-[5-isoquinolin-4-yl-1-(4-methoxy-benzyl)-1H-indazol-3-yl]-1H-benzoimidazol-4-ylmethyl}-amine By a procedure similar to 31 b, alcohol 31a (511.4 mg, 1.00 mmol) was treated with methanesulfonyl chloride and diisopropylethyl amine at 0° C. for 2.5 hours. Diethylamine (731.4 mg, 10.0 mmol) was then added, and stirring continued at room temperature for 25 hours. After extractive workup and column chromatography similar to 31 b, intermediate 36a (434.6 mg, 77%) was obtained as a yellow foam: $R_f$=0.22 (1:20:400 concentrated aqueous NH$_4$OH: ethanol:dichloromethane); $^1$H NMR (DMSO-d$_6$) [Some peaks are doubled due to tautomeric isomerization] δ 0.87 and 1.01 (2 br s, 6H together), 2.41 and 2.56 (2 br s, 4H together), 3.71 (s, 3H), 3.89 and 3.94 (2 br s, 2H together), 5.82 (s, 2H), 6.92 (d, 2H, J=8.7 Hz), 7.13 (m, 2H), 7.37 (d, 2H, J=8.5 Hz), 7.50 (m, 1H), 7.67 (d, 1H, J=8.7 Hz), 7.76 (m, 2H), 7.91 (m, 1H), 8.01 (d, 1H, J=8.7 Hz), 8.25 (dd, 1H, J=6.6, 1.9 Hz), 8.53 (s, 1H), 8.63 and 8.77 (2 br s, 1H together), 9.38 (s, 1H), 13.02 (s, 1H). Anal. (C$_{36}$H$_{34}$N$_6$O$_{0.4}$H$_2$O) C, H, N.

(b) Example 36—Diethyl-[2-(5-isoquinolin-4-yl-1H-indazol-3-yl)-1H-benzoimidazol-4-ylmethyl]-amine Similar to example 33, treatment of 36a (266.5 mg, 0.47 mmol) with 3:1 trifluoroacetic acid/sulfuric acid yielded 36 (67.5 mg, 32%) as a white powder: $R_f$=0.30 (1:20:200 concentrated aqueous NH$_4$OH:ethanol:dichloromethane); $^1$H NMR (DMSO-d$_6$) [Some peaks are doubled due to tautomeric isomerization] δ 0.94 (br m, 6H), 2.44 and 2.55 (2 br s, 4H together), 3.94 (br s, 2H), 7.14 (br s, 2H), 7.39 and 7.50 (2 br s, 1H together), 7.64 (dd, 1H, J=8.7, 1.5 Hz), 7.77 (m, 4H), 8.25 (d, 1H, J=7.4 Hz), 8.54 (s, 1H), 8.63 and 8.74 (2 br s, 1H together), 9.39 (s, 1H), 12.99 (s, 1H), 13.81 (s, 1H). Anal. (C$_{28}$H$_{26}$N$_6$.0.5EtOH) C, H, N.

EXAMPLE 37

Ethyl-[2-(5-isoquinolin-4-yl-1H-indazol-3-yl)-1H-benzoimidazol-4-ylmethyl]-amine

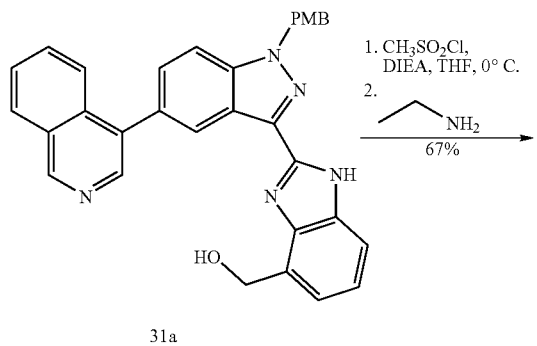

31a

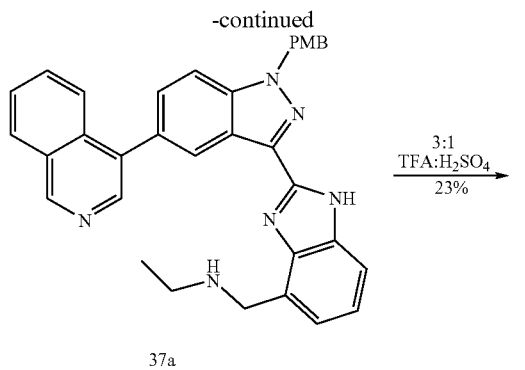

37a

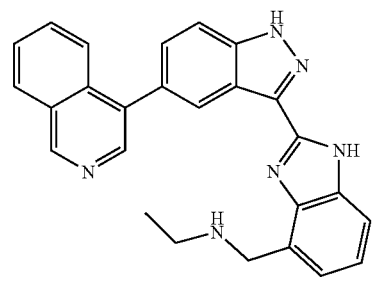

37

(a) Intermediate 37a—Ethyl-{2-[5-isoquinolin-4-yl-1-(4-methoxy-benzyl)-1H-indazol-3-yl]-1H-benzoimidazol-4-ylmethyl}-amine By a synthetic method similar to 31b, alcohol 31a (371.5 mg, 0.726 mmol) was treated with methanesulfonyl chloride and diisopropylethyl amine at 0° C. for 2.5 hours. The reaction flask was then fitted with a dry ice-cooled cold finger condenser, and ethylamine gas was condensed into the reaction solution until the volume had increased by about 5 mL. Stirring was continued at room temperature for 15 hours. After extractive workup and column chromatography similar to 31b, intermediate 37a (260.1 mg, 67%) was obtained as a pale yellow foam: $^1$H NMR (DMSO-d$_6$) δ 0.84 (br s, 3H), 3.39 (br s, 2H), 3.71 (s, 3H), 4.04 (s, 2H), 5.82 (s, 2H), 6.93 (d, 2H, J=8.7 Hz), 7.12 (m, 2H), 7.37 (d, 2H, J=8.7 Hz), 7.44 (m, 1H), 7.67 (dd, 1H, J=8.7, 1.5 Hz), 7.76 (m, 2H), 7.89 (m, 1H), 8.01 (d, 1H, J=8.7 Hz), 8.25 (dd, 1H, J=6.6, 1.9 Hz), 8.54 (s, 1H), 8.67 (s, 1H), 9.39 (s, 1H). Anal. (C$_{34}$H$_{30}$N$_6$O$_{00.7}$H$_2$O) C, H, N.

(b) Example 37—Ethyl-[2-(5-isoquinolin-4-yl-1H-indazol-3-yl)-1H-benzoimidazol-4-ylmethyl]-amine Similar to example 33, treatment of 37a (123.3 mg, 0.229 mmol) with 3:1 trifluoroacetic acid/sulfuric acid yielded 37 (21.8 mg, 23%) as an off-white powder: $^1$H NMR (DMSO-d$_6$) δ 0.84 (br s, 3H), 2.57 (br s, 2H), 4.10 (s, 2H), 7.13 (m, 2H), 7.46 (m, 1H), 7.64 (dd, 1H, J=8.7, 1.7 Hz), 7.80 (m, 4H), 8.26 (dd, 1H, J=7.2, 1.7 Hz), 8.55 (s, 1H), 8.66 (s, 1H), 9.39 (s, 1H), 13.85 (br s, 1H). Anal. (C$_{26}$H$_{22}$N$_6$.0.6EtOH.1.0CH$_2$Cl$_2$) C, H, N.

EXAMPLE 38

Isopropyl-[2-(5-isoquinolin-4-yl-1H-indazol-3-yl)-1H-benzoimidazol-4-ylmethyl]-amine

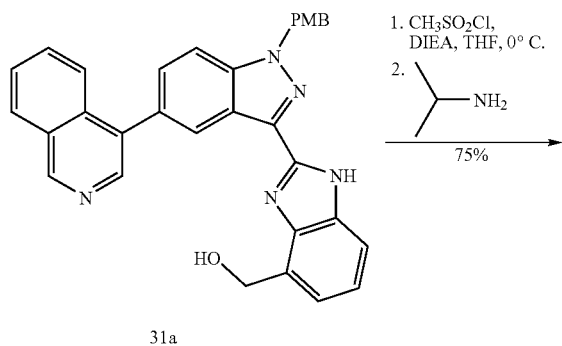

31a (a) Intermediate 38a—Isopropyl-{2-[5-isoquinolin-4-yl-1-(4methoxy-benzyl)-1H-indazol-3-yl]-1H-benzoimidazol-4-ylmethyl}-amine By a procedure similar to 31 b, alcohol 31a (518.0 mg, 1.01 mmol) was treated with methanesulfonyl chloride and diisopropylethyl amine at 0° C. for 2.5 hours. Isopropyl amine (597 mg, 10.1 mmol) was then added, and stirring continued at room temperature for 24 hours. After extractive workup and column chromatography similar to 31 b, intermediate 38a (417.8 mg, 75%) was obtained as a yellow foam: $^1$H NMR (DMSO-$d_6$) δ 0.77 (br s, 6H), 2.63 (br s, 1H), 3.71 (s, 3H), 4.02 (br s, 2H), 5.82 (s, 2H), 6.93 (d, 2H, J=8.7 Hz), 7.11 (m, 2H), 7.37 (d, 2H, J=8.7 Hz), 7.42 (m, 1H), 7.67 (dd, 1H, J=8.7, 1.5 Hz), 7.76 (m, 2H), 7.88 (d, 1H, J=7.7 Hz), 8.02 (d, 1H, J=8.7 Hz), 8.25 (dd, 1H, J=6.6, 2.1 Hz), 8.53 (s, 1H), 8.69 (br s, 1H), 9.38 (s, 1H). Anal. ($C_{35}H_{32}N_6O.0.7H_2O$) C, H, N.

(b) Example 38—Isopropyl-[2-(5-isoquinolin-4-yl-1H-indazol-3-yl)-1H-benzo-imidazol-4-ylmethyl]-amine 38 was prepared similar to example 33. Treatment of 38a (243.3 mg, 0.44 mmol) with 3:1 trifluoroacetic acid/sulfuric acid yielded 38 (89.9 mg, 47%) as an off-white powder: $^1$H NMR (CD$_3$OD) δ 1.03 (d, 6H, J=6.4 Hz), 2.99 (septet, 1H, J=6.4 Hz), 4.27 (s, 2H), 7.23 (m, 2H), 7.57 (dd, 1H, J=7.7, 1.1 Hz), 7.67 (dd, 1H, J=8.7, 1.7 Hz), 7.81 (m, 3H), 8.01 (d, 1H, J=8.3 Hz), 8.23 (d, 1H, J=7.5 Hz), 8.51 (s, 1H), 8.71 (br s, 1H), 9.30 (s, 1H).

EXAMPLE 39 tert-Butyl-[2-(5-isoquinolin-4-yl-1H-indazol-3-yl)-1H-benzoimidazol-4-ylmethyl]-amine

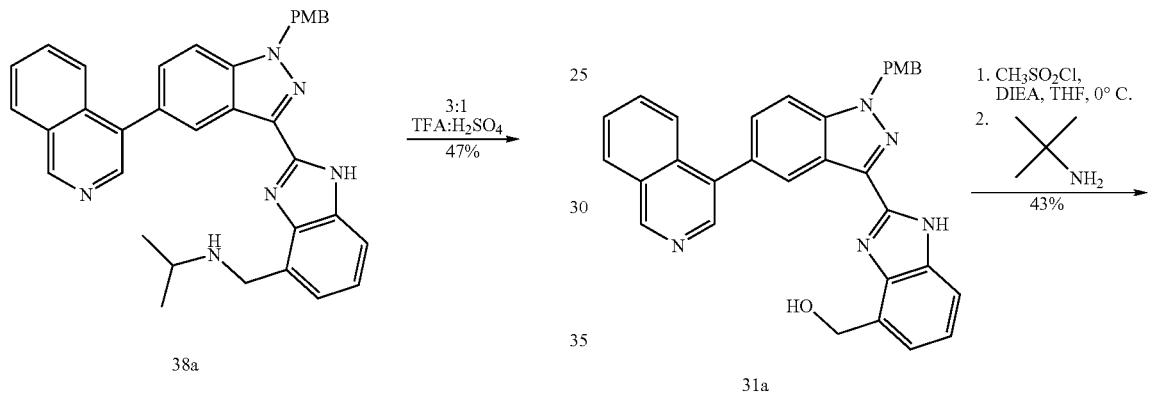

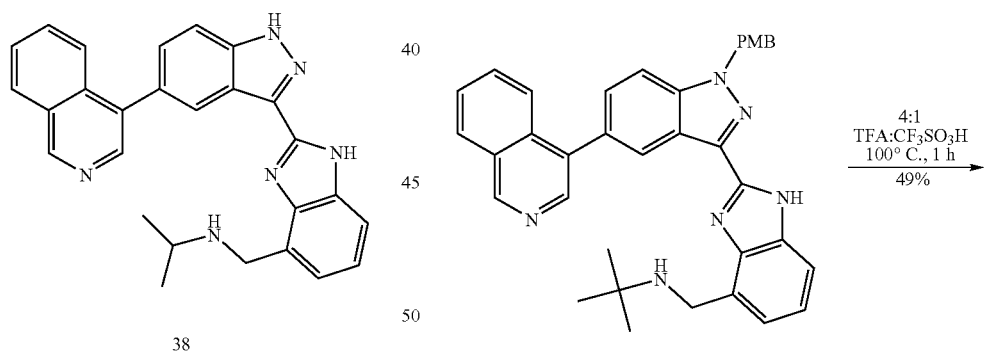

(a) Intermediate 39a—tert-Butyl-{2-[5-isoquinolin-4-yl-1-(4methoxy-benzyl)-1H-indazol-3-yl]-1H-benzoimidazol-4-ylmethyl}-amine By an analogous method to 31 b, alcohol 31a (623.2 mg, 1.22 mmol) was treated with methanesulfonyl chloride and diisopropylethyl amine at 0° C. for 1 hour. tert-Butylamine (890 mg, 12.2 mmol) was then added, and stirring continued at room temperature for 20 hours. After extractive workup and column chromatography similar to 31b, intermediate 39a (299.7 mg, 43%) was obtained as a yellow foam: $^1$H NMR (CD$_3$OD) δ 1.01 (s, 9H), 3.76 (s, 3H), 4.11 (s, 2H), 5.78 (s, 2H), 6.91 (d, 2H, J=8.7 Hz), 7.19 (m, 2H), 7.36 (d, 2H, J=8.7 Hz), 7.50 (dd, 1H, J=7.9, 1.1 Hz), 7.62 (dd, 1H, J=8.7, 1.7 Hz), 7.77 (m, 3H), 7.95 (d, 1H, J=7.9 Hz), 8.22 (dd, 1H, J=7.0, 1.7 Hz), 8.48 (s, 1H), 8.74 (s, 1H), 9.29 (s, 1H). Anal. (C$_{36}$H$_{34}$N$_6$O·0.3H$_2$O) C, H, N.

(b) Example 39—tert-Butyl-[2-(5-isoquinolin-4-yl-1H-indazol-3-yl)-1H-benzo-imidazol-4-ylmethyl]-amine A solution of 39b (103.7 mg, 0.183 mmol), trifluoromethanesulfonic acid (0.48 mL), and trifluoroacetic acid (1.6 mL) was stirred at room temperature for 17 hours, and then at 100° C. for 1.5 hours. The solution was added dropwise to a rapidly stirred mixture of concentrated aqueous NH$_4$OH (10 mL), water (10 mL), and ethyl acetate (10 mL). Extraction and purification similar to example 33, afforded 39 (40.2 mg, 49%) as a white powder: $^1$H NMR (CD$_3$OD) δ 1.30 (s, 9H), 4.56 (s, 2H), 7.33 (m, 2H), 7.68 (m, 2H), 7.81 (m, 3H), 8.01 (d, 1H, J=8.5 Hz), 8.25 (d, 1H, J=8.5 Hz), 8.51 (s, 1H), 8.73 (s, 1H), 9.32 (s, 1H). Anal. (C$_{28}$H$_{26}$N$_6$·1.6 HOAc) C, H, N.

EXAMPLE 40

4-[3-(4-Imidazol-1-ylmethyl-1H-benzoimidazol-2-yl)-1H-indazol-5-yl]-isoquinoline

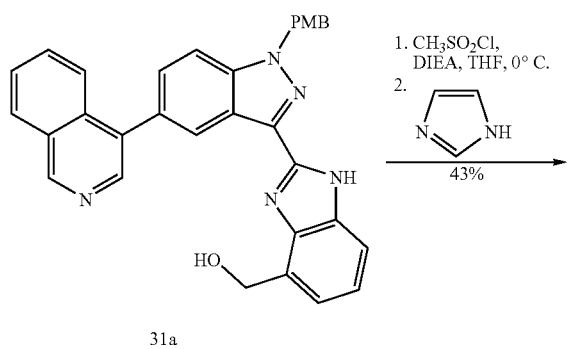

31a

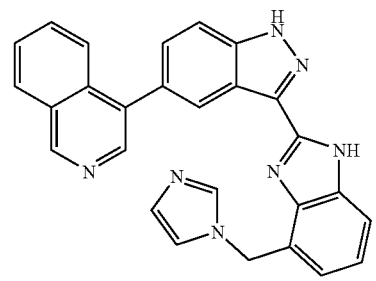

40a

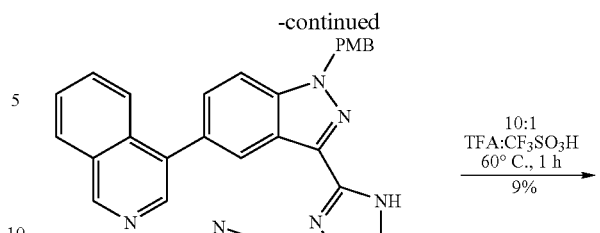

40

(a) Intermediate 40a—4-[3-(4-Imidazol-1-ylmethyl-1H-benzoimidazol-2-yl)-1-(4-methoxy-benzyl)-1H-indazol-5-yl]-isoquinoline By an analogous method to 31b, alcohol 31a (572.0 mg, 1.12 mmol) was treated with methanesulfonyl chloride and diisopropylethyl amine at 0° C. for 1 hour. Imidazole (761 mg, 11.2 mmol) was then added, and stirring was continued at room temperature for 24 hours. After extractive workup and column chromatography similar to 31b, intermediate 40a (269.1 mg, 43%) was obtained as a white powder: $^1$H NMR (CD$_3$OD) δ 3.77 (s, 3H), 5.58 (s, 2H), 5.79 (s, 2H), 6.73 (br s, 1H), 6.91 (d, 2H, J=8.8 Hz), 7.07 (d, 1H, J=7.4 Hz), 7.23 (m, 2H), 7.36 (d, 2H, J=8.8 Hz), 7.53–7.83 (m, 6H), 8.03 (d, 1H, J=7.9 Hz), 8.22 (d, 1H, J=7.9 Hz), 8.51 (s, 1H), 8.73 (br s, 1H), 9.28 (s, 1H). Anal. (C$_{35}$H$_{27}$N$_7$O) C, H, N.

(b) Example 40—4-[3-(4-Imidazol-1-ylmethyl-1H-benzoimidazol-2-yl)-1H-indazol-5-yl]-isoquinoline A solution of 40a (152.0 mg, 0.271 mmol), trifluoromethanesulfonic acid (0.271 mL), and trifluoroacetic acid (2.71 mL) was stirred at 60° C. for 1 hour. The solution was added dropwise to a rapidly stirred mixture of concentrated aqueous NH$_4$OH (10 mL), water (10 mL), THF (10 mL), and ethyl acetate (20 mL). Extraction and purification similar to example 33, afforded crude 40 as a pink solid (24.9 mg), which still showed impurities in the $^1$H NMR spectrum.

Trituration from acetonitrile afforded pure 40 (11.0 mg, 9%) as a pink powder: $^1$H NMR (CD$_3$OD) δ 5.59 (s, 2H), 6.74 (br s, 1H), 7.08 (d, 1H, J=7.4 Hz), 7.25 (m, 2H), 7.55–7.85 (m, 6H), 8.07 (d, 1H, J=7.9 Hz), 8.24 (d, 1H, J=7.5 Hz), 8.54 (s, 1H), 8.72 (br s, 1H), 9.30 (s, 1H). HRMS calculated for C$_{27}$H$_{20}$N$_7$ 442.1780 (MH$^+$). found 442.1794.

EXAMPLE 41

5-(3-Methyl-pyridin-4-yl)-3-(E)-styryl-1H-indazole

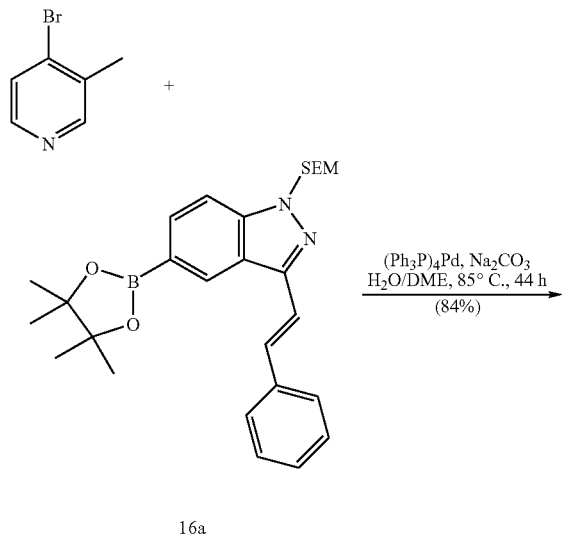

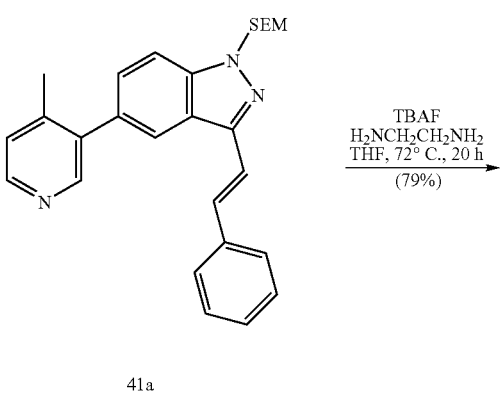

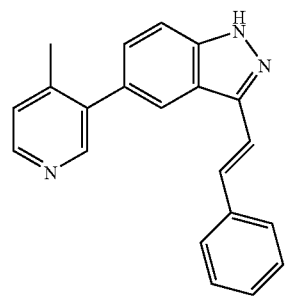

(a) Intermediate 41a—5-(3-Methyl-pyridin-4-yl)-3-((E)-styryl)-1-(2-trimethylsilanyl-ethoxymethyl)-1H-indazole Intermediate 16a (300 mg, 0.63 mmol), 4-bromo-3-methyl-pyridine (see Baliki et al., *Gazz. Chim. Ital.* 124, 9, 1994, 385–386) (112 mg, 0.65 mmol), and sodium carbonate (140 mg, 1.3 mmol) were stirred in DME (6 mL)/H$_2$O (1 mL) in a flask purged with argon. Tetrakis(triphenylphosphine)palladium (0) (60 mg, 0.05 mmol) was added, and the reaction stirred at reflux under argon for 24 hours. The solution was diluted with ethyl acetate, washed with H$_2$O and brine, dried over Na$_2$SO$_4$, and concentrated in vacuo. Purification by silica gel chromatography (20% ethyl acetate/hexanes) gave 234 mg (84%) of intermediate 41a as a clear oil. $^1$H NMR (300 MHz, CDCl$_3$) δ 8.56 (s, 1H), 8.52 (d, 1H, J=7.8 Hz), 7.95 (s, 1H), 7.24–7.67 (m, 10H), 5.78 (s, 2H), 3.64 (t, 2H, J=8.1 Hz), 2.33 (s, 3H), 0.94 (t, 2H, J=8.1 Hz), −0.04 (s, 9H). Anal. (C$_{27}$H$_{31}$N$_3$OSi. 0.2H$_2$O) C, H, N.

(b) Example 41—5-(3-Methyl-pyridin-4-yl)-3-(E)-styryl-1H-indazole

Intermediate 41a (218 mg, 0.49 mmol) was stirred in a mixture of ethylenediamine (0.34 mL, 4.9 mmol) and TBAF (1M in THF, 2.5 mL, 2.5 mmol) at 72° C. for 20 hours. The solution was diluted with ethyl acetate, washed with sat. NaHCO$_3$ and brine, dried (Na$_2$SO$_4$), and concentrated in vacuo. Purification by silica gel chromatography (1:1:1 ethyl acetate/THF/hexanes) gave 122 mg (79%) of the title compound as a white solid. $^1$H NMR (300 MHz, DMSO-d$_6$) δ 13.29 (s, 1H), 8.52 (s, 1H), 8.46 (d, 1H, J=4.8 Hz), 8.22 (s, 1H), 7.55–7.73 (m, 5H), 7.26–7.44 (m, 5H), 2.31 (s, 3H). Anal. (C$_{21}$H$_{17}$N$_3$) C, H, N. MS (ES) [m+H]/z calculated 312. found 312; [m−H]z calculated 310. found 310.

EXAMPLE 42

5-(4-Chloro-pyridin-3-yl)-3-(E)-styryl-1H-indazole

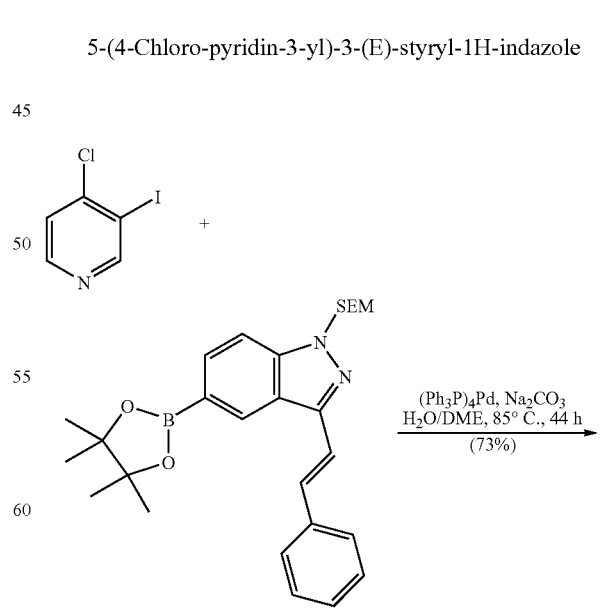

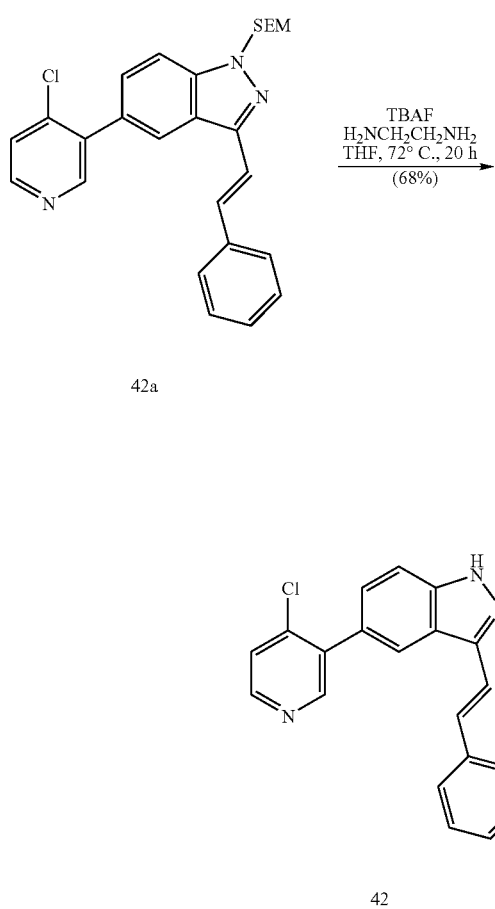

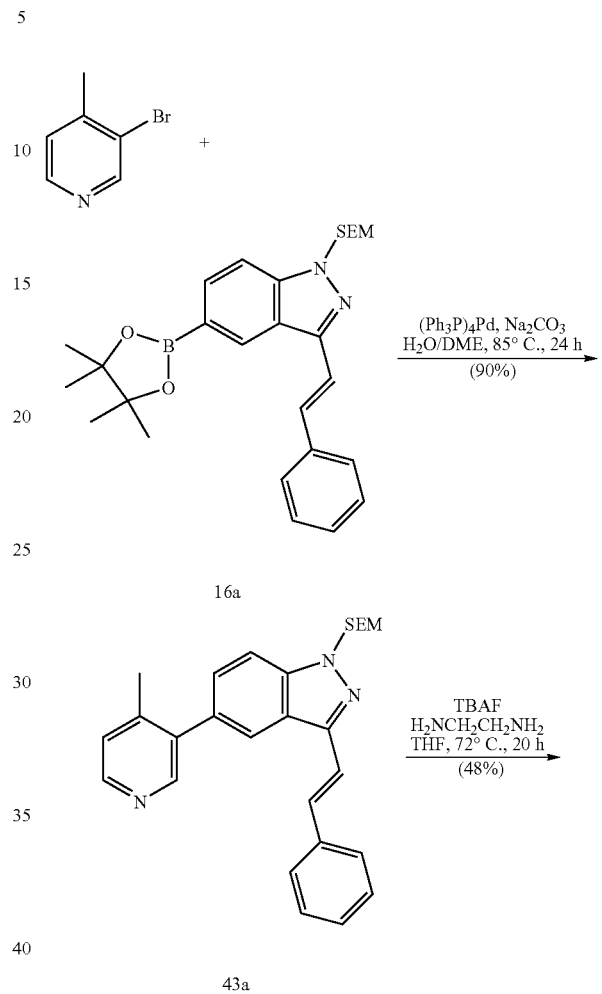

(a) Intermediate 42a—5-(4-Chloro-pyridin-3-yl)-3-((E)styryl)-1-(2-trimethylsilanyl-ethoxymethyl)-1H-indazole The title compound was prepared in 73% yield from intermediate 16a and 4-chloro-3-iodo-pyridine (see Cho et al., *Heterocycles*, 43, 8, 1996, 1641–1652) analogous to intermediate 41a. $^1$H NMR (300 MHz, CDCl$_3$) δ 8.67 (s, 1H), 8.52 (d, 1H, J=7.8 Hz), 8.08 (s, 1H), 7.26–7.70 (m, 10H), 5.79 (s, 2H), 3.64 (t, 2H, J=8.1 Hz), 0.94 (t, 2H, J=8.1 Hz), –0.03 (s, 9H). Anal. (C$_{26}$H$_{28}$ClN$_3$OSi.0.3H$_2$O) C, H, N.

(b) Example 42—5-(4-Chloro-pyridin-3-yl)-3-(E)-styryl-1H-indazole

The title compound was prepared in 66% yield by the SEM-deprotection of intermediate 42a in a method analogous to example 41. $^1$H NMR (300 MHz, DMSO-d$_6$) δ 13.30 (s, 1H), 8.70 (s, 1H), 8.56 (d, 1H, J=5.4 Hz), 8.31 (s, 1H), 7.63–7.73 (m, 4H), 7.57 (d, 2H, J=4.2 Hz), 7.50 (dd, 1H, J=8.4, 1.2 Hz), 7.26–7.40 (m, 3H). Anal. (C$_{20}$H$_{14}$ClN$_3$. 0.05H$_2$O) C, H, N. MS (ES) [m+H]/z calculated 332/334. found 332/334; [m–H]/z calculated 330/332. found 330/332.

EXAMPLE 43

5-(4Methyl-pyridin-3-yl)-3-(E)styryl-1H-indazole

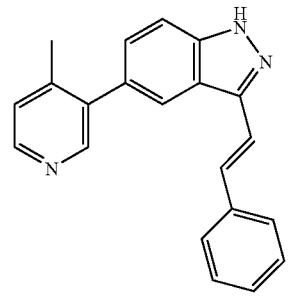

(a) Intermediate 43a—5-(4-Methyl-pyridin-3-yl)-3-((E)-styryl)-1-(2-trimethylsilanyl-ethoxymethyl)-1H-indazole The title compound was prepared in 90% yield from intermediate 16a and 3-bromo-4-methyl-pyridine similar to the procedure for intermediate 41a. $^1$H NMR (300 MHz, CDCl$_3$) δ 8.54 (s, 1H), 8.50 (d, 1H, J=7.8 Hz), 7.95 (s, 1H), 7.23–7.67 (m, 10H), 5.78 (s, 2H), 3.64 (t, 2H, J=8.1 Hz), 2.33 (s, 3H), 0.94 (t, 2H, J=8.1 Hz), −0.04 (s, 9H). Anal. ($C_{27}H_{31}N_3OSi$) C, H, N.

(b) Example 43—5-(4Methyl-pyridin-3-yl)-3-(E)-styryl-1H-indazole

The title compound was prepared in 48% yield by the SEM-deprotection of intermediate 43a in a method analogous to example 41. $^1$H NMR (300 MHz, DMSO-$d_6$) δ 13.26 (s, 1H), 8.47 (s, 1H), 8.44 (d, 1H, J=4.8 Hz), 8.20 (s, 1H), 7.71 (d, 2H, J=7.2 Hz), 7.55–7.64 (m, 3H), 7.26–7.42 (m, 5H), 2.31 (s, 3H). Anal. ($C_{21}H_{17}N_3$. 0.13$H_2O$) C, H, N. MS (ES) [m+H]/z calculated 312. found 312; [m−H]/z calculated 310. found 310.

EXAMPLE 44

5-Fluoro-4-((E)-styryl)-1H-indazol-5-yl]-isoquinoline

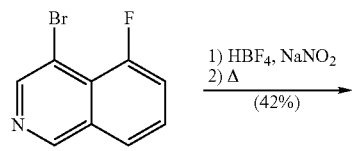

44a

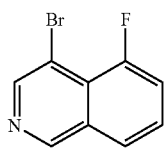

+

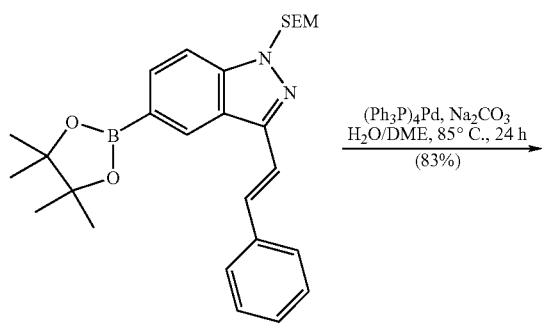

16a

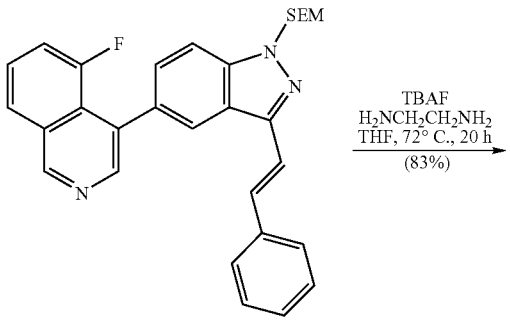

44b

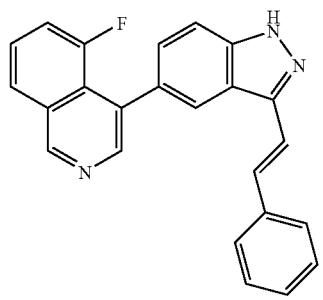

44

(a) Intermediate 44a—4-Bromo-5-fluoro-isoquinoline

5-Amino-4-bromo-isoquinoline (see Gordon et al., *J. Heterocycl. Chem.*, 4, 1967, 410–411) (1.86 g, 8.34 mmol) was stirred in 48% fluoroboric acid (15 mL)/EtOH (15 mL) until completely dissolved. The solution was cooled to 0° C., and sodium nitrite (660 mg, 9.59 mmol) in $H_2O$ (1 mL) was added dropwise. The solution was diluted with $Et_2O$ (30 mL), and the tan diazonium fluoroborate salt was collected by filtration and dried under vacuum. The solid was placed in a flask and carefully heated over a flame to expel nitrogen. The dark brown residue was diluted with 10% NaOH and extracted with chloroform. Organics were washed with brine, dried over $MgSO_4$, and concentrated in vacuo. Purification by silica gel chromatography (40% to 50% ethyl acetate/hexanes) gave 798 mg (42%) of 4-bromo-5-fluoro-isoquinoline as a white solid. $^1$H NMR (300 MHz, $CDCl_3$) δ 9.36 (d, 1H, J=2.4 Hz), 8.74 (s, 1H), 8.07–8.11 (m, 1H), 7.70–7.80 (m, 2H). Anal. ($C_9H_5BrFN$)C, H, N.

(b) Intermediate 44b—5-Fluoro-4-[3-((E)-styryl)-1-(2-trimethylsilanyl-ethoxymethyl)-1H-indazol-5-yl]-isoquinoline The title compound was prepared in 83% yield from intermediate 16a and 4-bromo-5-fluoro-isoquinoline similar to intermediate 41a. $^1$H NMR (300 MHz, CDCl$_3$) δ 9.32 (d, 1H, J=251.8 Hz), 8.52 (s, 1H), 8.07 (s, 1H), 7.91 (dd, 1H, J=8.1, 0.9 Hz), 7.26–7.66 (m, 11H), 5.80 (s, 2H), 3.67 (t, 2H, J=8.1 Hz), 0.95 (t, 2H, J=8.1 Hz), -0.03 (s, 9H). Anal. (C$_{30}$H$_{30}$FN$_3$OSi.0.2H$_2$O) C, H, N.

(c) Example 44—5-Fluoro-4-[3-((E)-styryl)-1H-indazol-5-yl]-isoquinoline

The title compound was prepared in 83% yield by the SEM-deprotection of intermediate 44b in a manner analogous to example 41. $^1$H NMR (300 MHz, DMSO-d$_6$) δ 13.26 (s, 1H), 9.44 (d, 1H, J=1.8 Hz), 8.47 (s, 1H), 8.29 (s, 1H), 8.12 (d, 1H, J=7.2 Hz), 7.44–7.78 (m, 8H), 7.35 (t, 2H, J=7.2 Hz), 7.24 (t, 1H, J=7.2 Hz). Anal. (C$_{24}$H$_{16}$FN$_3$.0.6H$_2$O) C, H, N. MS (ES) [m+H]/z calculated 366. found 366; [m−H]/z calculated 364. found 364.

EXAMPLE 45

4-[3-((E)-Styryl)-1H-indazol-5-yl-isoquinolin-8-ylamine

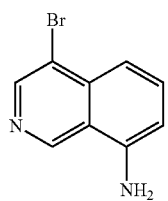

+

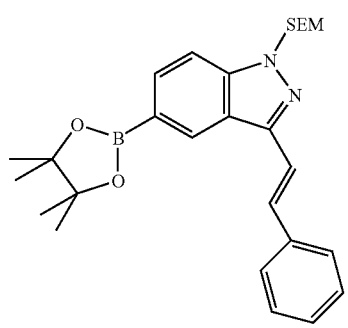

16a

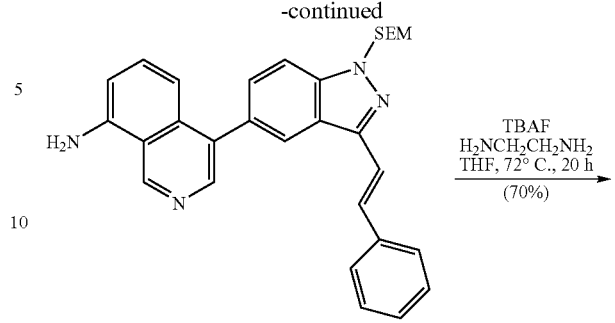

45a

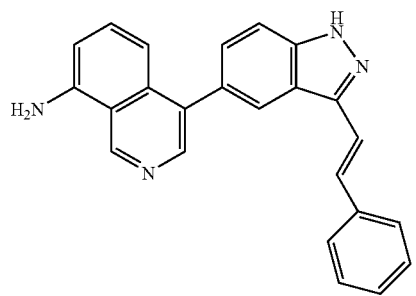

45

(a) Intermediate 45a—4-[3-((E)-Styryl)-1-(2-trimethylsilanyl-ethoxymethyl)-1H-indazol-5-yl]-isoquinolin-8-ylamine The title compound was prepared in 82% yield from intermediate 16a and 8-amino-4-bromo-isoquinoline (see Elpern et al., *J. Amer. Chem. Soc.*, 68, 1946, 1436) similar to the procedure for intermediate 41a. $^1$H NMR (300 MHz, CDCl$_3$) δ 9.36 (d, 1H, J=0.6 Hz), 8.53 (s, 1H), 8.13 (s, 1H) 7.26–7.72 (m, 11H), 6.86 (dd, 1H, J=7.5, 0.6 Hz), 5.81 (s, 2H), 4.51 (s, 2H), 3.66 (t, 2H, J=8.1 Hz), 0.96 (t, 2H, J=8.1 Hz), −0.03 (s, 9H). Anal. (C$_{30}$H$_{32}$N$_4$OSi) C, H, N.

(b) Example 45—4-[3-((E)-Styryl)-1H-indazol-5-yl]-isoquinolin-8-ylamine

The title compound was prepared in 70% yield by the SEM-deprotection of intermediate 45a in a manner analogous to the procedure for example 41. $^1$H NMR (300 MHz, DMSO-d$_6$) δ 13.30 (s, 1H), 9.50 (s, 1H), 8.36 (s, 1H), 8.26 (s, 1H), 7.24–7.71 (m, 10H), 6.91 (d, 1H, J=207.8 Hz), 6.77 (t, 1H, J=7.8 Hz), 6.33 (s, 2H). Anal. (C$_{24}$H$_8$N$_4$. 0.45H$_2$O) C, H, N. MS (ES) [m+H]/z calculated 363. found 363.

EXAMPLE 46

5-(4-Chloro-5-ethyl-pyridin-3-yl)-3-(E)-styryl-1H-indazole

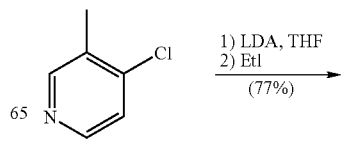

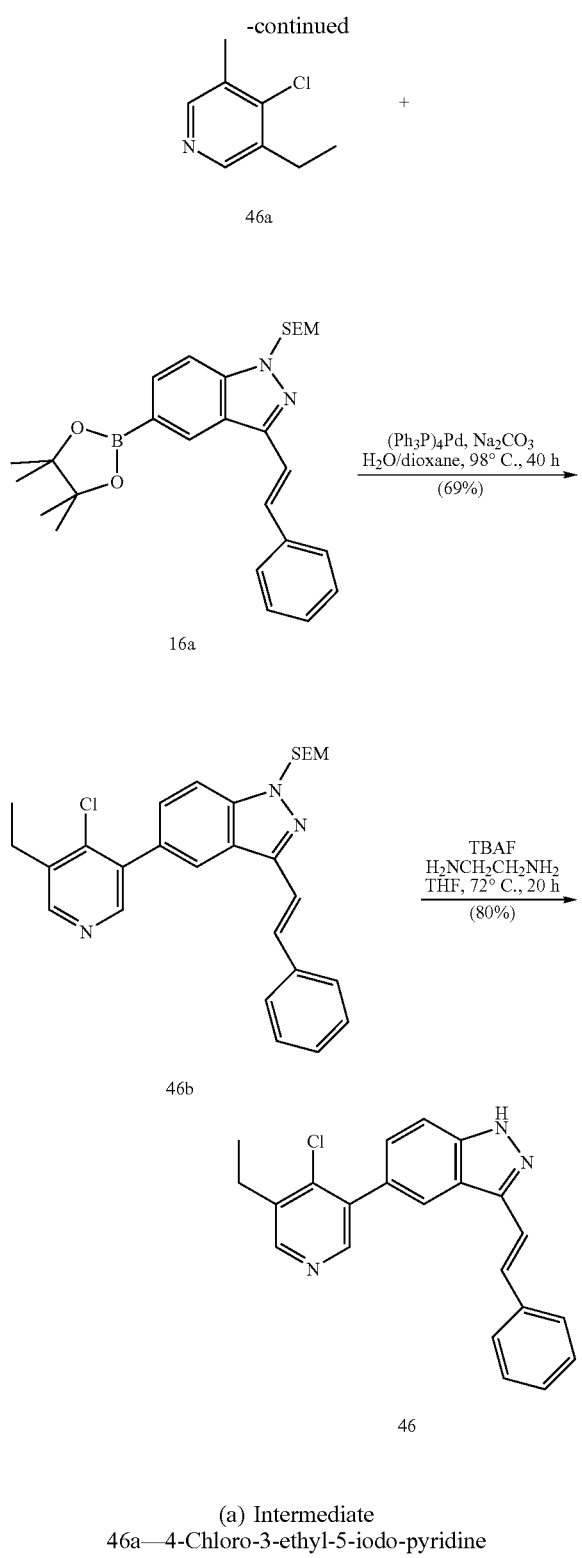

reaction was stirred for 1 hour at −78° C., then 1 hour while warming to 0° C. The reaction was quenched with sat. NH₄Cl, made basic with saturated NaHCO₃, and extracted with ethyl acetate. Organics were washed with brine, dried over Na₂SO₄, and concentrated in vacuo. Purification by silica gel chromatography (20% ethyl acetate/hexanes) gave 429 mg (77%) of 4-chloro-3-ethyl-5-iodo-pyridine as a waxy white solid.

$^1$H NMR (300 MHz, CDCl₃) δ 8.78 (s, 1H), 8.33 (s, 1H), 2.83 (q, 2H, J=7.5 Hz), 1.26 (t, 3H, J=7.5 Hz). Anal. (C₇H₇ClIN) C, H, N.

(b) Intermediate 46b—5-(4-Chloro-5-ethyl-pyridin-3-yl)-3-((E)-styryl)-1-(2-trimethylsilanyl-ethoxymethyl)-1H-indazole The title compound was prepared in 69% yield from intermediate 16a and 4-chloro-3-ethyl-5-iodo-pyridine similar to the procedure for intermediate 41a. $^1$H NMR (300 MHz, CDCl₃) δ 8.49 (d, 2H, J=3.3 Hz), 8.06 (s, 1H) 7.26–7.69 (m, 9H), 5.79 (s, 2H), 3.65 (t, 2H, J=8.1 Hz), 2.88 (q, 2H, J=7.5 Hz), 1.35 (t, 3H, J=7.5 Hz), 0.95 (t, 2H, J=8.1 Hz), −0.03 (s, 9H). Anal. (C₂₈H₃₂ClN₃OSi) C, H, N.

(c) Example 46—5-(4Chloro-5-ethyl-pyridin-3-yl)-3-(E)-styryl-1H-indazole

The title compound was prepared in 80% yield by the SEM-deprotection of intermediate 46b in a manner analogous to the procedure for example 41. $^1$H NMR (300 MHz, DMSO-d₆) δ 13.25 (s, 1H), 8.55 (s, 1H), 8.50 (s, 1H), 8.27 (s, 1H), 7.55–7.72 (m, 5H), 7.26–7.48 (m, 4H), 2.83 (q, 2H, J=7.5 Hz), 1.26 (t, 2H, J=7.5 Hz). Anal. (C₂₂H₁₈N₃Cl.0.3 H₂O) C, H, N. MS (ES) [m+H]/z calculated 360. found 360.

EXAMPLE 47

3-[3-(1H-benzoimidazol-2-yl)-1H-indazol-5-yl]-2-methoxy-phenol

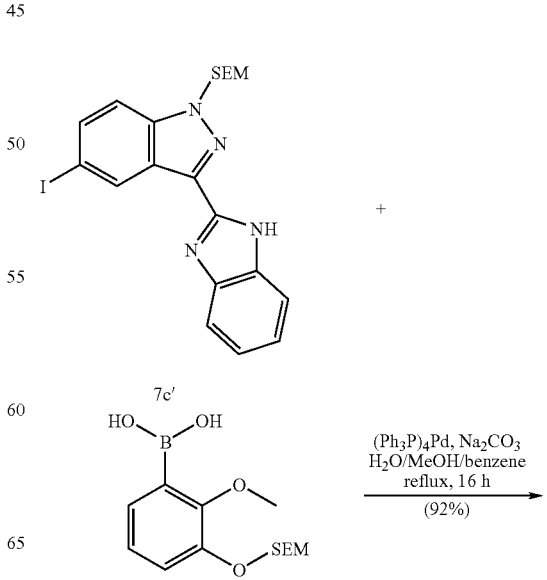

(a) Intermediate 46a—4-Chloro-3-ethyl-5-iodo-pyridine

LDA was prepared by the addition of n-butyllithium (2.5 M in hexanes, 0.95 mL, 2.38 mmol) to a solution of diisopropylamine (0.345 mL, 2.42 mmol) in THF (5 mL) at −20° C. After 10 minutes, the solution was cooled to −78° C. 4-Chloro-3-iodo-pyridine (500 mg, 2.09 mmol) in THF (3 mL) was added dropwise, and the reaction stirred for 30 minutes Iodoethane (0.2 mL, 2.5 mmol) was added, and the -continued

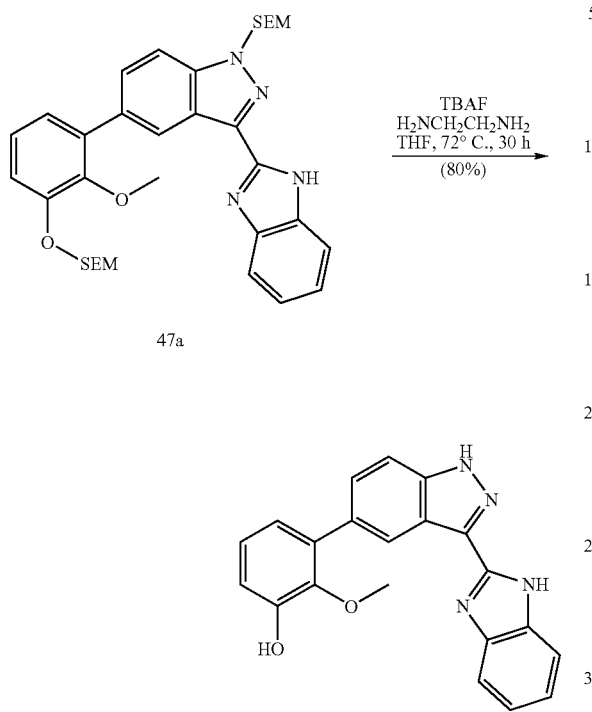

(a) Intermediate 47a—3-(1H-Benzoimidazol-2-yl)-5-{2-methoxy-3-{2-(2-trimethylsilanyl-ethoxymethyl)-ethoxy]-phenyl}-1-(2-trimethylsilanyl-ethoxymethyl)-1H-indazole The title compound was prepared in 92% yield from intermediate 7c' and 2-methoxy-3-[2-(2-trimethylsilanyl-ethoxy)-ethoxy]-boronic acid (Found in: Kania, Braganza, et al., patent application "Compounds and Pharmaceutical Compositions for Inhibiting Protein Kinases, and Methods for Their Use", p. 52, line 10 to p. 53, line 26; and p. 59, line 16 to p. 60, line 4, U.S. Provisional Ser. No. 60/142,130, filed Jul. 2, 1999, incorporated by reference herein in its entirety.), similar to the procedure for intermediate 7d'. $^1$H NMR (300 MHz, CDCl$_3$) δ 9.92 (s, 1H), 8.79 (s, 1H), 7.86–7.89 (m, 1H), 7.79 (dd, 1H, J=8.7, 1.5 Hz), 7.63 (d, 1H, J=8.7 Hz), 7.49–7.52 (m, 1H), 7.28–7.31 (m, 3H), 7.19 (dd, 1H, J=8.4, 1.8 Hz), 7.15 (d, 1H, J=7.8 Hz), 5.82 (s, 2H), 5.34 (s, 2H), 3.86 (t, 2H, J=8.4 Hz), 3.65 (t, 2H, J=8.1 Hz), 3.59 (s, 3H), 0.92–1.02 (m, 4H), 0.02 (s, 9H), −0.03 (s, 9H).

(b) Example 47—3-[3-(1H-benzoimidazol-2-yl)-1H-indazol-5-yl]-2-methoxy-phenol

The title compound was prepared in 61% yield by the SEM-deprotection of intermediate 47a in a manner analogous to the procedure for example 41. $^1$H NMR (300 MHz, DMSO-d$_6$) δ 13.64 (s, 1H), 12.98 (s, 1H), 9.36 (s, 1H), 8.59 (s, 1H), 7.68 (dd, 1H, J=8.4, 0.6 Hz), 7.60 (br s, 2H), 7.59 (dd, 1H, J=8.4, 1.5 Hz), 7.18–7.22 (m, 2H), 7.03 (t, 1H, J=7.8 Hz), 6.83–6.92 (m, 2H), 3.46 (s, 3H). Anal. ($C_{21}H_{16}N_4O_2 \cdot 1.0H_2O$) C, H, N. MS (ES) [m+H]/z calculated 357. found 357; [m−H]/z calculated 355. found 355.

EXAMPLE 48

3-(1H-Benzoimidazol-2-yl)-5-(1H-indol-4-yl)-1H-indazole

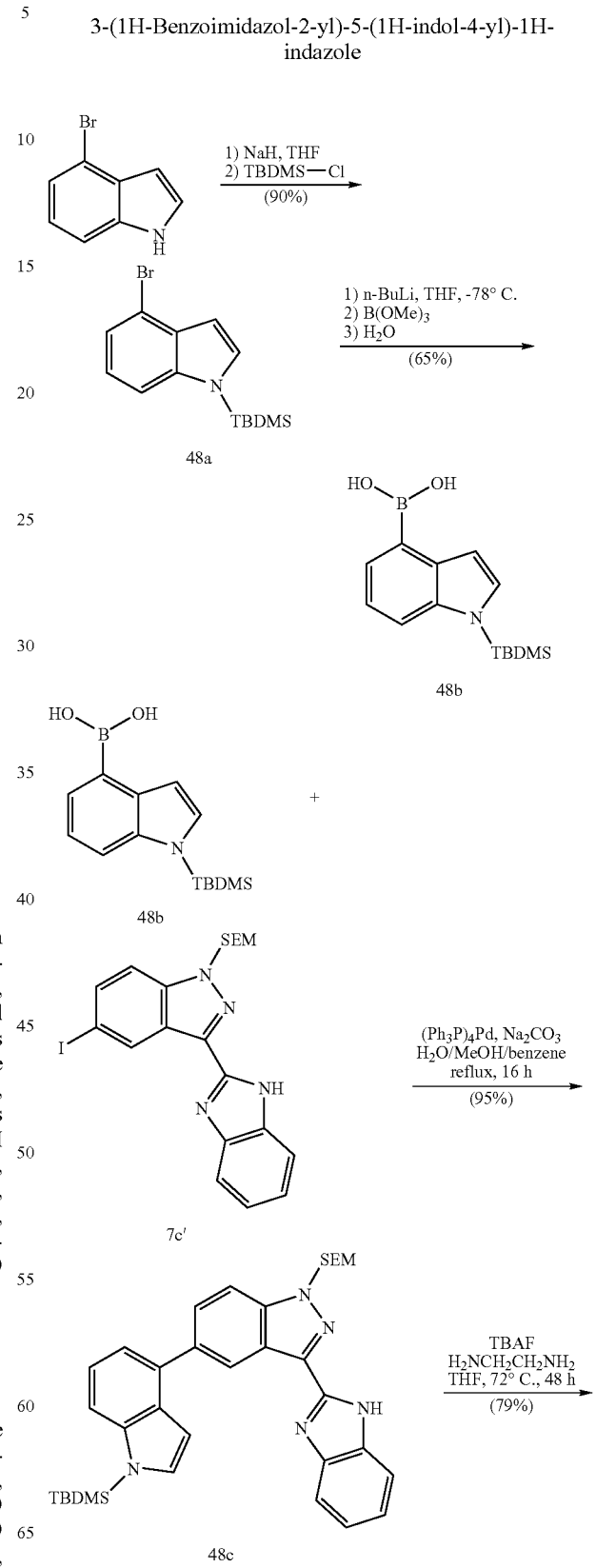

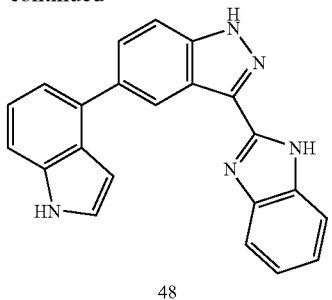

48

(a) Intermediate 48a—4Bromo-(tert-butyl-dimethyl-silanyl)-1H-indole

Sodium hydride (60% dispersion in mineral oil, 1.84 g, 46 mmol) was washed with hexanes and then stirred in THF (30 mL) under argon at 0° C. 4-Bromoindole (3.0 g, 15.3 mmol) in THF (10 mL) was added slowly, and the reaction stirred 1 hour while warming to room temperature. tert-Butyl-dimethylsilyl chloride (3.5 g, 23 mmol) was added, and the reaction stirred 16 hours before it was diluted with ether (100 mL) and slowly quenched with $H_2O$. Organics were separated and washed with brine, dried over $Na_2SO_4$, and concentrated in vacuo. Purification by silica gel chromatography (5% ether/hexanes) gave 4.28 g (90%) intermediate 48a as a white solid. $^1$H NMR (300 MHz, $CDCl_3$) δ 7.44 (d, 1H, J=8.4 Hz), 7.27 (d, 1H, J=8.4 Hz), 7.22 (d, 1H, J=3.3 Hz), 7.00 (t, 1H, J=8.1 Hz), 6.67 (dd, 1H, J=3.3, 0.9 Hz), 0.92 (s, 9H), 0.60 (s, 6H). Anal. ($C_{14}H_{20}BrNSi$) C, H, N.

(b) Intermediate 48b—1-(tert-Butyl-dimethyl-silanyl)-1H-indole-4boronic acid

Intermediate 48a (2.22 g, 7.16 mmol) was stirred in dry THF (15 mL) at −78° C. n-Butyllithium (2.5 M in hexanes, 3.45 mL, 8.6 mmol) was added slowly. The reaction stirred for 20 minutes before it was transferred via cannula to a flask of trimethyl borate (8.0 mL, 72 mmol) in dry THF (10 mL) at −78° C. The reaction stirred for 30 minutes at −78° C. and then 3 hours while warming to room temperature. It was quenched with $H_2O$ and extracted with ether. Organics were washed with brine, dried over $Na_2SO_4$, and concentrated in vacuo. Purification by silica gel chromatography (33% ethyl acetate/hexanes) gave 1.28 g (65%) of intermediate 48b as a white foam. $^1$H NMR (300 MHz, DMSO-$d_6$w/$D_2O$) δ 7.55 (d, 1H, J=8.4 Hz), 7.45 (d, 1H, J=8.4 Hz), 7.28 (s, 1H), 7.03–7.09 (m, 1H), 6.96 (s, 1H), 0.84 (s, 9H), 0.57 (s, 6H). Anal. ($C_{14}H_{22}BNO_2Si$·0.9$H_2O$) C, H, N.

(c) Intermediate 48c—3-(1H-Benzoimidazol-2-yl)-5-[1-(tert-butyl-dimethyl-silanyl)-1H-indol-4-yl]-1-(2-trimethylsilanyl-ethoxymethyl)-1H-indazole The title compound was prepared in 95% yield from intermediate 7c' and intermediate 48b similar to the procedure for intermediate 7d'. $^1$H NMR (300 MHz, $CDCl_3$) δ 9.90 (s, 1H), 8.96 (d, 1H, J=0.9 Hz), 7.84–7.90 (m, 2H), 7.69 (d, 1H, J=8.7 Hz), 7.48–7.53 (m, 2H), 7.23–7.33 (m, 5H), 6.82 (d, 1H, J=3.3 Hz), 5.84 (s, 2H), 3.67 (t, 2H, J=8.1 Hz), 0.96 (s, 9H), 0.94 (t, 2H, J=8.1 Hz), 0.65 (s, 6H), −0.03 (s, 9H). Anal. ($C_{34}H_{43}N_5OSi_2$) C, H, N.

(d) Example 48—3-(1H-Benzoimidazol-2-yl)-5-(1H-indol-4-yl)-1H-indazole

The title compound was prepared in 79% yield by the SEM, TBDMS-deprotection of intermediate 48c in a manner analogous to the procedure for example 41. $^1$H NMR (300 MHz, DMSO-$d_6$) δ 13.66 (s, 1H), 12.97 (s, 1H), 11.25 (s, 1H), 8.78 (s, 1H), 7.68–7.81 (m, 3H), 7.51 (d, 1H, J=7.2 Hz), 7.42–7.46 (m, 2H), 7.14–7.26 (m, 4H), 6.59 (t, 1H, J=2.1 Hz). Anal. ($C_{22}H_{15}N_5$·0.3$H_2O$) C, H, N. MS (ES) [m+H]/z calculated 350. found 350; [m−H]/z calculated 348. found 348.

EXAMPLE 49

3-[-3-(1H-Benzoimidazol-2-yl)-1H-indazol-5-yl]-2,4-difluoro-phenol

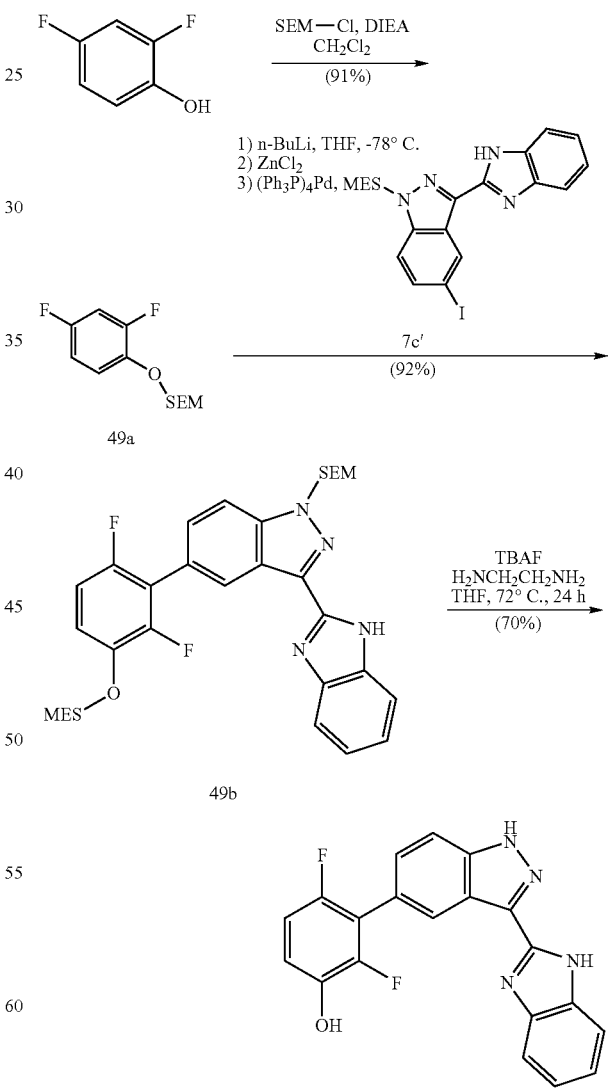

49

(a) Intermediate 49a—[2-(2,4-Difluoro-phenoxymethoxy)-ethyl]-trimethyl-silane 2,4-Difluoro-phenol (6.0 g, 46.1 mmol) and DIEA (9.64 mL, 55.3 mmol) were stirred in dry $CH_2Cl_2$ (100 mL) at room temperature. 2-(Trimethylsilyl)ethoxymethyl chloride (9.0 mL, 50.8 mmol) was added, and the reaction stirred 1 for hour. The solution was washed with $H_2O$ and brine, dried over $Na_2SO_4$, and concentrated in vacuo. Purification by silica gel chromatography gave 10.88 g (91%) of the title compound as a clear oil. $^1$H NMR (300 MHz, CDCl$_3$) δ 7.11–7.20 (m, 1H), 6.74–6.89 (m, 2H), 5.20 (s, 2H), 3.77–3.83 (m, 2H), 0.93–0.99 (m, 2H), 0.01 (s, 9H).

(b) Intermediate 49b—3-(1H-Benzoimidazol-2-yl)-5{2,6-difluoro-3-[2-(2-trimethylsilanyl-ethoxy-ethoxy]-phenyl}-1-(2-trimethylsilanyl-ethoxymethyl)-1H-indazole Intermediate 49a (1.4 g, 5.38 mmol) was stirred in dry THF (16 mL) under argon at −78° C. n-Butyllithium (2.5 M in hexanes, 2.32 mL, 5.8 mmol) was added dropwise, and the reaction stirred for 20 minutes. The solution was then transferred via cannula to a flask of dry zinc chloride under argon at room temperature. After 30 minutes intermediate 7c' (320 mg, 0.65 mmol) and tetrakis(triphenylphosphine)palladium (0) (60 mg, 0.05 mmol) were added, and the reaction stirred at room temperature for 2 hours. The solution was diluted with ether and washed with $H_2O$, saturated NaHCO$_3$, and brine. Organics were dried over Na$_2$SO$_4$ and concentrated in vacuo. Purification by silica gel chromatography (20% to 30% Et$_2$O/hexanes) gave 372 mg (92%) of the title compound as a white solid. $^1$H NMR (300 MHz, CDCl$_3$) δ 9.89 (s, 1H), 8.80 (s, 1H), 7.86–7.89 (m, 1H), 7.70 (dd, 1H, J=8.7, 0.9 Hz), 7.58 (dd, 1H, J=8.7, 1.2 Hz), 7.49–7.53 (m, 1H), 7.17–7.31 (m, 3H), 6.90–6.97 (m, 1H), 5.82 (s, 2H), 5.28 (s, 2H), 3.86 (t, 2H, J=8.4 Hz), 3.67 (t, 2H, J=8.1 Hz), 0.92–1.04 (m, 4H), 0.02 (s, 9H), −0.02 (s, 9H). Anal. ($C_{32}H_{40}F_2N_4O_3S_2$. 0.25 $H_2O$) C, H, N.

(c) Example 49—3-[-3-(1H-Benzoimidazol-2-yl)-1H-indazol-5-yl]-2,4difluoro-phenol The title compound was prepared in 70% yield by the SEM-deprotection of intermediate 49b in a manner analogous to the procedure for example 41. $^1$H NMR (300 MHz, DMSO-d$_6$) δ 13.75 (s, 1H), 13.00 (s, 1H), 9.88 (s, 1H), 8.56 (s, 1H), 7.70–7.78 (m, 2H), 7.48–7.53 (m, 2H), 7.17–7.25 (m, 2H), 6.99–7.05 (m, 2H). Anal. ($C_{20}H_{12}FN_4O.0.33H_2O$) C, H, N. MS (ES) [m+H]/z calculated 363. found 363; [m−H]/z calculated 361. found 361.

EXAMPLE 50

4-[-3-(1H-Benzoimidazol-2-yl)-1H-indazol-5-yl]-3,5-difluoro-phenol and

EXAMPLE 51

2-[-3-(1H-Benzoimidazol-2-yl)-1H-indazol-5-yl-3,5-difluoro-phenol

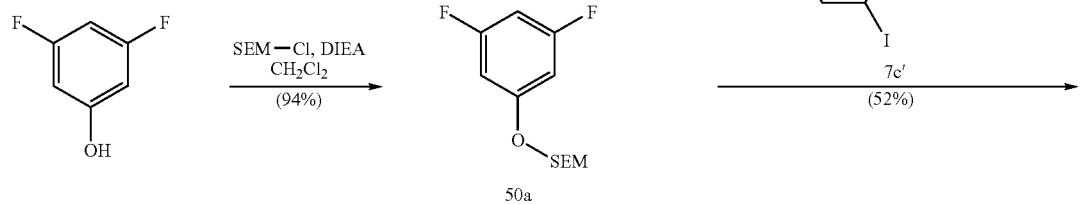

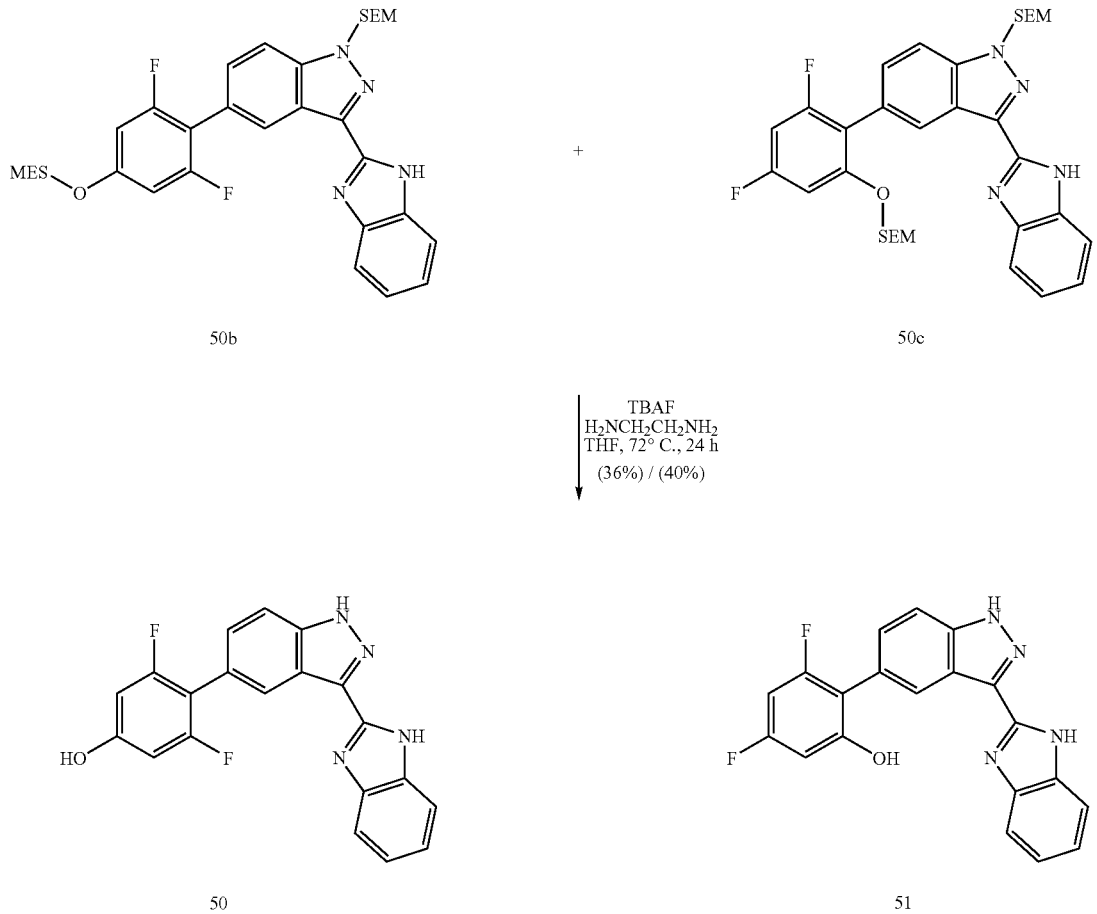

(a) Intermediate 50a—[2-(3,5-Difluoro-phenoxymethoxy)-ethyl]-trimethyl-silane

The title compound was prepared in 94% yield from 3,5-difluorophenol analogous to the procedure to intermediate 49a. $^1$H NMR (300 MHz, CDCl$_3$) δ 6.55–6.60 (m, 2H), 6.40–6.48 (m, 1H), 5.18 (s, 2H), 3.70–3.76 (m, 2H), 0.92–0.98 (m, 2H), 0.01 (s, 9H).

(b) Intermediate mixture 50b and 50c-3-(1H-Benzoimidazol-2-yl)-5{2,6-difluoro-4-[2-(2-trimethylsilanyl-ethoxy-ethoxy]-phenyl}-1-(2-trimethylsilanyl-ethoxymethyl)-1H indazole and 3-(1H-Benzoimidazol-2-yl)-5{2,4-difluoro-6-[2-(2-trimethylsilanyl-ethoxy-ethoxy]-phenyl}-1-(2-trimethylsilanyl-ethoxymethyl)-1H-indazole The title compounds were prepared in 52% yield as an inseparable mixture from intermediate 50a similar to the procedure for intermediate 49b. $^1$H NMR (300 MHz, CDCl$_3$) δ 9.89 (s, 1H), 8.44–8.75 (m, 1H), 7.83–7.93 (m, 1H), 7.45–7.69 (m, 3H), 7.26–7.39 (m, 2.5H), 6.58–6.88 (m, 1.5H), 5.81 (s, 1H), 5.80 (s, 1H), 5.26 (s, 1H), 5.13 (s, 1H), 3.57–3.82 (m, 4H), 0.86–1.04 (m, 4H), −0.06–0.02 (m, 18H).

(c) Example 50—4-[-3-(1H-Benzoimidazol-2-yl)-1H-indazol-5-yl]-3,5-difluoro-phenol The title compound was prepared in 36% yield by the SEM-deprotection of intermediate mixture 50b and 50c in a manner analogous to the procedure for example 41. $^1$H NMR (300 MHz, DMSO-d$_6$) δ 13.73 (s, 1H), 13.01 (s, 1H), 10.50 (s, 1H), 8.50 (s, 1H), 7.70–7.74 (m, 2H), 7.43–7.52 (m, 2H), 7.15–7.25 (m, 2H), 6.62 (dd, 2H, J=13.8, 1.5 Hz). Anal. (C$_{20}$H$_{12}$FN$_4$O . 0.7H$_2$O) C, H, N. MS (ES) [m+H]/z calculated 363. found 363; [m−H]/z calculated 361. found 361.

(d) Example 51—2-[-3-(1H-Benzoimidazol-2-yl)-1H-indazol-5-yl]-3,5-difluoro-phenol The title compound was prepared in 40% yield by the SEM-deprotection of intermediate mixture 50b and 50c in a manner analogous to the procedure for example 41. $^1$H NMR (300 MHz, DMSO-d$_6$) δ 13.65 (s, 1H), 12.98 (s, 1H), 10.39 (s, 1H), 8.47 (s, 1H), 7.66–7.72 (m, 2H), 7.50 (d, 1H, J=7.2 Hz), 7.40 (d, 1H, J=8.4 Hz), 7.14–7.24 (m, 2H), 6.73–6.80 (m, 1H), 6.64 (d, 1H, J=10.5 Hz). Anal. (C$_{20}$H$_{12}$FN$_4$O . 0.9H$_2$O) C, H, N. MS (ES) [m+H]/z calculated 363. found 363; [m−H]/z calculated 361. found 361.

EXAMPLE 52

3-(1H-Benzoimidazol-2-yl)-5-(4-chloro-pyridin-3-yl)-1H-indazole

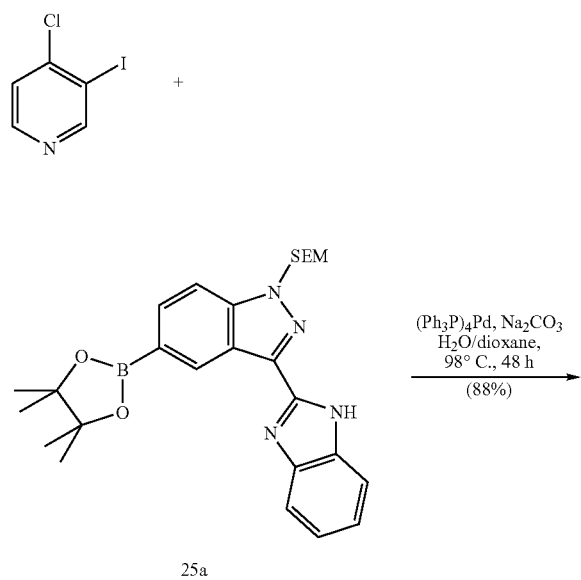

(a) Intermediate 52a—3-(1H-Benzoimidazol-2-yl)-5-(4-chloro-pyridin-3-yl)-1-(2-trimethylsilanyl-ethoxymethyl)-1H-indazole The title compound was prepared in 88% yield from intermediate 25a and 4-chloro-3-iodo-pyridine similar to the procedure for intermediate 41a. $^1$H NMR (300 MHz, CDCl$_3$) δ 9.96 (s, 1H), 8.77 (s, 1H), 8.72 (s, 1H), 8.53 (d, 1H, J=5.4 Hz), 7.85–7.89 (m, 1H), 7.72 (dd, 1H, J=8.7, 0.9 Hz), 7.61 (dd, 1H, J=8.7, 1.5 Hz), 7.50–7.53 (m, 1H), 7.47 (d, 1H, J=5.4 Hz), 7.28–7.35 (m, 2H), 5.84 (s, 2H), 3.65 (t, 2H, J=8.1 Hz), 0.95 (t, 2H, J=8.1 Hz), −0.03 (s, 9H).

(b) Example 52—3-(1H-Benzoimidazol-2-yl)-5-(4-chloro-pyridin-3-yl)-1H-indazole The title compound was prepared in 54% yield by the SEM-deprotection of intermediate 52a in a manner analogous to the procedure for example 41. $^1$H NMR (300 MHz, DMSO-d$_6$) δ 13.81 (s, 1H), 13.02 (s, 1H), 8.70 (s, 1H), 8.56–8.60 (m, 2H), 8.22 (s, 1H), 7.55–7.80 (m, 5H), 7.20 (d, 5H, J=3.6 Hz). Anal. (C$_{22}$H$_{18}$ClN$_3$.0.5H$_2$O) C, H, N. MS (ES) [m+H]/z calculated 346. found 346.

EXAMPLE 53

5-[3-(1H-Benzoimidazol-2-yl)-1H-indazol-5-yl]-4-methyl-[3,4']bipyridinyl

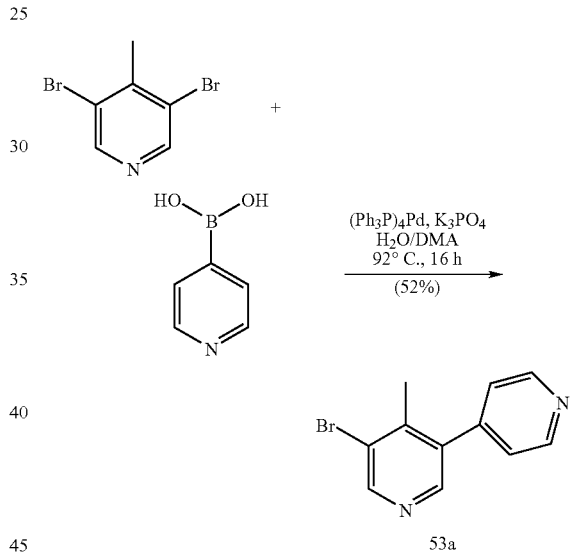

131

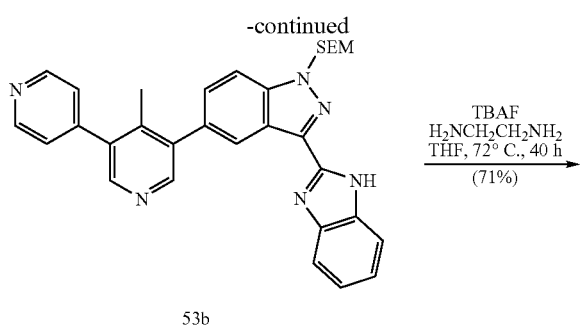

(a) Intermediate 53a—5-(Bromo-4-methyl-[3,4']bipyridinyl 3,5-Dibromo-4-methyl-pyridine (2.21 g, 8.8 mmol), 4-pyridylboronic acid (1.08 g, 8.8 mmol) and potassium phosphate (2.8 g, 13.2 mmol) were stirred in DMA (50 mL)/H₂O (6 mL) in a flask purged with argon. Tetrakis(triphenylphosphine)palladium (0) (812 mg, 0.7 mmol) was added, and the reaction stirred at 92° C. under argon for 16 hours. The solution was concentrated in vacuo, and the residue was dissolved in ethyl acetate. Organics were washed with H₂O and brine, dried (Na₂SO₄), and concentrated in vacuo. Purification by silica gel chromatography (40% to 50% ethyl acetate/hexanes) gave 1.14 g (60%) of intermediate 53a as a white solid. $^1$H NMR (300 MHz, CDCl$_3$) δ 8.73 (dd, 2H, J=4.5, 1.5 Hz), 8.72 (s, 1H), 8.32 (s, 1H), 7.25 (dd, 2H, J=4.5, 1.5 Hz), 2.35 (s, 3H). Anal. ($C_{11}H_9BrN_2$) C, H, N.

(b) Intermediate 53b—5-[3-(1H-Benzoimidazol-2-yl)-1-(2-trimethylsilanyl-ethoxymethyl)-1H-indazol-5-yl]-4-methyl-[3,4']bipyridinyl The title compound was prepared in 64% yield from intermediate 25a and intermediate 53a similar to the procedure for intermediate 41a. $^1$H NMR (300 MHz, CDCl$_3$) δ 10.21 (s, 1H), 8.70–8.76 (m, 3H), 8.61 (s, 1H), 8.46 (s, 1H), 7.85–7.88 (m, 1H), 7.72 (dd, 1H, J=8.7, 0.9 Hz), 7.47–7.53 (m, 2H), 7.24–7.37 (m, 4H), 5.84 (s, 2H), 3.64 (t, 2H, J=8.1 Hz), 2.19 (s, 3H), 0.94 (t, 2H, J=8.1 Hz), −0.04 (s, 9H).

132

(c) Example 53—5-[3-(1H-Benzoimidazol-2-yl)-1H-indazol-5-yl]-4-methyl-[3,4']bipyridinyl The title compound was prepared in 71% yield by the SEM-deprotection of intermediate 53b in a manner analogous to the procedure for example 41. $^1$H NMR (300 MHz, DMSO-d$_6$) δ 13.79 (s, 1H), 13.02 (s, 1H), 8.71 (d, 2H, J=4.8 Hz), 8.55 (s, 1H), 8.51 (s, 1H), 8.47 (s, 1H), 7.78 (d, 1H, J=8.7 Hz), 7.52–7.58 (m, 5H), 7.18–7.21 (m, 2H), 2.17 (s, 3H). Anal. ($C_{25}H_{18}N_6$·0.75H$_2$O) C, H, N. MS (ES) [m+H]/z calculated 403. found 403; [m−H]/z calculated 401. found 401.

EXAMPLE 54

5-[3-(1H-Benzolimidazol-2-yl)-1H-indazol-5-yl]-1,2,3,4,4a,8a-hexahydro-[1,7]naphthyridine

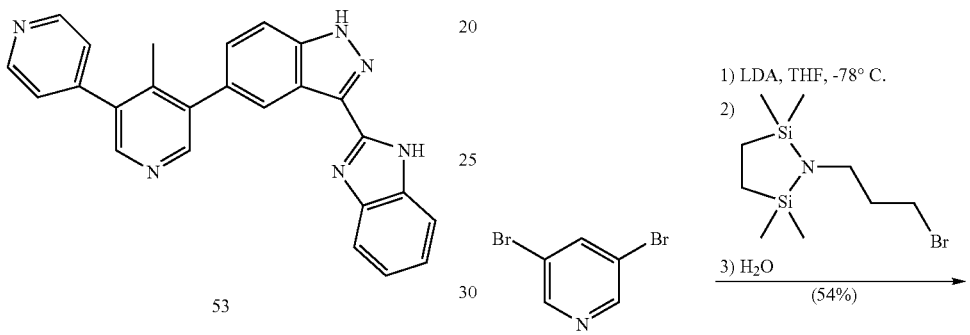

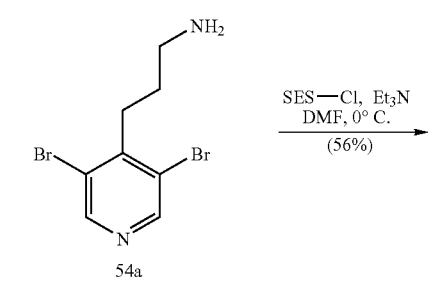

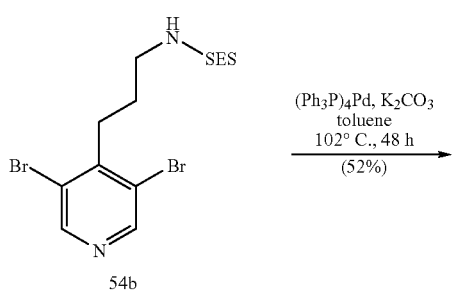

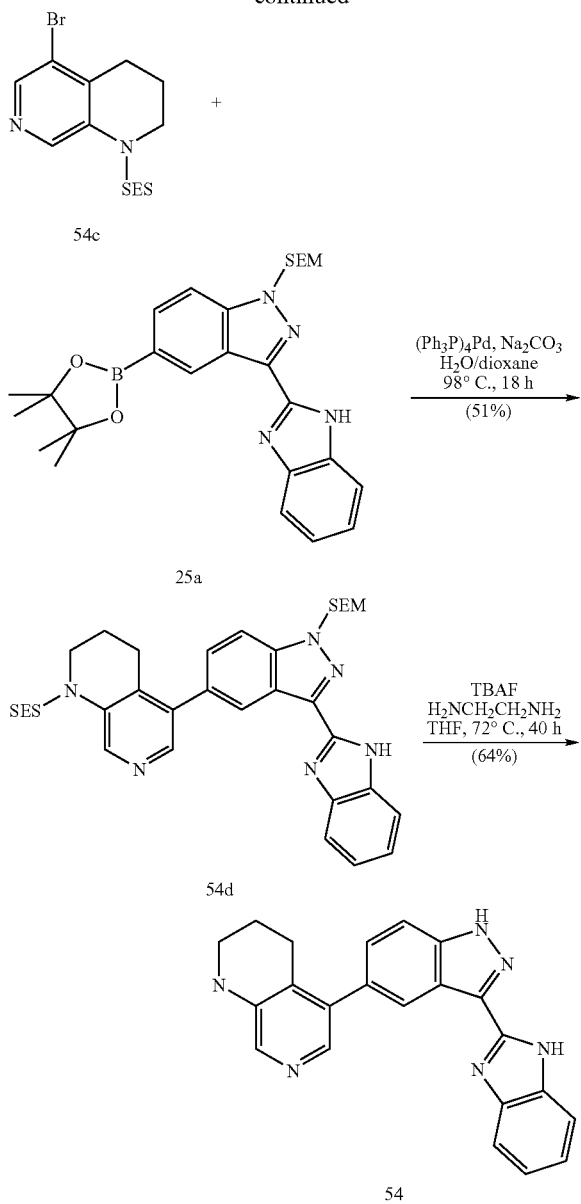

(a) Intermediate
54a—3-(3,5-Dibromo-pyridin-4-yl)-propylamine

LDA was prepared by the addition of n-butyllithium (2.5 M in hexanes, 6.8 mL, 17.0 mmol) to a solution of diisopropylamine (2.5 mL, 17.8 mmol) in THF (40 mL) at −20° C. After 10 minutes, the solution was cooled to −78° C. 3,5-Dibromopyridine (3.84 g, 16.2 mmol) in THF (25 mL) was added dropwise, and the reaction stirred for 30 minutes 1-(3-Bromopropyl)-2,2,5,5-tetramethyl-1-aza-2,5-disilacyclopentate (5 g, 17.8 mmol) was added, and the reaction stirred for 1 hour at −78° C. and then for 1 hour while warming to 0° C. The reaction was quenched with sat. NH$_4$Cl, made basic with saturated NaHCO$_3$, and extracted with ethyl acetate. Organics were washed with brine, dried over Na$_2$SO$_4$, and concentrated in vacuo. Purification by silica gel chromatography (15% MeOH/CHCl$_3$) gave 2.72 g (54%) of intermediate 54a as a tight brown oil. $^1$H NMR (300 MHz, CDCl$_3$) δ 8.55 (d, 2H), 2.72–3.05 (m, 6H), 1.70–1.77 (m, 2H).

(b) Intermediate 54b—2-Trimethylsilanyl-ethanesulfonic acid [3-(3,5-dibromo-pyridin-4yl)-propyl]-amide Intermediate 54a (2.7 g, 9.2 mmol) was stirred with triethylamine (1.92 mL, 13.8 mmol) in dry DMF (20 mL) at 0° C. 2-Trimethylsilyanyl-ethanesulfonyl chloride, SES-Cl, (see Weinreb et al., Tet. Lett. 27, 19, 1986, 2099–2102) (1.9 g, 9.5 mmol) was added slowly, and the reaction stirred for 1.5 hours at 0° C. The reaction was diluted with H$_2$O and extracted with ether. Organics were washed with brine, dried over Na$_2$SO$_4$, and concentrated in vacuo. Purification by silica gel chromatography (33% ethyl acetate/hexanes) gave 2.37 g (56%) of intermediate 54b as a white solid. $^1$H NMR (300 MHz, CDCl$_3$) δ 8.58 (s, 2H), 4.36 (t, 1H, J=6.3 Hz), 3.26 (q, 2H, J=6.3 Hz), 2.93–3.06 (m, 4H), 1.81–1.89 (m, 2H), 1.00–1.07 (m, 2H), 0.07 (s, 9H). Anal. (C$_{13}$H$_{22}$Br$_2$N$_2$O$_2$SSi) C, H, N, S.

(c) Intermediate 54c—5-Bromo-1-(2-trimethylsilanyl-ethanesulfonyl)-1,2,3,4-tetrahydro-[1,7]naphthyridine Intermediate 54b (860 mg, 1.88 mmol) and potassium carbonate (390 mg, 2.82 mmol) were stirred in dry toluene (15 mL) in a flask purged with argon. Tetrakis(triphenylphosphine)palladium (0) (218 mg, 0.19 mmol) was added, and the reaction stirred under argon at 102° C. for 48 hours. The reaction was diluted with ethyl acetate and washed with brine, dried (Na$_2$SO$_4$), and concentrated in vacuo. Purification by silica gel chromatography (25% ethyl acetate/hexanes) gave 372 mg (52%) of intermediate 54c as a waxy white solid. $^1$H NMR (300 MHz, CDCl$_3$) δ 8.70 (s, 1H), 8.42 (s, 1H), 3.72–3.76 (m, 2H), 3.07–3.14 (m, 2H), 2.83 (t, 2H, J=6.9 Hz), 2.07–2.12 (m, 2H), 1.04–1.11 (m, 2H), 0.05 (s, 9H). Anal. (C$_{13}$H$_{21}$BrN$_2$O$_2$SSi) C, H, N, S.

(d) Intermediate 54d—5-[3-(11Benzolimidazol-2-yl)-1-(2-trimethylsilanl-ethoxymethyl)-1H-indazol-5-yl]-1-(2-trimethylsilanyl-ethanesulfonyl)-1,2,3,4,4a,8a-hexahydro-[1,7]naphthyridine The title compound was prepared in 51% yield from intermediate 25a and intermediate 54c similar to the procedure for intermediate 41a. $^1$H NMR (300 MHz, CDCl$_3$) δ 10.36 (s, 1H), 8.88 (s, 1H), 8.64 (t, 1H, J=0.9 Hz), 8.29 (s, 1H), 3.82–3.86 (m, 1H), 7.69 (dd, 1H, J=8.7, 0.9 Hz), 7.50–7.52 (m, 1H), 7.41 (dd, 1H, J=8.7, 1.5 Hz), 7.26–7.33 (m, 2H), 5.83 (s, 2H), 3.80 (t, 2H, J=5.7 Hz), 3.63 (t, 2H, J=8.1 Hz), 3.13–3.20 (m, 2H), 2.72 (t, 2H, J=6.6 Hz), 1.93–1.99 (m, 2H), 1.10–1.16 (m, 2H), 0.94 (t, 2H, J=8.1 Hz), 0.09 (s, 9H), −0.05 (s, 9H).

(e) Example 54—5-[3-(1H-Benzolimidazol-2-yl)-1H-indazol-5-yl]-1,2,3,4,4a,8a-hexahydro-[1,7]naphthyridine The title compound was prepared in 64% yield by the SEM, SES-deprotection of intermediate 54d in a manner analogous to the procedure for example 41. $^1$H NMR (300 MHz, DMSO-d$_6$) δ 13.71 (s, 1H), 13.00 (s, 1H), 8.41 (s, 1H), 7.82 (s, 1H), 7.69 (d, 2H, J=8.7 Hz), 7.63 (s, 1H), 7.50 (d, 1H, J=7.2 Hz), 7.44 (dd, 1H, J=8.7, 1.5 Hz), 7.16–7.22

(m, 2H), 6.11 (s, 1H), 3.23 (br s, 2H), 2.55 (t, 2H, J=6.0 Hz), 1.68–1.73 (m, 2H). Anal. (C$_{22}$H$_{18}$N$_6$·0.45H$_2$O) C, H, N. MS (ES) [m+H]/z calculated 366. found 366.

EXAMPLE 55

N-{4-[3-(1H-Benzoimidazol-2-yl)-1H-indazol-5-yl]-isoquinolin-8-yl}-nicotinamide

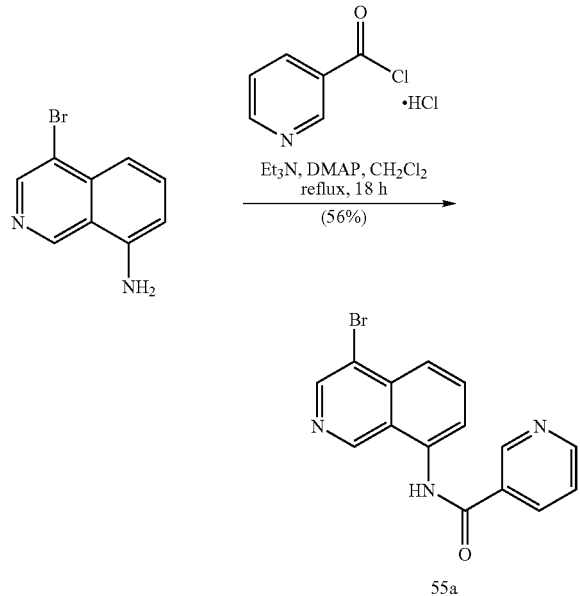

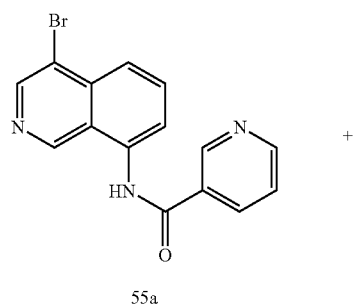

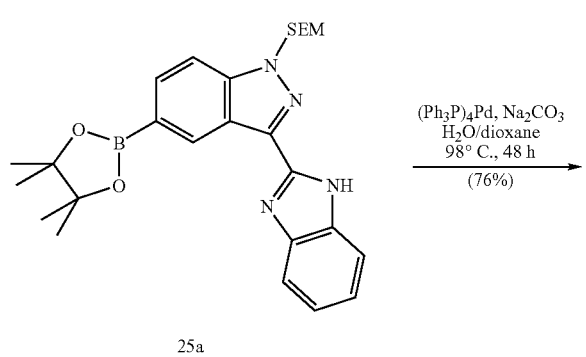

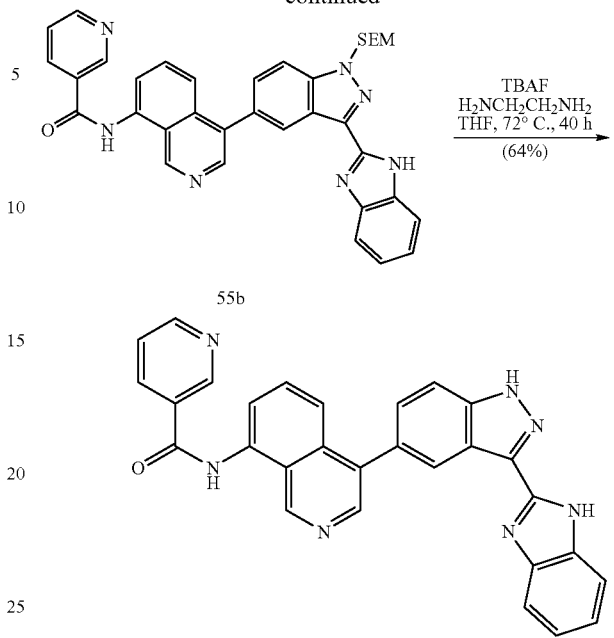

(a) Intermediate 55a—N-(4-Bromo-isoquinolin-8-yl)-nicotinamide

8-Amino-4-bromo-isoquinoline (328 mg, 1.47 mmol), triethylamine (820 μL, 5.9 mmol), and DMAP (10 mg) were stirred in CH$_2$Cl$_2$ (50 mL). Nicotinoyl chloride, hydrochloride (395 mg, 2.2 mmol) was added, and the reaction stirred at reflux for 18 hours. The reaction was concentrated in vacuo and purified by silica gel chromatography (3% MeOH/ethyl acetate) to give 272 mg (56%) of intermediate 55a as a white solid. $^1$H NMR (300 MHz, CDCl$_3$) δ 10.95 (s, 1H), 9.46 (s, 1H), 9.25 (d, 1H, J=1.5 Hz), 8.81 (dd, 2H, J=4.8, 1.5 Hz), 8.40–8.45 (m, 1H), 7.92–8.06 (m, 3H), 7.59–7.64 (m, 1H). Anal. (C$_{15}$H$_{10}$BrN$_3$O) C, H, N.

(b) Intermediate 55b—N-{4-[3-(1H-Benzoimidazol-2-yl)-1-(2-trimethylsilanyl-ethyoxymethyl)-1H-indazol-5-yl]-isoquinolin-8-yl}-nicotinamide The title compound was prepared in 76% yield from intermediate 25a and intermediate 55a similar to the procedure for intermediate 41a. $^1$H NMR (300 MHz, CDCl$_3$) δ 10.27 (s, 1H), 9.48 (s, 1H), 9.29 (d, 1H, J=1.8 Hz), 8.83–8.88 (m, 2H), 8.79 (s, 1H), 8.58 (s, 1H), 8.36 (d, 1H, J 20=7.8 Hz), 8.02 (d, 1H, J=6.9 Hz), 7.73–7.81 (m, 3H), 7.58–7.65 (m, 2H), 7.47–7.53 (m, 2H), 7.24–7.29 (m, 2H), 5.86 (s, 2H), 3.67 (t, 2H, J=8.1 Hz), 0.96 (t, 2H, J=8.1 Hz), –0.04 (s, 9H).

(c) Example 55—N{4-[3-(1H-Benzoimidazol-2-yl)-11 indazol-5-yl]-isoquinolin-8-yl}-nicotinamide The title compound was prepared in 78% yield by the SEM-deprotection of intermediate 55b in a manner analogous to the procedure for example 41. $^1$H NMR (300 MHz, DMSO-d$_6$) δ 13.85 (s, 1H), 13.04 (s, 1H), 10.98 (s, 1H), 9.54 (s, 1H), 9.30 (d, 2H, J=1.8 Hz), 8.83 (dd, 1H, J=4.8, 1.8 Hz), 8.65 (s, 1H), 8.59 (s, 1H), 8.45–8.50 (m, 4H), 7.52–7.66 (m, 4H), 7.18 (br s, 2H). Anal. (C$_{29}$H$_{19}$N$_7$O.0.5H$_2$O) C, H, N. MS (ES) [m+H]/z calculated 482. found 482.

EXAMPLE 56

N-{4-[3-(1H-Benzoimidazol-2-yl)1H-indazol-5-yl]-isoquinolin-8-yl}-acetamide

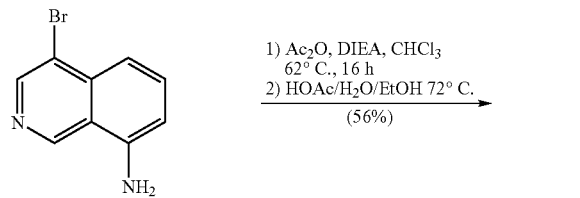

(a) Intermediate 56a—N(4-Bromo-isoquinolin-8-yl)-acetamide

8-Amino-4-bromo-isoquinoline (300 mg, 1.35 mmol), DIEA (0.94 mL, 5.38 mmol), and acetic anhydride (255 µL, 2.7 mmol) were stirred in chloroform (20 mL) at reflux for 16 hours. The solution was washed with H$_2$O and brine, dried (Na$_2$SO$_4$), and concentrated in vacuo. The residue was stirred in ethanol (6 mL) with HOAc (2 mL) at 72° C. for 20 hours. The solution was allowed to cool and was diluted with ethyl acetate. Organics were washed with 1 N NaOH and brine, dried (MgSO$_4$), and concentrated in vacuo. Purification by silica gel chromatography (ethyl acetate) gave 232 mg (65%) of intermediate 56a as a white solid. $^1$H NMR (300 MHz, CDCl$_3$) δ 10.31 (s, 1H), 9.47 (s, 1H), 8.77 (s, 1H), 7.90–7.97 (m, 3H), 2.21 (s, 3H). Anal. (C$_{11}$H$_9$BrN$_2$O) C, H, N.

(b) Intermediate 56b—N{4-[3-(1H-Benzoimidazol-2-yl)-1-(2-trimethylsilanyl-ethyoxymethyl)-1H-indazol-5-yl]-isoquinolin-8-yl}-acetamide The title compound was prepared in 80% yield from intermediate 25a and intermediate 56a similar to the procedure for intermediate 41a. $^1$H NMR (300 MHz, CDCl$_3$) δ 10.39 (s, 1H), 9.46 (s, 1H), 8.76 (s, 1H), 8.53 (s, 1H), 8.42 (s, 1H), 7.91 (d, 1H, J=7.2 Hz), 7.89 (d, 1H, J=7.2 Hz), 7.62–7.72 (m, 3H), 7.48–7.57 (m, 3H), 7.24–7.28 (m, 1H), 5.83 (s, 2H), 3.65 (t, 2H, J=8.1 Hz), 2.35 (s, 3H), 0.95 (t, 2H, J=8.1 Hz), –0.04 (s, 9H).

(c) Example 56—N-{4-[3-(1H-Benzoimidazol-2-yl)1H-indazol-5-yl]-isoquinolin-8-yl}-acetamide The title compound was prepared in 68% yield by the SEM-deprotection of intermediate 56b in a manner analogous to the procedure for example 41. $^1$H NMR (300 MHz, DMSO-d$_6$) δ 13.84 (s, 1H), 13.03 (s, 1H), 10.34 (s, 1H), 9.56 (s, 1H), 8.61 (s, 1H), 8.55 (s, 1H), 7.82–7.89 (m, 2H), 7.74 (t, $_1$H, J=7.2 Hz), 7.59–7.66 (m, 3H), 7.51 (d, 1H, J=7.2 Hz), 7.13–7.21 (m, 2H), 2.25 (s, 3H). Anal. (C$_{25}$H$_{18}$N$_6$O.0.4H$_2$O) C, H, N. MS (ES) [m+H]/z calculated 419. found 419.

EXAMPLE 57

N-{4-[3-(1H-Benzoimidazol-2-yl)1H-indazol-5-yl-isoquinolin-8-yl}-benzyl-amine

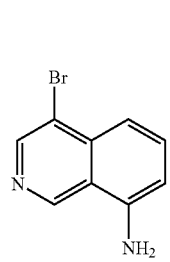

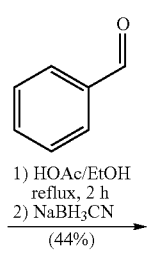

57a

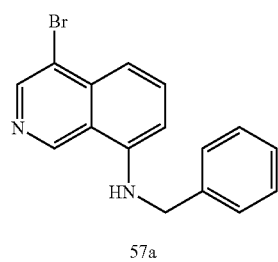
57a

+

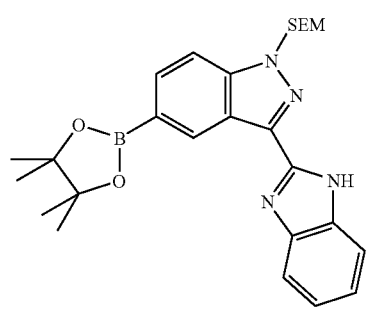
25a

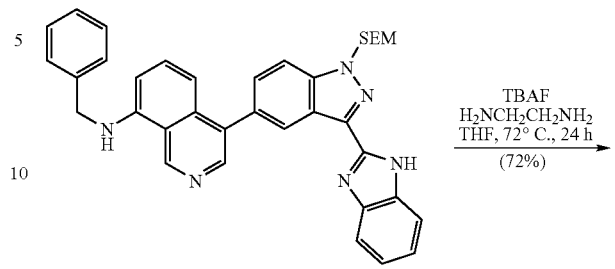
57b

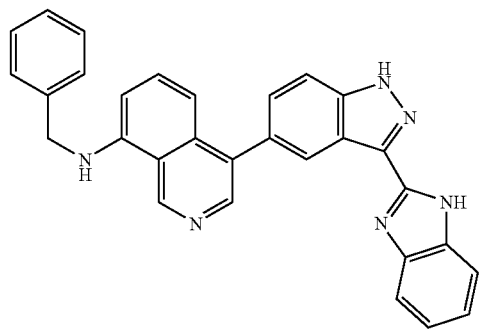
57

(a) Intermediate 57a—Benzyl-(4-bromo-isoquinoline-8-yl)-amine

8-Amino-4-bromo-isoquinoline (220 mg, 0.99 mmol) and benzaldehyde (110 μL, 1.1 mmol) were stirred in ethanol (15 mL)/HOAc (0.2 mL) at reflux for 24 hours. The reaction was cooled to 0° C., and sodium cyanoborohydride (622 mg, 9.9 mmol) was added in portions. After stirring for 1 hour, the reaction was diluted with H$_2$O and extracted with ethyl acetate. Organics were washed with brine, dried (Na$_2$SO$_4$) and concentrated in vacuo. Purification by silica gel chromatography (33% ethyl acetate/hexanes) gave 136 mg (44%) of intermediate 57a as a light yellow solid. $^1$H NMR (300 MHz, CDCl$_3$) δ 9.61 (s, 1H), 8.64 (s, 1H), 7.79 (t, 1H, J=5.7 Hz), 7.55 (t, 1H, J=8.1 Hz), 7.28–7.42 (m, 4H), 7.15–7.24 (m, 2H), 6.58 (d, 1H, J=8.4 Hz), 4.53 (d, 2H, J=5.7 Hz). Anal. (C$_{16}$H$_{13}$BrN$_3$) C, H, N.

(b) Intermediate 57b—N{4-[3-(1H-Benzoimidazol-2-yl)-1-(2-trimethylsilanyl-ethyoxymethyl)-1H-indazol-5-yl]-isoquinolin-8-yl}-benzyl-amine The title compound was prepared in 72% yield from intermediate 25a and intermediate 57a similar to the procedure for intermediate 41a. $^1$H NMR (300 MHz, CDCl$_3$) δ 10.02 (s, 1H), 9.38 (s, 1H), 8.82 (s, 1H), 8.56 (s, 1H), 7.82 (d, 1H, J=8.7 Hz), 7.73 (d, 1H, J=8.7 Hz), 7.63 (dd, 1H, J=8.4, 1.5 Hz), 7.24–7.52 (m, 9H), 7.17 (d, 1H, J=8.4 Hz), 6.69 (d, 1H, J=7.5 Hz), 5.86 (s, 2H), 5.23 (s, 1H), 4.58 (d, 2H, J=4.5 Hz), 3.67 (t, 2H, J=8.1 Hz), 0.97 (t, 2H, J=8.1 Hz), −0.03 (s, 9H).

(c) Example 57—N-{4-[3-(1H-Benzoimidazol-2-yl)-1H-indazol-5-yl]-isoquinolin-8-yl}-benzyl-amine The title compound was prepared in 72% yield by the SEM-deprotection of intermediate 57b in a manner analogous to the procedure for example 41. $^1$H NMR (300 MHz, DMSO-$d_6$) δ 13.80 (s, 1H), 13.01 (s, 1H), 9.71 (s, 1H), 8.56 (s, 1H), 8.42 (s, 1H), 7.71–7.81 (m, 2H), 7.30–7.63 (m, 8H), 7.17–7.25 (m, 3H), 6.90 (d, 1H, J=7.2 Hz), 6.52 (d, 1H, J=7.2 Hz), 4.57 (d, 2H, J=5.4 Hz). Anal. ($C_{30}H_{22}N_6 \cdot 0.5H_2O$) C, H, N. MS (ES) [m+H]/z calculated 467. found 467.

EXAMPLE 58

3-[3-(1H-Benzoimidazol-2-yl)-1H-indazol-5-yl]-4-methyl-[3,3']bipyridinyl

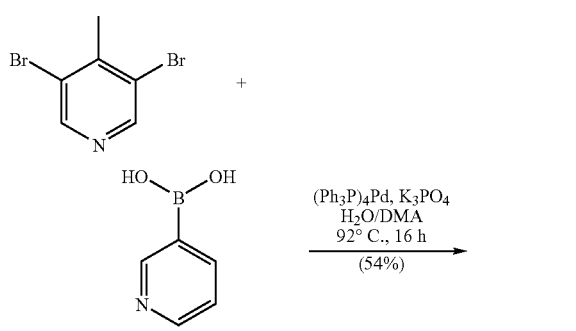

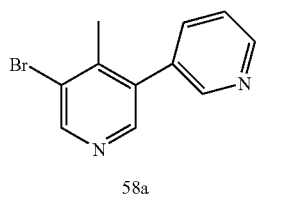

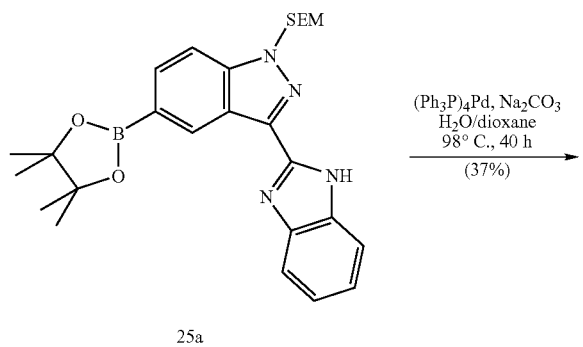

(a) Intermediate 58a—5-Bromo-4-methyl-[3,3']bipyridinyl

The title compound was prepared in 54% yield from 3,5-dibromo-4-methyl-pyridine and 3-pyridyl boronic acid analogous to the procedure for intermediate 53a. $^1$H NMR (300 MHz, CDCl$_3$) δ 8.67–8.71 (m, 2H), 8.59 (dd, 1H, J=2.4, 0.6 Hz), 8.33 (s, 1H), 7.62–7.66 (m, 1H), 7.39–7.44 (m, 1H), 2.35 (m, 3H). Anal. ($C_{11}H_9BrN_2 \cdot 0.1H_2O$) C, H, N.

(b) Intermediate 58b—3-[3-(1H-Benzoimidazol-2-yl)-1-(2-trimethylsilanyl-ethoxymethyl)-1H-indazol-5-yl]-4-methyl-[3,3']bipyridinyl The title compound was prepared in 37% yield from intermediate 25a and intermediate 58a analogous to the procedure for intermediate 41a. $^1$H NMR (300 MHz, CDCl$_3$) δ 10.24 (s, 1H), 8.68–8.71 (m, 3H), 8.61 (s, 1H), 8.47 (s, 1H), 7.85–7.88 (m, 1H), 7.70–7.78 (m, 2H), 7.42–7.53 (m, 3H), 7.26–7.33 (m, 2H), 5.83 (s, 2H), 3.64 (t, 2H, J=8.1 Hz), 2.19 (s, 3H), 0.95 (t, 2H, J=8.1 Hz), −0.05 (s, 9H).

(c) Example 58—3-[3-(1H-Benzoimidazol-2-yl)-1H-indazol-5-yl]-4-methyl-[3,3']bipyridinyl The title compound was prepared in 74% yield by the SEM-deprotection of intermediate 58b in a manner analogous to the procedure for example 41. $^1$H NMR (300 MHz, DMSO-$d_6$) δ 13.79 (s, 1H), 13.02 (s, 1H), 8.72 (d, 1H, J=1.5 Hz), 8.65 (dd, 1H, J=4.8, 1.5 Hz), 8.54 (s, 1H), 8.52 (s, 1H), 8.48 (s, 1H), 7.96–8.00 (m, 1H), 7.78 (d, 1H, J=8.7 Hz), 7.69 (d, 1H, J=7.5 Hz), 7.49–7.57 (m, 3H), 7.17–7.23 (m, 2H), 2.16 (s, 3H). Anal. ($C_{25}H_{18}N_6 \cdot 0.6H_2O$) C, H, N. MS (ES) [m+H]/z calculated 403. found 403.

EXAMPLE 59
(E)-3-{5-[3-(1H-Benzoimidazol-2-yl)-1H-indazol-5-yl]-4-methyl-pyridin-3-yl}-prop-2-en-1-ol and
EXAMPLE 60
(E)-3-{5-[3-(1H-Benzoimidazol-2-yl)-1H-indazol-5-yl]-4-methyl-pyridin-3-yl}-propan-1-ol
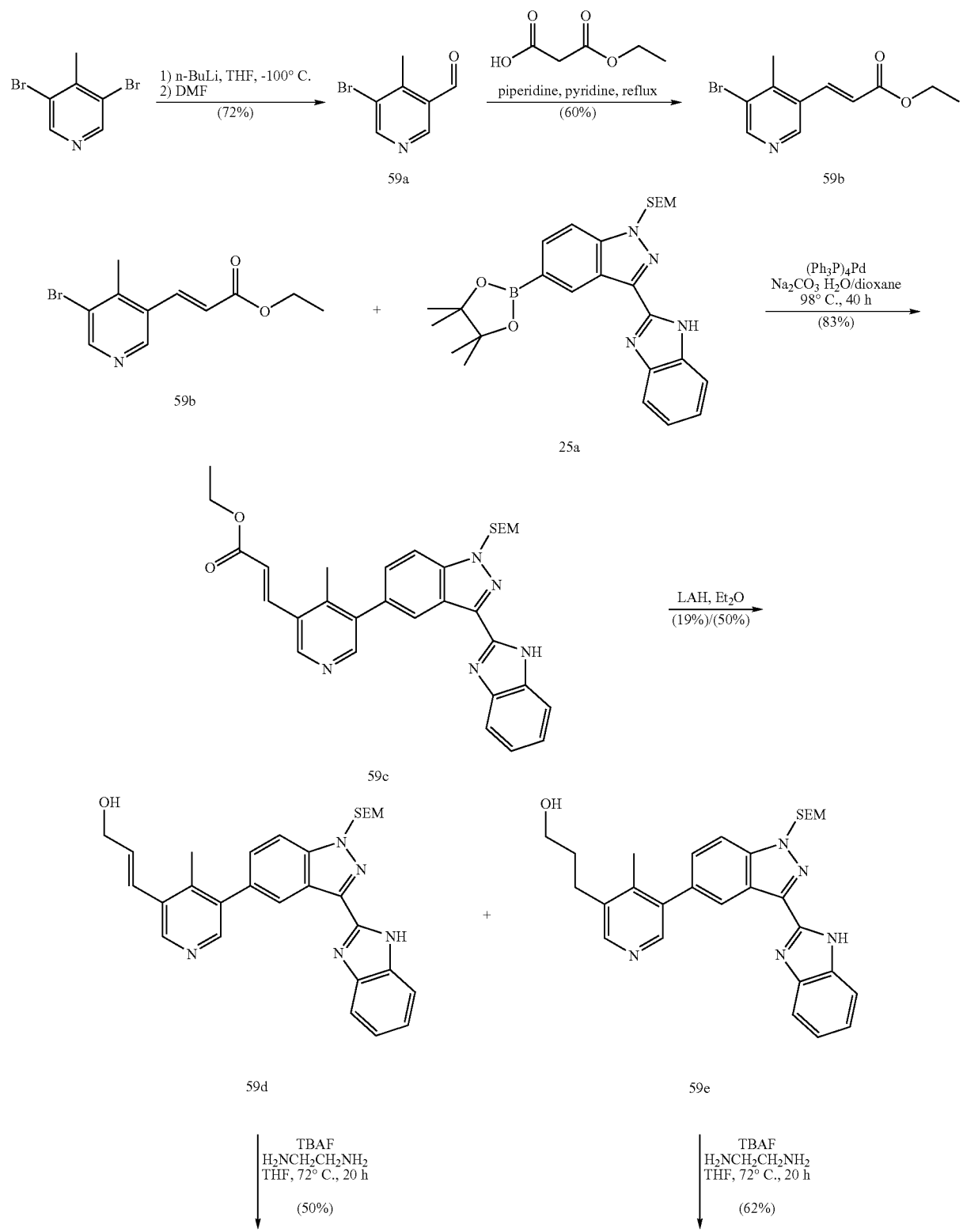

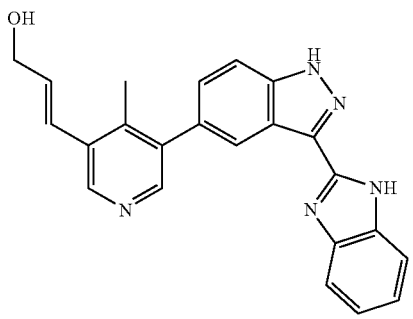

59

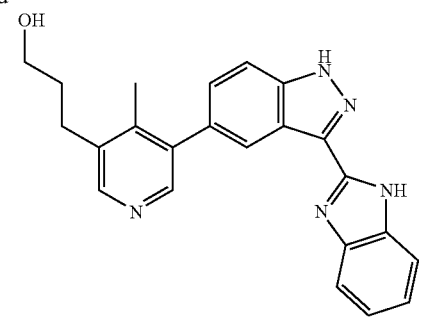

60

(a) Intermediate 59a—5-Bromo-4-methyl-pyridine-3-carbaldehyde 3,5-Dibromo-4-methyl-pyridine (3.8 g, 15.1 mmol) was stirred in dry THF (150 mL) at −100° C. ($N_2$/ether) under argon. n-Butyllithium (2.5 M in hexanes, 6.2 mL, 15.4 mmol) was added dropwise, and the reaction stirred for 5 minutes DMF (1.8 mL, 23.2 mmol) was added, and the reaction was stirred for 20 minutes at −100° C. and then for 1 hour at −78° C. The reaction was quenched with sat. $NH_4Cl$ and extracted with ether. Organics were washed with brine, dried over $Na_2SO_4$, and concentrated in vacuo. Purification by silica gel chromatography (20% ethyl acetate/hexanes) gave 2.18 g (72%) of intermediate 59a as a clear oil which slowly solidified. $^1H$ NMR (300 MHz, $CDCl_3$) δ 10.25 (s, 1H), 8.84 (s, 1H), 8.83 (s, 1H), 2.76 (s, 3H). Anal. ($C_7H_6BrNO$) C, H, N.

(b) Intermediate 59b—(E)-3-(5-Bromo-4-methyl-pyridin-3-yl)-acrylic acid ethyl ester Intermediate 59a (690 mg, 3.45 mmol), ethyl hydrogen malonate (600 mg, 4.5 mmol), and piperidine (170 µL, 1.73 mmol) were refluxed in pyridine (5 mL) for 7 hours The reaction was concentrated in vacuo and purified by silica gel chromatography (20% ethyl acetate/hexanes) to give 560 mg (60%) of intermediate 59b as a waxy white solid. $^1H$ NMR (300 MHz, $CDCl_3$) δ 8.65 (s, 1H), 8.57 (s, 1H), 7.87 (d, 1H, J=15.9 Hz), 6.39 (d, 1H, J=15.9 Hz), 4.29 (q, 2H, J=7.2 Hz), 2.50 (s, 3H), 1.35 (t, 3H, J=7.2 Hz). Anal. ($C_{11}H_{12}BrNO_2$) C, H, N.

(c) Intermediate 59c—(E)-3-{5-[3-(1H-Benzoimidazol-2-yl)-1-(2-trimethylsilanyl-ethoxymethyl)-1H-indazol-5-yl]-4-methyl-pyridin-3-yl}-acrylic acid ethyl ester The title compound was prepared in 83% yield from intermediate 25a and intermediate 59b similar to the procedure for intermediate 41a. $^1H$ NMR (300 MHz, $CDCl_3$) δ 10.00 (s, 1H), 8.74 (s, 1H), 8.65 (s, 1H), 8.55 (s, 1H), 7.99 (d, 1H, J=15.9 Hz), 7.83–7.87 (m, 1H), 7.71 (d, 1H, J=8.7 Hz), 7.50–7.53 (m, 1H), 7.43 (dd, 1H, J=8.7, 1.5 Hz), 7.27–7.32 (m, 2H), 6.50 (d, 1H, J=15.9 Hz), 5.84 (s, 2H), 4.31 (q, 2H, J=7.2 Hz), 3.65 (t, 2H, J=8.1 Hz), 2.36 (s, 3H), 1.37 (t, 3H, J=7.2 Hz), 0.95 (t, 2H, J=8.1 Hz), −0.04 (s, 9H).

(d) Intermediate 59d—(E)-3-{5-[3-(1H-Benzoimidazol-2-yl)-1-(2-trimethylsilanyl-ethoxymethyl)-1H-indazol-5-yl]-4-methyl-pyridin-3-yl}-prop-2-en-1-ol A solution of intermediate 59c (402 mg, 0.73 mmol) in ether (10 mL) was added dropwise to a stirred suspension of LAH (180 mg, 4.74 mmol) in ether (10 mL) at 0° C. The reaction was allowed to stir for 3 hours while warming to room temperature. The reaction was quenched with water and extracted with ethyl acetate. Organics were washed with brine, dried over $Na_2SO_4$, and concentrated in vacuo. Purification by silica gel chromatography (50% to 100% ethyl acetate/hexanes) gave 72 mg (19%) of intermediate 59d as a white foam (followed by 186 mg (50%) of intermediate 59e). $^1H$ NMR (300 MHz, $CDCl_3$) δ 9.99 (s, 1H), 8.64 (s, 1H), 8.63 (s, 1H), 8.45 (s, 1H), 7.83–7.87 (m, 1H), 7.69 (d, 1H, J=8.7 Hz), 7.50–7.53 (m, 1H), 7.43 (dd, 1H, J=8.7, 1.5 Hz), 7.26–7.32 (m, 2H), 6.86 (d, 1H, J=15.9 Hz), 6.33–6.41 (m, 1H), 5.84 (s, 2H), 4.42 (br s, 2H), 3.65 (t, 2H, J=8.1 Hz), 2.28 (s, 3H), 1.73 (br s, 1H), 0.95 (t, 2H, J=8.1 Hz), −0.04 (s, 9H).

(e) Intermediate 59e—(E)₃-{5-[3-(1H-Benzoimidazol-2-yl)-1-(2-trimethylsilanyl-ethoxymethyl)-1H-indazol-5-yl]-4-methyl-pyridin-3-yl}-propan-1-ol See the procedure for intermediate 59d above. $^1H$ NMR (300 MHz, $CDCl_3$) δ 10.17 (s, 1H), 8.63 (s, 1H), 8.40 (s, 2H), 7.83–7.87 (m, 1H), 7.68 (d, 1H, J=8.7 Hz), 7.49–7.52 (m, 1H), 7.43 (dd, 1H, J=8.7, 1.5 Hz), 7.26–7.31 (m, 2H), 5.83 (s, 2H), 3.77 (t, 2H, J=6.3 Hz), 3.65 (t, 2H, J=8.1 Hz), 2.82 (t, 2H, J=7.5 Hz), 2.24 (s, 3H), 1.88–1.95 (m, 2H), 1.74 (br s, 1H), 0.94 (t, 2H, J=8.1 Hz), −0.05 (s, 9H).

(f) Example 59—(E)-3-{5-[3-(1H-Benzoimidazol-2-yl)-1H-indazol-5-yl]-4-methyl-pyridin-3-yl}-prop-2-en-1-ol The title compound was prepared in 50% yield by the SEM-deprotection of intermediate 59d in a manner analogous to the procedure for example 41. $^1H$ NMR (300 MHz, DMSO-$d_6$) δ 13.78 (s, 1H), 13.02 (s, 1H), 8.63 (s, 1H), 8.43 (s, 1H), 8.35 (s, 1H), 7.75 (d, 1H, J=8.7 Hz), 7.63 (br.s, 1H), 7.55 (br s, 1H), 7.46 (dd, 1H, J=8.7, 1.5 Hz), 7.20 (br s, 2H), 6.83 (d, 1H, J=15.9 Hz), 6.37–6.46 (m, 1H), 4.99 (t, 1H, J=5.4 Hz), 4.19 (s, 2H), 2.23 (s, 3H). Anal. ($C_{23}H_{19}N_5O$ ·0.6$H_2O$) C, H, N. MS (ES) [m+H]/z calculated 382. found 382.

(g) EXAMPLE 60

(E)-3-{5-[3-(1H-Benzoimidazol-2-yl)-1H-indazol-5-yl]-4-methyl-pyridin-3-yl}-propan-1-ol The title compound was prepared in 62% yield by the SEM-deprotection of intermediate 59e in a manner analogous to the procedure for example 41. $^1$H NMR (300 MHz, DMSO-$d_6$) δ 13.77 (s, 1H), 13.02 (s, 1H), 8.41 (s, 1H), 8.37 (s, 1H), 8.30 (s, 1H), 7.73 (d, 1H, J=8.7 Hz), 7.67 (br.s, 1H), 7.52 (br s, 1H), 7.44 (dd, 1H, J=8.7, 1.5 Hz), 7.19 (br s, 2H), 4.57 (t, 1H, J=5.1 Hz), 3.49 (q, 2H, J=6.0 Hz), 2.74 (t, 2H, J=7.8 Hz), 2.21 (s, 3H), 1.69–1.79 (m, 2H). Anal. ($C_{23}H_{21}N_5O\cdot0.5\,H_2O$) C, H, N. MS (ES) [m+H]/z calculated 384. found 384.

EXAMPLE 61

5-[3-(1H-Benzoimidazol-2yl)-1H-indazol-5-yl]-4ethyl-[3,4']bipyridinyl

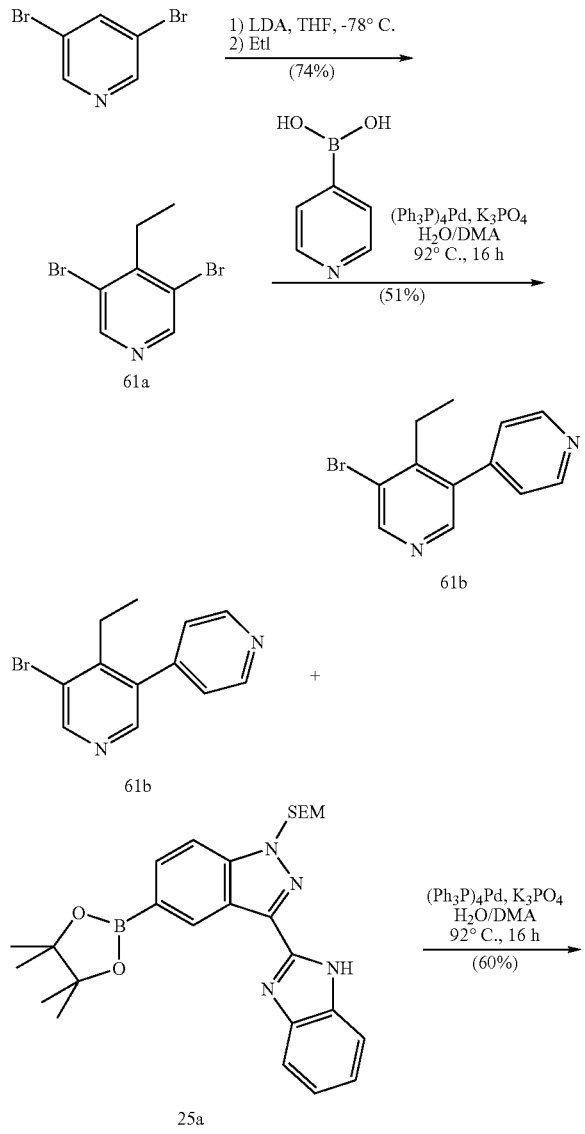

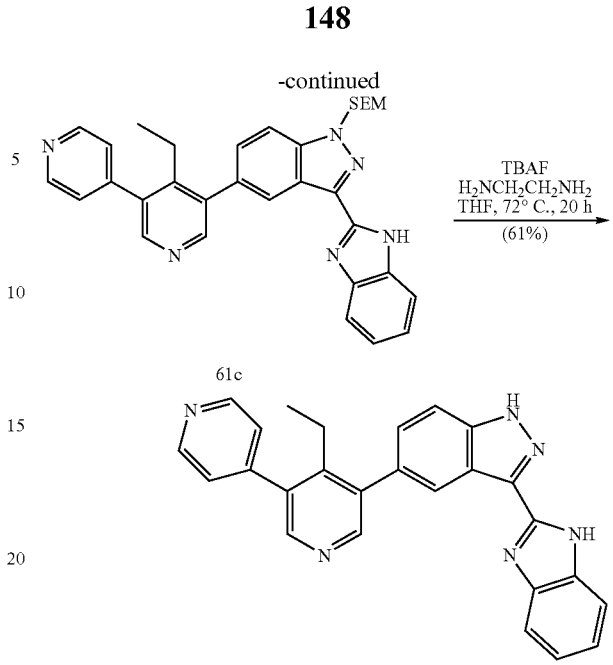

(a) Intermediate 61a—3,5-Dibromo-4-ethyl-pyridine

The title compound was prepared in 74% yield by the substitution of iodoethane for iodomethane in the procedure for the preparation of 3,5-dibromo-4-methyl-pyridine (see Gu, et al., *Tet. Lett.*, 37, 15, 1996, 2565–2568). $^1$H NMR (300 MHz, CDCl$_3$) δ 8.49 (s, 2H), 2.92 (q, 2H, J=7.5 Hz), 1.12 (t, 3H, J=7.5 Hz).

(b) Intermediate 61b—5-(Bromo-4-ethyl-[3,4']bipyridinyl

The title compound was prepared in 51% yield from intermediate 61a and 4-pyridyl boronic acid similar to the procedure for intermediate 53a. $^1$H NMR (300 MHz, CDCl$_3$) δ 8.71–8.74 (m, 3H), 8.28 (s, 1H), 7.24 (dd, 2H, J=4.5, 1.5 Hz), 2.70 (q, 2H, J=7.5 Hz), 1.10 (t, 3H, J=7.5 Hz). Anal. ($C_{12}H_{11}BrN_2$) C, H, N. MS (ES) [m+H]/z calculated 263/265. found 263/265.

(c) Intermediate 61c—5-[3-(1H-Benzoimidazol-2yl)-1-(2-trimethylsilanyl-ethoxymethyl)-1H-indazol-5-yl]-4-ethyl-[3,4']bipyridinyl Intermediate 61b (188 mg, 0.71 mmol), intermediate 25a (385 mg, 0.79 mmol) and potassium phosphate (226 mg, 1.06 mmol) were stirred in DMA (6 mL)/H$_2$O (0.8 mL) in a flask purged with argon. Tetrakis(triphenylphosphine)palladium (0) (82 mg, 0.07 mmol) was added, and the reaction stirred at 92° C. under argon for 16 hours The solution was diluted with ethyl acetate, washed with H$_2$O and brine, dried over Na$_2$SO$_4$, and concentrated in vacuo. Purification by silica gel chromatography (75% to 100% ethyl acetate/hexanes) gave 232 mg (60%) of intermediate 61c as a clear oil. $^1$H NMR (300 MHz, CDCl$_3$) δ 10.18 (s, 1H), 8.71–8.75 (m, 3H), 8.57 (s, 1H), 8.41 (s, 1H), 7.84–7.87 (m, 1H), 7.71 (d, 1H. J=8.Hz), 7.48–7.53 (m, 2H), 7.36 (dd, 2H, J=4.5, 1.5 Hz), 7.26–7.32 (m, 2H), 5.84 (s, 2H), 3.65 (t, 2H, J=8.1 Hz), 2.64 (q, 2H, J=7.5 Hz), 0.94 (t, 2H, J=8.1 Hz), 0.77 (t, 3H, J=7.5 Hz), −0.04 (s, 9H).

(d) Example 61—5-[3-(1H-benzoimidazol-2yl)-1H-indazol-5-yl]-4-ethyl-[3,4']bipyridinyl The title compound was prepared in 61% yield by the SEM-deprotection of intermediate 61c in a manner analogous to the procedure for example 41. $^1$H NMR (300 MHz, DMSO-$d_6$) δ 13.79 (s, 1H), 13.02 (s, 1H), 8.71 (dd, 2H, J=4.5, 1.5 Hz), 8.51 (s, 2H), 8.40 (s, 1H), 7.78 (d, 1H, J=8.7 Hz), 7.68 (d, 1H, J=7.5 Hz), 7.49–7.56 (m, 4H), 7.14–7.25 (m, 2H), 2.59 (q, 2H, J=7.5 Hz), 0.69 (t, 3H, J=7.5 Hz). Anal. ($C_{26}H_{20}N_6 \cdot 0.3H_2O$) C, H, N. MS (ES) [m+H]/z calculated 417. found 417.

EXAMPLE 62

3-[3-(1H-Benzoimidazol-2-yl)-1H-indazol-5-yl]-4-methyl-[2,3']bipyridinyl

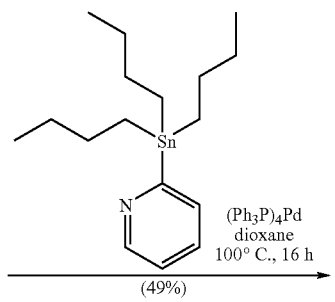

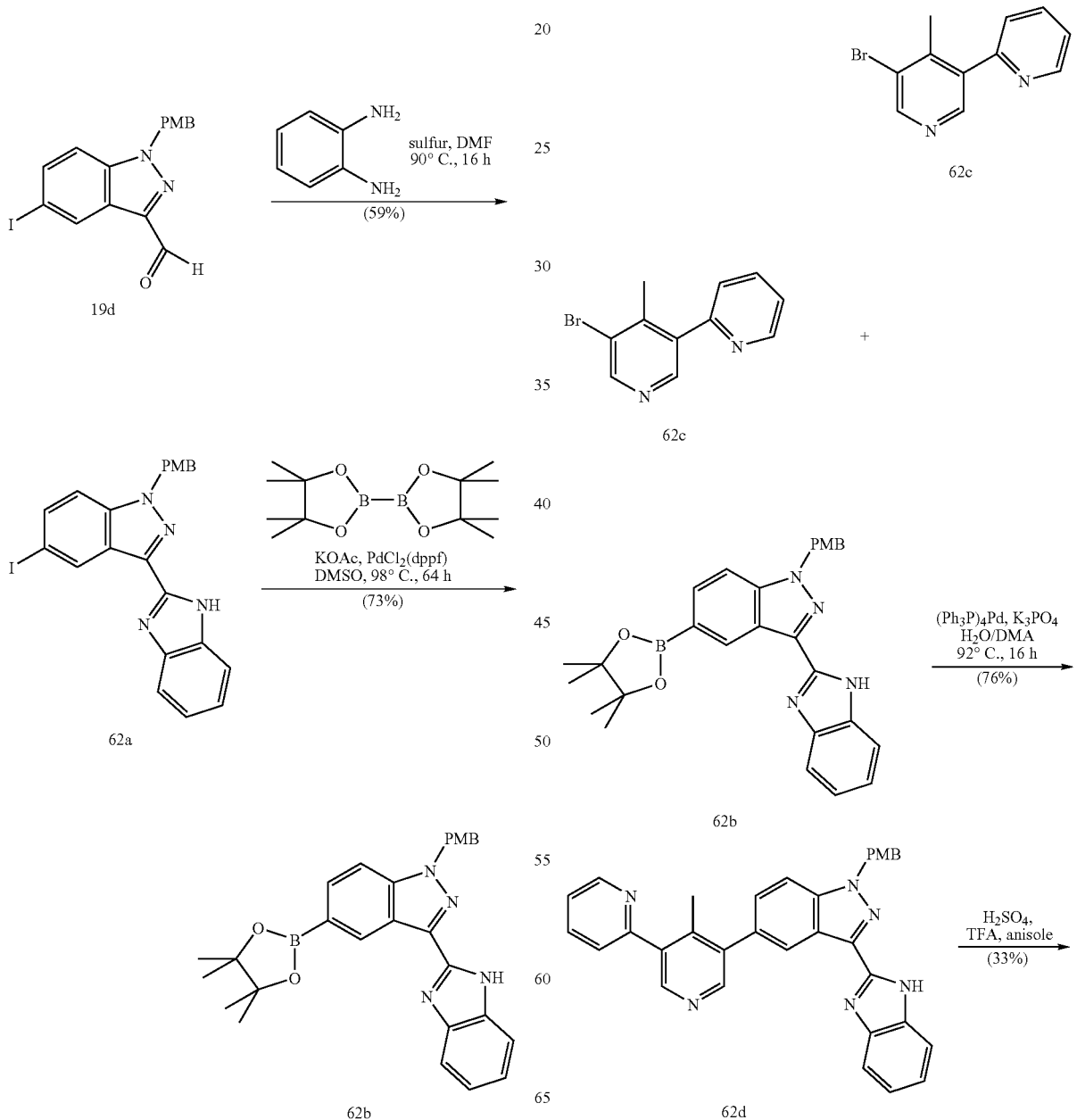

-continued

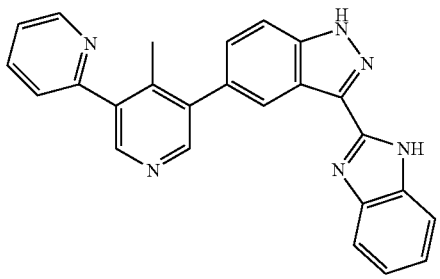

62

(a) Intermediate 62a—3-(1H-Benzoimidazol-2-yl)-5-iodo-1-(4-methoxy-benzyl)-1H-indazole The title compound was prepared in 59% yield from intermediate 19d and phenylenediamine similar to the procedure for intermediate 7c'. $^1$H NMR (300 MHz, DMSO-$d_6$) δ 13.06 (s, 1H), 8.91 (s, 1H), 7.70–7.78 (m, 3H), 7.51 (dd, 1H, J=6.3, 2.1 Hz), 7.19–7.28 (m, 4H), 6.88 (dd, 2H, J=6.6, 2.1 Hz), 5.72 (s, 2H), 3.69 (s, 3H). Anal. ($C_{22}H_{17}IN_4O$) C, H, N.

(b) Intermediate 62b—3-(1H-Benzoimidazol-2-yl)-1-(4-methoxy-benzyl)-5-(4,4,5,5-tetramethyl[1,3,2]dioxaborolan-2-yl)-1H-indazole The title compound was prepared in 73% yield from intermediate 62a in a manner analogous to the preparation of intermediate 19e. $^1$H NMR (300 MHz, DMSO-$d_6$) δ 13.03 (s, 1H), 8.93 (d, 1H, J=4.2 Hz), 7.78–7.84 (m, 2H), 7.73 (dd, 1H, J=8.7, 0.9 Hz), 7.51 (d, 1H, J=7.2 Hz), 7.20–7.27 (m, 4H), 6.87 (d, 2H, J=8.7 Hz), 5.74 (s, 2H), 3.68 (s, 3H), 1.34 (s, 12H). Anal. ($C_{28}H_{29}BN_4O_3$) C, H, N.

(c) Intermediate 62c—5'-Bromo-4'-methyl-[2,3']bipyridinyl 3,5-Dibromo-4-methyl-pyridine (2.0 g, 7.8 mmol) and 2-tributylstannanyl-pyridine (2.4 g, 6.5 mmol) were stirred in dioxane (20 mL) in a flask purged with argon. Tetrakis(triphenylphosphine)-palladium(0) (600 mg, 0.5 mmol) was added, and the reaction stirred at 100° C. for 80 hours. The solution was concentrated in vacuo and purified by silica gel chromatography (30% to 50% ethyl acetate/hexanes, two purifications) to give 788 mg (49%) of intermediate 62c as a white solid. $^1$H NMR (300 MHz, CDCl$_3$) δ 8.72–8.75 (m, 1H), 8.70 (s, 1H), 8.46 (s, 1H), 7.78–7.84 (m, 1H), 7.31–7.42 (m, 2H), 2.42 (s, 3H). Anal. ($C_{11}H_9BrN_2$) C, H, N.

(d) Intermediate 62d—3-[3-(1H-Benzoimidazol-2-yl)-1-(4-methoxy-benzyl)-1H-indazol-5-yl]-4-methyl-[2,3']bipyridinyl The title compound was prepared in 76% yield from intermediate 62b and intermediate 62c similar to the procedure for intermediate 61c. $^1$H NMR (300 MHz, DMSO-$d_6$) δ 13.08 (s, 1H), 8.73 (d, 1H, J=4.2 Hz), 8.52–8.57 (m, 3H), 7.92–7.98 (m, 2H), 7.68–7.72 (m, 2H), 7.58 (dd, 1H, J=8.7, 1.5 Hz), 7.51 (d, 1H, J=7.2 Hz), 7.43–7.47 (m, 1H), 7.36 (d, 2H, J=8.7 Hz), 7.17–7.23 (m, 2H), 6.91 (d, 2H, J=8.7 Hz), 5.79 (s, 2H), 3.70 (s, 3H), 2.21 (s, 3H). Anal. ($C_{33}H_{26}N_6O$) C, H, N.

(e) Example 62—3-[3-(1H-Benzoimidazol-2-yl)-1H-indazol-5-yl]-4-methyl-[2,3']bipyridinyl Intermediate 62d (400 mg, 9.77 mmol) was stirred in a solution of concentrated $H_2SO_4$ (1 mL) and anisole (1 mL) in TFA (8 mL) for 48 hours. The solution was concentrated to 3 mL in vacuo, and was then quenched with sat. NaHCO$_3$ and extracted with 4:1 ethyl acetate/THF. Organics were washed with brine, dried (MgSO$_4$), and concentrated in vacuo. Purification by silica gel chromatography (0.2% NH$_4$OH/6% to 10% MeOH/ethyl acetate) gave 102 mg (33%) of example 62 as a white solid. $^1$H NMR (300 MHz, DMSO-$d_6$) δ 13.78 (s, 1H), 13.02 (s, 1H), 8.74 (d, 1H, J=4.2 Hz), 8.57 (s, 1H), 8.53 (s, 1H), 7.51 (s, 1H), 7.93–7.99 (m, 1H), 7.77 (d, 1H, J=8.7 Hz), 7.70 (d, 2H, J=7.8 Hz), 7.43–7.56 (m, 3H), 7.20 (br s, 2H), 2.23 (s, 3H). Anal. ($C_{25}H_{18}N_6 \cdot 0.5\ H_2O$) C, H, N. MS (ES) [m+H]/z calculated 403. found 403.

EXAMPLE 63

1-{5-[3-(1H-Benzoimidazol-2yl)-1H-indazol-5-yl]-3,4-dihydro-2H-[1,7]naphthyridin-1-yl}-ethanone

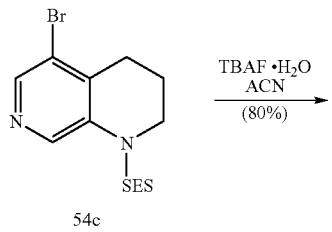

54c

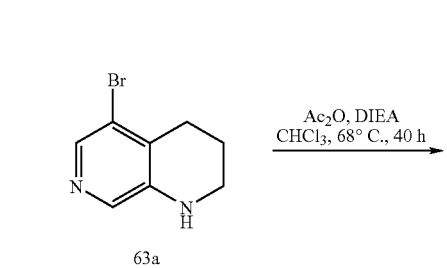

63a

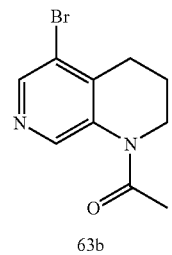

63b

-continued

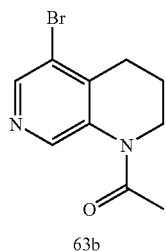

63b

+

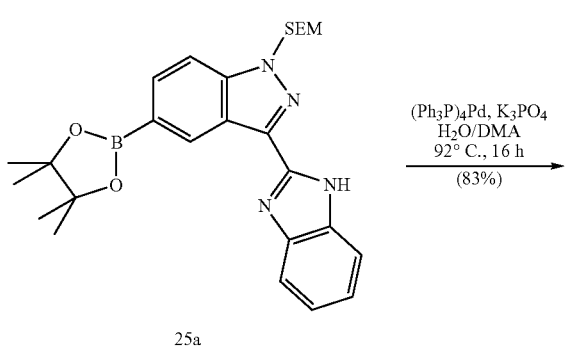

(a) Intermediate 63a—5-Bromo-1,2,3,4-tetrahydro-[1,7]naphthyridine

Intermediate 54c (1.16 g, 3.08 mmol) was stirred with tetrabutylammonium fluoride hydrate (2.0 g, 7.65 mmol) in acetonitrile (16 mL) at 72° C. for 18 hours. The solution was allowed to cool and was diluted with ethyl acetate. Organics were washed with sat. NaHCO$_3$ and brine, dried (Na$_2$SO$_4$), and concentrated in vacuo. Purification by silica gel chromatography gave 524 mg (80%) of intermediate 63a as a white solid. $^1$H NMR (300 MHz, CDCl$_3$) δ 7.96 (s, 1H), 7.74 (s, 1H), 4.00 (br s, 1H), 3.28–3.33 (m, 2H), 2.74 (q, 2H, J=6.6 Hz), 1.92–2.01 (m, 2H). Anal. (C$_8$H$_9$BrN$_2$) C, H, N.

(b) Intermediate 63b—1-(5-Bromo-3,4-dihydro-2S[1,7]naphthyridin-1-yl)-ethanone

Intermediate 63a (212 mg, 1.0 mmol), DIEA (1.4 mL, 8.0 mmol), and acetic anhydride (4.0 mmol) were stirred in dry chloroform (10 mL) at 68° C. for 40 hours. The solution was washed with saturated NaHCO$_3$ and brine, dried (Na$_2$SO$_4$), and concentrated in vacuo. Purification by silica gel chromatography (70% ethyl acetate/hexanes) gave 242 mg (95%) of intermediate 63b as a white solid. $^1$H NMR (300 MHz, CDCl$_3$) δ 8.61 (br s, 1H), 8.46 (s, 1H), 3.79 (q, 2H, J=6.0 Hz), 2.83 (t, 2H, J=6.9 Hz), 2.93 (s, 3H), 2.01–2.08 (m, 2H). Anal. (C$_{10}$H$_{11}$BrN$_2$O) C, H, N.

(c) Intermediate 63c—1-{5-[3-(1H-Benzoimidazol-2yl)-1-(2-trimethylsilanyl-ethoxymethyl)-1H-indazol-5-yl]-3,4dihydro-2H-[1,7]naphthyridin-1-yl}-ethanone The title compound was prepared in 83% yield from intermediate 25a and intermediate 63c similar to the procedure for intermediate 61c. $^1$H NMR (300 MHz, CDCl$_3$) δ 10.06 (s, 1H), 8.68 (s, 1H), 8.55 (br s, 1H), 8.42 (s, 1H), 7.84–7.87 (m, 1H), 7.71 (d, 1H, J=8.7 Hz), 7.50–7.53 (m, 1H), 7.46 (dd, 1H, J=8.7, 1.5 Hz), 7.27–7.32 (m, 2H), 5.84 (s, 2H), 3.84 (t, 2H, J=6.6 Hz), 3.64 (t, 2H, J=8.1 Hz), 2.70 (t, 2H, J=6.6 Hz), 2.36 (s, 3H), 1.87–1.93 (m, 2H), 0.94 (t, 2H, J=8.1 Hz), −0.04 (s, 9H). Anal. (C$_{30}$H$_{34}$N$_6$O$_2$Si.0.5H$_2$O) C, H, N.

(d) Example 63—1-{5-[3-(1H-Benzoimidazol-2yl)-1H-indazol-5-yl]-3,4-dihydro-2H-[1,7]naphthyridin-1-yl}-ethanone The title compound was prepared in 65% yield by the SEM-deprotection of intermediate 63c in a manner analogous to the procedure for example 41. $^1$H NMR (300 MHz, DMSO-d$_6$) δ 13.77 (s, 1H), 13.02 (s, 1H), 8.78 (s, 1H), 8.46 (br s, 1H), 8.27 (s, 1H), 7.75 (d, 1H, J=8.7 Hz), 7.67 (br.s, 1H), 7.49 (dd, 2H, J=5.7, 1.5 Hz), 7.20 (br s, 2H), 3.74 (t, 2H, J=6.3 Hz), 2.63 (t, 2H, J=6.3 Hz), 2.27 (s, 3H), 1.79–1.85 (m, 2H). Anal. (C$_{24}$H$_{20}$N$_6$O) C, H, N. MS (ES) [m+H]/z calculated 409. found 409.

EXAMPLE 64

5-[3-(1H-Benzoimidazol-2-yl)-1H-indazol-5-yl]-4-methyl-nicotinamide

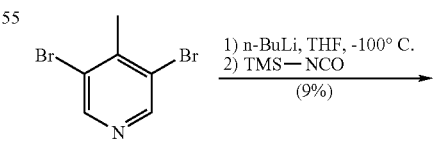

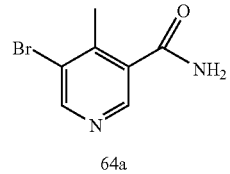

64a

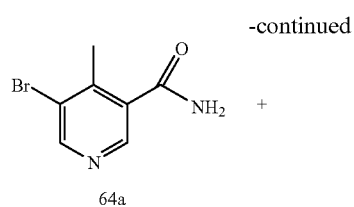

64a

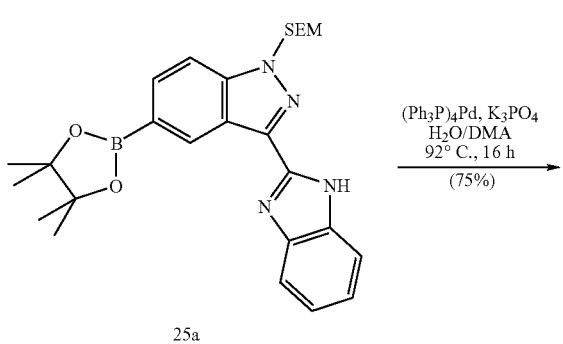

25a

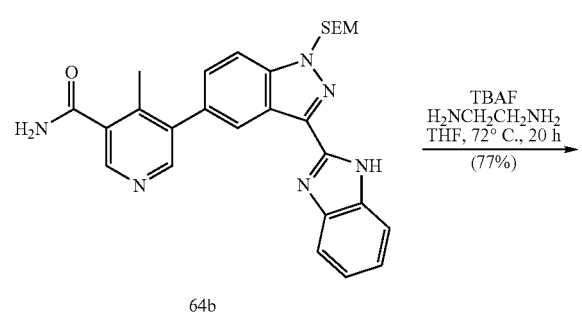

64b

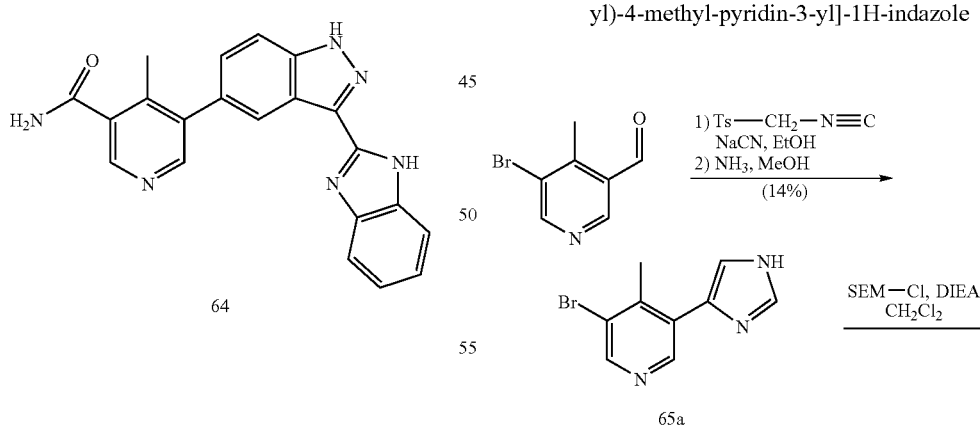

64

(a) Intermediate 64a—3-Bromo-4-methyl-5-carboxamoyl-pyridine

A solution of 3,5-dibromopyridine (3g, 11.9 mmol) in 150 mL dry THF was cooled to −100° C. (ether-N$_2$ bath) and BuLi (5 mL of a 2.5 M solution in hexanes, 12.5 mmol) was added dropwise over 3 minutes. After 2 additional minutes trimethylsilylisocyanate (3.8 mL of 85% solution, 3.24 g, 24 mmol) was added to the yellow-anion and the whole was stirred for 30 minutes at −10° C., 30 minutes at −6° C. and then it was allowed to reach 25° C. and stirred for 12 hours. The reaction was poured into saturated aqueous NH$_4$Cl, extracted with ethyl acetate, the organic layers were washed with brine, dried (Na$_2$SO$_4$), and concentrated. Purification of the residue by chromatography on silica (5:1 to 10:1 hexanes-ethyl acetate then 100% ethyl acetate) afforded 236 mg (9%) of amide 64a. R$_f$=0.09 (50% ethyl acetate in hexanes); $^1$H NMR (300 MHz, CDCl$_3$) δ 8.70 (bs, 1H), 8.54 (bs, 1H), 5.98 (bs, 1H), 5.93 (bs, 1H). (LCMS: M+215).

(b) Intermediate 64b—5-[3-(1H-Benzoimidazol-2-yl)-1-(2-trimethylsilanyl-ethoxymethyl)-1H-indazol-5-yl]-4-methyl-nicotinamide The title compound was prepared in 75% yield from intermediate 25a and intermediate 64a similar to the procedure for intermediate 61c. $^1$H NMR (300 MHz, CDCl$_3$) δ 10.18 (s, 1H), 8.66 (s, 1H), 8.64 (s, 1H), 8.59 (s, 1H), 7.82–7.86 (m, 1H), 7.70 (d, 1H, J=8.4 Hz), 7.48–7.52 (m, 1H), 7.42 (dd, 1H, J=8.4, 1.5 Hz), 7.26–7.31 (m, 2H), 6.13 (br s, 1H), 5.91 (br s, 1H), 5.83 (s, 2H), 3.64 (t, 2H, J=8.1 Hz), 2.40 (s, 3H), 0.94 (t, 2H, J=8.1 Hz), −0.04 (s, 9H).

(c) Example 64—5-[3-(1H-Benzoimidazol-2-yl)-1H-indazol-5-yl]-4-methyl-nicotinamide The title compound was prepared in 77% yield by the SEM-deprotection of intermediate 64b in a manner analogous to the procedure for example 41. $^1$H NMR (300 MHz, DMSO-d$_6$) δ 13.80 (s, 1H), 13.03 (s, 1H), 8.54 (s, 1H), 8.50 (s, 1H), 8.45 (s, 1H), 8.05 (s, 1H), 7.76 (d, 1H, J=8.7 Hz), 7.68 (br.s, 2H), 7.44–7.52 (m, 2H), 7.16–7.22 (m, 2H), 2.29 (s, 3H). Anal. (C$_{21}$H$_{16}$N$_6$O.0.55H$_2$O) C, H, N. MS (ES) [m+H]/z calculated 369. found 369.

EXAMPLE 65

3-(1H-Benzoimidazol-2-yl)-5-[5-(1H-imidazol-4-yl)-4-methyl-pyridin-3-yl]-1H-indazole

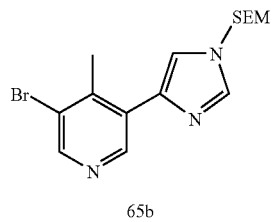

65b

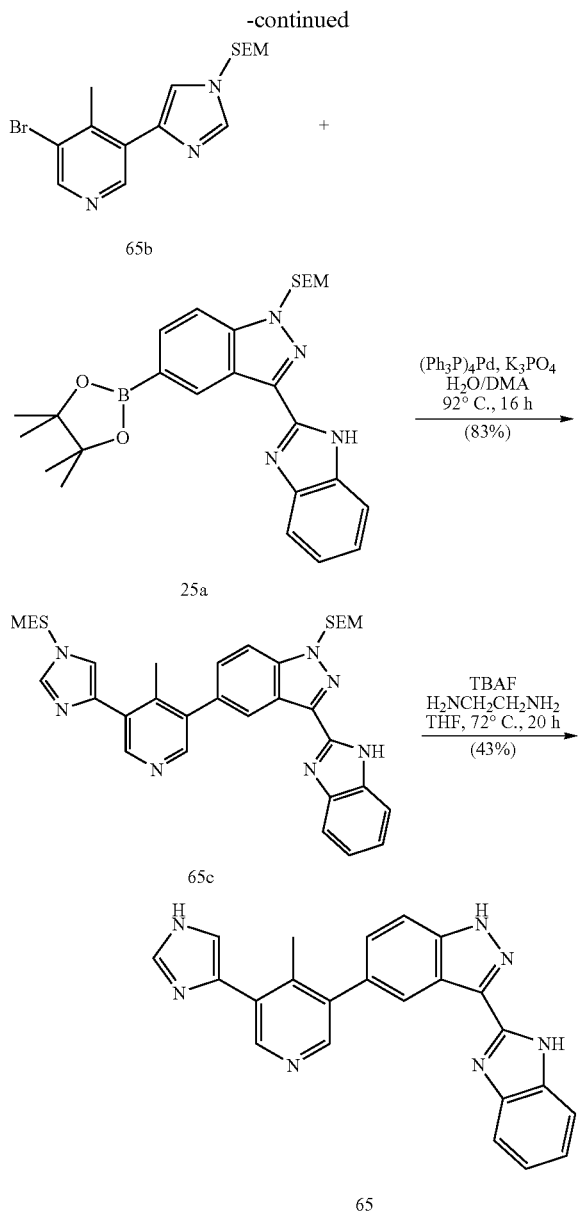

(a) Intermediate 65a—3-Bromo-4-methyl-5-1H-imidazol-4-yl-pyridine

To a stirred suspension of tosylmethyl isocyanide (1.02 g, 5.25 mmol) and 3-bromo-4-methyl-5-formyl pyridine (1.0 g, 5 mmol) in 5 mL of dry ethanol was added finely powdered NaCN (25 mg, 0.5 mmol) at 25° C. After 30 minutes the reaction was concentrated to an oil. The resulting oil was added to a saturated solution of ammonia in dry methanol in a sealed tube and heated to 100° C. for 24 hours. Cooling and concentration followed by chromatography on silica (10:1 ethyl acetate-hexanes) afforded 167 mg (14%) of 65a as a white solid. $^1$H NMR (300 MHz, DMSO-$d_6$) δ 12.45 (bs, 1H), 8.71 (s, 1H), 8.55 (s, 1H), 7.83 (s, 1H), 7.52 (s, 1H), 2.56 (s, 3H).

(b) Intermediate 65b—3-Bromo-4-methyl-5-[1-(2-trimethylsilanyl-ethoxymethyl)-1H-imidazol-4-yl]-pyridine Intermediate 65a was SEM-protected in 45% yield in a manner analogous to the procedure for intermediate 49a. $^1$H NMR (300 MHz, CDCl$_3$) δ 8.67 (s, 1H), 8.60 (s, 1H), 7.70 (s, 1H), 7.21 (d, 1H, J=1.2 Hz), 5.33 (s, 2H), 3.56 (t, 2H, J=8.1 Hz), 2.58 (s, 3H), 0.94 (t, 2H, J=8.1 Hz), 0.00 (s, 9H). Anal. ($C_{15}H_{22}BrN_3OSi$) C, H, N.

(c) Intermediate 65c—3-(1H-Benzoimidazol-2-yl)-5-{5-[1-(2-trimethylsilanyl-ethoxymethyl)-1H-imidazol-4-yl]-4-methyl-pyridin-3-yl}-1-(2-trimethylsilanyl-ethoxymethyl)-1H-indazole The title compound was prepared in 83% yield from intermediate 25a and intermediate 65b similar to the procedure for intermediate 61c. $^1$H NMR (300 MHz, CDCl$_3$) δ 10.09 (s, 1H), 8.85 (s, 1H), 7.70 (s, 1H), 8.50 (s, 1H), 7.84–7.88 (m, 1H), 7.68–7.74 (m, 2H), 7.47–7.52 (m, 2H), 7.26–7.31 (m, 3H), 5.84 (s, 2H), 5.36 (s, 2H), 3.55–3.68 (m, 4H), 2.41 (s, 3H), 0.92–0.98 (m, 4H), −0.01 (s, 9H), −0.05 (s, 9H).

(d) Example 65—3-(1H-Benzoimidazol-2-yl)-5-[5-(1H-imidazol-4-yl)-4-methyl-pyridin-3-yl]-1H-indazole The title compound was prepared in 43% yield by the SEM-deprotection of intermediate 65c in a manner analogous to the procedure for example 41. $^1$H NMR (300 MHz, DMSO-$d_6$) δ 13.78 (s, 1H), 13.02 (s, 1H), 12.38 (s, 1H), 8.83 (s, 1H), 8.47 (s, 1H), 8.35 (s, 1H), 7.83 (d, 1H, J=0.9 Hz), 7.76 (d, 1H, J=8.4 Hz), 8.69 (d, 1H, J=7.5 Hz), 7.47–7.51 (m, 3H), 7.16–7.22 (m, 2H), 2.37 (s, 3H). Anal. ($C_{23}H_{17}N_7$·2.5H$_2$O) C, H, N. MS (ES) [m+H]/z calculated 392. found 392.

EXAMPLE 66

4-[3-(4,5,6,7-Tetrahydro-1H-benzoimidazol-2-yl)-1H-indazol-5-yl]-isoquinoline

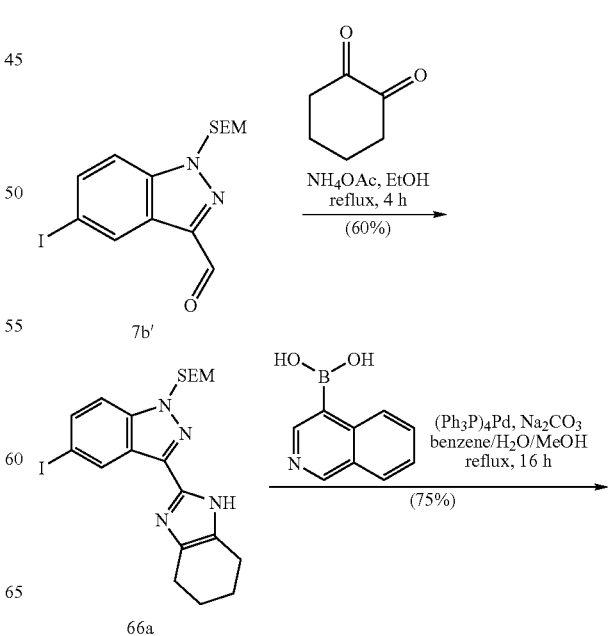

159

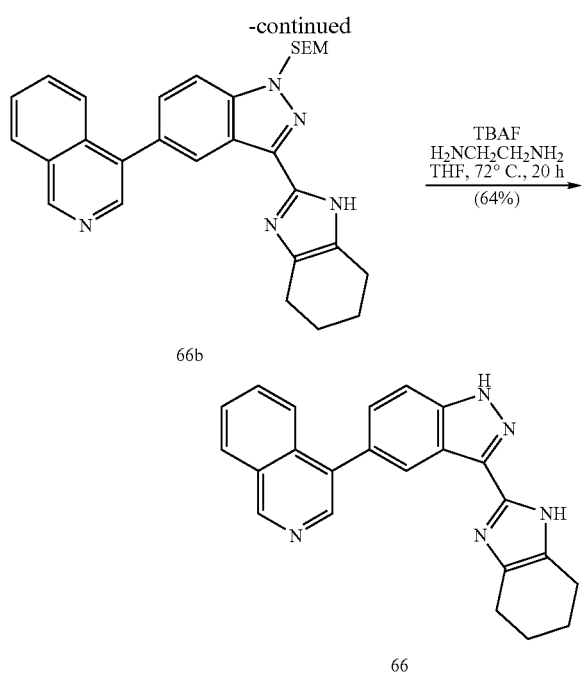

(a) Intermediate 66a—5-Iodo-3-(4,5,6,7-tetrahydro-1H-benzoimidazol-2-yl)-1H indazole A solution of intermediate 7b' (500 mg, 1.24 mmol), 1,2-cyclohexanedione (146 mg, 1.3 mmol), and ammonium acetate (575 mg, 7.44 mmol) in ethanol (12 mL) was stirred at reflux for 4 hours. The reaction was diluted with ethyl acetate and washed with brine, dried ($Na_2SO_4$), and concentrated in vacuo. Purification by silica gel chromatography (20% ethyl acetate/hexanes) gave 366 mg (60%) of the title compound as a light yellow foam. $^1$H NMR (300 MHz, $CDCl_3$) δ 9.47 (br s, 1H), 8.88 (d, 1H, J=0.9 Hz), 7.69 (dd, 1H, J=8.7, 1.5 Hz), 7.31 (d, 1H, J=8.7 Hz), 5.67 (s, 2H), 3.52 (t, 2H, J=8.1 Hz), 2.70 (br s, 4H), 1.89 (br s, 4H), 0.88 (t, 2H, J=8.1 Hz), –0.06 (s, 9H). Anal. ($C_{20}H_{27}IN_4OSi$) C, H, N.

(b) Intermediate 66b—4-[3-(4,5,6,7-Tetrahydro-1H-benzoimidazol-2-yl)-1-(2-trimethylsilanyl-ethoxymethyl)-1H-indazol-5-yl]-isoquinoline The title compound was prepared in 75% yield from intermediate 66a and isoquinoline-4-boronic acid (EP 976747) similar to the procedure for intermediate 7d'. $^1$H NMR (300 MHz, $CDCl_3$) δ 9.57 (br s, 1H), 9.28 (s, 1H), 8.67 (s, 1H), 8.58 (s, 1H), 8.04–8.08 (m, 1H), 7.85–7.89 (s, 1H), 7.57–7.70 (m, 4H), 5.80 (s, 2H), 3.63 (t, 2H, J=8.1 Hz), 2.7 (br s, 4H), 1.86 (br s, 4H), 0.96 (t, 2H, J=8.1 Hz), -0.03 (s, 9H).

(c) Example 66—4-[3-(4,5,6,7-Tetrahydro-1H-benzoimidazol-2-yl)-1H-indazol-5-yl]-isoquinoline The title compound was prepared in 64% yield by the SEM-deprotection of intermediate 66b in a manner analogous to the procedure for example 41. $^1$H NMR (300 MHz, DMSO-$d_6$) δ 13.31 (s, 1H), 12.25 (s, 1H), 9.36 (s, 1H), 8.49 (s, 1H), 8.43 (s, 1H), 8.24 (d, 1H, J=7.8 Hz), 7.69–7.85 (m, 4H), 7.53 (dd, 1H, J=8.7, 1.8 Hz), 2.50 (br s, 4H), 1.73 (br s, 4H). Anal. ($C_{23}H_{19}N_5 \cdot 0.2H_2O$) C, H, N. MS (ES) [m+H]/z calculated 366. found 366.

160

EXAMPLE 67

4-[3-(4-Methyl-5-phenyl-1H-imidazol-2-yl)-1H-indazol-5-yl]-isoquinoline

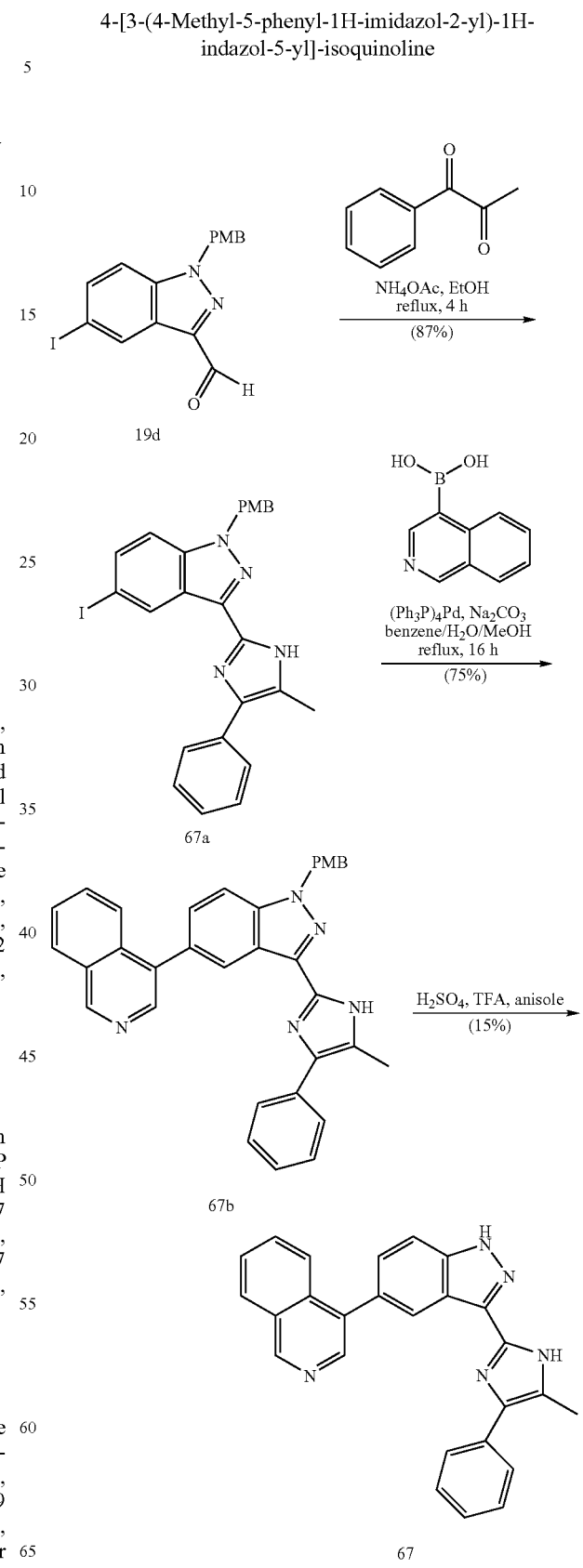

(a) Intermediate 67a—5-Iodo-1-(4-methoxy-benzyl)-3-(4-methyl-5-phenyl-1H imidazol-2-yl)-1H-indazole The title compound was prepared from intermediate 19d and 1-phenyl-1,2-propanedione similar to the procedure for intermediate 66a. $^1$H NMR (300 MHz, CDCl$_3$) δ 9.87 (br s, 0.5H), 9.71 (br s, 0.5H), 8.98 (br s, 0.5H), 8.92 (br s, 0.5H), 7.84 (d, 1H, J=7.2 Hz), 7.61 (dd, 1H, J=8.7, 1.5 Hz), 7.44–7.53 (m, 3H), 7.31 (d, 1H, J=7.5 Hz), 7.11 (app d, 3H, J=8.7 Hz), 6.81 (dd, 2H, J=6.6, 1.8 Hz), 5.49 (s, 2H), 3.77 (s, 3H), 2.55 (s, 3H). Anal. (C$_{25}$H$_{21}$IN$_4$O) C, H, N.

(b) Intermediate 67b—4-[1-(4-Methoxy-benzyl)-3-(4-methyl-5-phenyl-1H-imidazol-2-yl)-1H-indazol-5-yl]-isoquinoline The title compound was prepared in 75% yield from intermediate 67a and isoquinoline-4-boronic acid (EP 976747) in a manner analogous to the procedure for intermediate 7d' $^1$H NMR (300 MHz, CDCl$_3$) δ 9.97 (br s, 0.5H), 9.85 (br s, 0.5H), 9.28 (s, 1H), 8.76 (br s, 0.5H), 8.70 (br s, 0.5H), 8.59 (s, 1H), 8.03–8.10 (m, 1H), 7.90 (br s, 1H), 7.75 (br s, 1H), 7.37–7.68 (m, 8H), 7.20–7.26 (m, 2H), 6.86 (dd, 2H, J=6.6, 1.5 Hz), 5.60 (s, 2H), 3.78 (s, 3H), 2.54 (br s, 1.5H), 2.49 (br s, 1.5H).

(c) Example 67—4-[3-(4-Methyl-5-phenyl-1H-imidazol-2-yl)-1H-indazol-5-yl]-isoquinoline The title compound was prepared in 15% yield by the PMB-deprotection of intermediate 67b in a manner analogous to the procedure for example 62. $^1$H NMR (300 MHz, DMSO-d$_6$) δ 12.67 (s, 1H), 13.02 (s, 1H), 9.38 (s, 1H), 8.57 (s, 1H), 8.53 (s, 1H), 8.25 (d, 1H, J=7.5 Hz), 7.66–7.91 (m, 6H), 7.57 (dd, 1H, J=8.7, 1.5 Hz), 7.30–7.33 (m, 2H), 7.15–7.18 (m, 1H), 2.50 (s, 3H). Anal. (C$_{26}$H$_{19}$N$_5$·0.5H$_2$O) C, H, N. MS (ES) [m+H]/z calculated 402. found 402.

EXAMPLE 68

Dimethyl-{2-[5-(4-methyl-[3,4']bipyridinyl-5-yl)-1H-indazol-3-yl]-1H-benzoimidazol-4-ylmethyl}-amine

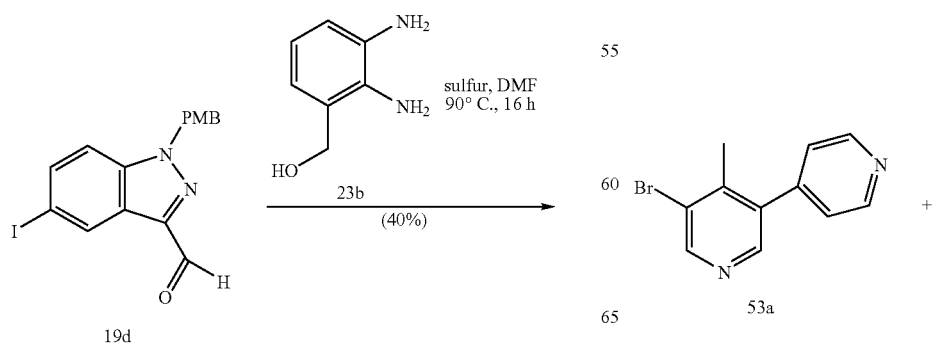

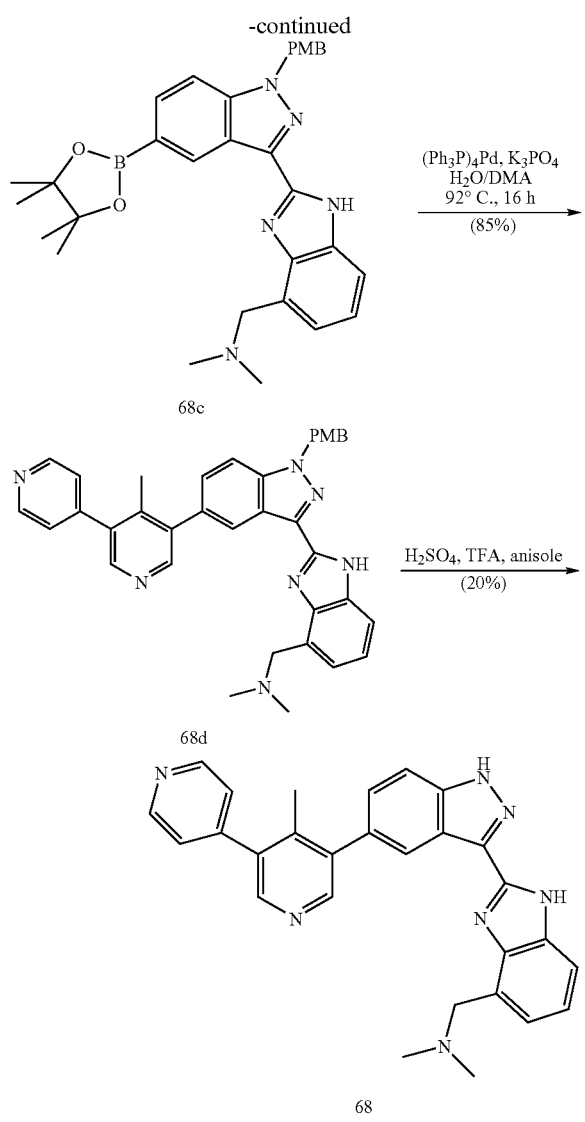

was allowed to stir for 2 hours while warming to room temperature. The solution was quenched with H₂O and extracted with ethyl acetate. Organics were washed with sat. NaHCO₃ and brine, dried (Na₂SO₄), and concentrated in vacuo. Purification by silica gel chromatography (0.2% NH₄OH/3% MeOH/ethyl acetate) gave 2.56 g (97%) of intermediate 68b as a white foam. $^1$H NMR (300 MHz, CDCl₃) δ 9.07 (d, 1H, J=0.9 Hz), 7.80 (d, 1H, J=7.8 Hz), 7.63 (dd, 1H, J=8.7, 1.5 Hz), 7.07–7.25 (m, 5H), 6.85 (dd, 2H, J=6.6, 1.8 Hz), 5.61 (s, 2H), 3.77 (app s, 5H), 2.33 (s, 6H).

(c) Intermediate 68c—{2-[1-(4-Methoxy-benzyl)-5-(4,4,5,5-tetramethyl-[1,3,2]dioxaborolan-2-yl)-1H-indazol-3-yl]-1H-benzoimidazol-4-ylmethyl}-dimethyl-amine The title compound was prepared in 62% yield from intermediate 68b similar to the method for the preparation of intermediate 19e. $^1$H NMR (300 MHz, CDCl₃) δ 9.11 (s, 1H), 7.82 (dd, 2H, J=8.4, 0.9 Hz), 7.35 (dd, 1H, J=8.4, 0.9 Hz), 7.16–7.21 (m, 4H), 6.85 (dd, 2H, J=6.9, 1.8 Hz), 5.64 (s, 2H), 3.80 (br s, 2H), 3.76 (s, 3H), 2.35 (s, 6H), 1.37 (s, 12H).

(d) Intermediate 68d—Dimethyl-{2-[5-(4-methyl-[3,4']bipyridinyl-5-yl)-1-(4-methoxy-benzyl)-1H-indazol-3-yl]-1H-benzoimidazol-4-ylmethyl}-amine The title compound was prepared in 85% yield from intermediate 68c and intermediate 53a similar to the procedure for intermediate 61c. $^1$H NMR (300 MHz, CDCl₃) δ 8.69–8.75 (m, 4H), 8.57 (s, 1H), 8.43 (s, 1H), 7.75 (d, 1H, J=8.1 Hz), 7.46 (d, 1H, J=8.7 Hz), 7.34–7.40 (m, 3H), 7.25–7.28 (m, 1H), 7.19 (t, 1H, J=7.6 Hz), 7.08 (d, 1H, J=7.2 Hz), 6.89 (d, 2H, J=8.7 Hz), 5.70 (s, 2H), 3.79 (app s, 5H), 2.34 (s, 6H), 2.19 (s, 3H).

(e) Example 68—Dimethyl-{2-[5-(4-methyl-[3,4']bipyridinyl-5-yl)-1H-indazol-3-yl]-1H-benzoimidazol-4-ylmethyl}-amine The title compound was prepared in 20% yield by the PMB-deprotection of intermediate 68d in a manner analogous to the procedure for example 62. $^1$H NMR (300 MHz, DMSO-d₆) δ 13.80 (s, 1H), 13.01 (s, 1H), 8.71 (dd, 2H, J=4.5, 1.5 Hz), 8.56 (br s, 2H), 8.47 (s, 1H), 7.78 (d, 1H, J=8.7 Hz), 7.39–7.58 (m, 4H), 7.17 (br s, 2H), 3.76–3.99 (m, 2H), 2.14–7.29 (m, 9H). Anal. (C₂₈H₂₅N₇·1.5H₂O) C, H, N. MS (ES) [m+H]/z calculated 460. found 460.

(a) Intermediate 68a—(2-[5-Iodo-1-(4methoxy-benzyl)-1H-indazol-3-yl]-1H-benzoimidazol-4-ylmethyl}-methanol The title compound was prepared in 40% yield from intermediate 19d and intermediate 23b similar to the procedure for intermediate 7c'. $^1$H NMR (300 MHz, DMSO-d₆) δ 13.02 (s, 0.5H), 12.87 (s, 0.5H), 8.91 (s, 1H), 7.64–7.77 (m, 2.5H), 7.37 (dd, 0.5H, J=7.5, 1.5 Hz), 7.18–7.27 (m, 4H), 6.88 (d, 2H, J=8.4 Hz), 5.73 (s, 1H), 5.71 (s, 1H), 5.14–5.24 (m, 1H), 5.03 (d, 1H, J=5.7 Hz), 4.86 (d, 1H, J=5.7 Hz), 3.69 (s, 3H).

(b) Intermediate 68b—{2-[5-Iodo-1-(4methoxy-benzyl)-1H-indazol-3-yl]-1H-benzoimidazol-4-ylmethyl}-dimethyl-amine Intermediate 68a (2.5 g, 4.9 mmol) and DIEA (1.38 mL, 10 mmol) were stirred in THF (90 mL) at 0° C. Methanesulfonyl chloride (0.76 mL, 9.8 mmol) was added, and the reaction stirred for 2.5 hours at 0° C. Dimethylamine was bubbled through the solution for 1 minute, and the reaction

EXAMPLE 69

(3-{5-[3-(1H-Benzoimidazol-2-yl)-1H-indazol-5-yl]-4-methyl-pyridin-3-yl}-phenyl)-methanol

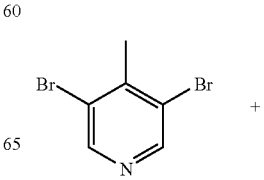

+

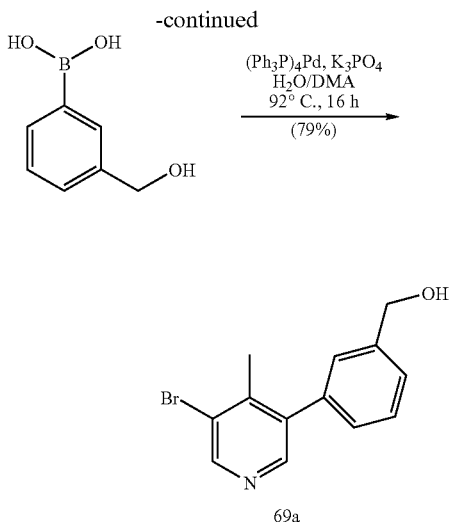

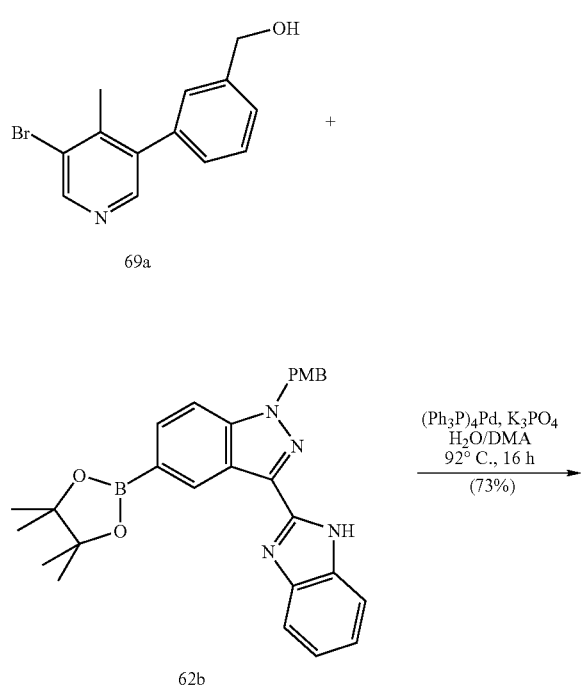

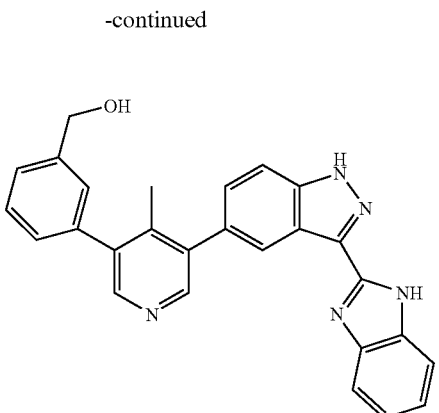

(a) Intermediate 69a—[3-(5-Bromomethyl-pyridin-3-yl)-phenyl]-methanol

The title compound was prepared in 79% yield from 3,5-dibromo-4-methyl-pyridine and 3-(hydroxymethyl)-phenyl-boronic acid similar to the procedure for intermediate 53a. $^1$H NMR (300 MHz, CDCl$_3$) 8.62 (s, 1H), 8.22 (s, 1H), 7.42–7.46 (m, 2H), 7.29 (s, 1H), 7.16–7.20 (m, 1H), 4.76 (d, 2H, J=5.7 Hz), 2.48 (t, 1H, J=5.7 Hz), 2.32 (s, 3H). Anal. (C$_{13}$H$_{12}$BrNO.0.2H$_2$O) C, H, N.

(b) Intermediate 69b—(3-{5-[3-(1H-Benzoimidazol-2-yl)-1-(4-methoxy-benzyl)-1H-indazol-5-yl]-4-methyl-pyridin-3-yl}-phenyl)-methanol The title compound was prepared in 83% yield from intermediate 62b and intermediate 69a similar to the procedure for intermediate 61c. $^1$H NMR (300 MHz, CDCl$_3$) δ 10.39 (s, 1H), 8.69 (s, 1H), 8.45 (s, 1H), 8.36 (s, 1H), 7.83–7.87 (m, 1H), 7.36–7.49 (m, 7H), 7.22–7.31 (m, 4H), 6.84 (d, 2H, J=8.7 Hz), 5.60 (s, 2H), 4.79 (s, 2H), 3.76 (s, 3H), 2.51 (br s, 1H), 2.11 (s, 3H).

(c) Example 69—(3-{5-[3-(1H-Benzoimidazol-2-yl)-1H-indazol-5-yl]-4-methyl-pyridin-3-yl}-phenyl)-methanol The title compound was prepared in 41% yield by the PMB-deprotection of intermediate 69b in a manner analogous to the procedure for example 62. $^1$H NMR (300 MHz, DMSO-d$_6$) δ 13.79 (s, 1H), 13.02 (s, 1H), 849 (d, 2H, J=6.3 Hz), 8.41 (s, 1H), 7.76 (d, 1H, J=8.7 Hz), 7.34–7.69 (m, 7H), 7.19–7.22 (m, 2H), 5.25 (br s, 1H), 4.58 (s, 2H), 2.15 (s, 3H). Anal. (C$_{27}$H$_{21}$N$_5$O$_2$. 1.2H$_2$O) C, H, N. MS (ES) [m+H]/z calculated 432. found 432.

EXAMPLE 70

N-[2-(5-Isoquinolin-4-yl-1H-indazol-3-yl)-3H-benzoimidazol-5-yl]-methanesulfonamide

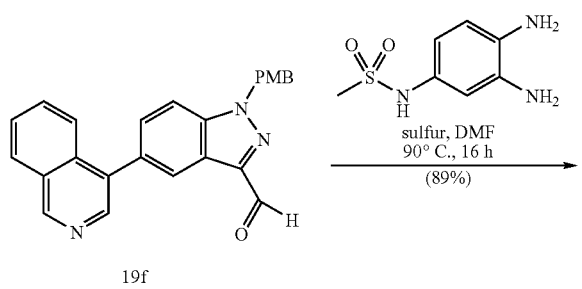

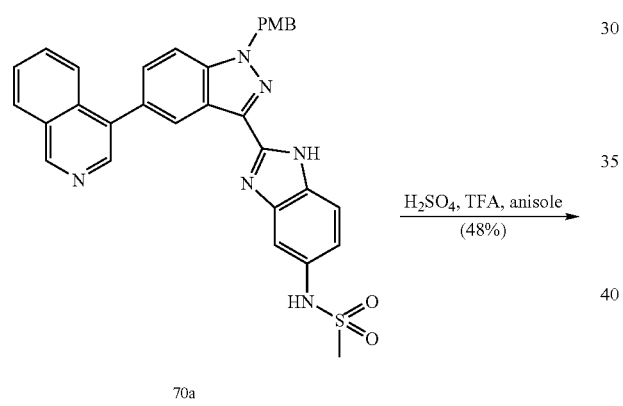

(a) Intermediate 70a—N-{2-[5-Isoquinolin-4-yl-1-(4-methoxy-benzyl)-1H-indazol-3-yl]-3H-benzoimidazol-5-yl}-methanesulfonamide The title compound was prepared in 89% yield from intermediate 19f and N-(3,4-diaminophenyl)methanesulfonamide (see Rajappa et al., *Indian J. Chem. Sect B*, 19, 7,1980, 533–535) similar to the procedure for intermediate 7c'. $^1$H NMR (300 MHz, MeOD-$d_4$) δ 9.26 (s, 1H), 8.63 (s, 1H), 8.49 (s, 1H), 8.20 (d, 1H, J=7.8 Hz), 7.96 (d, 1H, J=7.8 Hz), 7.72–7.81 (m, 3H), 7.58–7.63 (m, 3H), 7.35 (d, 2H, J=8.7 Hz), 7.16 (br s, 1H), 6.89 (d, 2H, J=8.7 Hz), 5.76 (s, 2H), 3.75 (s, 3H), 2.93 (s, 3H).

(b) Example 70—N[2-(5-Isoquinolin-4-yl-1H-indazol-3-yl)-3H-benzoimidazol-5-yl]-methanesulfonamide The title compound was prepared in 48% yield by the PMB-deprotection of intermediate 70a in a manner analogous to the procedure for example 62. $^1$H NMR (300 MHz, DMSO-$d_6$) δ 13.83 (s, 1H), 13.04 (s, 1H), 9.54 (br s, 1H), 9.40 (s, 1H), 8.60 (s, 1H), 8.55 (s, 1H), 8.27 (d, 1H, J=8.7 Hz), 7.72–7.88 (m, 4H), 7.63 (dd, 1H, J=8.7, 1.5 Hz), 7.54 (br s, 1H), 7.46 (s, 1H), 7.07 (d, 1H, J=7.8 Hz), 2.91 (s, 3H). Anal. ($C_{24}H_{18}N_6O_2S$·1.05$H_2O$) C, H, N, S. MS (ES) [m+H]/z calculated 455. found 455.

EXAMPLE 71

N-{2-[5-(4-methyl-[3,4']bipyridinyl-5-yl)-1H-indazol-3-yl)-3H-benzoimidazol-5-yl]-methanesulfonamide

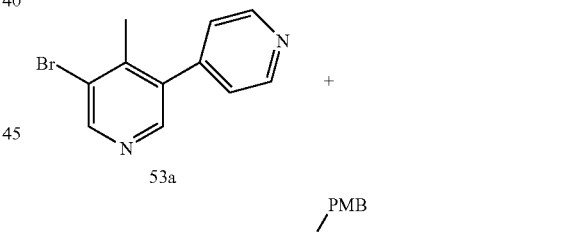

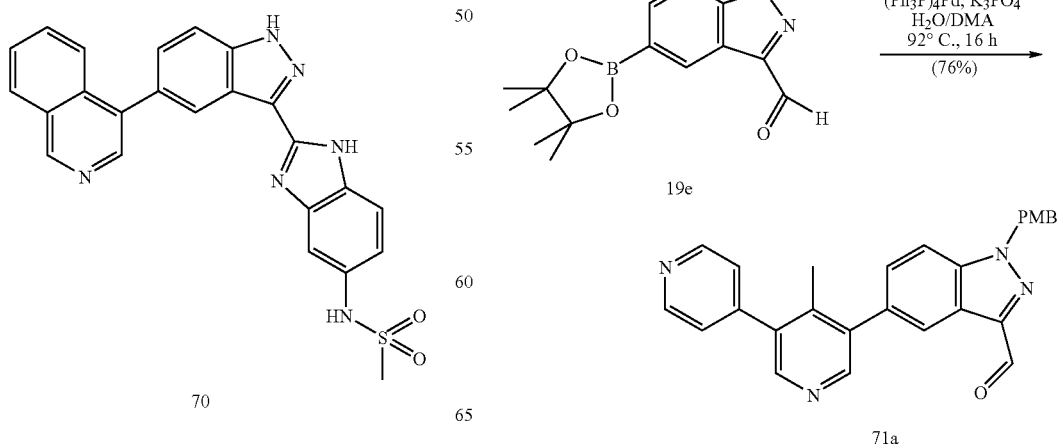

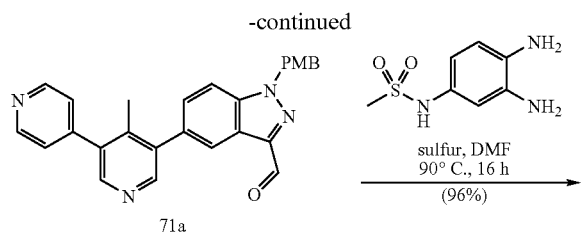

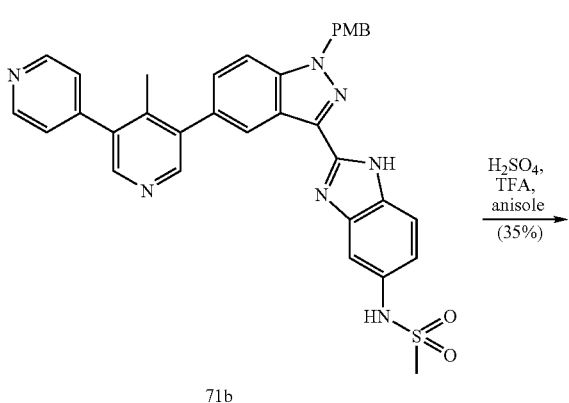

(a) Intermediate 71a—1-(4Methoxy-benzyl)-5-(4-methyl-[3,4']bipyridinyl-5-yl)-1H-indazole-3-carbaldehyde The title compound was prepared in 76% yield from intermediate 19e and intermediate 53a similar to the procedure for intermediate 61c. $^1$H NMR (300 MHz, CDCl$_3$) δ 10.28 (s, 1H), 8.73 (dd, 2H, J=4.5, 1.5 Hz), 8.49 (s, 1H), 8.43 (s, 1H), 8.31 (s, 1H), 7.53 (d, 1H, J=8.7 Hz), 7.40 (dd, 1H, J=8.7, 1.5 Hz), 7.26–7.34 (m, 4H), 6.89 (d, 2H, J=8.7 Hz), 5.67 (s, 2H), 3.79 (s, 3H), 2.15 (s, 3H). Anal. (C$_{27}$H$_{22}$N$_4$O$_2$·0.25H$_2$O) C, H, N.

(b) Intermediate 71b—N-{2-[5-(4-methyl-[3,4'] bipyridinyl-5-yl)-1-(4-methoxy-benzyl)-1H-indazol-3-yl]-3H-benzoimidazol-5-yl]-methanesulfonamide The title compound was prepared in 96% yield from intermediate 71a and N-(3,4-diaminophenyl)methane-sulfonamide similar to the procedure for intermediate 7c'. $^1$H NMR (300 MHz, MeOD-d$_4$) δ 8.66 (dd, 2H, J=4.5, 1.5 Hz), 8.52 (s, 2H), 8.39 (s, 1H), 7.73 (d, 1H, J=8.7 Hz), 7.47–7.65 (m, 5H), 7.35 (d, 2H, J=8.7 Hz), 7.17 (br s, 1H), 6.86 (d, 2H, J=8.7 Hz), 5.72 (s, 2H), 3.73 (s, 3H), 2.94 (s, 3H), 2.24 (s, 3H).

(c) Example 71—N-{2-[5-(4-methyl-[3,4']bipyridinyl-5-yl)-1H-indazol-3-yl)-3]benzoimidazol-5-yl]-methanesulfonamide The title compound was prepared in 35% yield by the PMB-deprotection of intermediate 71b in a manner analogous to the procedure for example 62. $^1$H NMR (300 MHz, DMSO-d$_6$) δ 13.79 (s, 1H), 13.02 (s, 1H), 9.56 (s, 1H), 8.70 (d, 2H, J=5.7 Hz), 8.54 (s, 1H), 8.47 (d, 2H, J=7.8 Hz), 7.78 (d, 1H, J=8.7 Hz), 7.49–7.58 (m, 5H), 7.10 (d, 1H, J=8.7 Hz), 2.93 (s, 3H), 2.17 (s, 3H). Anal. (C$_{26}$H$_{21}$N$_7$O$_2$S·1.45H$_2$O) C, H, N, S. MS (ES) [m+H]/z calculated 496. found 496.

EXAMPLE 72

{5-[3-(1H-Benzoimidazol-2-yl)-1H-indazol-5-yl]-4-methyl-pyridin-3-yl}-methanol

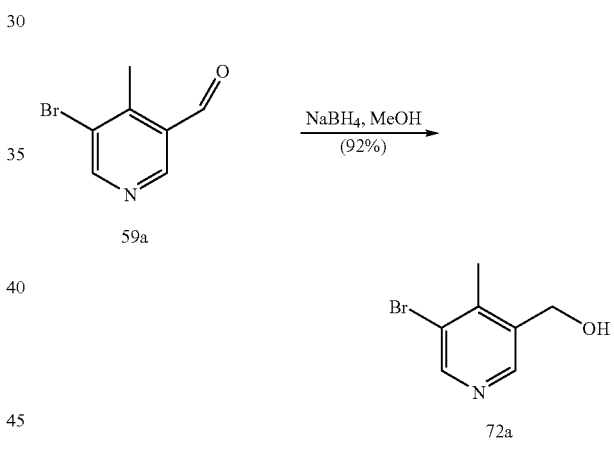

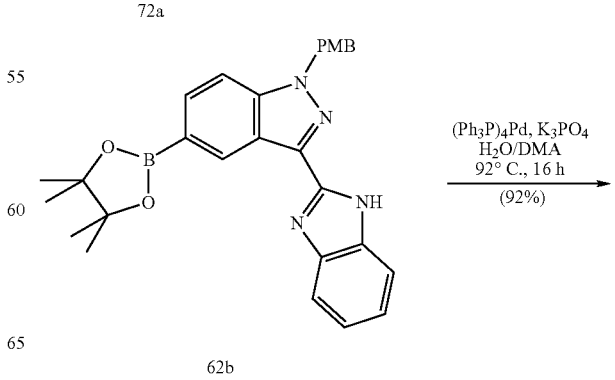

EXAMPLE 73

{5-[3-(1H-Benzoimidazol-2-yl)-1H-indazol-5-yl]-4-methyl-pyridin-3-ylmethyl}-dimethyl-amine

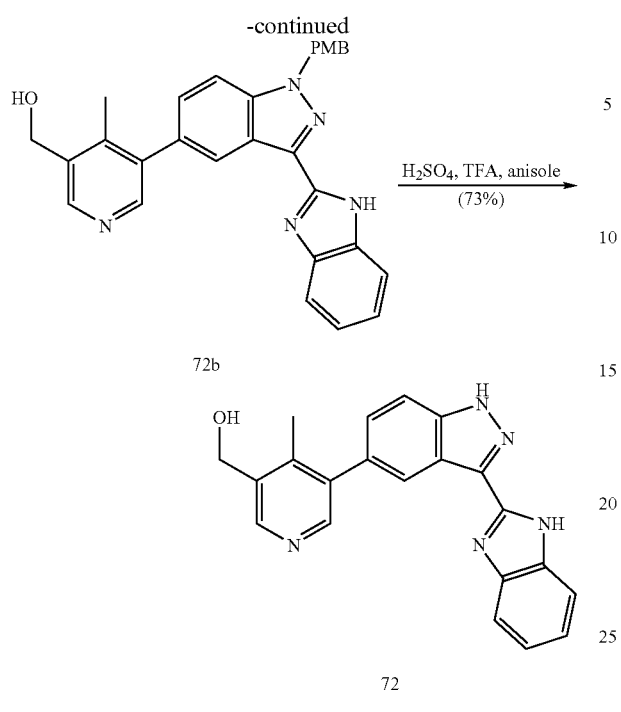

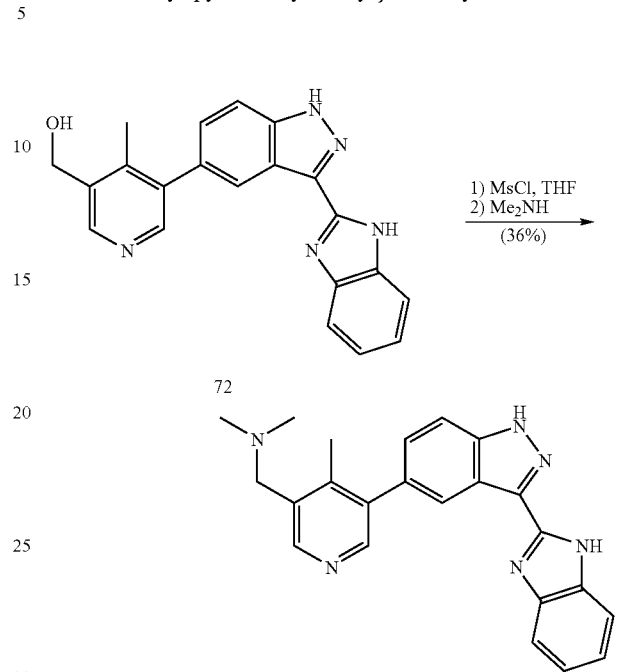

(a) Intermediate 72a—(5-Bromomethyl-pyridin-3-yl)-methanol

Intermediate 59a (1.5 g, 7.5 mmol) was stirred in MeOH at 0° C. Sodium borohydride (850 mg, 22.5 mmol) was added in portions, and the reaction was stirred for 1 hour. The solution was diluted with ethyl acetate, and organics were washed with $H_2O$ and brine, dried ($MgSO_4$), and concentrated in vacuo. Purification by silica gel chromatography (80% to 100% ethyl acetate/hexanes) gave 1.39 g (92%) of intermediate 72a as a white solid. $^1$H NMR (300 MHz, $CDCl_3$) δ 8.59 (s, 1H), 8.38 (s, 1H), 8.43 (s, 1H), 4.75 (d, 1H, J=5.4 Hz), 2.45 (s, 3H), 2.37 (t, 1H, J=5.4 Hz).

(b) Intermediate 72b—{5-[3-(1H-Benzoimidazol-2-yl)-1-(4-methoxy-benzyl)-1H-indazol-5-yl]-4-methyl-pyridin-3-yl}-methanol The title compound was prepared in 92% yield from intermediate 62b and intermediate 72a similar to the procedure for intermediate 61c. $^1$H NMR (300 MHz, $CDCl_3$) δ 10.48 (s, 1H), 8.62 (s, 1H), 8.48 (s, 1H), 8.42 (s, 1H), 7.83 (br s, 1H), 7.45 (d, 2H, J=8.7 Hz), 7.21–7.32 (m, 5H), 6.83 (d, 2H, J=8.7 Hz), 5.60 (d, 2H, J=4.5 Hz), 4.80 (s, 2H), 3.76 (s, 3H), 2.25 (s, 3H), 1.94 (br s, 1H).

(c) Example 72—{5-[3-(1H-Benzoimidazol-2-yl)-1H-indazol-5-yl]-4-methyl-pyridin-3-yl}-methanol The title compound was prepared in 59% yield by the PMB-deprotection of intermediate 72b in a manner analogous to the procedure for example 62. $^1$H NMR (300 MHz, DMSO-$d_6$) δ 13.78 (s, 1H), 13.01 (s, 1H), 8.52 (s, 1H), 8.43 (s, 1H), 8.39 (s, 1H), 7.75 (dd, 1H, J=8.4, 0.6 Hz), 7.68 (d, 1H, J=7.2 Hz), 7.50 (d, 1H, J=7.2 Hz), 7.44 (dd, 1H, J=8.4, 1.5 Hz), 7.15–7.23 (m, 2H), 5.29 (t, 1H, J=5.4 Hz), 4.64 (d, 2H, J=5.4 Hz), 2.22 (s, 3H). Anal. ($C_{21}H_{17}N_5O \cdot 1.25H_2O$) C, H, N. MS (ES) [m+H]/z calculated 356. found 356.

(a) Example 73—{5-[3-(1H-Benzoimidazol-2-yl)-1H-indazol-5-yl]-4-methyl-pyridin-3-ylmethyl}-dimethyl-amine The title compound was prepared in 36% yield from example 72 and dimethylamine by a synthetic method analogous to intermediate 68b. $^1$H NMR (300 MHz, DMSO-$d_6$) δ 13.77 (s, 1H), 13.02 (s, 1H), 8.38–8.42 (m, 3H), 7.67–7.76 (m, 2H), 7.50 (d, 1H, J=7.8 Hz), 7.44 (dd, 1H, J=8.7, 1.5 Hz), 7.14–7.24 (m, 2H), 3.48 (br s, 2H), 2.28 (s, 3H), 2.21 (s, 6H). Anal. ($C_{23}H_{22}N_6 \cdot 0.8H_2O$) C, H, N. MS (ES) [m+H]/z calculated 383. found 383.

EXAMPLE 74

{5-[3-(1H-Benzoimidazol-2-yl)-1H-indazol-5-yl]-4-methyl-pyridin-3-ylmethyl}-ethyl-amine

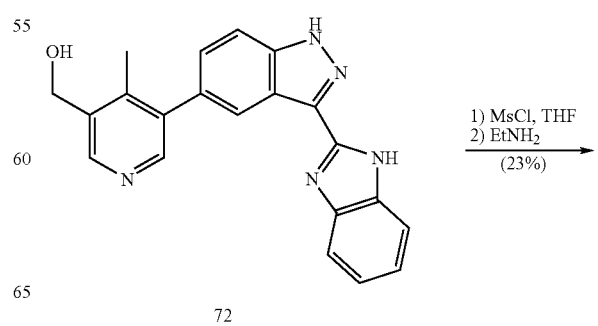

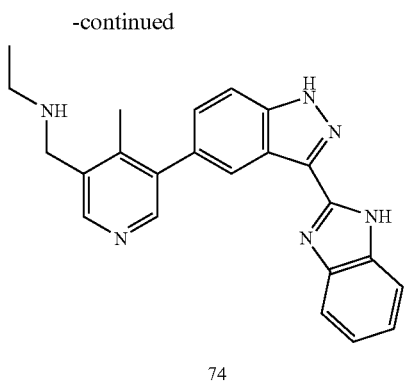
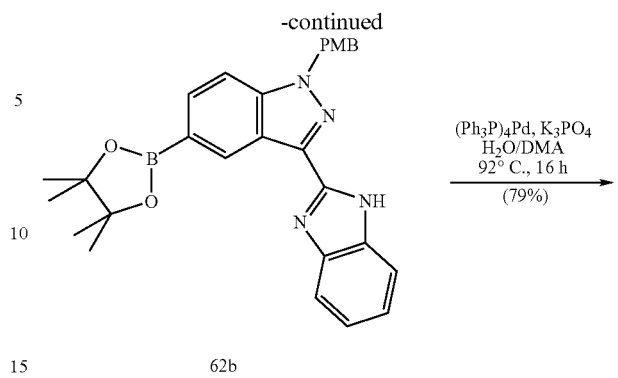

(a) Example 74—{5-[3-(1H-Benzoimidazol-2-yl)-1H-indazol-5-yl]-4-methyl-pyridin-3-ylmethyl}-ethyl-amine The title compound was prepared in 23% yield from example 72 and ethylamine by a synthetic method analogous to intermediate 68b. $^1$H NMR (300 MHz, DMSO-d$_6$) δ13.76 (s, 1H), 13.01 (s, 1H), 8.48 (s, 1H), 8.42 (s, 1H), 8.36 (s, 1H), 7.74 (d, 1H, J=8.7 Hz), 7.68 (d, 1H, J=7.5 Hz), 7.50 (d, 1H, J=7.5 Hz), 7.43 (dd, 1H, J=8.7, 1.5 Hz), 7.14–7.23 (m, 2H), 3.81 (s, 2H), 2.65 (q, 2H, J=7.2 Hz), 2.26 (s, 3H), 1.08 (t, 3H, J=7.2 Hz). Anal. (C$_{23}$H$_{22}$N$_6$.0.5H$_2$O) C, H, N. MS(ES)[m+H]/z calculated 383. found 383.

EXAMPLE 75

(3-(1H-Benzoimidazol-2-yl)-5-(4,5-dimethyl-pyridin-3-yl)-1H-indazole

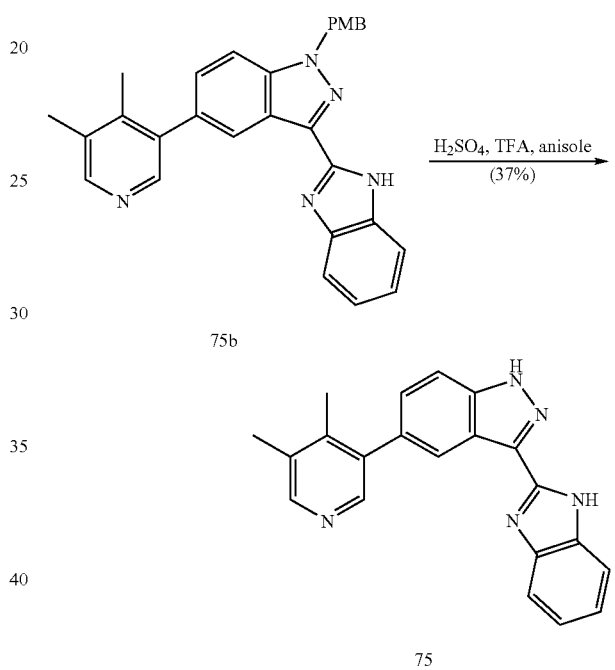

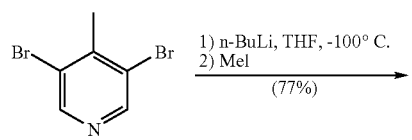

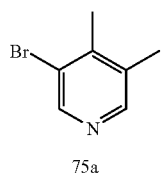

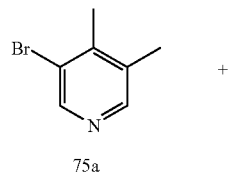

(a) Intermediate 75a—5-Bromo-3,4dimethyl-pyridine

The title compound was prepared from 3,5-dibromo-4-methyl-pyridine and iodomethane similar to the procedure for intermediate 59a. $^1$H NMR (300 MHz, CDCl$_3$) δ 8.50 (s, 1H), 8.22 (s, 1H), 2.36 (s, 3H), 2.30 (s, 3H).

(b) Intermediate 75b—3-(1H-Benzoimidazol-2-yl)-5-(4,5-dimethyl-pyridin-3-yl)-1-(4-methoxy-benzyl)-1H-indazole The title compound was prepared in 79% yield from intermediate 62b and intermediate 75a similar to the procedure for intermediate 61c. $^1$H NMR (300 MHz, CDCl$_3$) δ 10.66 (s, 1H), 8.64 (s, 1H), 8.40 (s, 1H), 8.36 (s, 1H), 7.81–7.85 (m, 1H), 7.41–7.49 (m, 2H), 7.18–7.27 (m, 5H), 6.81 (d, 2H, J=4.5 Hz), 5.57 (s, 2H), 3.74 (s, 3H), 2.31 (s, 3H), 2.16 (s, 3H).

(c) Example 75—3-(1H-Benzoimidazol-2-yl)-5-(4,5-dimethyl-pyridin-3-yl)-1H-indazole The title compound was prepared in 37% yield by the PMB-deprotection of intermediate 75b in a manner analogous to example 62. $^1$H NMR (300 MHz, DMSO-$d_6$) δ 13.76 (s, 1H), 13.02 (s, 1H), 842 (s, 1H), 8.38 (s, 1H), 8.31 (s, 1H), 7.74 (dd, 1H, J=8.4, 0.6 Hz), 7.51–7.69 (m, 2H), 7.44 (dd, 1H, J=8.7, 1.8 Hz), 7.17–7.22 (m, 2H) 2.33 (s, 3H), 2.18 (s, 3H). Anal. ($C_{21}H_{17}N_5$·1.0$H_2O$) C, H, N. MS (ES) [m+H]/z calculated 340. found 340.

EXAMPLE 76

3-[3-(1H-Benzoimidazol-2-yl)-1H-indazol-5-yl]-4-methyl-quinoline

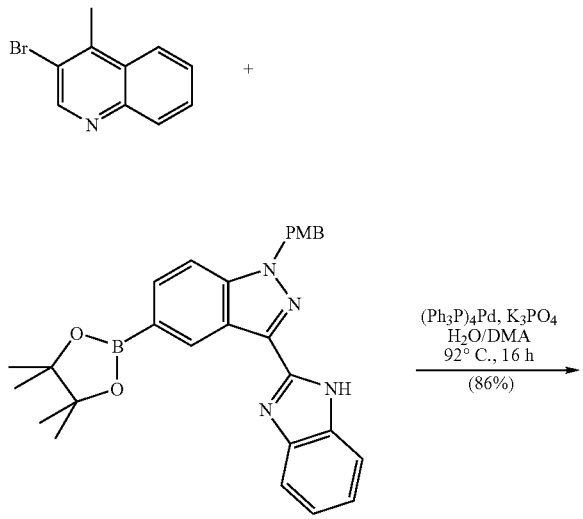

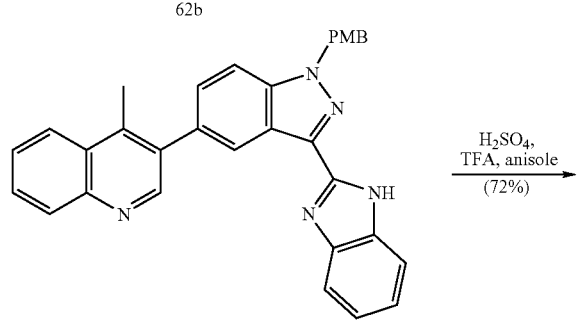

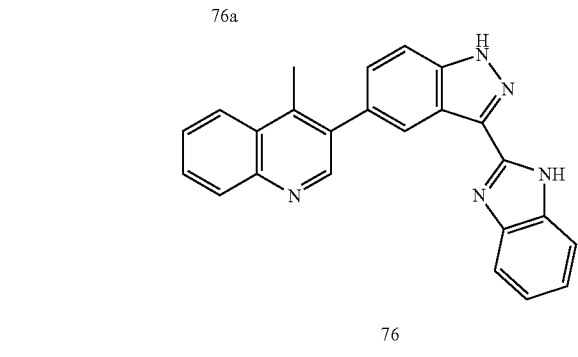

(a) Intermediate 76a—3-[3-(1H-Benzoimidazol-2-yl)-1-(4-methoxy-benzyl)-1H-indazol-5-yl]-4-methyl-quinoline The title compound was prepared in 86% yield from intermediate 62b and 3-bromo-4-methylquinoline (see Kwon et al., *Synthesis*, 1976, 249) similar to the procedure for intermediate 61c. $^1$H NMR (300 MHz, CDCl$_3$) 810.24 (s, 1H), 8.94 (s, 1H), 8.78 (s, 1H), 8.25 (dd, 1H, J=7.8, 0.3 Hz), 8.14 (dd, 1H, J=7.8, 0.3 Hz), 7.75–7.88 (m, 2H), 7.64–7.70 (m, 1H), 7.45–7.57 (m, 3H), 7.27–7.35 (m, 4H), 6.91 (d, 2H, J=6.9 Hz), 5.68 (s, 2H), 3.82 (s, 3H), 2.70 (s, 3H). Anal. ($C_{32}H_{25}N_5O$·0.15$H_2O$) C, H, N.

(b) Example 76—3-[3-(1H-Benzoimidazol-2-yl)-1H-indazol-5-yl]-4-methyl-quinoline

The title compound was prepared in 72% yield by the PMB-deprotection of intermediate 76a in a manner analogous to the procedure for example 62. $^1$H NMR (300 MHz, DMSO-$d_6$) δ 13.81 (s, 1H), 13.06 (s, 1H), 8.86 (s, 1H), 8.55 (s, 1H), 8.23 (d, 1H, J=7.8 Hz), 8.09 (d, 1H, J=7.2 Hz), 7.68–7.84 (m, 3H), 7.55–7.59 (m, 3H), 7.17–7.23 (m, 2H), 2.66 (s, 3H). Anal. ($C_{24}H_{17}N_5$·0.8$H_2O$) C, H, N. MS (ES) [m+H]/z calculated 376. found 376.

EXAMPLE 77

5-[3-(1H-Benzoimidazol-2-yl)-1H-indazol-5-yl]-4-methyl-pyridin-3-ol

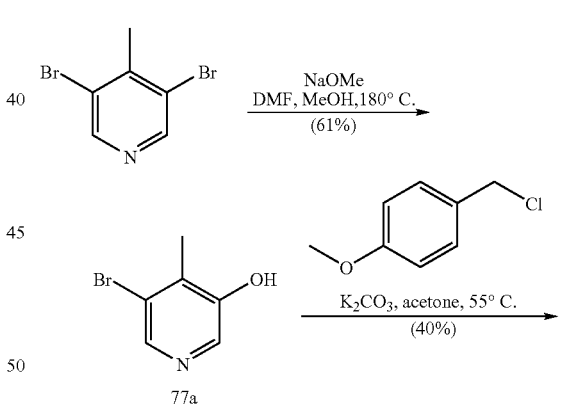

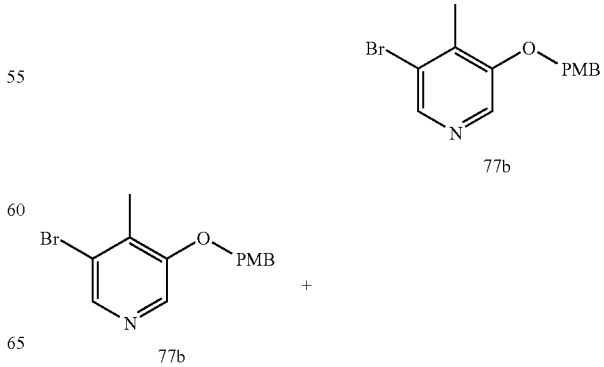

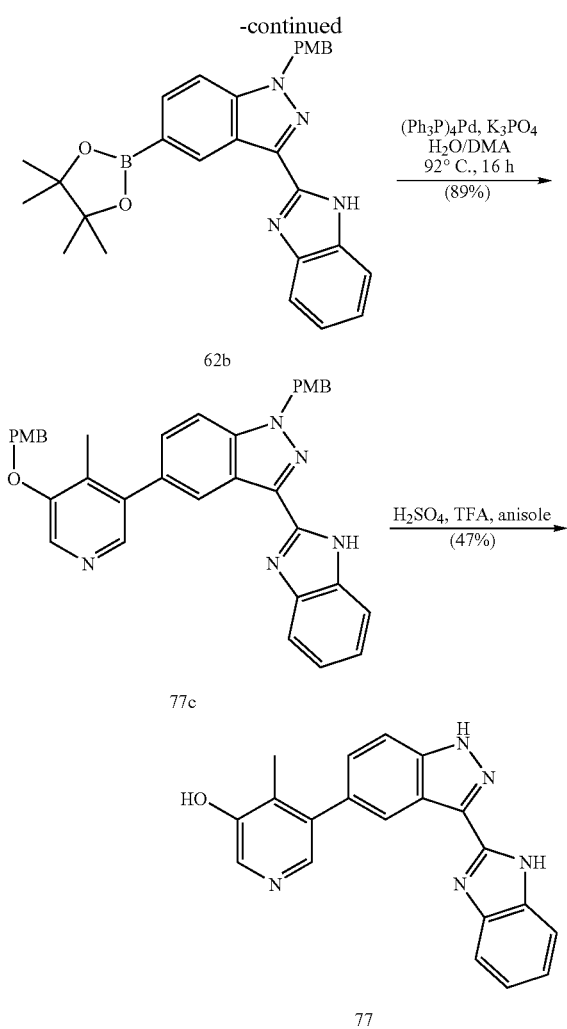

solid. ¹H NMR (300 MHz, CDCl₃) δ 8.33 (s, 1H), 8.16 (s, 1H), 7.34 (d, 2H, J=8.7 Hz), 7.93 (d, 2H, J=8.7 Hz), 5.08 (s, 2H), 3.83 (s, 3H), 2.34 (s, 3H). Anal. ($C_{14}H_{14}BrNO_2$) C, H, N.

(c) Intermediate 77c—5-[3-(1H-Benzoimidazol-2-yl)-1-(4methoxy-benzyl)-1H-indazol-5-yl]-4-methyl-pyridin-3-ol The title compound was prepared in 89% yield from intermediate 62b and intermediate 77b similar to the procedure for intermediate 61c. ¹H NMR (300 MHz, CDCl₃) δ 10.17 (s, 1H), 8.64 (s, 1H), 8.29 (s, 1H), 8.25 (s, 1H), 7.81–7.86 (m, 1H), 7.34–7.49 (m, 5H), 7.21–7.29 (m, 4H), 6.95 (d, 2H, J=8.7 Hz), 6.85 (d, 2H, J=8.7 Hz), 5.61 (s, 2H), 5.16 (s, 2H), 3.83 (s, 3H), 3.76 (s, 3H), 2.20 (s, 3H).

(d) Example 77—5-[3-(1H-Benzoimidazol-2-yl)-1H-indazol-5-yl]-4-methyl-pyridin-3-ol The title compound was prepared in 47% yield by the PMB-deprotection of intermediate 77c in a manner analogous to the procedure for example 62. ¹H NMR (300 MHz, DMSO-d₆) δ 13.74 (s, 1H), 13.01 (s, 1H), 9.91 (s, 1H), 8.43 (s, 1H), 8.14 (s, 1H), 7.98 (s, 1H), 7.72 (dd, 1H, J=8.4, 0.6 Hz), 7.69 (bs, 1H), 7.51 (bs, 1H), 7.45 (dd, 1H, J=8.7, 1.5 Hz), 7.17–7.22 (m, 2H) 2.09 (s, 3H). Anal. ($C_{20}H_{15}N_5O·0.3H_2O$) C, H, N. MS (ES) [m+H]/z calculated 340. found 340.

EXAMPLE 78

{5-[3-(1H-Benzoimidazol-2-yl)-1H-indazol-5-yl]-4-methyl-pyridin-3-ylmethyl}-isopropyl-amine

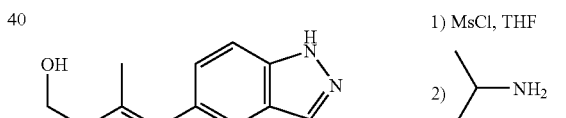

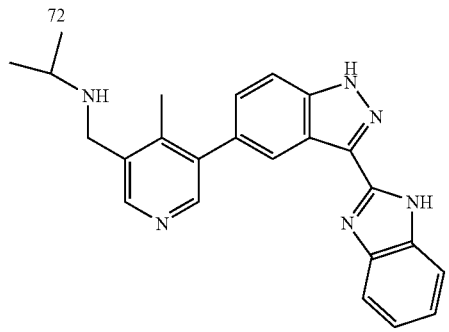

(a) Intermediate 77a—5-Bromo-4-methyl-pyridin-3-ol 3,5-Dibromo-4-methyl-pyridine (2.42 g, 9.64 mmol) and sodium methoxide (3.12 g, 57.8 mmol) were stirred in a mixture of DMF (8 mL) and MeOH (2 mL) in a sealed tube at 180° C. for 24 hours. The reaction was allowed to cool and was concentrated in vacuo. Purification by silica gel chromatography (100% ethyl acetate) gave 1.10 g (61%) of intermediate 77a as a white solid. ¹H NMR (300 MHz, DMSO-d₆) 610.31 (s, 1H), 8.12 (s, 1H), 8.04 (s, 1H), 2.21 (s, 3H). Anal. ($C_6H_6BrNO$) C, H, N.

(b) Intermediate 77b—3-Bromo-5-(4-methoxy-benzyloxy)-4-methyl-pyridine

Intermediate 77a (1.0 g, 5.3 mmol), tetramethylammonium iodide (107 mg, 0.53 mmol), and potassium carbonate (1.47g, 10.6 mmol) were stirred in acetone (30 mL). p-Methoxybenzyl chloride (1.08 mL, 7.98 mmol) was added, and the reaction stirred at 55° C. for 8 hours. The solution was diluted with ethyl acetate. Organics were washed with H₂O and brine, dried (MgSO₄), and concentrated in vacuo. Purification by silica gel chromatography (25% ethyl acetate/hexanes) gave 648 mg (40%) of intermediate 77b as a white

(a) Example 78—{5-[3-(1H-Benzoimidazol-2-yl)-1H-indazol-5-yl]-4-methyl-pyridin-3-ylmethyl}-iospropyl-amine The title compound was prepared in 28% yield from example 72 and isopropylamine using an analogous procedure to the preparation of intermediate 68b. $^1$H NMR (300 MHz, DMSO-d$_6$) δ 13.76 (s, 1H), 13.01 (s, 1H), 8.48 (s, 1H), 8.42 (s, 1H), 8.35 (s, 1H), 7.74 (d, 1H, J=8.7 Hz), 7.68 (d, 1H, J=7.8 Hz), 7.50 (d, 1H, J=7.2 Hz), 7.43 (dd, 1H, J=8.7, 1.5 Hz), 7.15–7.25 (m, 2H), 3.79 (s, 2H), 2.80–2.86 (m, 1H), 2.27 (s, 3H), 1.07 (d, 6H, J=6.6 Hz). Anal. (C$_{24}$H$_{24}$N$_6$ · 0.7H$_2$O) C, H, N. MS (ES) [m+H]/z calculated 397. found 397.

EXAMPLE 79

(5-Isoquinolin-4-yl-1H-indazol-3-ylmethylene)-pyrrol-1-yl-amine

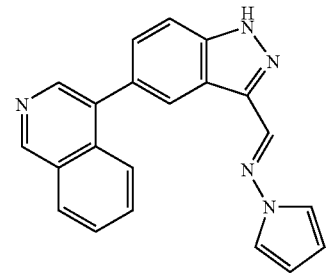

79

(a) Intermediate 79a—5-Isoquinolin-4-yl-1-(2-trimethylsilanyl-ethoxymethyl)-1H indazole-3-carbaldehyde The title compound was prepared in a manner analogous to the preparation of intermediate 19f, substituting a SEM-protection (see intermediate 3a) for the PMB-protection of intermediate 19c. $^1$H NMR (300 MHz, CDCl$_3$) δ 10.30 (s, 1H), 9.30 (s, 1H), 8.54 (s, 1H), 8.48 (s, 1H), 8.08 (dd, 1H, J=6.6, 2.4 Hz), 7.86 (dd, 1H, J=6.6, 0.6 Hz), 7.81 (dd, 1H, J=8.7, 0.9 Hz), 7.64–7.70 (m, 3H), 5.91 (s, 2H), 3.66 (t, 2H, J=8.4 Hz), 0.97 (t, 2H, J=8.4 Hz), −0.02 (s, 9H).

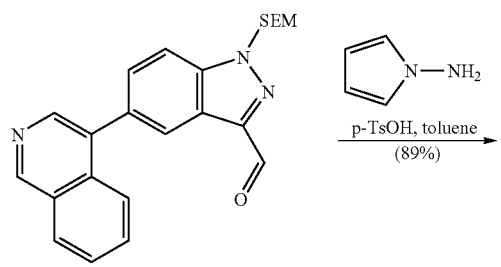

79a

(b) Intermediate 79b—[5-Isoquinolin-4-yl-1-(2-trimethylsilanyl-ethoxymethyl)-1H-indazol-3-ylmethylene]-pyrrol-1-yl-amine Intermediate 79a (400 mg, 0.99 mmol) and 1-aminopyrrole (98 mg, 1.2 mmol) were stirred with p-toluenesulfonic acid (10 mg) in toluene (6 mL) at 80° C. for 2 hours. The solution was concentrated in vacuo and purified by silica gel chromatography (50% ethyl acetate/hexanes) to give 410 mg (89%) of intermediate 79b as a yellow oil. $^1$H NMR (300 MHz, CDCl$_3$) δ 9.31 (s, 1H), 8.77 (s, 1H), 8.58–8.60 (m, 2H), 8.09 (dd, 1H, J=7.2, 0.9 Hz), 7.92 (d, 1H, J=7.8 Hz), 7.76 (dd, 1H, J=8.7, 0.9 Hz), 7.63–7.70 (m, 3H), 7.19 (t, 2H, J=2.4 Hz), 6.26 (t, 2H, J=2.4 Hz), 5.85 (s, 2H), 3.66 (t, 2H, J=8.4 Hz), 0.97 (t, 2H, J=8.4 Hz), −0.02 (s, 9H).

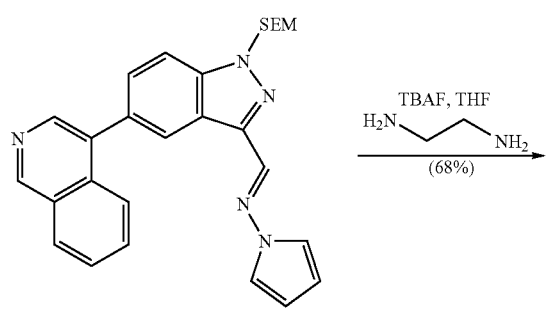

79b

(c) Example 79—(5-Isoquinolin-4-yl-1H-indazol-3-ylmethylene)-pyrrol-1-yl-amine The title compound was prepared in 68% yield by the SEM-deprotection of intermediate 79b in a manner analogous to the procedure for example 41. $^1$H NMR (300 MHz, DMSO-d$_6$) δ 13.82 (s, 1H), 9.38 (s, 1H), 9.09 (s, 1H), 8.52 (s, 1H), 8.41 (s, 1H), 8.24 (dd, 1H, J=7.2, 1.5 Hz), 7.71–7.85 (m, 4H), 7.61 (dd, 1H, J=8.4, 1.5 Hz), 7.46 (t, 2H, J=2.4 Hz), 6.15 (t, 2H, J=2.4 Hz). Anal. ($C_{21}H_{15}N_5$) C, H, N. MS (ES) [m+H]/z calculated 338. found 338.

EXAMPLE 80

2-[5-(5-Ethylaminomethyl-4-methyl-pyridin-3-yl)-1H-indazol-3-yl]-1H benzoimidazole-4carboxylic acid methylamide

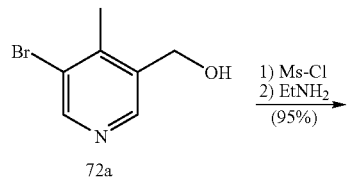

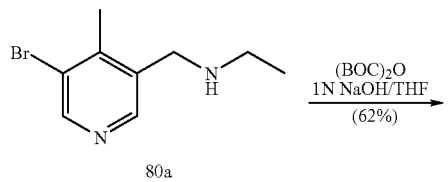

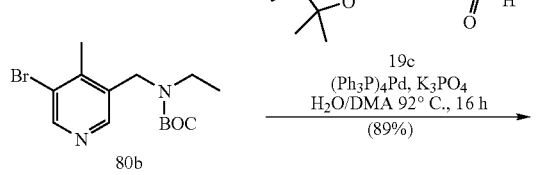

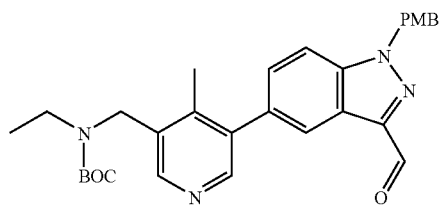

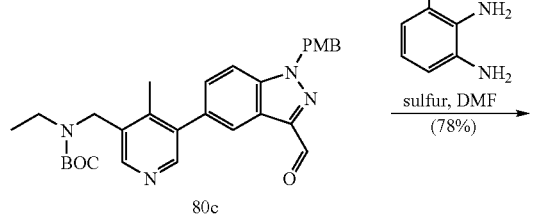

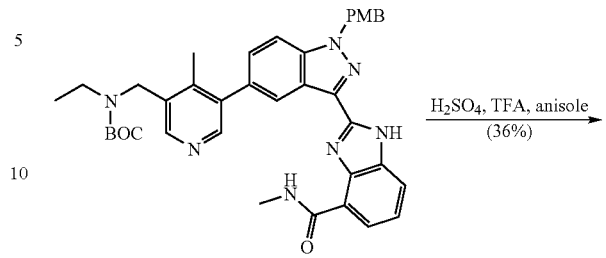

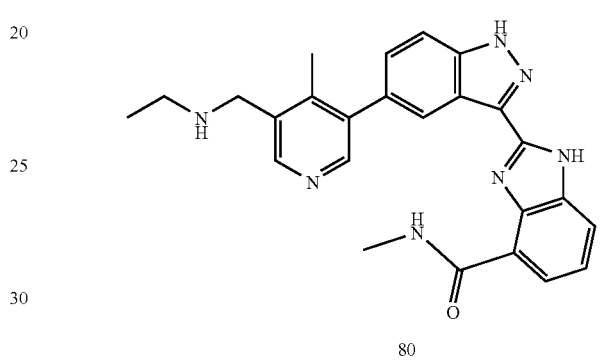

(a) Intermediate 80a—(5-Bromo-4-methyl-pyridin-3-ylmethyl)-ethyl-amine

The title compound was prepared in 95% yield from intermediate 72a and ethylamine using an analogous procedure to the method outlined for the preparation of intermediate 68b. $^1$H NMR (300 MHz, CDCl$_3$) δ 8.59 (s, 1H), 8.37 (s, 1H), 3.83 (s, 2H), 2.73 (q, 2H, J=7.2 Hz), 2.48 (s, 3H), 1.16 (t, 3H, J=7.2 Hz).

(b) Intermediate 80b—5-Bromo-4-methyl-pyridin-3-ylmethyl)-ethyl-carbamic acid dimethyl-ethyl ester Intermediate 80a (850 mg, 3.7 mmol) was stirred in a solution of THF (80 mL) and 1 N NaOH (10 mL). Di-tert-butyl dicarbonate (1.09 g, 5 mmol) was added, and the reaction stirred for 2 hours at room temperature. The solution was diluted with ethyl acetate. Organics were washed with H$_2$O and brine, dried (MgSO$_4$), and concentrated in vacuo. Purification by silica gel chromatography (33% ethyl acetate/hexanes) gave 760 mg (62%) of intermediate 80b as a clear oil. $^1$H NMR (300 MHz, CDCl$_3$) δ 8.60 (s, 1H), 8.24 (s, 1H), 4.49 (s, 2H), 3.18 (bs, 2H), 2.39 (s, 3H), 1.47 (s, 9H), 1.05 (t, 3H, J=7.2 Hz).-

(c) Intermediate 80c—Ethyl-[5-(3-formyl-1H-indazol-5-yl)-4-methyl-pyridin-3-ylmethyl] carbamic acid dimethyl-ethyl ester The title compound was prepared in 85% yield from intermediate 19e and intermediate 80b similar to the procedure for intermediate 61c. ¹H NMR (300 MHz, CDCl₃) δ 10.27 (s, 1H), 8.38 (s, 1H), 8.35 (s, 1H), 8.23 (s, 1H), 7.49 (dd, 1H, J=8.7, 0.6 Hz), 7.26–7.51 (m, 3H), 6.89 (dd, 2H, J=6.6, 2.1 Hz), 5.66 (s, 2H), 4.53 (s, 2H), 3.79 (s, 3H), 3.24 (bs, 2H), 2.18 (s, 3H), 1.48 (s, 9H), 1.10 (t, 3H, J=7.2 Hz).

(d) Intermediate 80d—Ethyl-{5-[1-(4methoxy-benzyl)-3-(4-methylcarbamoyl-1H-benzoimidazol-2-yl)-1H-indazol-5-yl]-4-methyl-pyridin-3-ylmethyl}-carbamic acid dimethyl-ethyl ester The title compound was prepared in 78% yield from intermediate 80c and 2-amino-N-methyl-3-nitro-benzamide (Found in: Kania, Braganza, et al., patent application "Compounds and Pharmaceutical Compositions for Inhibiting Protein Kinases, and Methods for Their Use", p. 52, line 10 to p. 53, line 26; and p. 59, line 16 to p. 60, line 4, U.S. Provisional Ser. No. 60/142,130, filed Jul. 2, 1999, incorporated by reference herein in its entirety.), similar to the procedure for intermediate 7c'. ¹H NMR (300 MHz, CDCl₃) δ 11.50 (s, 0.3H), 10.21 (s, 0.7H), 9.86 (bs, 1H), 8.36–8.57 (m, 3H), 8.18 (dd, 0.7H, J=7.8, 1.2 Hz), 7.97 (dd, 0.3H, J=7.8, 1.2 Hz), 7.63 (dd, 0.7H, J=7.8, 1.2 Hz), 7.24 (m, 5.3H), 6.88 (d, 2H, J=6.3 Hz), 5.65 (s, 1.4H), 5.63 (s, 0.6H), 4.57 (bs, 2H), 3.79 (s, 3H), 3.27 (bs, 2H), 3.12 (d, 0.9H, J=4.8 Hz), 3.06 (d, 2.1H, J=4.8 Hz), 2.29 (s, 2.1H), 2.21 (s, 0.9H), 1.48 (s, 9H), 1.11 (t, 3H, J=6.9 Hz).

(e) Example 80—2-[5-(5-Ethylaminomethyl-4-methyl-pyridin-3-yl)-1H-indazol-3-yl]-1H-benzoimidazole-4-carboxylic acid methylamide The title compound was prepared in 36% yield by the PMB-deprotection of intermediate 80d in a manner analogous to the procedure for example 62, with a final purification by preparatory HPLC (0.1% TFA-ACN/0.1% TFA-H₂O). ¹H NMR (300 MHz, DMSO-d₆) δ 14.02 (s, 1H), 13.62 (bs, 1H), 9.72 (bs, 1H), 8.88 (bs, 2H), 8.63 (s, 2H), 8.44 (s, 1H), 7.83–7.88 (m, 2H), 7.72 (d, 1H, J=7.2 Hz), 7.52 (dd, 1H, J=8.4, 1.5 Hz), 7.36 (t, 1H, J=7.8 Hz), 4.33 (bs, 2H), 3.15 (q, 2H, J=7.2 Hz), 2.90 (d, 3H, J=4.5 Hz), 2.43 (s, 3H), 1.27 (t, 3H, J=7.2 Hz). Anal. (C₂₅H₂₅N₇O.3TFA) C, H, N. MS (ES) [m+H]/z calculated 440. found 440.

EXAMPLE 81

Ethyl-4-{methyl-5-[3-(4-methylsulfanyl-1H-benzoimidazol-2-yl)-1H-indazol-5-yl]-pyridin-3-ylmethyl}-amine

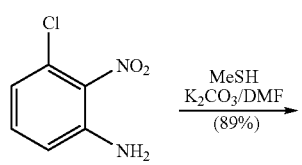

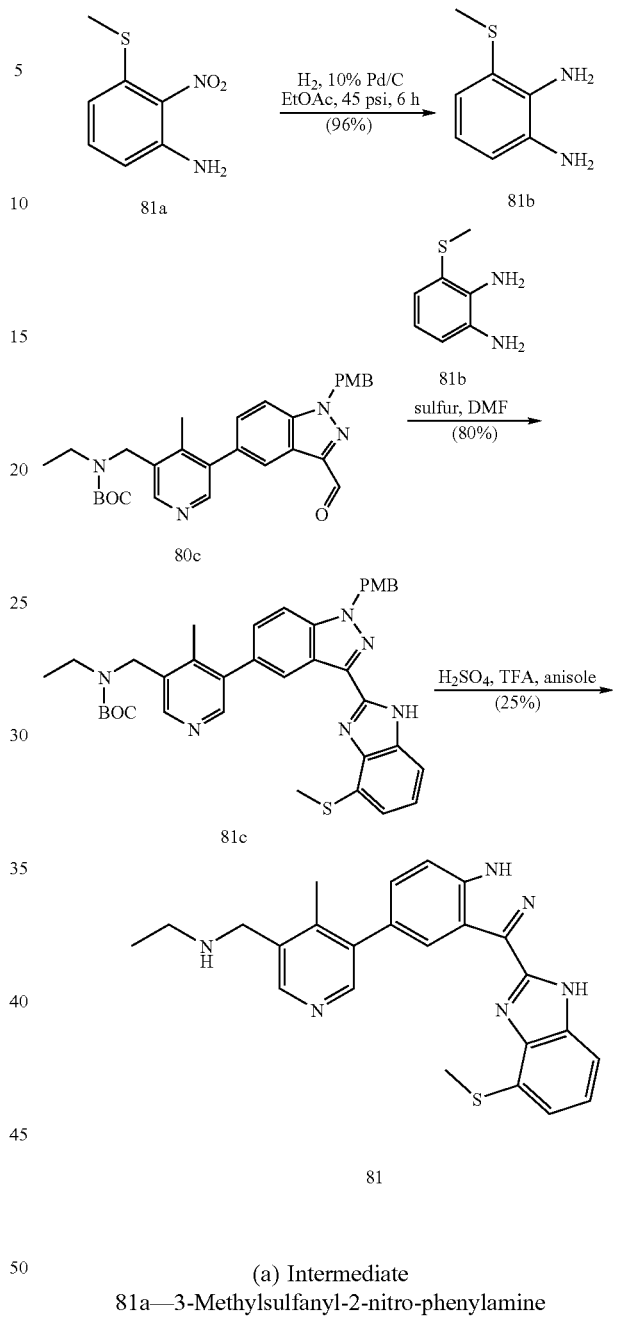

(a) Intermediate 81a—3-Methylsulfanyl-2-nitro-phenylamine

3-Chloro-2-nitro-aniline (1.0 g, 5.8 mmol) and potassium carbonate (880 mg, 6.4 mmol) were stirred in dry DMF (15 mL) in a sealable tube at 0° C. Methanethiol was bubbled through the solution for 4 minutes. The tube was sealed and the reaction stirred at 122° C. for 16 hours. The cooled reaction was diluted with H₂O and extracted with ethyl acetate. Organics were washed with brine, dried (Na₂SO₄), and concentrated in vacuo. Purification by silica gel chromatography (33% ethyl acetate/hexanes) gave 950 mg (89%) of intermediate 81a as a bright red-orange solid. ¹H NMR (300 MHz, CDCl₃) δ 7.21 (t, 1H, J=8.1 Hz), 6.55 (d, 2H, J=8.1 Hz), 5.93 (bs, 2H), 2.42 (s, 3H). Anal. (C₇H₈N₂O₂S)C, H, N, S.

(b) Intermediate 81b—3-Methylsulfanyl-benzene-1,2-diamine

The title compound was prepared in 96% yield from intermediate 81a similar to the hydrogenation procedure outlined for intermediate 9a'. $^1$H NMR (300 MHz, CDCl$_3$) δ 6.93–6.97 (m, 1H), 6.63–6.70 (m, 2H), 3.71 (bs, 4H), 2.36 (s, 3H). Anal. (C$_7$H$_{10}$N$_2$S)C, H, N, S.

(c) Intermediate 81c—Ethyl-{5-[1-(4-methoxy-benzyl)-3-(4-methylsulfanyl-1H benzoimidazol-2-yl)-1H-indazol-5-yl]-4-methyl-pyridin-3-ylmethyl}-carbamic acid dimethyl-ethyl ester The title compound was prepared in 80% yield from intermediate 81 b and intermediate 80c similar to the procedure for intermediate 7c'. $^1$H NMR (300 MHz, CDCl$_3$) δ 10.15 (s, 0.6H), 10.12 (s, 0.4H), 8.64 (s, 0.4H), 8.59 (s, 0.6H), 8.47 (s, 1H), 8.37 (s, 1H), 7.72 (d, 0.6H, J=7.5 Hz), 7.45 (t, 1H, J=7.2 Hz), 7.19–7.34 (m, 5H), 7.10 (d, 0.4H, J=7.5 Hz), 6.83–6.89 (m, 2H), 5.65 (s, 1.2H), 5.61 (s, 0.8H), 4.55 (bs, 2H), 3.78 (s, 1.8H), 3.77 (s, 1.2H), 3.26 (bs, 2H), 2.67 (s, 1.2H), 2.57 (s, 1.8H), 2.24 (s, 1.2H), 2.22 (s, 1.8H), 1.49 (s, 9H), 1.12 (t, 3H, J=6.9 Hz).

(d) Example 81—Ethyl-4-{methyl-5-[3-(4-methylsulfanyl-1H-benzoimidazol-2-yl)-1H-indazol-5-yl]-pyridin-3-ylmethyl}-amine The title compound was prepared in 25% yield by the PMB-deprotection of intermediate 81c in a manner analogous to the procedure for example 62. $^1$H NMR (300 MHz, DMSO-d$_6$) δ 13.78 (s, 1H), 13.10 (s, 1H), 8.48 (s, 1H), 8.44 (s, 1H), 8.39 (s, 1H), 7.75 (d, 1H, J=8.7 Hz), 7.44 (d, 1H, J=8.7, 1.8 Hz), 7.30 (d, 1H, J=7.8 Hz), 7.19 (t, 1H, J=7.8 Hz), 6.99 (d, 1H, J=7.2 Hz), 3.82 (s, 2H), 2.66 (q, 2H, J=7.2 Hz), 2.56 (s, 3H), 2.28 (s, 3H), 1.08 (t, 3H, J=7.2 Hz). Anal. (C$_{24}$H$_{24}$N$_6$S.1.5H$_2$O) C, H, N, S. MS (ES) [m+H]/z calculated 429. found 429.

EXAMPLE 82

N-2-[5-(5-Ethylaminomethyl-4-methyl-pyridin-3-yl)-1H-indazol-3-yl-1 benzoimidazol-4-yl]-acetamide

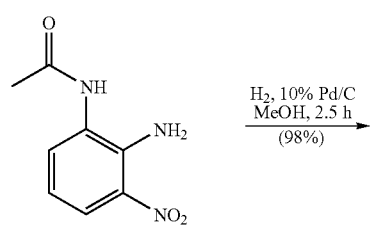

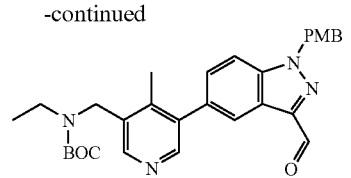

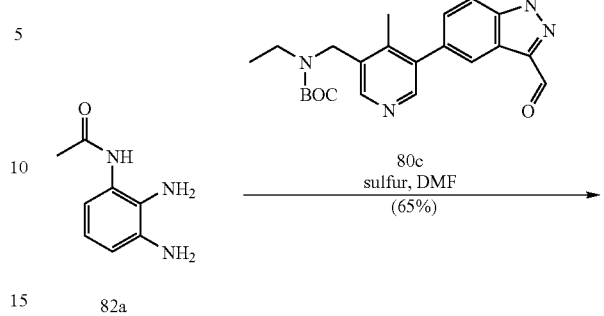

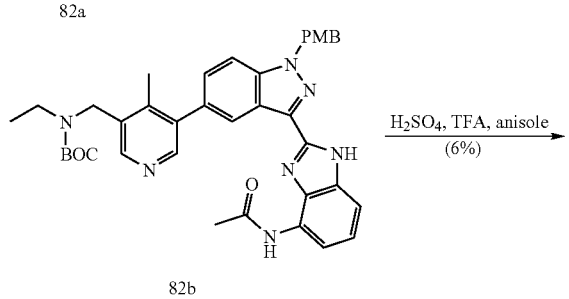

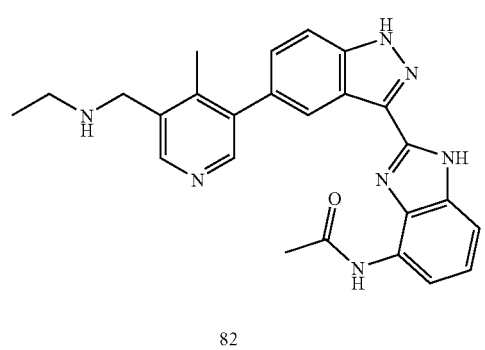

(a) Intermediate 82a—N(2,3-diamino-phenyl)-acetamide

The title compound was prepared in 98% yield from N-(2-amino-3-nitro-phenyl)-acetamide (see Harvey et al., *J. Chem. Soc. Perk. Trans. 1*, 1988,1939–1944) in a manner analogous to the hydrogenation of intermediate 9a'. $^1$H NMR (300 MHz, CDCl$_3$) δ 9.04 (s, 1H), 6.35–6.49 (m, 3H), 4.38 (bs, 4H), 2.00 (s, 3H).

(b) Intermediate 82b—{5-[3-(4-Acetylamino-1H-benzoimidazol-2-yl)-1-(4-methoxy-benzyl)-1H-indazol-5-yl]-4-methyl-pyridin-3-ylmethyl}-ethyl-carbamic acid dimethyl-ethyl ester The title compound was prepared in 65% yield from intermediate 82a and intermediate 80c similar to the procedure for intermediate 7c'. $^1$H NMR (300 MHz, CDCl$_3$) δ 12.35 (bs, 1H), 10.80 (bs, 1H), 7.90–8.85 (m, 4H), 6.76–7.46 (m, 8H), 5.60 (bs, 2H), 4.51 (bs, 2H), 3.78 (s, 3H), 3.61 (bs, 2H), 3.19 (bs, 3H), 1.74 (bs, 12H), 1.18 (bs, 3H). MS (ES) [m+H]/z calculated 660, found 660.

(c) Example 82—N{2-[5-(5-Ethylaminomethyl-4-methyl-pyridin-3-yl)-1H-indazol-3-yl]-1H-benzoimidazol-4-yl}-acetamide The title compound was prepared in 6% yield by the PMB-deprotection of intermediate 82b in a manner analogous to the procedure for example 62. $^1$H NMR (300 MHz, MeOD-d$_4$) δ 8.64 (s, 1H), 8.58 (s, 1H), 8.45 (s, 1H), 7.82 (d, 1H, J=8.4 Hz), 7.57 (d, 1H, J=7.2 Hz), 7.50 (d, 2H, J=7.2 Hz), 7.34 (t, 1H, J=8.4 Hz), 4.44 (s, 2H), 3.27 (q, 2H, J=7.5 Hz), 2.43 (s, 3H), 2.22 (s, 3H), 1.41 (t, 3H, J=7.5 Hz). MS (ES) [m+H]/z calculated 440. found 440.

EXAMPLE 83

5-(2,6-Difluorophenyl)-3-Phenyl-1H-indazole

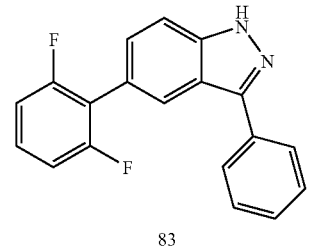

83

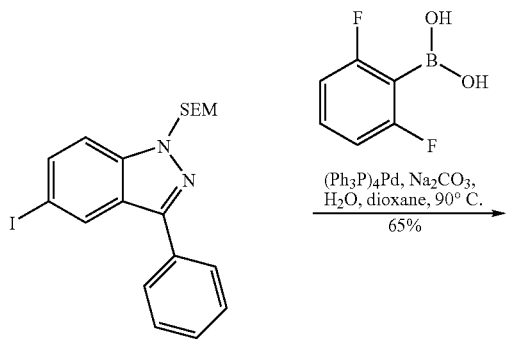

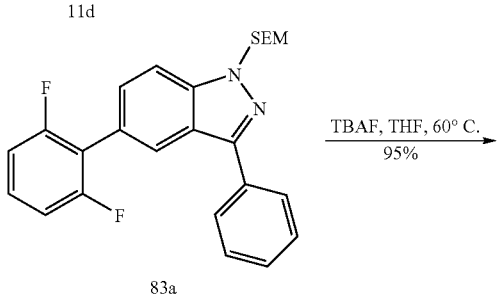

83a (a) Intermediate 83a—5-(2,6-Difluorophenyl)-3-phenyl-1-[2-(trimethylsilanyl)ethoxymethyl]-1H-indazole By a synthetic method analogous to intermediate 11e, palladium catalyzed coupling of intermediate 11d with 2,6-difluorophenylboronic acid yielded 83a (65%) as a pale yellow foam: $^1$H NMR (DMSO-d$_6$) δ −0.09 (s, 9H), 0.84 (t, 2H, J=8.0 Hz), 3.62 (t, 2H, J=8.0 Hz), 5.86 (s, 2H), 7.24 (dd, 2H, J=8.1, 8.3 Hz), 7.44 (tt, 1H, J=1.3, 7.2 Hz), 7.47–7.58 (m, 4H), 7.92 (dd, 1H, J=0.5, 8.8 Hz), 7.98 (dd, 2H, J=1.3, 8.2 Hz), 8.14 (d, 1H, J=0.5 Hz).

(a) Example 83—5-(2,6-Difluorophenyl)-3-phenyl-1H-indazole

Similar to example 7', treatment of 83a with tetrabutylammonium fluoride afforded 5-(2,6-difluorophenyl)-3-phenyl-1H-indazole 83 (95%) as a yellow solid:: $^1$H NMR (DMSO-d$_6$) δ 7.23 (dd, 2H, J=8.1, 8.3 Hz), 7.40 (tt, 1H, J=1.3, 7.2 Hz), 7.43–7.56 (m, 4H), 7.70 (dd, 1H, J=0.6, 8.7 Hz), 7.98 (dd, 2H, J=1.3, 8.4 Hz), 8.11 (d, 1H, J=0.6 Hz), 13.38 (s, 1H). Anal. (C$_{19}$H$_{12}$N$_2$F$_2$) C, H, N.

EXAMPLE 84

5-Amino-3-(2-Pyrrolyl)-1H-indazole

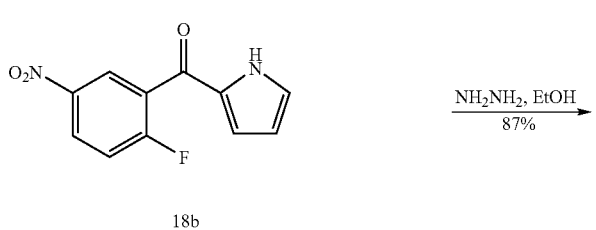

18b

NH$_2$NH$_2$, EtOH
87%

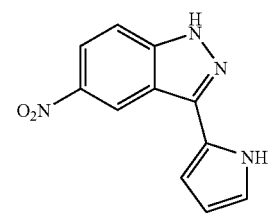

18b'

H$_2$, Pd/C, EtOAc
99%

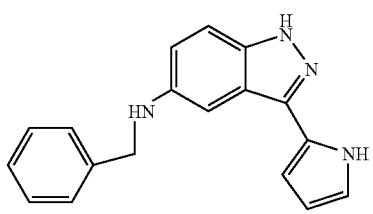 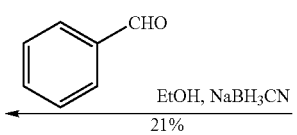 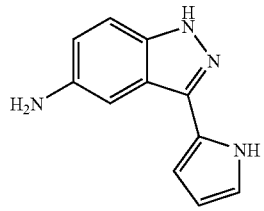

85    84

By a synthetic method analogous to intermediate 18c, hydrogenation of 5-nitro-3-(2-pyrrolyl)-1H-indazole 18b' over 10% palladium on carbon afforded 5-amino-3-(2-pyrrolyl)-1H-indazole 84 (99%) as a beige solid: $^1$H NMR (DMSO-t*) δ 6.13 (dd, 1H, J=2.4, 2.6 Hz), 6.49 (dd, 1H, J=1.5, 2.4 Hz), 6.76 (dd, 1H, J=1.5, 2.6 Hz), 6.79 (dd, 1H, J=2.1, 8.9 Hz), 7.03 (d, 1H, J=2.1 Hz), 7.22 (d, 1H, J=8.9 Hz), 11.16 (s, 1H), 12.45 (s, 1H). Anal. ($C_{11}H_{10}N_4$·0.2 ethyl acetate) C, H, N.

EXAMPLE 85

5-(Benzylamino)-3-(2-Pyrrolyl)-1H-indazole

Benzaldehyde (100 mg, 1 mmol) was added to a solution of 5-amino-3-(2-pyrrolyl)-1H-indazole 84 (100 mg, 0.5 mmol) in EtOH (100 ml). The resultant solution was stirred for 2 hours at ambient temperature prior to addition of NaBH$_3$CN (50 mg, 0.8 mmol) in a single portion as the solid. After stirring for an additional 2 hours, the crude reaction mixture was poured into H$_2$O (200 ml) and extracted with ethyl acetate (2×100 ml). The combined organic extracts were dried over sodium sulfate and concentrated. Silica gel chromatography (60% ethyl acetate/hexanes) provided 85 (21%) as a beige solid: $^1$H NMR (DMSO-d$_6$) δ 4.33 (s, 2H), 6.11 (dd, 1H, J=2.5, 2.6 Hz), 6.38 (dd, 1H, J=1.5, 2.5 Hz), 6.74 (dd, 1H, J=1.5, 2.6 Hz), 6.81 (s, 1H), 6.91 (dd, 1H, J=1.9, 8.9 Hz), 7.17–7.36 (m, 5H), 7.43 (d, 1H, J=8.9 Hz), 7.45 (d, 1H, J=1.9 Hz), 11.13 (s, 1H), 12.48 (s, 1H). Anal. ($C_{18}H_{16}N_4$·0.33H$_2$O) C, H, N.

EXAMPLE 86

5-(3-Methoxyphenyl)-3-(phenyl)-1H-indazole

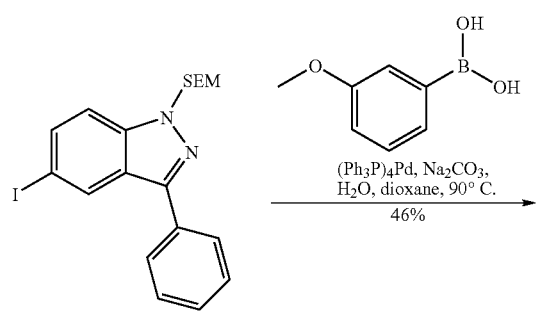

11d

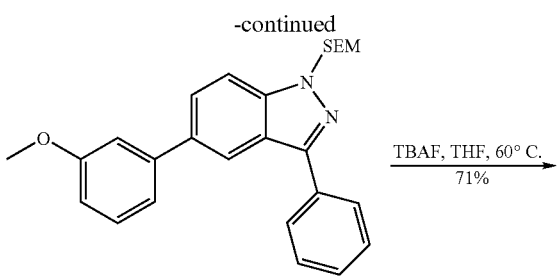

86a

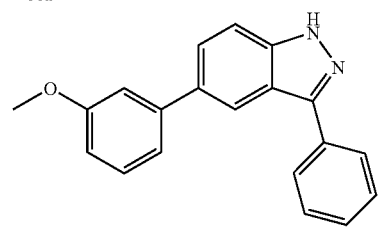

86

(a) Intermediate 86a—5-(3-Methoxyphenyl)-3-phenyl-1-[2-(trimethylsilanyl)ethoxymethyl]-1H-indazole By a synthetic method to intermediate 11e, palladium catalyzed coupling of intermediate 11d with 3-methoxyphenylboronic acid yielded 86a (46%) as a pale yellow solid: $^1$H NMR (DMSO-d$_6$) δ −0.10 (s, 9H), 0.84 (t, 2H, J=8.0 Hz), 3.62 (t, 2H, J=8.0 Hz), 5.86 (s, 2H), 7.24–7.34 (m, 4H), 7.38–7.56 (m, 4H), 7.84 (d, 1H, J=8.3 Hz), 7.91–8.03 (m, 3H).

(b) Example 86

5-(3-Methoxyphenyl)-3-phenyl-1H-indazole

Similar to example 11, treatment of 86a with tetrabutylammonium fluoride afforded 5-(3-methoxyphenyl)-3-phenyl-1H-indazole 86 (71%) as a white solid:: $^1$H NMR (DMSO-d$_6$) δ 3.83 (s, 3H), 6.93 (dd, 1H, J=1.9, 8.0 Hz), 7.22–7.75 (m, 8H), 8.04 (dd, 2H, J=1.3, 7.2 Hz), 8.20 (d, 1H, J=0.3 Hz), 13.27(s, 1H). Anal. ($C_{20}H_{16}N_2$000.2H$_2$O) C, H, N.

EXAMPLE 87

{5-[3-(1H-Benzoimidazol-2-yl)-1H-indazol-5-yl]-4-methyl-pyridin-3-ylmethyl}-isobutyl-amine

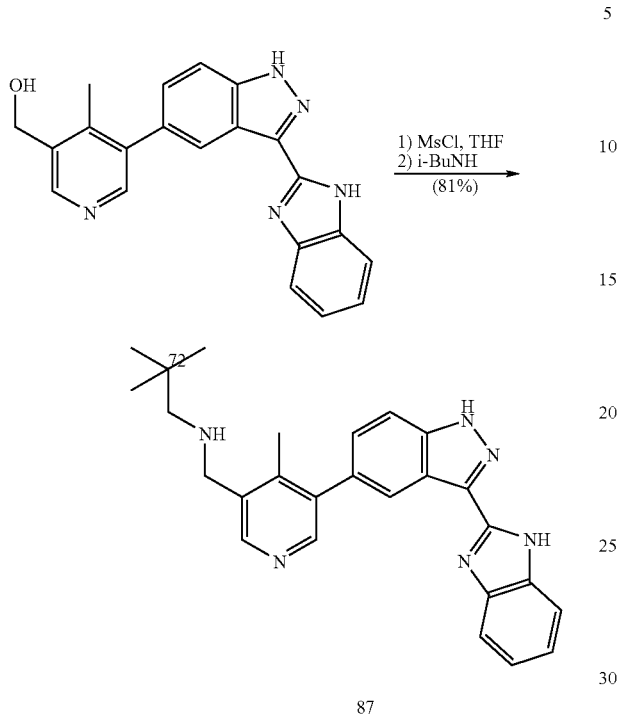

87

(a) Example 87—{5-[3-(1H-Benzoimidazol-2-yl)-1H-indazol-5-yl]-4-methyl-pyridin-3-ylmethyl}-isobutyl-amine The title compound was prepared in 81% yield from example 72 and isobutylamine using an analogous procedure to the preparation of intermediate 68b. $^1$H NMR (300 MHz, DMSO-$d_6$) 13.77 (s, 1H), 13.02 (s, 1H), 8.50 (s, 1H), 8.42 (s, 1H), 8.37 (s, 1H), 7.74 (d, 1H, J=8.7 Hz), 7.68 (d, 1H, J=7.5 Hz), 7.50 (d, 1H, J=7.5 Hz), 7.43 (dd, 1H, J=8.7, 1.5 Hz), 7.14–7.24 (m, 2H), 3.85 (s, 2H), 2.49 (bs, 2H), 2.27 (s, 3H), 1.73–1.79 (m, 1H), 0.90 (d, 6H, J=6.6 Hz). Anal. ($C_{25}H_{26}N_6$·0.3$H_2O$) C, H, N. MS (ES) [m+H]/z calculated 411. found 411.

EXAMPLE 88

{5-[3-(1H-Benzoimidazol-2-yl)-1H-indazol-5-yl]-4-methyl-pyridin-3-ylmethyl}-benzyl-amine

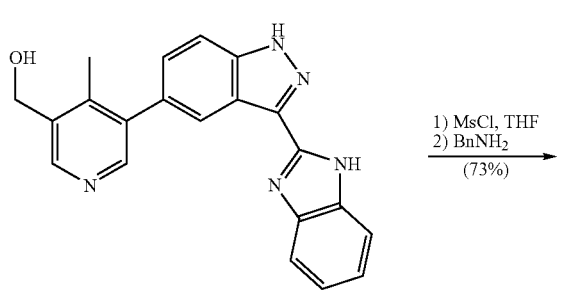

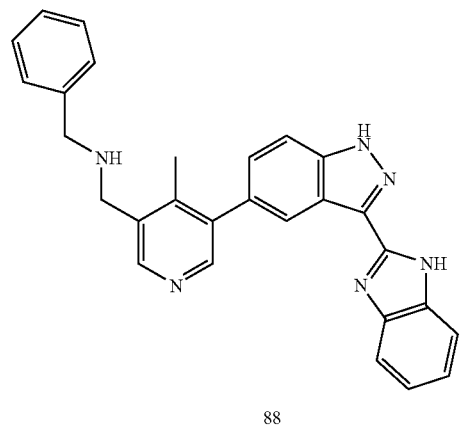

88

(a) Example 88—{5-[3-(1H-Benzoimidazol-2-yl)-1H-indazol-5-yl]-4-methyl-pyridin-3-ylmethyl}-benzyl-amine The title compound was prepared in 73% yield from example 72 and benzylamine similar to intermediate 68b. $^1$H NMR (300 MHz, DMSO-$d_6$) δ 13.77 (s, 1H), 13.02 (s, 1H), 8.51 (s, 1H), 8.42 (s, 1H), 8.38 (s, 1H), 7.74 (d, 1H, J=8.7 Hz), 7.68 (d, 1H, J=7.5 Hz), 7.50 (d, 1H, J=7.5 Hz), 7.16–7.44 (m, 8H), 3.90 (bs, 4H), 2.23 (s, 3H). Anal. ($C_{28}H_{24}N_6$·1.2$H_2O$) C, H, N. MS (ES) [m+H]/z calculated 445. found 445.

EXAMPLE 89

2-({5-[3-(1H-Benzoimidazol-2-yl)-1H-indazol-5-yl]-4-methyl-pyridin-3-ylmethyl}-amino)-ethanol

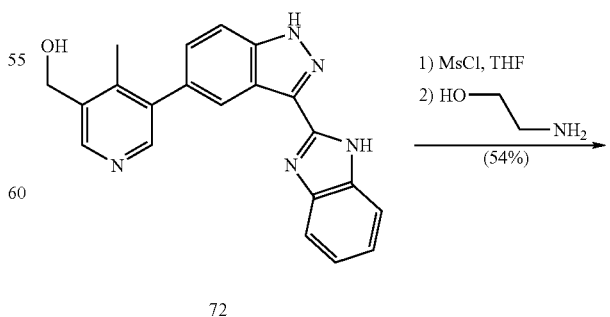

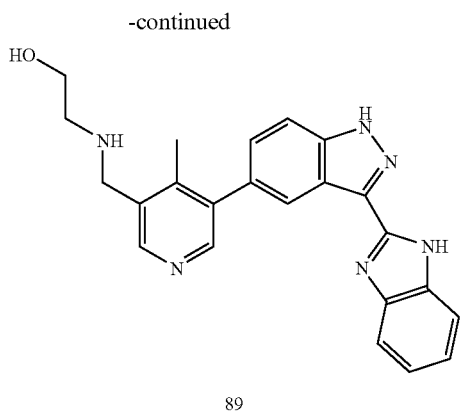

(a) Example 89—2-({5-[3-(1H-Benzoimidazol-2-yl)-1H-indazol-5-yl]-4-methyl-pyridin-3-ylmethyl}-amino)-ethanol The title compound was prepared in 54% yield from example 72 and ethanolamine similar to intermediate 68b. $^1$H NMR (300 MHz, DMSO-d$_6$) δ 13.78 (s, 1H), 13.01 (s, 1H), 8.54 (s, 1H), 8.43 (s, 1H), 8.42 (s, 1H), 7.75 (d, 1H, J=8.7 Hz), 7.67 (d, 1H, J=7.5 Hz), 7.51 (d, 1H, J=7.5 Hz), 7.43 (dd, 1H, J=8.7, 1.5 Hz), 7.15–7.23 (m, 2H), 4.82 (bs, 1H), 4.03 (s, 2H), 3.60 (d, 2H, J=2.7 Hz), 2.87 (t, 2H, J=2.7 Hz), 2.29 (s, 3H). Anal. (C$_{23}$H$_{22}$N$_6$O.0.1H$_2$O) C, H, N. MS (ES) [m+H]/z calculated 399. found 399.

EXAMPLE 90

{1-[2-(5-Isoquinolin-4-yl-1H-indazol-3-yl)-1H-benzoimidazol-4-yl]-ethyl}-methyl-amine

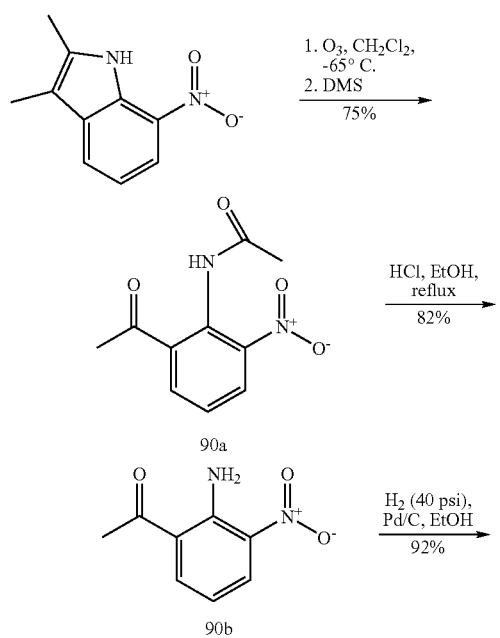

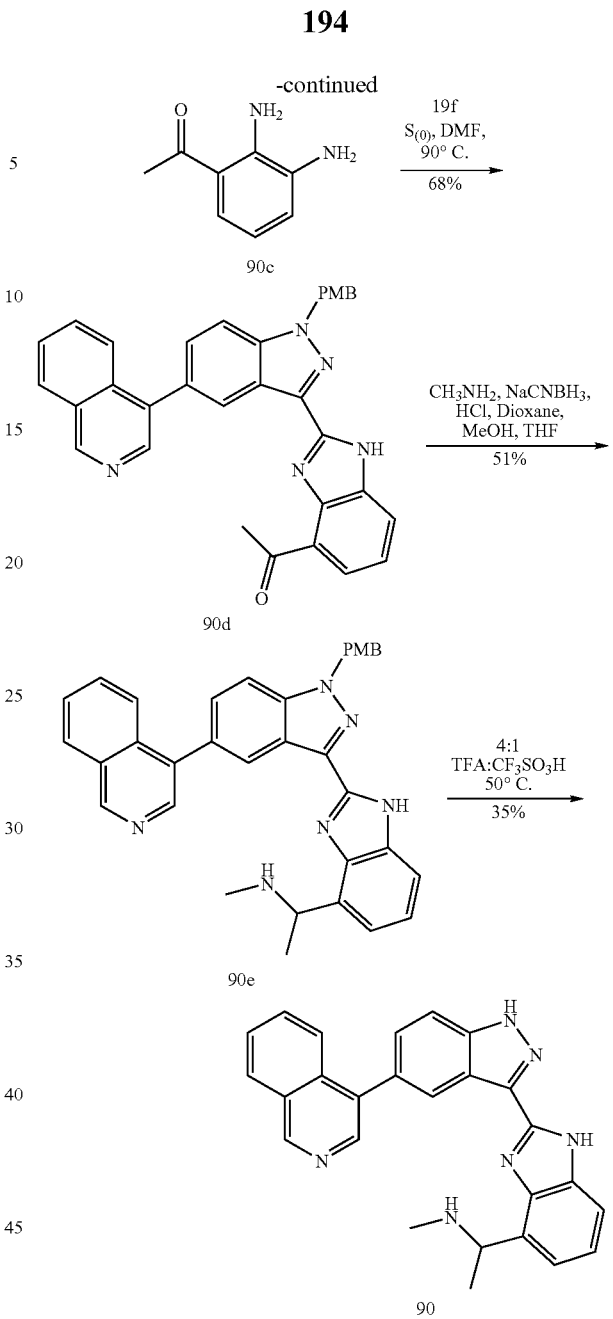

(a) Intermediate 90a—N-(2-Acetyl-6-nitro-phenyl)-acetamide

A solution of 2,3-dimethyl-7-nitroindole (Acros Organics, 13.55 g, 71.24 mmol) in dichloromethane (1.0 L) was cooled to −60° C. internal temperature and treated with ozone gas for 1.5 hours. A color change from orange to yellow-green was observed in this time. Argon was bubbled through the solution for one hour, causing the color to change to yellow. Dimethylsulfide (10.5 mL, 142.5 mmol) was added, and stirring continued at −60° C. for 1.5 hours. After warming to room temperature, the solution was concentrated in vacuo to 200 mL, washed with water (2×50 mL), dried over magnesium sulfate, filtered, concentrated, and purified by silica gel chromatography (50 to 100% ethyl acetate in hexanes), affording 90a (11.85 g, 75%) as an orange solid. R$_f$=0.36 (75% ethyl acetate/hexanes); $^1$H NMR (DMSO-d$_6$) δ 2.02

(s, 3H), 2.52 (s, 3H), 7.52 (t, 1H, J=7.9 Hz), 8.00 (dd 1H, J=7.9, 1.5 Hz), 8.05 (dd, 1H, J=8.1, 1.5 Hz), 10.32 (s, 1H). Anal. ($C_{10}H_{10}N_2O_4 \cdot 0.4H_2O$) C, H, N.

(b) Intermediate 90b—1-(2-Amino-3-nitro-phenyl)-ethanone

Concentrated hydrochloric acid (40 mL) was added to a solution of 90a (4.00 g, 18.0 mmol) in absolute ethanol (80 mL) and water (40 mL). The mixture was heated to reflux (87° C. internal temperature) for 1 hour. After cooling to room temperature, saturated aqueous sodium bicarbonate solution was added to bring the pH to 8. The solution was extracted with ethyl acetate (2×200 mL). The combined organic extracts were dried over magnesium sulfate, filtered, concentrated and purified by silica gel chromatography (20 to 70% ethyl acetate in hexanes) to give 90b (2.67 g, 82%) as a yellow solid. $R_f$=0.45 (50% ethyl acetate/hexanes); $^1$H NMR (DMSO-$d_6$) δ 2.62 (s, 3H), 6.74 (t, 1H, J=8.1 Hz), 8.31 (m. 2H), 8.85 (br s, 2H). Anal. ($C_8H_8N_2O_3$) C, H, N.

(c) Intermediate 90c—1-(2,3-Diamino-phenyl)-ethanone

By a synthetic method analogous to the synthesis of 9a, hydrogenation of 90b (2.00 g, 11.1 mmol) in ethanol afforded 90c (1.54 g, 92%) as bright yellow crystals. $R_f$=0.34 (50% ethyl acetate/hexanes); $^1$H NMR (DMSO-$d_6$) δ 2.47 (s, 3H), 4.75 (br s, 2H), 6.40 (dd, 1H, J=7.5, 8.1 Hz), 6.69 (dd, 1H, J=7.5, 1.3 Hz), 6.79 (br s, 2H), 7.10 (dd, 1H, J=8.1, 1.3 Hz). Anal. ($C_8H_{10}N_2O$) C, H, N.

(d) Intermediate 90d—1-{2-[5-Isoquinolin-4-yl-1-(4methoxy-benzyl)-1H-indazol-3-yl]-1H-benzoimidazol-4-yl}-ethanone Similar to the synthesis of 19h, aldehyde 19f (2.02 g, 5.13 mmol) and diamine 90c (771 mg, 5.13 mmol) were condensed in the presence of sulfur to give 90d (1.83 g, 68%) as a bright yellow solid. $R_f$=0.19 (75% ethyl acetate/hexanes); $^1$H NMR (DMSO-$d_6$) [Some peaks are doubled due to tautomeric isomerization] δ 2.72 and 2.87 (2 br s, 3H together), 3.71 (s, 3H), 5.85 (s, 2H), 6.93 (d, 2H, J=8.7 Hz), 7.34 (m, 3H), 7.75 (m, 5H), 8.07 (m, 2H), 8.25 (d, 1H, J=7.5 Hz), 8.56 and 8.80 (2 br s, 2H together), 9.38 (s, 1H), 11.83 (s, 1H), 13.53 (s, 1H).

(e) Intermediate 90e—(1-{2-[5-Isoquinolin-4-yl-1-(4-methoxy-benzyl)-1H-indazol-3-yl]-1H-benzoimidazol-4-yl}-ethyl)-methyl-amine A solution of methylamine in methanol (2.0 M, 3.02 mL, 6.04 mmol) was added to ketone 90d (527.8 mg, 1.01 mmol) at room temperature, followed by hydrochloric acid (4.0 mL in dioxane, 0.504 mL, 2.02 mmol), methanol (6.0 mL), and sodium cyanoborohydride (38.0 mg, 0.605 mmol). The suspension was stirred at room temperature for 23 hours, but no reaction was observed by TLC analysis. Anhydrous THF (10 mL) was added to increase solubility, and stirring continued for 70 hours. The mixture was partitioned between ethyl acetate and saturated aqueous sodium bicarbonate solution. The organic phase was dried over magnesium sulfate, filtered, concentrated and purified by silica gel chromatography (1:20:200 aq. NH$_4$OH:ethanol:dichloromethane), yielding 90e (275.0 mg, 51%) as a yellow foam. $R_f$=0.09 (1:20:400 aqueous NH$_4$OH: ethanol: dichloromethane); $^1$H NMR (CD$_3$OD) δ 1.53 (d, 3H, J=6.8 Hz), 2.24 (s, 3H), 3.75 (s, 3H), 4.28 (q, 1H, J=6.8 Hz), 5.45 (s, 1H), 5.77 (s, 2H), 6.89 (d, 2H, J=8.7 Hz), 7.22 (m, 2H), 7.34 (d, 2H, J=8.7 Hz), 7.52 (d, 1H, J=7.9 Hz),7.61 (dd, 1H, J=8.7, 1.5 Hz), 7.76 (m, 3H), 7.99 (d, 1H, J=8.3 Hz), 8.20 (dd, 1H, J=7.2, 1.7 Hz), 8.48 (s, 1H), 8.70 (s, 1H), 9.27 (s, 1H). Anal. ($C_{34}H_{30}N_6O_{01.0}H_2O$) C, H, N.

(f) Example 90—{1-[2-(5-Isoquinolin-4-yl-1H-indazol-3-yl)-1H-benzoimidazol-4-yl]-ethyl}-methyl-amine A solution of 90e (179.7 mg, 0.334 mmol), trifluoromethanesulfonic acid (0.84 mL), and trifluoroacetic acid (3.34 mL) was stirred at 50° C. for 2 hours. The solution was then added dropwise to a rapidly stirred mixture of concentrated aqueous NH$_4$OH (10 mL) and ethyl acetate (30 mL). Extraction and purification similar to example 33, afforded 90 as an off-white solid (140.9 mg). Although this material appeared pure by HPLC and $^1$H NMR analysis, the elemental analysis showed significant impurities. The impure material was dissolved in ethyl acetate (50 mL) and washed with water (10 mL), saturated aqueous sodium bicarbonate solution (10 mL), and saturated aqueous sodium chloride solution (10 mL). The organic layer was dried over magnesium sulfate, filtered and concentrated to give 90 (49.4 mg, 35%) as a white solid: $^1$H NMR (CD$_3$OD) δ 1.71 (d, 3H, J=6.8 Hz), 2.45 (s, 3H), 4.66 (q, 1H, J=7.0 Hz), 7.24 (d, 1H, J=7.5 Hz), 7.32 (t, 1H, J=7.7 Hz), 7.61 (dd, 1H, J=7.9, 1.0 Hz),7.67 (dd, 1H, J=8.5, 1.5 Hz), 7.82 (m, 3H), 8.03 (d, 1H, J=8.3 Hz), 8.24 (d, 1H, J=7.5 Hz), 8.53 (s, 1H), 8.71 (s, 1H), 9.30 (s, 1H). Anal. ($C_{26}H_{22}N_6 \cdot 0.4$ CH$_2$Cl$_2$) C, H, N.

EXAMPLE 91

3-(1H-Benzoimidazol-2-yl)-5-(4-methyl-5-morpholin-4-ylmethyl-pyridin-3-yl)-1H-indazole

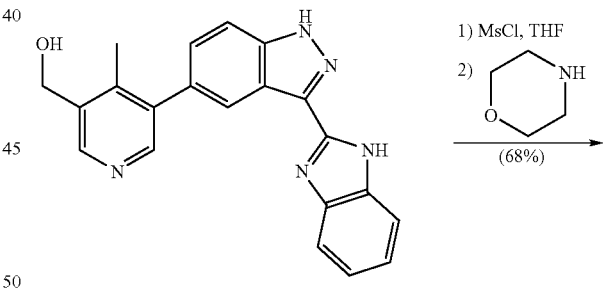

72

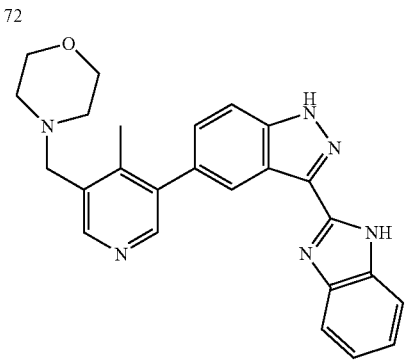

91

(a) Example 91—3-(1H-Benzoimidazol-2-yl)-5-(4-methyl-5-morpholin-4-ylmethyl-pyridin-3-yl)-1H-indazole The title compound was prepared in 68% yield from example 72 and morpholine using an analogous procedure to the preparation of intermediate 68b. $^1$H NMR (300 MHz, DMSO-$d_6$) δ 13.78 (s, 1H), 13.02 (s, 1H), 8.42 (s, 2H), 8.40 (s, 1H), 7.75 (d, 1H, J=8.7 Hz), 7.59 (br s, 2H), 7.44 (dd, 1H, J=8.7, 1.5 Hz), 7.17–7.22 (m, 2H), 3.58–3.67 (m, 6H), 2.48 (br s, 4H), 2.30 (s, 3H). Anal. ($C_{25}H_{24}N_6O \cdot 0.7H_2O$) C, H, N. MS (ES) [m+H]/z calculated 425. found 425.

EXAMPLE 92

{5-[3-(1H-Benzoimidazol-2-yl)-1H-indazol-5-yl]-4-methyl-pyridin-3-ylmethyl}-cyclopentyl-amine

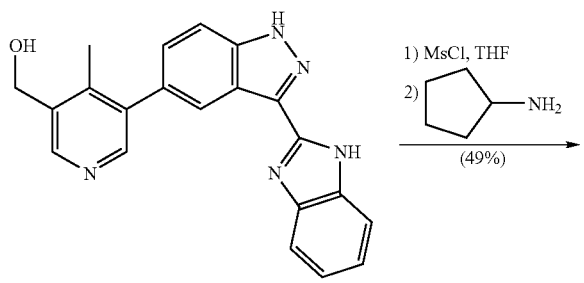

72

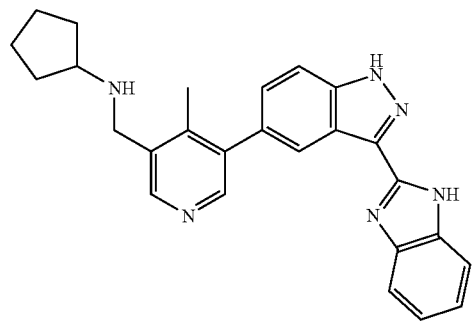

92

(a) Example 92—{5-[3-(1H-Benzoimidazol-2-yl)-1H-indazol-5-yl]-4-methyl-pyridin-3-ylmethyl}-cyclopentyl-amine The title compound was prepared in 49% yield from example 72 and cyclopentylamine using an analogous procedure to the preparation of intermediate 68b. $^1$H NMR (300 MHz, MeOD-$d_4$) δ 8.49 (s, 1H), 8.46 (s, 1H), 8.42 (s, 1H), 7.73 (d, 1H, J=8.7 Hz), 7.64 (br s, 2H), 7.45 (d, H, J=8.7 Hz), 7.24–7.28 (m, 2H), 3.95 (s, 2H), 3.25 (br s, 1H), 2.39 (s, 3H) 1.96–2.02 (m, 2H), 1.71–1.78 (m, 2H), 1.46–1.67 (m, 4H). Anal. ($C_{26}H_{26}N_6 \cdot 0.25H_2O$) C, H, N. MS (ES) [m+H]/z calc'd 423. found 423.

EXAMPLE 93

{5-[3-(1H-Benzoimidazol-2-yl)-1H-indazol-5-yl]-4-methyl-pyridin-3-ylmethyl}-pyridin-3-yl-amine

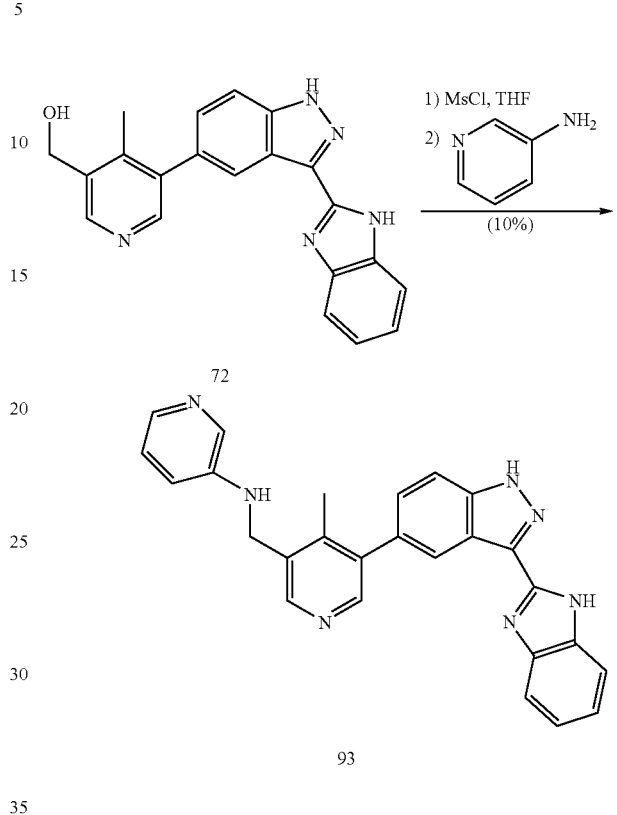

(a) Example 93—{5-[3-(1H-Benzoimidazol-2-yl)-1H-indazol-5-yl]-4-methyl-pyridin-3-ylmethyl}-pyridin-3-yl-amine The title compound was prepared in 10% yield from example 72 and 3-amino-pyridine using an analogous procedure to the preparation of intermediate 68b. $^1$H NMR (300 MHz, DMSO-$d_6$) δ 13.79 (s, 1H), 13.03 (s, 1H), 8.49 (s, 1H), 8.45 (s, 1H), 8.42 (s, 1H), 8.09 (s, 1H), 7.83 (s, 1H), 7.75 (d, 1H, J=8.7 Hz), 7.59 (br s, 2H), 7.45 (d, 1H, J=8.7 Hz), 7.09–7.22 (m, 4H), 6.55 (br s, 1H), 4.40 (d, 1H, J=6.0 Hz), 2.28 (s, 3H). Anal. ($C_{26}H_{21}N_7 \cdot 0.5H_2O$) C, H, N. MS (ES) [m+H]/z calc'd 432. found 432.

Biochemical and Biological Evaluation

Cyclin-dependent kinase activity was measured by quantifying the enzyme-catalyzed, time-dependent incorporation of radioactive phosphate from [$^{32}$P]ATP or [$^{33}$P]ATP into a protein substrate. Unless noted otherwise, assays were performed in 96-well plates in a total volume of 50 μL, in the presence of 10 mM HEPES (N-[2-hydroxyethyl]piperazine-N'-[2-ethanesulfonic acid]) (pH 7.4), 10 mM MgCl$_2$, 25 μM adenosine triphosphate (ATP), 1 mg/mL ovalbumin, 5 μg/mL leupeptin, 1 mM dithiothreitol, 10 mM beta-glycerophosphate, 0.1 mM sodium vanadate, 1 mM sodium fluoride, 2.5 mM ethylene glycol-bis(β-aminoethyl ethKer)-N, N,N',N'-tetraacetic acid (EGTA), 2% (v/v) dimethylsulfoxide, and 0.03–0.4 μCi [$^{32/33}$P]ATP per reaction. Reactions were initiated with appropriate enzyme, incubated at 30° C., and terminated after 20 minutes by the addition of ethylenediaminetetraacetic acid (EDTA) to 250 mM. The phosphorylated substrate was then captured on a nitrocellulose or phosphocellulose membrane using a 96-well filtration manifold, and unincorporated radioactivity was removed by repeated washing with 0.85% phosphoric acid. Radioactivity was quantified by exposing the dried membranes to a phosphorimager.

Apparent $K_i$ values were measured by assaying enzyme activity in the presence of different inhibitor compound concentrations and subtracting the background radioactivity measured in the absence of enzyme. Inhibition data were fit to an equation for competitive inhibition using Kaleidagraph (Synergy Software), or were fit to an equation for competitive tight-binding inhibition using the software KineTic (BioKin, Ltd.).

Inhibition of CDK4/Cyclin D Retinoblastoma Kinase Activity

A complex of human CDK4 and cyclin D3, or a complex of human CDK4 and genetically truncated (1–264) cyclin D3, was purified using traditional biochemical chromatographic techniques from insect cells that had been co-infected with the corresponding baculovirus expression vectors (see e.g., Meijer and Kim, "Chemical Inhibitors of Cyclin-Dependent Kinases," Methods in Enzymol,. vol. 283 (1997), pp. 113–128.). The enzyme complex (5 or 50 nM) was assayed with 0.3–0.5 µg of purified recombinant retinoblastoma protein fragment (Rb) as a substrate. The engineered Rb fragment (residues 386–928 of the native retinoblastoma protein; 62.3 kDa) contains the majority of the phosphorylation sites found in the native 106-kDa protein, as well as a tag of six histidine residues for ease of purification. Phosphorylated Rb substrate was captured by microfiltration on a nitrocellulose membrane and quantified using a phosphorimager as described above. For measurement of tight-binding inhibitors, the enzyme complex concentration was lowered to 5 nM, and the assay duration was extended to 60 minutes, during which the time-dependence of product formation was linear.

Inhibition of CDK2/Cyclin A Retinoblastoma Kinase Activity

CDK2 was purified using published methodology (Rosenblatt et al., "Purification and Crystallization of Human Cyclin-dependent Kinase 2," J. Mol. Biol., vol. 230, 1993, pp. 1317–1319) from insect cells that had been infected with a baculovirus expression vector. Cyclin A was purified from E. coli cells expressing full-length recombinant cyclin A, and a truncated cyclin A construct was generated by limited proteolysis and purified as described previously (Jeffrey et al., "Mechanism of CDK activation revealed by the structure of a cyclin A-CDK2 complex," Nature, vol. 376 (27 Jul. 1995), pp. 313–320). A complex of CDK2 and proteolyzed cyclin A was prepared and purified by gel filtration. The substrate for this assay was the same Rb substrate fragment used for the CDK4 assays, and the methodology of the CDK2/cyclin A and the CDK4/cyclin D3 assays was essentially the same, except that CDK2 was present at 150 nM or 5 nM. $K_i$ values were measured as described above.

The stimulation of cell proliferation by growth factors such as VEGF and others is dependent upon their induction of autophosphorylation of each of their respective receptor's tyrosine kinases. Therefore, the ability of a protein kinase inhibitor to block cellular proliferation induced by these growth factors is directly correlated with its ability to block receptor autophosphorylation. To measure the protein kinase inhibition activity of the compounds, the following constructs were used.

VEGF-R2 Construct for Assay

This construct determines the ability of a test compound to inhibit tyrosine kinase activity. A construct (VEGF-R2Δ50) of the cytosolic domain of human vascular endothelial growth factor receptor 2 (VEGF-R2) lacking the 50 central residues of the 68 residues of the kinase insert domain was expressed in a baculovirus/insect cell system. Of the 1356 residues of full-length VEGF-R2, VEGF-R2Δ50 contains residues 806–939 and 990–1171, and also one point mutation (E990V) within the kinase insert domain relative to wild-type VEGF-R2. Autophosphorylation of the purified construct was performed by incubation of the enzyme at a concentration of 4 µM in the presence of 3 mM ATP and 40 mM $MgCl_2$ in 100 mM Hepes, pH 7.5, containing 5% glycerol and 5 mM DTT, at 4° C. for 2 hours After autophosphorylation, this construct has been shown to possess catalytic activity essentially equivalent to the wild-type autophosphorylated kinase domain construct. See Parast et al., Biochemistry, 37,16788–16801 (1998).

CHK1 Construct for Assay

C-terminally His-tagged full-length human CHK1 (FL-CHK1) was expressed using the baculovirus/insect cell system. It contains 6 histidine residues (6×His-tag) at the C-terminus of the 476 amino acid human CHK1. The protein was purified by conventional chromatographic techniques.

VEGF-R2 Assay

Coupled Spectrophotometric (FLVK-P) Assay

The production of ADP from ATP that accompanies phosphoryl transfer was coupled to oxidation of NADH using phosphoenolpyruvate (PEP) and a system having pyruvate kinase (PK) and lactic dehydrogenase (LDH). The oxidation of NADH was monitored by following the decrease of absorbance at 340 nm ($e_{340}$=6.22 $cm^1$ $mM^{-1}$) using a Beckman DU 650 spectrophotometer. Assay conditions for phosphorylated VEGF-R2A50 (indicated as FLVK-P in the tables below) were the following: 1 mM PEP; 250 µM NADH; 50 units of LDH/mL; 20 units of PK/mL; 5 mM DTT; 5.1 mM poly($E_4Y_1$); 1 mM ATP; and 25 mM $MgCl_2$ in 200 mM Hepes, pH 7.5. Assay conditions for unphosphorylated VEGF-R2A50 (indicated as FLVK in the tables) were the following: 1 mM PEP; 250 µM NADH; 50 units of LDH/mL; 20 units of PK/mL; 5 mM DTT; 20 mM poly($E_4Y_1$); 3 mM ATP; and 60 mM $MgCl_2$ and 2 mM $MnCl_2$ in 200 mM Hepes, pH 7.5. Assays were initiated with 5 to 40 nM of enzyme. $K_i$ values were determined by measuring enzyme activity in the presence of varying concentrations of test compounds. The data were analyzed using Enzyme Kinetic and Kaleidagraph software.

ELISA Assay

Formation of phosphogastrin was monitored using biotinylated gastrin peptide (1–17) as substrate. Biotinylated phosphogastrin was immobilized using streptavidin coated 96-well microtiter plates followed by detection using anti-phosphotyrosine-antibody conjugated to horseradish peroxidase. The activity of horseradish peroxidase was monitored using 2,2'-azino-di-[3-ethylbenzathiazoline sulfonate(6)] diammonium salt (ABTS). Typical assay solutions contained: 2 µM biotinylated gastrin peptide; 5 mM DTT; 20 µM ATP; 26 mM $MgCl_2$; and 2 mM $MnCl_2$ in 200 mM Hepes, pH 7.5. The assay was initiated with 0.8 nM of phosphorylated VEGF-R2Δ50. Horseradish peroxidase activity was assayed using ABTS, 10 mM. The horseradish peroxidase reaction was quenched by addition of acid ($H_2SO_4$), followed by absorbance reading at 405 nm. $K_i$ values were determined by measuring enzyme activity in the presence of varying concentrations of test compounds. The data were analyzed using Enzyme Kinetic and Kaleidagraph software.

CHK1 Assay

The production of ADP from ATP that accompanies phosphoryl transfer to the synthetic substrate peptide Syntide-2 (PLARTLSVAGLPGKK) was coupled to oxidation of NADH using phosphoenolpyruvate (PEP) through the actions of pyruvate kinase (PK) and lactic dehydrogenase (LDH). The oxidation of NADH was monitored by following the decrease of absorbance at 340 nm ($\epsilon 340 = 6.22$ cm$^{-1}$ mM$^{-1}$) using a HP8452 spectrophotometer. Typical reaction solutions contained: 4 mN PEP; 0.15 mM NADH; 28 units of LDH/ml; 16 units of PK/ml; 3 mM DTT; 0.125 mM Syntide-2; 0.15 mM ATP; 25 mM $MgCl_2$ in 50 mM TRIS, pH 7.5; and 400 mM NaCl. Assays were initiated with 10 nM of FL-CHK1. $K_i$ values were determined by measuring initial enzyme activity in the presence of varying concentrations of test compounds. The data were analyzed using Enzyme Kinetic and Kaleidagraph software.

Inhibition of Phosphorylated FGF Receptor and LCK Tyrosine Kinase Activity

Cloning, expression and purification of the cytosolic domain of FGFR1 tyrosine kinase (amino acids 456–766) containing three amino acid substitutions (L457V, C488A, and C584S) were conducted as previously described (Mohammadi, M., Schlessinger, J., & Hubbard, S. R. (1996) Cell 86, 577–587). This domain was expressed in Sf9 insect cells using a baculovirus expression vector, and protein was purified using conventional techniques. The LCK tyrosine kinase was expressed in insect cells as an N-terminal deletion starting from amino acid 223 to the end of the protein at amino acid 509. The N-terminus of the protein also had two amino acid substitutions, P223M and C 224D. Kinases were purified using conventional chromatographic methods.

Tyrosine kinase activity was measured using a coupled, continuous spectrophotometric assay, in which production of phosphorylated poly(Glu, Tyr; 4:1) substrate and ADP is coupled to the pyruvate kinase-catalyzed transfer of a phosphate from phosphoenolpyruvate to ADP, with generation of pyruvate and regeneration of ATP. Pyruvate production is in turn coupled to the lactate dehydrogenase-catalyzed reduction of pyruvate to form lactate, with concomitant conversion of NADH to NAD+. Loss of NADH is monitored by measuring absorbance at 340 nm (see e.g., Technikova-Dobrova et al., "Spectrophotometric determination of functional characteristics of protein kinases with coupled enzymatic assay," FEBS Letters, vol. 292 (1991), pp. 69–72). Enzyme activity was measured in the presence of 200 mM HEPES (pH 7.5), 2 mM phosphoenolpyruvate, 0.3 mM NADH, 20 mM $MgCl_2$, 100 µM ATP, 5 mM DTT, 5.1 or 25 mM poly (Glu,Tyr) 4:1 for P-FGF or P-LCK assays, respectively, and 15 units/mL each of pyruvate kinase and lactate dehydrogenase. Phosphorylated FGF receptor kinase was present at 100 nM and phosphorylated LCK kinase was present at 50 nM. Assays were performed under initial rate conditions at 37° C., and rates were corrected for any background rate measured in the absence of enzyme. Percent inhibition was calculated relative to control enzyme assayed in the presence of 2% (v/v) DMSO. The results are shown in Table 1.

Coupled Spectrophotometric (FAK) Assay

Tyrosine kinase assays were monitored using a Beckman DU 650 Spectrophotometer. Production of ADP was coupled to oxidation of NADH using phosphoenolpyruvate (PEP) through the actions of pyruvate kinase (PK) and lactic dehydrogenase (LDH). The oxidation of NADH was monitored by following the decrease in absorbance at 340 nm ($\epsilon_{340} = 6.22$ cm$^{-1}$ mM$^{-1}$). Typical reaction solutions contained: 1 mM PEP, 250 µM NADH, 50 units of LDH/mL, 20 units of PK/mL, 5 mM DTT, in 200 mM Hepes, pH 7.5 and varying concentrations of poly($E_4Y_1$), ATP and $MgCl_2$. Assays were initiated with 40 nM of cdFGFR1.

Results of assays performed on compounds, which include the specific examples described above are provided below in Table I. Unless indicated otherwise in a particular entry, the units and assays used are as indicated in the applicable column of the table.

TABLE I

| | | | | $K_i$ with Kinases | | | |
|---|---|---|---|---|---|---|---|
| Ex. No. | $K_i$ CDK4/D (µM) | $K_i$ CDK2/A (µM) | $K_i$ CHK1 (µM) or % Inhib. | $K_i$ VEGF (µM) or % Inhib. at 1 µM | $K_i$ LCK (µM) or % Inhib. at 1 µM | $K_i$ FGF (µM) or % Inhib. at 1 µM | FAK % Inhibition at 1 µM |
| 1 | 1.7 +/− 0.6 | 11 +/− 2 | 6.7 +/− 0.09 | NT | NT | NT | 32 |
| 2 | 7.9 +/− 3.0 | NT | NT | NT | NT | NT | NT |

TABLE I-continued

K_i with Kinases

| Ex. No. | K_i CDK4/D (μM) | K_i CDK2/A (μM) | K_i CHK1 (μM) or % Inhib. | K_i VEGF (μM) or % Inhib. at 1 μM | K_i LCK (μM) or % Inhib. at 1 μM | K_i FGF (μM) or % Inhib. at 1 μM | FAK % Inhibition at 1 μM |
|---|---|---|---|---|---|---|---|
| 3 | 0.37 +/− 0.05 | 0.24 +/− 0.01 | 75% inhibition at 20 μM | NT | NT | NT | NT |

TABLE I

K_i with Kinases

| Ex. No. | K_i CDK4/D (μM) | K_i CDK2/A (μM) | K_i CHK1 (μM) or % Inhib. | K_i VEGF (μM) or % Inhib. at 1 μM | K_i LCK (μM) or % Inhib. at 1 μM | K_i FGF (μM) or % Inhib. at 1 μM | FAK % Inhibition at 1 μM |
|---|---|---|---|---|---|---|---|
| 4 | 0.11 +/− 0.02 | 0.14 +/− 0.01 | 1.09 +/− 0.12 | 0.0264 +/− 0.002 | NT | NT | NT |
| 5 | 0.48 +/− 0.04 | 0.69 +/− 0.03 | 56% inhibition at 20 μM | NT | NT | NT | NT |
| 6 | 0.2 +/− 0.03 | 0.16 +/− 0.02 | 80% inhibition at 20 μM | 64% | 11% | 53% | NT |
| 7' | 1.2 +/− 0.3 | 0.79 +/− 0.12 | NT | NT | NT | NT | NT |
| 8' | 0.59 +/− 0.10 | 0.37 +/− 0.04 | NT | NT | NT | NT | NT |
| 9' | 2.2 +/− 0.3 | 0.67 +/− 0.07 | NT | NT | NT | NT | NT |
| 10' | 0.074 +/− 0.009 | 0.033 +/− 0.003 | 5% inhibition @ 10 μM | NT | 21% | 61% | NT |
| 11 | 39% inhibition at 10 μM | 2.6 +/− 0.3 | NT | NT | NT | NT | NT |
| 11a | 48% inhibition at 100 μM | 13 | NT | NT | NT | NT | NT |
| 12 | 19% inhibition at 5 μM | 6.3 +/− 1.1 | NT | NT | NT | NT | NT |
| 13 | 3.4 +/− 0.7 | 2.7 +/− 0.7 | NT | NT | NT | NT | NT |
| 14 | 2.4 +/− 0.5 | 2.5 +/− 0.4 | NT | NT | NT | NT | NT |
| 14b | 20% inhibition at 1 μM | NT | NT | NT | NT | NT | NT |
| 15' | 0.018 | 0.062 +/− 0.007 | 16% inhibition at 1 μM | NT | 17% | 87% | NT |
| 16 | 0.035 | 0.015 | 81 | 36% | NT | 1 | 47% |
| 17 | NT | 1.4 | NT | NT | NT | 42.6% | NT |
| 18 | 0.96 | NT | NT | NT | NT | NT | NT |
| 18b' | 6.6 | 3.3 | NT | NT | NT | NT | NT |
| 19 | 0.054 | 0.001 | NT | NT | NT | 31.3% inhibition | NT |
| 20 | 0.0021 | 0.00093 | NT | NT | NT | 96.9% | NT |
| 21 | 0.237 | 0.049 | 8.55 | NT | 23% | 54% | NT |
| 22 | 0.015 | 0.094 | NT | NT | NT | 93.5% | NT |
| 23 | 0.065 | 0.041 | NT | NT | NT | 0.8 | NT |
| 24 | 0.69 | 1.1 | NT | NT | NT | 45.4% | NT |
| 25 | 0.01 | 0.001 | NT | NT | NT | 0.44 | NT |
| 26 | 0.083 | 0.072 | NT | NT | NT | NT | NT |
| 27 | 1.5 | 1.6 | NT | NT | NT | NT | 44% |
| 28 | 0.68 | 0.72 | NT | NT | NT | NT | 61% |
| 29 | 0.0077 | 0.00047 | NT | 6% | NT | 2.2 | NT |
| 30 | 0.011 | 0.001 | NT | NT | NT | 52.4% | NT |
| 31 | 0.00037 | 0.00021 | NT | 2.9; 17% | NT | 55.5% | NT |
| 32 | 0.00041 | 0.00025 | NT | NT | NT | 29.7% | NT |
| 33 | 0.0011 | 0.001 | NT | NT | NT | 51.6% | NT |
| 34 | 0.019 | 0.001 | NT | NT | NT | 26.9% | NT |
| 35 | 0.0032 | 0.001 | NT | NT | NT | 40.5% | NT |
| 36 | 0.0023 | 0.001 | NT | 15% | NT | 55.8% | NT |
| 37 | 0.00076 | 0.00022 | NT | 17% | NT | 34.4% | NT |
| 38 | 0.000798 | 0.001 | NT | 9% | NT | 42.4% | NT |
| 39 | 0.009 | 0.0011 | NT | NT | NT | NT | NT |

TABLE I-continued

K<sub>i</sub> with Kinases

| Ex. No. | $K_i$ CDK4/D (μM) | $K_i$ CDK2/A (μM) | $K_i$ CHK1 (μM) or % Inhib. | $K_i$ VEGF (μM) or % Inhib. at 1 μM | $K_i$ LCK (μM) or % Inhib. at 1 μM | $K_i$ FGF (μM) or % Inhib. at 1 μM | FAK % Inhibition at 1 μM |
|---|---|---|---|---|---|---|---|
| 40 | 0.0022 | 0.00038 | NT | NT | NT | NT | NT |
| 41 | 0.078 | 0.25 | NT | NT | NT | NT | NT |
| 42 | 0.0082 | 0.0172 | NT | NT | NT | 70.3% | 78% |
| 43 | 0.015 | 0.029 | NT | NT | NT | 59.6% | NT |
| 44 | 0.019 | 0.029 | NT | NT | NT | 56.2% | NT |
| 45 | 0.012 | 0.017 | NT | NT | NT | 58.7% | 63% |
| 46 | 0.03 | 0.028 | NT | 51% | NT | 50.5% | NT |
| 47 | 0.094 | 0.1 | NT | NT | NT | 81.1% | NT |
| 48 | 0.021 | 0.055 | 7.82 | NT | NT | 68.5% | NT |
| 49 | 0.095 | 0.049 | NT | NT | NT | 86.7% | NT |
| 50 | 0.253 | 0.073 | NT | NT | NT | 89.6% | NT |
| 51 | 1.1 | 0.4 | NT | NT | NT | NT | NT |
| 52 | 0.0035 | 0.0026 | NT | 38% | NT | 55% | NT |
| 53 | 0.0026 | 0.00029 | NT | 32% | NT | 32% | NT |
| 54 | 0.026 | 0.00027 | NT | 46% | NT | 81.5% | NT |
| 55 | 0.041 | 0.0011 | NT | 32% | NT | 83.6% | NT |
| 56 | 0.036 | 0.001 | NT | NT | NT | NT | NT |
| 57 | 0.65 | 0.037 | NT | NT | NT | NT | NT |
| 58 | 0.0067 | 0.001 | NT | 17% | NT | 3; 20.3% | NT |
| 59 | 0.0016 | 0.00058 | NT | 31% | NT | 47.6% | NT |
| 60 | 0.0016 | 0.0006 | NT | 26% | NT | 40.8% | NT |
| 61 | 0.017 | 0.0012 | NT | 18% | NT | 0.48; 60.7% | NT |
| 62 | 0.05 | 0.0037 | NT | NT | NT | NT | NT |
| 63 | 0.22 | 0.0012 | NT | NT | NT | NT | NT |
| 64 | 0.19 | 0.014 | NT | NT | NT | NT | NT |
| 65 | 0.0028 | 0.001 | NT | NT | NT | 44.1% | NT |
| 66 | 0.055 | 0.001 | NT | NT | NT | NT | NT |
| 67 | 0.22 | 0.016 | NT | NT | NT | NT | NT |
| 68 | 0.0047 | 0.0011 | NT | NT | NT | 12.6% | NT |
| 69 | 0.015 | 0.0041 | NT | 38% | NT | 25.6% | NT |
| 70 | 0.0018 | 0.00023 | NT | 45% | NT | 63% | NT |
| 71 | 0.00085 | 0.001 | NT | 42% | NT | 28.8% | NT |
| 72 | 0.012 | 0.0076 | NT | 24% | NT | 48.6% | NT |
| 73 | 0.0069 | 0.0027 | NT | 15% | NT | 42.9 | NT |
| 74 | 0.00052 | 0.0016 | NT | 14% | NT | 82.6 | NT |
| 75 | 0.0098 | 0.0014 | NT | NT | NT | NT | NT |
| 76 | 0.15 | 0.027 | NT | NT | NT | NT | NT |
| 77 | 0.0058 | 0.00038 | NT | NT | NT | NT | NT |
| 78 | 0.0055 | 0.0007 | NT | NT | NT | NT | NT |
| 79 | 0.0022 | 0.00042 | NT | NT | NT | NT | NT |
| 80 | 0.014 | 0.00025 | NT | NT | NT | NT | NT |
| 81 | 0.0008 | 0.0049 | NT | NT | NT | NT | NT |
| 82 | 0.11 | 0.0024 | NT | NT | NT | NT | NT |
| 83 | 30% at 10 μM | 30% at 10 μM | NT | NT | NT | NT | NT |
| 84 | 34 | 28 | 22.5 | NT | NT | NT | NT |
| 85 | 16 | 6.6 | NT | NT | NT | NT | NT |
| 86 | 18% at 10 μM | 45% at 10 μM | NT | NT | NT | NT | NT |
| 87 | 0.0042 | 0.0019 | NT | NT | NT | NT | NT |
| 88 | 0.0035 | 0.0014 | NT | NT | NT | NT | NT |
| 89 | 0.001 | 0.00094 | NT | NT | NT | NT | NT |
| 90 | 0.00009 | 0.0003 | NT | NT | NT | NT | NT |
| 91 | 0.0075 | 0.0028 | NT | NT | NT | NT | NT |
| 92 | 0.0078 | 0.0027 | NT | NT | NT | NT | NT |
| 93 | 0.0019 | 0.00061 | NT | NT | NT | NT | NT |

Note:
NT = not tested.

Inhibition of Cell Growth: Assessment of Cytotoxicity

Inhibition of cell growth was measured using the tetrazolium salt assay, which is based on the ability of viable cells to reduce 3-(4,5-dimethylthiazol-2-yl)-2,5-[2H]-diphenyltetrazolium bromide (MTT) to formazan (Mossman, Journal of Immunological Methods, vol. 65 (1983), pp. 55–58). The water-insoluble purple formazan product was then detected spectrophotometrically. The HCT 116 cell line was grown in 96-well plates. Cells were plated in the appropriate medium at a volume of 135 μl/well in McCoy's 5A Medium. Plates were incubated for four hours before addition of inhibitor compounds. Different concentrations of inhibitor compounds were added in 0.5% (v/v) dimethylsulfoxide (15 μL/well), and cells were incubated at 37° C.

(5% CO$_2$) for four to six days (depending on cell type). At the end of the incubation, MTT was added to a final concentration of 0.2 mg/mL, and cells were incubated for 4 hours more at 37° C. After centrifugation of the plates and removal of medium, the absorbance of the formazan (solubilized in dimethylsulfoxide) was measured at 540 nm. The concentration of inhibitor compound causing 50% inhibition of growth was determined from the linear portion of a semi-log plot of inhibitor concentration versus percentage inhibition. All results were compared to control cells treated only with 0.5% (v/v) dimethylsulfoxide.

TABLE II

| Example No. | HCT 116 IC50 (uM) | HCT 116 IC90 (uM) |
|---|---|---|
| 4 | 2.7 | 6.2 |
| 6 | 6 | 21 |
| 10 | 1.5 | 3.8 |
| 15 | 1.2 | 2.5 |
| 16 | 3 | 5 |
| 17 | 3.2 | 5 |
| 19 | 0.78 | 1.6 |
| 20 | 0.07 | 0.4 |
| 22 | 5 | 5 |
| 23 | 4 | 5 |
| 25 | 0.33 | 1.1 |
| 26 | 2.8 | 5 |
| 29 | 0.18 | 0.8 |
| 30 | 0.18 | 0.62 |
| 31 | 0.22 | 0.058 |
| 32 | 0.086 | 0.23 |
| 33 | 0.055 | 0.16 |
| 34 | 0.2 | 0.58 |
| 35 | 0.13 | 0.37 |
| 36 | 0.024 | 0.06 |
| 37 | 0.041 | 0.12 |
| 38 | 0.029 | 0.06 |
| 39 | 0.018 | 0.06 |
| 42 | 3 | 5 |
| 43 | 1.9 | 5 |
| 44 | 5 | 5 |
| 45 | 2.1 | 5 |
| 47 | 2.1 | 5 |
| 48 | 3.9 | 5 |
| 49 | 2.3 | 4.8 |
| 50 | 1.8 | 5 |
| 52 | 0.5 | 2.2 |
| 53 | 0.2 | 0.75 |
| 54 | 0.079 | 0.23 |
| 55 | 1.5 | 5 |
| 56 | 0.48 | 1.3 |
| 57 | 2 | 5 |
| 58 | 0.46 | 1.3 |
| 59 | 0.2 | 0.48 |
| 60 | 0.2 | 0.5 |
| 61 | 0.22 | 0.5 |
| 62 | 1 | 2.4 |
| 63 | 0.43 | 1.3 |
| 64 | 1.3 | 5 |
| 65 | 0.39 | 1.3 |
| 66 | 0.49 | 1.6 |
| 67 | 2 | 4.7 |
| 68 | 0.16 | 0.6 |
| 69 | 0.69 | 2.1 |
| 70 | 0.18 | 0.44 |
| 71 | 0.7 | 2 |
| 72 | 0.15 | 0.53 |
| 73 | 0.2 | 0.6 |
| 75 | 0.4 | 1.3 |
| 76 | 0.5 | 0.5 |
| 77 | 0.31 | 0.5 |
| 78 | 0.085 | 0.22 |
| 79 | 0.5 | 0.5 |
| 80 | 0.09 | 0.22 |
| 81 | 0.086 | 0.21 |
| 82 | >0.5 | >0.5 |

TABLE II-continued

| Example No. | HCT 116 IC50 (uM) | HCT 116 IC90 (uM) |
|---|---|---|
| 87 | 0.16 | 0.42 |
| 88 | >0.5 | >0.5 |
| 89 | 0.15 | 0.25 |
| 90 | 0.03 | 0.12 |
| 91 | 0.34 | >0.5 |
| 92 | 0.18 | 0.5 |
| 93 | 0.32 | >0.5 |

The examples above illustrate compounds according to Formula I or II and assays that may readily be performed to determine their activity levels against the various kinase complexes. It will be apparent that such assays or other suitable assays known in the art may be used to select an inhibitor having a desired level of activity against a selected target.

The exemplary compounds described above may be formulated into pharmaceutical compositions according to the following general examples.

Parenteral Composition

To compare a parenteral pharmaceutical composition suitable for administration by injection, 100 mg of a water-soluble salt of a compound of Formula I or II is dissolved in DMSO and then mixed with 10 mL of 0.9% sterile saline. The mixture is incorporated into a dosage unit form suitable for administration by injection.

Oral Composition

To prepare a pharmaceutical composition for oral delivery, 100 mg of a compound of Formula I or II is mixed with 750 mg of lactose. The mixture is incorporated into an oral dosage unit for, such as a hard gelatin capsule, which is suitable for oral administration.

It is to be understood that the foregoing description is exemplary and explanatory in nature, and is intended to illustrate the invention and its preferred embodiments. Thus, the scope of the invention should be understood to be defined not by the foregoing description, but by the following claims and their equivalents.

We claim:

1. A compound having the formula

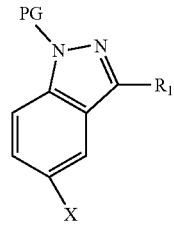

wherein PG is (trimethyl silyl) ethoxy methyl (SEM), benzyloxycarbonyl (CBZ), tert-butoxycarbonyl (BOC), tetra hydropyranyl (THP), or fluorene-9-methyloxycarbonyl;
X is halo or NO$_2$; and
R$_1$ is a substituted or unsubstituted benzimidazole.

2. The compound according to claim 1, wherein R$_1$ is a substituted benzimidazole.

* * * * *